US 12,043,674 B2

(12) United States Patent
Raj et al.

(10) Patent No.: US 12,043,674 B2
(45) Date of Patent: Jul. 23, 2024

(54) SYNTHETIC CYCLIC PEPTIDES AND METHODS OF PREPARATION AND USE THEREOF

(71) Applicant: Auburn University, Auburn, AL (US)

(72) Inventors: Monika Raj, Atlanta, GA (US); Victor Adebomi, Atlanta, GA (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 17/502,506

(22) Filed: Oct. 15, 2021

(65) Prior Publication Data

US 2022/0119445 A1     Apr. 21, 2022

Related U.S. Application Data

(60) Provisional application No. 63/092,343, filed on Oct. 15, 2020.

(51) Int. Cl.
    *A61K 38/00*     (2006.01)
    *C07K 5/12*     (2006.01)

(52) U.S. Cl.
    CPC .............. *C07K 5/123* (2013.01); *A61K 38/00* (2013.01)

(58) Field of Classification Search
    CPC ...... A61K 38/00; C07K 5/123; C07K 5/1016; C07K 7/06
    See application file for complete search history.

(56) References Cited

U.S. PATENT DOCUMENTS

| | | | |
|---|---|---|---|
| 9,040,462 B2 | 5/2015 | Lorens | |
| 9,073,975 B2 | 7/2015 | Klingler | |
| 9,394,561 B2 | 7/2016 | Barber | |
| 10,494,657 B2 | 12/2019 | Ibrahim | |

FOREIGN PATENT DOCUMENTS

WO      2011156686      12/2011

OTHER PUBLICATIONS

Roscic et al. Stereochemical Assignment of Diastereomeric Imidazolidinone-Ring-Containing Bicyclic Sugar-Peptide Adducts: NMR Spectroscopy and Molecular Calculations. Eur. J. Org. Chem. 2004, 4641-4647 (Year: 2004).*
"Click Chemistry Azide-Alkyne Cycloaddition," Organic Chemistry Portal, https://www.organic-chemistry.org/namedreactions/click-chemistry.shtm (accessed Nov. 23, 2022) 8 pages.
"Click Chemistry for peptide cyclization," Bio-Synthesis website, https://www.biosyn.com/cyclic-peptide-synthesis.aspx (accessed Nov. 23, 2022) 3 pages.
"Cyclic Custom Peptides," Biopeptek website, https://biopeptek.com/products-services/custom-peptides/cyclic-custom-peptides/ (accessed Nov. 23, 2022) 2 pages.
"Cyclizations," Pepscan website, https://www.pepscan.com/custom-peptide-synthesis/peptide-modifications/cyclizations/ (accessed Nov. 23, 2022) 3 pages.
"Peptide cyclization," Smart Bioscience website, https://www.sb-peptide.com/peptide-service/peptide-modification/peptide-cyclization/ (accessed Nov. 23, 2022) 9 pages.
Aboul-Enein MN et al., 2015, "Synthesis and Anticonvulsant Activity of Substituted-1,3-diazaspiro[4.5]decan-4-ones" Arch. Pharm., 348:575.
Adebomi et al., 2019, "CyClick Chemistry for the Synthesis of Cyclic Peptides" Angew. Chem. Int. Ed. 2019, 58:19073.
Adessi C et al., 2002, "Converting a peptide into a drug: strategies to improve stability and bioavailability" Curr. Med. Chem., 9:963.
Albericio F et al., 2012, "Therapeutic peptides" Future Med. Chem., 4:1527.
Bielawski CW et al., 2002, "An "endless" route to cyclic polymers" Science, 297:2041.
Cardote TAF et al., 2016, "Cyclic and Macrocyclic Peptides as Chemical Tools To Recognise Protein Surfaces and Probe Protein-Protein Interactions" ChemMedChem, 11:787.
Chang SD et al., 2015, "Novel Synthesis and Pharmacological Characterization of NOP Receptor Agonist 8-[(1S,3aS)-2,3,3a,4,5,6-Hexahydro-1H-phenalen-1-yl]-1-phenyl-1,3,8-triazaspiro[4.5]decan-4-one (Ro 64-6198)" ACS Chem. Neuroscie., 6:1956.
Chow H et al., 2019, "Ligation Technologies for the Synthesis of Cyclic Peptides" Chem. Rev., 119:9971.
Craik DJ et al., 2013, "The future of peptide-based drugs" Chem. Biol. Drug Des., 81:136.
Davis AC et al., 1951, "768. The interaction of α-amino-nitriles and aldehydes and ketones" J. Chem. Soc., 3479.
Dechantsreiter MA et al., 1999, "N-Methylated cyclic RGD peptides as highly active and selective alpha(V)beta(3) integrin antagonists" J. Med. Chem., 42:3033.
Driggers EM et al., 2008, "The exploration of macrocycles for drug discovery—an underexploited structural class" Nat. Rev. Drug Discovery, 7:608.
Ehrlich A et al., 1996, "Cyclization of all-L-Pentapeptides by Means of 1-Hydroxy-7-azabenzotriazole-Derived Uronium and Phosphonium Reagents" J. Org. Chem., 61:8831.
Empting, M., 2017 "Chapter 1: An Introduction to Cyclic Peptides," in Cyclic Peptides: From Bioorganic Synthesis to Applications, 1, 13 pages.
Federsel HJ et al., 1990, "Dichloromethane as reactant in synthesis: an expedient transformation of prolinamide to a novel pyrrolo[1,2-c]imidazolone" J. Org. Chem., 55:2254.
Frost JR et al., 2016, "Oxadiazole grafts in peptide macrocycles" Nat. Chem., 8:1105.
Heinis C et al., 2014, "Drug discovery: tools and rules for macrocycles" Nat. Chem. Biol., 10:696.

(Continued)

*Primary Examiner* — Aradhana Sasan
*Assistant Examiner* — Mercy H Sabila
(74) *Attorney, Agent, or Firm* — Riverside Law LLP

(57) ABSTRACT

The present invention relates, in part, to novel compounds comprising 4-imidazolidinone-fused cyclic peptides and compositions thereof. The present invention also relates to methods of generating said compounds and compositions thereof as well as methods of inhibiting protein-protein interaction using said compounds or compositions thereof. In another aspect, the present invention relates, in part, to methods of treating or preventing a various diseases or disorders using said compounds or compositions thereof.

13 Claims, 126 Drawing Sheets
Specification includes a Sequence Listing.

(56) References Cited

OTHER PUBLICATIONS

Hili R et al., 2010, "Macrocyclization of Linear Peptides Enabled by Amphoteric Molecules" J. Am. Chem. Soc., 132:2889.
Hill TA et al., 2014, "Constraining cyclic peptides to mimic protein structure motifs" Angew. Chem. Int. Ed., 53:13020.
Jain AN et al., 2019, "Complex macrocycle exploration: parallel, heuristic, and constraint-based conformer generation using ForceGen" J. Comput. Aided Mol. Des., 33:531.
Ji D et al., 2018, "[3+2]-Cycloaddition of Azaoxyallyl Cations with Hexahydro-1,3,5-triazines: Access to 4-Imidazolidinones" Org. Lett., 20:2745.
Kumagai H et al., 1991, "Effect of cyclic RGD peptide on cell adhesion and tumor metastasis" Biochem. Biophys. Res. Commun., 177:74.
Lambert JN et al., 2001, "The synthesis of cyclic peptides" J. Chem. Soc. Perkin Trans. 1, 471.
Lawson KV et al., 2013, "Template-constrained macrocyclic peptides prepared from native, unprotected precursors" Proc. Natl. Acad. Sci. USA, 110:E3753.
Lawson, K. V., et al, 2013 "Template-constrained macrocyclic peptides prepared from native, unprotected precursors," PNAS, E3753, 8 pages.
Li, Y., et al, "2009, Synthesis of Cyclic Peptides through Direct Aminolysis of Peptide Thioesters Catalyzed by Imidazole in Aqueous Organic Solutions," J. Comb. Chem. 11:1066.
Mach RH et al., 1992, "Effect of N-alkylation on the affinities of analogs of spiperone for dopamine D2 and serotonin 5-HT2 receptors" J. Med. Chem., 35:423.
Malesevic M et al., 2004, "An improved method for the solution cyclization of peptides under pseudo-high dilution conditions" J. Biotechnol., 112:73.
Malins LR et al., 2017, "Peptide Macrocyclization Inspired by Non-Ribosomal Imine Natural Products" J. Am. Chem. Soc., 139:5233.
Marti-Centelles V et al., 2015, "Macrocyclization Reactions: The Importance of Conformational, Configurational, and Template-Induced Preorganization" Chem. Rev., 115:8736.
Meutermans WDF et al., 2003, "Difficult Macrocyclizations: New Strategies for Synthesizing Highly Strained Cyclic Tetrapeptides" Org. Lett., 5:2711.
Molinski TF et al., 2011, "N, N'-Methyleno-didemnin A from the Ascidian Trididemnum solidum. Complete NMR Assignments and Confirmation of the Imidazolidinone Ring by Strategic Analysis of 1JCH" J. Nat. Prod., 74:882.
O'Reilly MC et al., 2013, "Development of Dual PLD1/2 and PLD2 Selective Inhibitors from a Common 1,3,8-Triazaspiro[4.5]decane Core: Discovery of ML298 and ML299 That Decrease Invasive Migration in U87-MG Glioblastoma Cells" J. Med. Chem., 56:2695.
Pagenkopf B et al., 2005, ""ACD/HNMR Predictor and ACD/CNMR Predictor Advanced Chemistry Development, Inc. (ACD/Labs), 90 Adelaide Street West, Suite 600, Toronto, ON M5H 2V9, Canada. www.acdlabs.com. See Web site for pricing information. J. Am. Chem. Soc., 127:3232.
Puentes AR et al., 2017, "Peptide Macrocyclization Assisted by Traceless Turn Inducers Derived from Ugi Peptide Ligation with Cleavable and Resin-Linked Amines" Org. Lett., 19:4022.
Rohrbacher, F., et al, 2015, "Spontaneous head-to-tail cyclization of unprotected linear peptides with the KAHA ligation," Chem Sci. 6:4889.
Royo-Gracia, S et al., 2009, "Synthesis of chemically modified bioactive peptides: recent advances, challenges and developments for medicinal chemistry" Future Med. Chem., 1:1289.
Schilling N et al., 2019, "Synthetic Lugdunin Analogues Reveal Essential Structural Motifs for Antimicrobial Action and Proton Translocation Capability" Angew. Chem. Int. Ed., 58:9234.
Skropeta D et al., 2004, "Pseudoprolines as removable turn inducers: tools for the cyclization of small peptides" J. Org. Chem., 69:8804.
Thombare, V. J., 2019, "New methods for the synthesis of biologically active cyclic peptides," University of Melbourne, PhD Thesis, 177 pages.
Vinogradov AA et al., 2019, "Macrocyclic Peptides as Drug Candidates: Recent Progress and Remaining Challenges" J. Am. Chem. Soc., 141:4167.
Wang G et al., 2003, "Solid-phase synthesis of peptide vinyl sulfones as potential inhibitors and activity-based probes of cysteine proteases" Org. Lett., 5:737.
Wessjohann LA et al., 2017, "One-Pot Assembly of Amino Acid Bridged Hybrid Macromulticyclic Cages through Multiple Multicomponent Macrocyclizations" Angew. Chem. Int. Ed., 56:3501.
White CJ et al., 2011, "Contemporary strategies for peptide macrocyclization" Nat. Chem., 3:509.
Witus LS et al., 2010, "Site-specific Protein Bioconjugation via a Pyridoxal 5'-Phosphate-Mediated N-Terminal Transamination Reaction" Curr. Protoc. Chem. Biol., 2:125.
Wong CTT et al., 2013, "Synthesis of constrained head-to-tail cyclic tetrapeptides by an imine-induced ring-closing/contraction strategy" Angew. Chem. Int. Ed., 52:10212.
Zhang X et al., 2018, "A general strategy for synthesis of cyclophane-braced peptide macrocycles via palladium-catalysed intramolecular sp3 C—H arylation" Nat. Chem., 10:540.
Zhang, X., et al, 2019, "Chemoselective Peptide Cyclization and Bicyclization Directly on Unprotected Peptides," JACS, 141:12274.

* cited by examiner

Control reaction

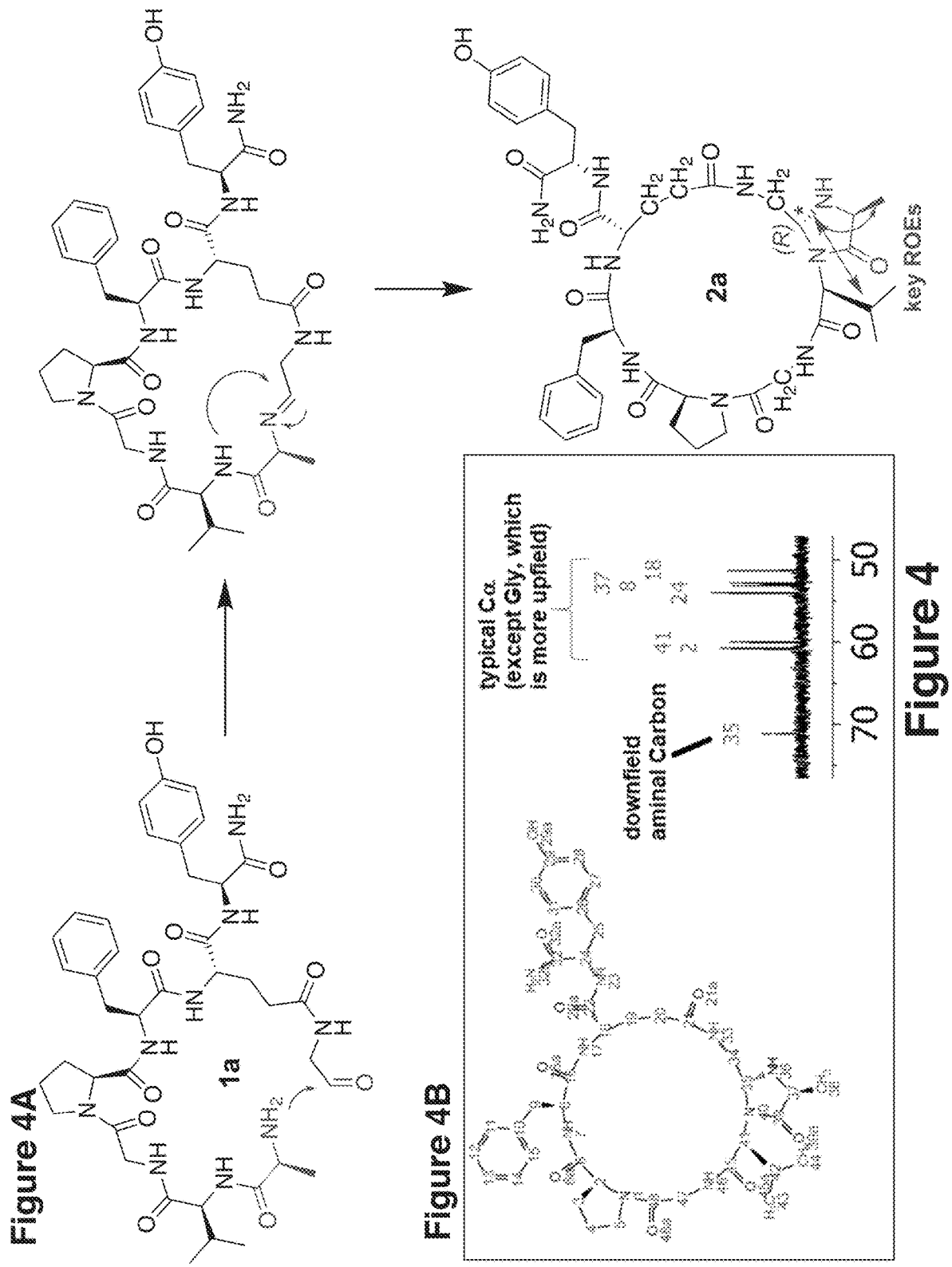

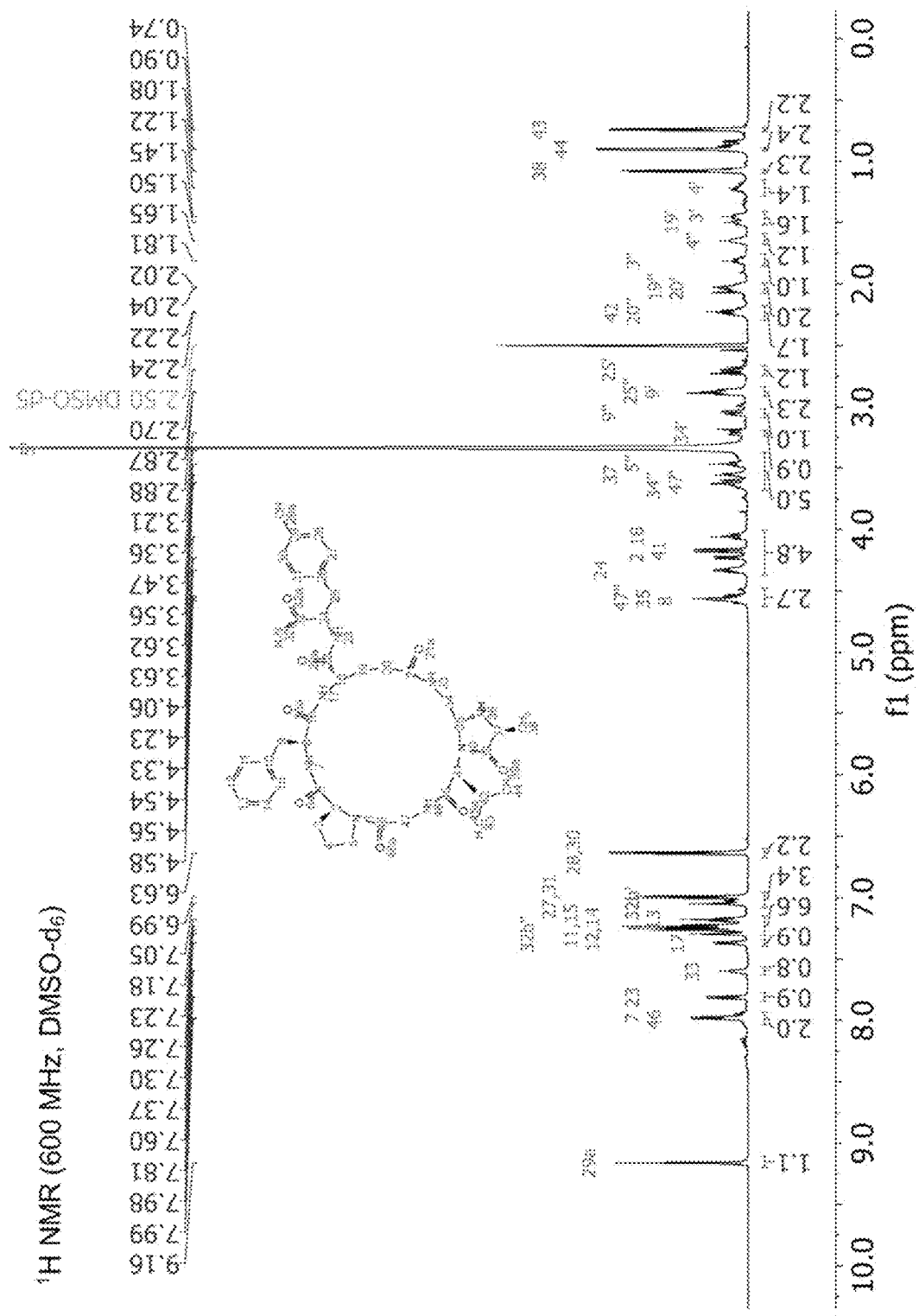

$^{13}$C NMR (151 MHz, DMSO-d$_6$)

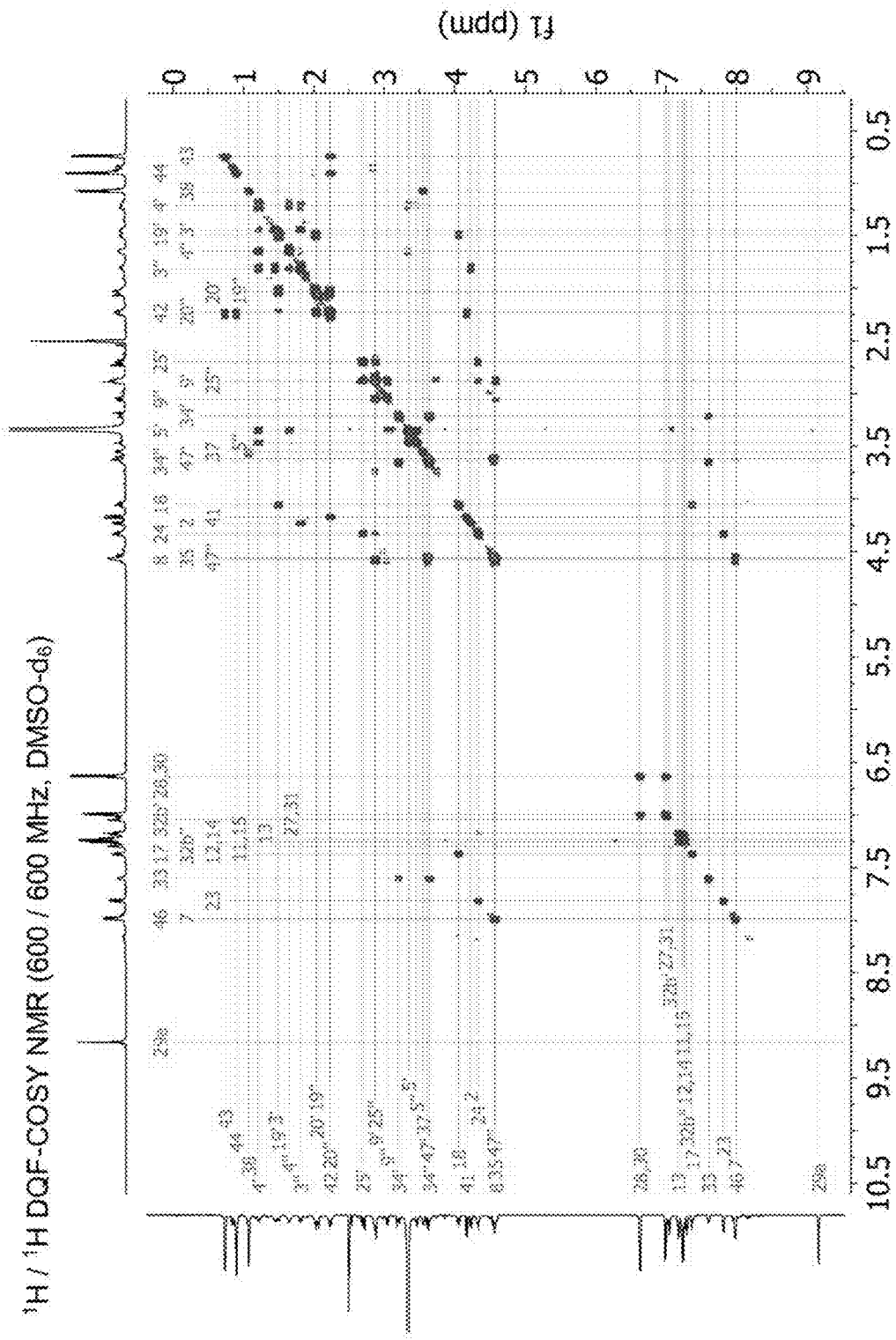

$^1$H / $^1$H TOCSY NMR (600 / 600 MHz, DMSO-d$_6$)

$^1H$ / $^{13}C$ HSQC NMR (600 / 151 MHz, DMSO-$d_6$)

$^1$H / $^1$H ROESY NMR (600 / 600 MHz, DMSO-$d_6$)

Figure 5B
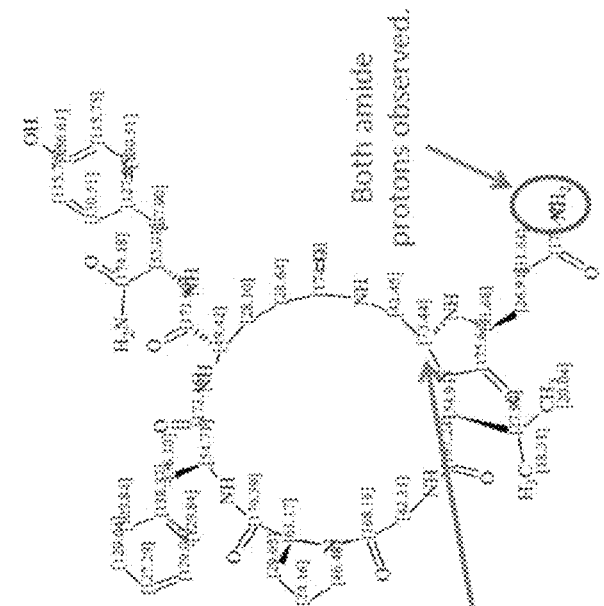
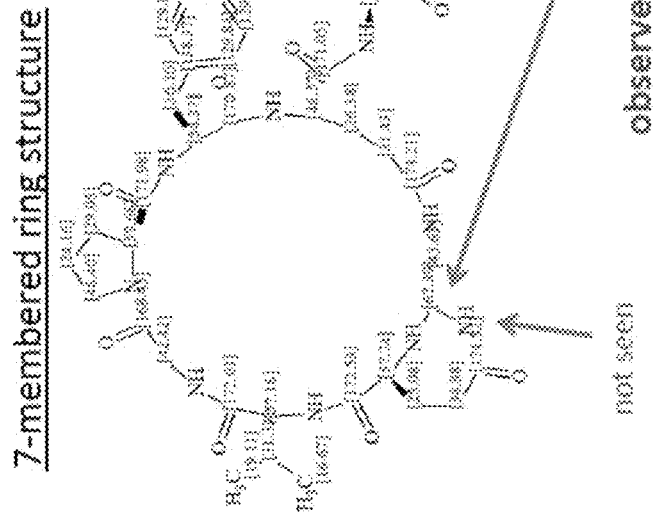
Figure 5 (cont.)

¹H NMR (600 MHz, DMSO-d₆)

$^{13}$C NMR (151 MHz, DMSO-$d_6$)

¹H / ¹H DQF-COSY NMR
(600 / 600 MHz, DMSO-d₆)

¹H / ¹H TOCSY NMR
(600 / 600 MHz, DMSO-d₆)

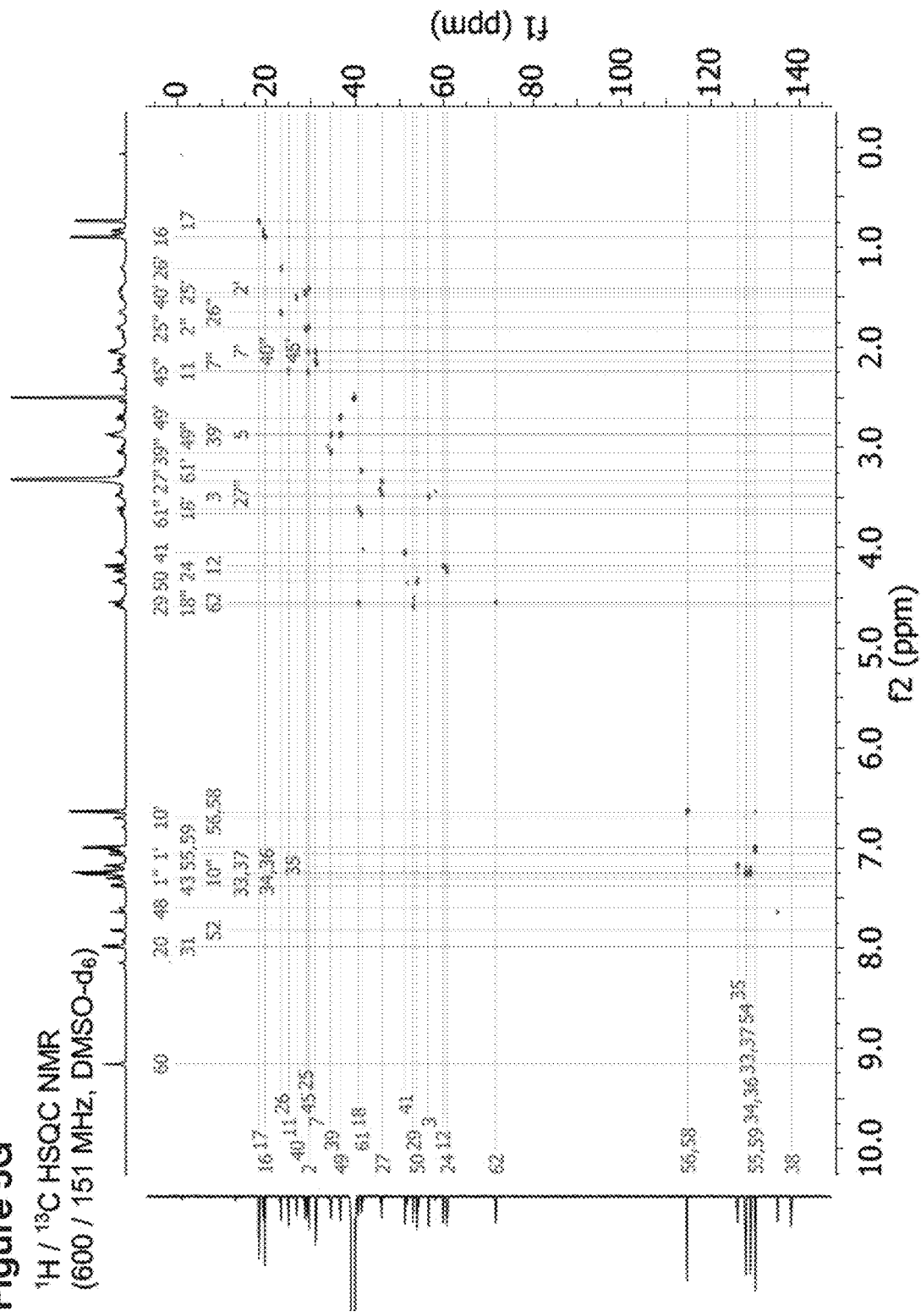

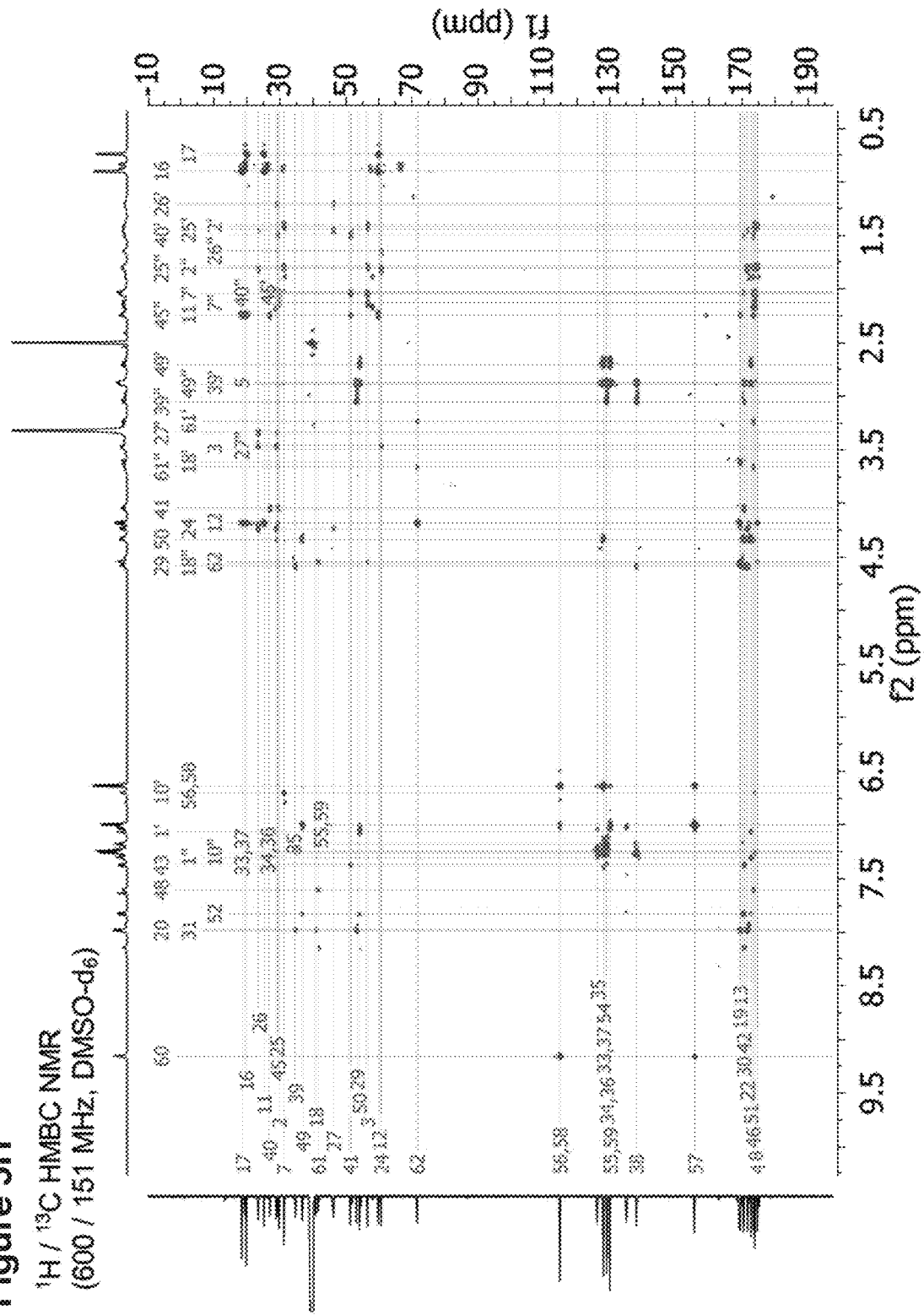

¹H / ¹H ROESY NMR
(600 / 600 MHz, DMSO-d₆)

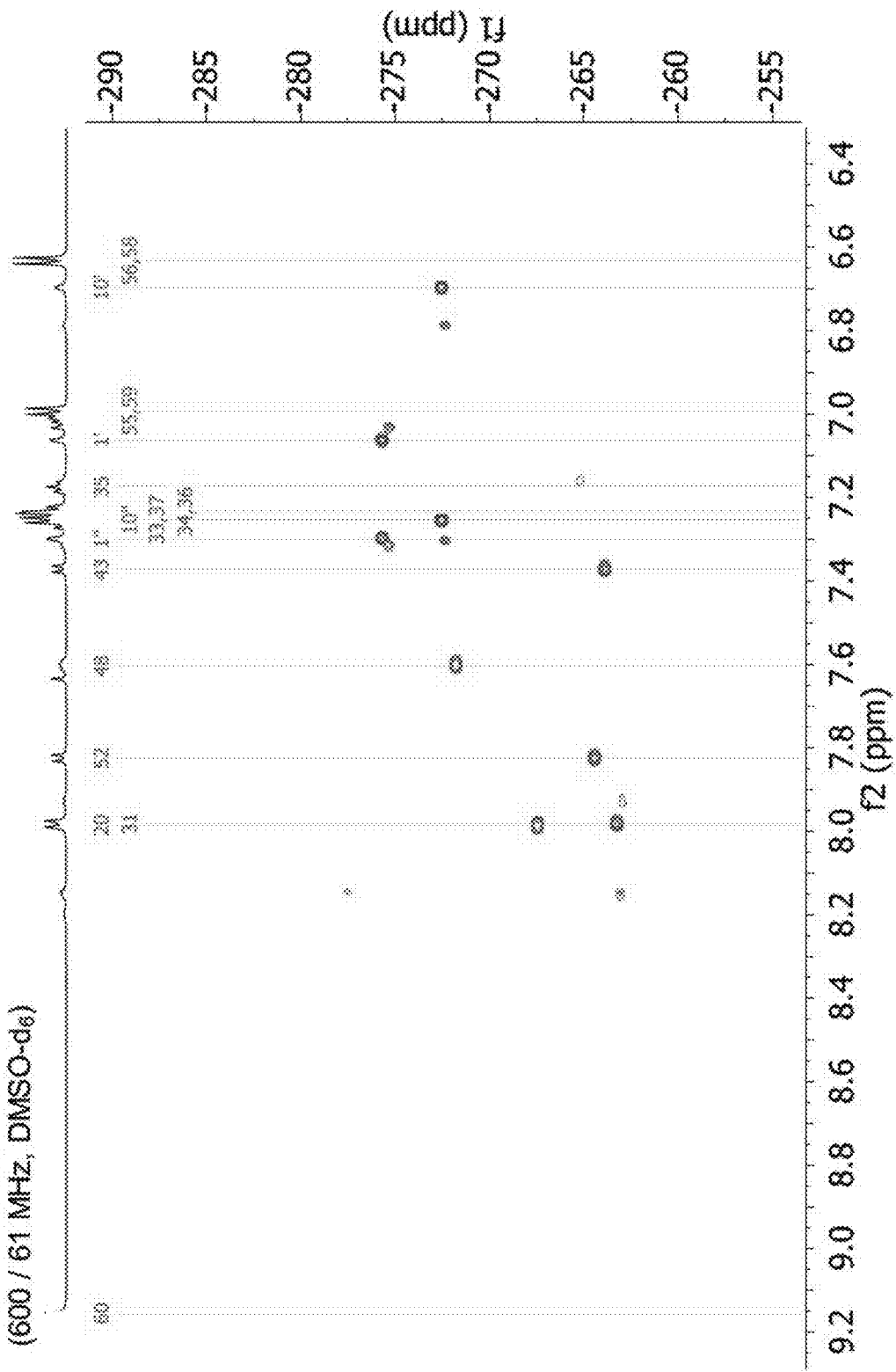

$^1$H NMR (500 MHz, DMSO-$d_6$)

¹H / ¹H COSY NMR
(500 / 500 MHz, DMSO-d₆)

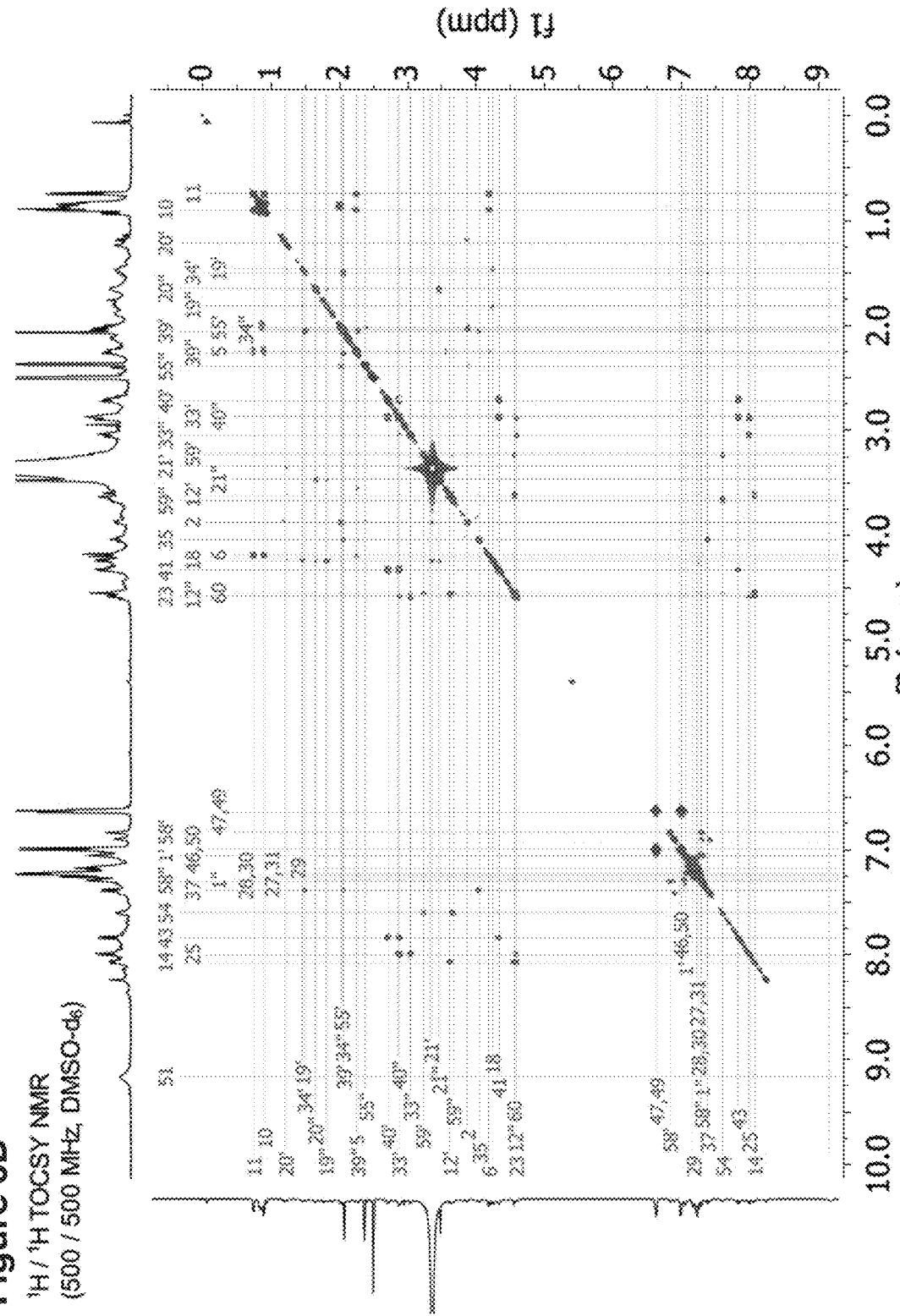

$^1H$ / $^{13}C$ HSQC NMR
(500 / 126 MHz, DMSO-$d_6$)

$^1H$ / $^{13}C$ HSQC-TOCSY NMR
(500 / 126 MHz, DMSO-$d_6$)

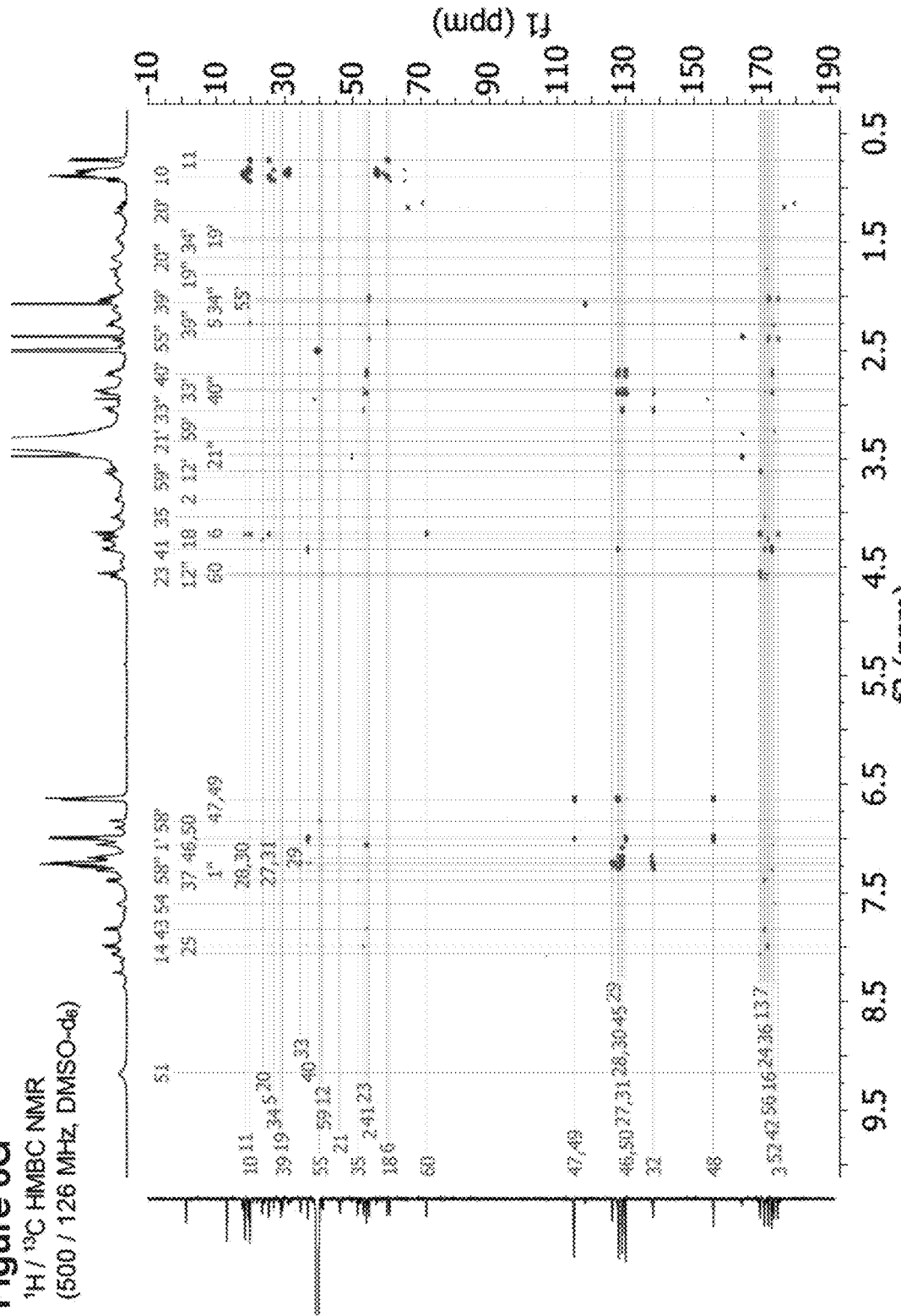

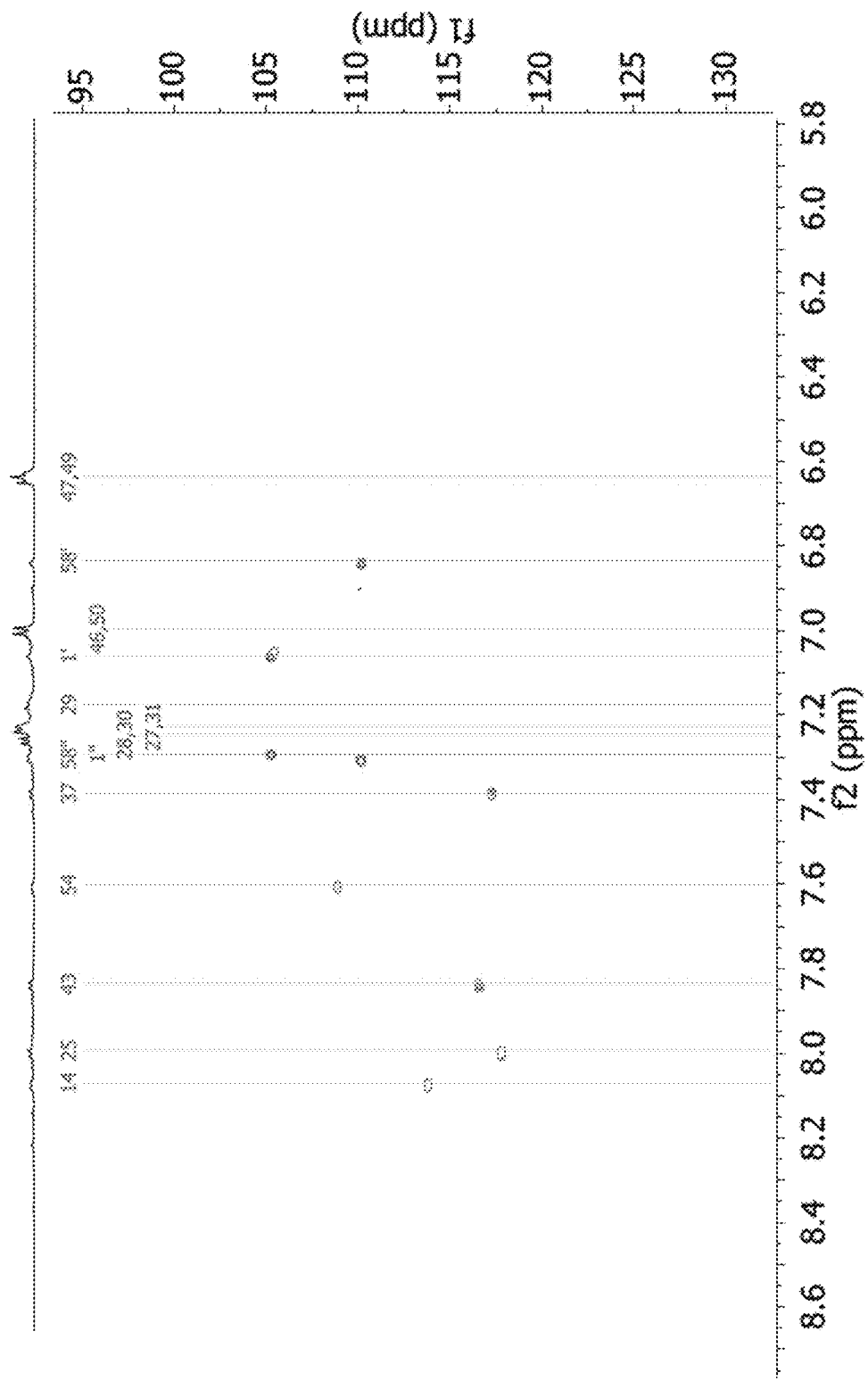

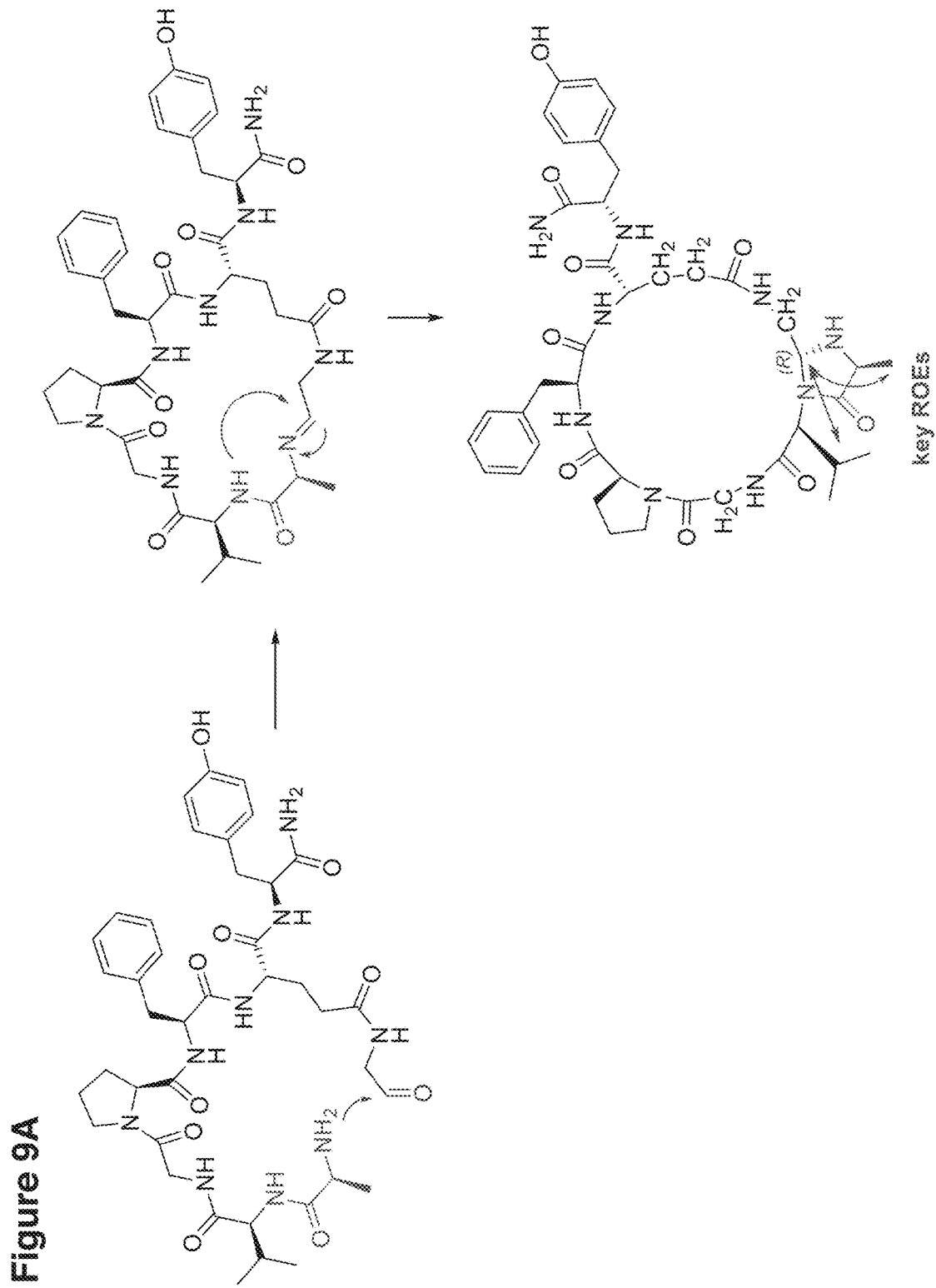

$^1H / ^1H$ ROESY NMR (600 / 600 MHz, DMSO-$d_6$)

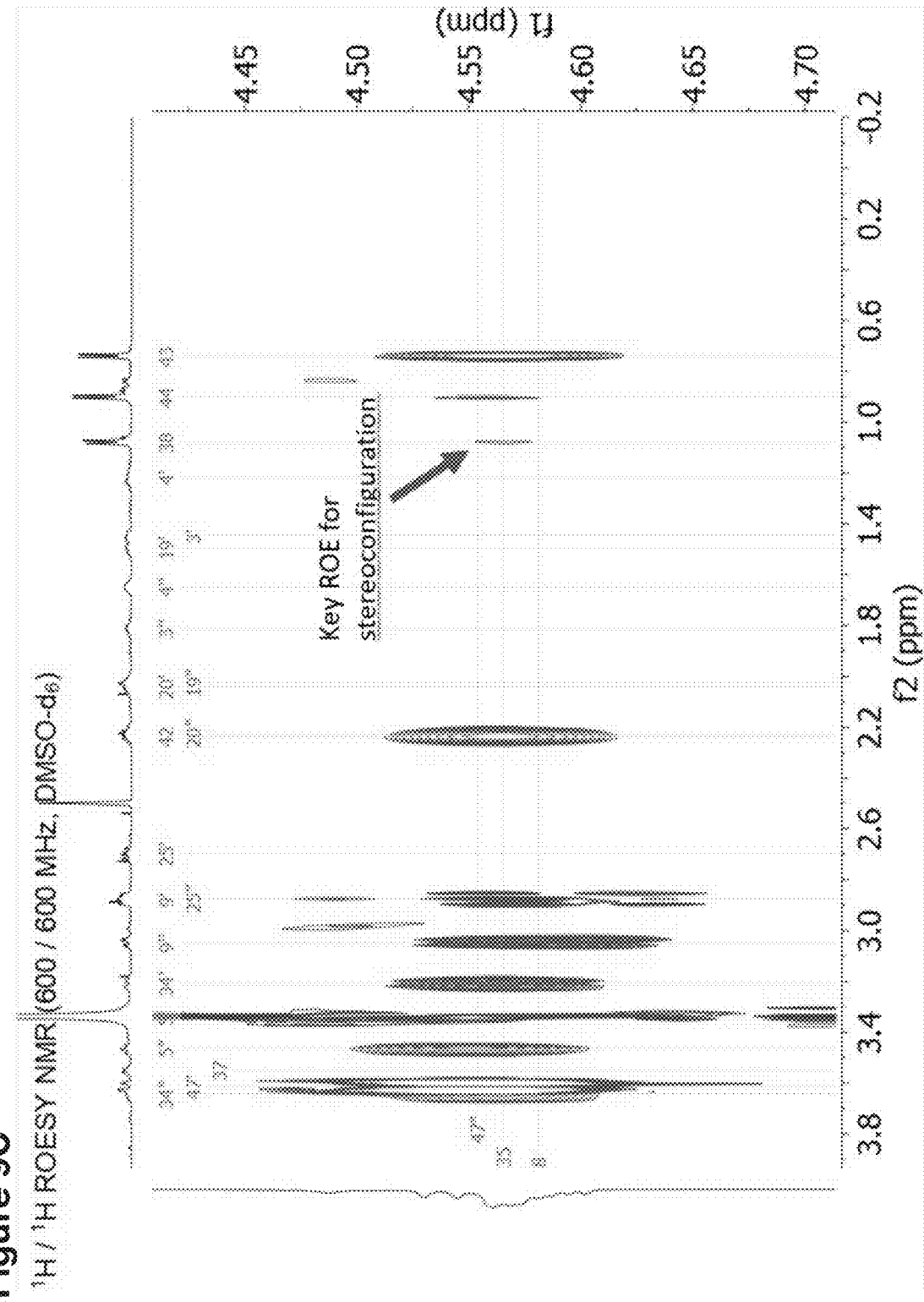

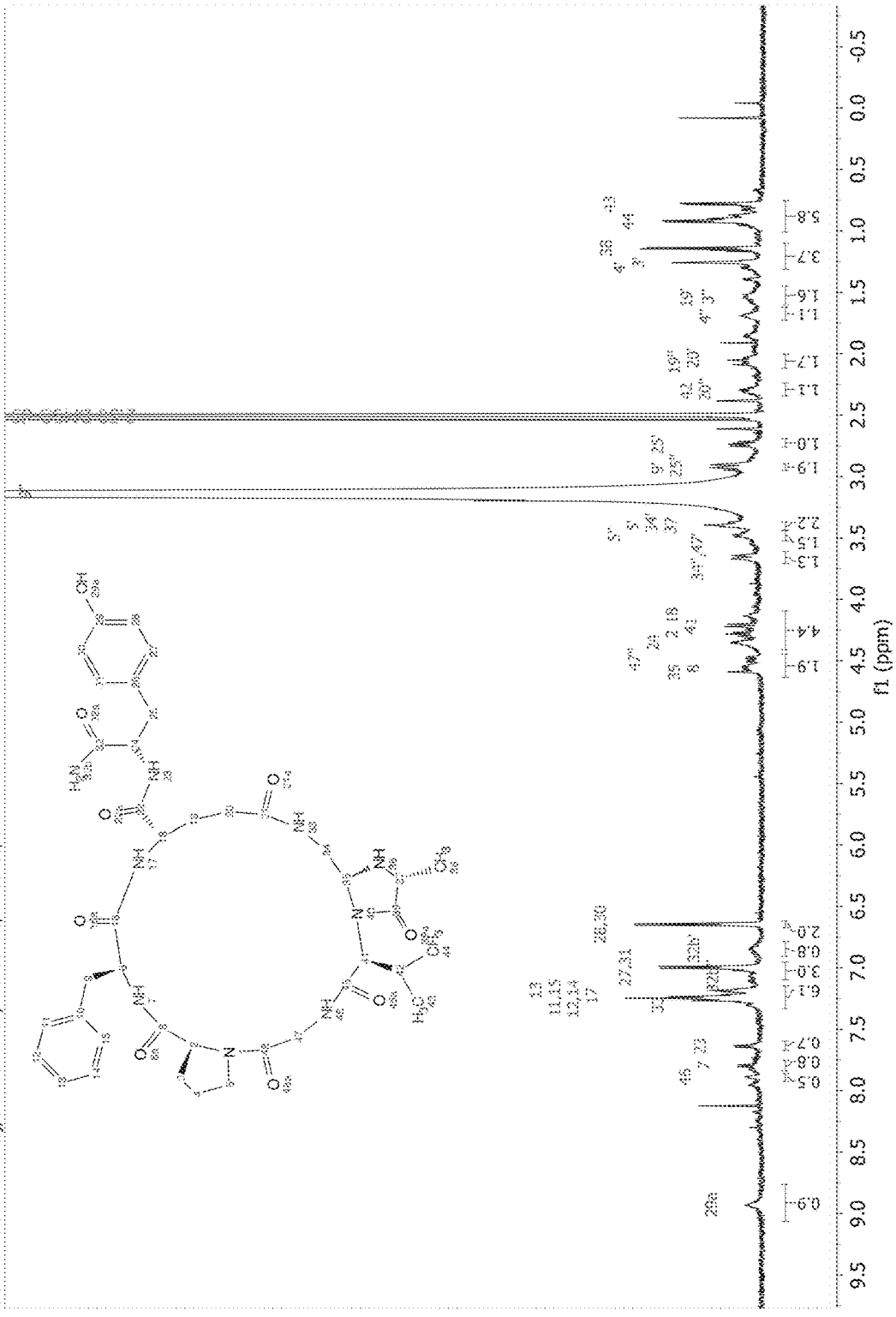

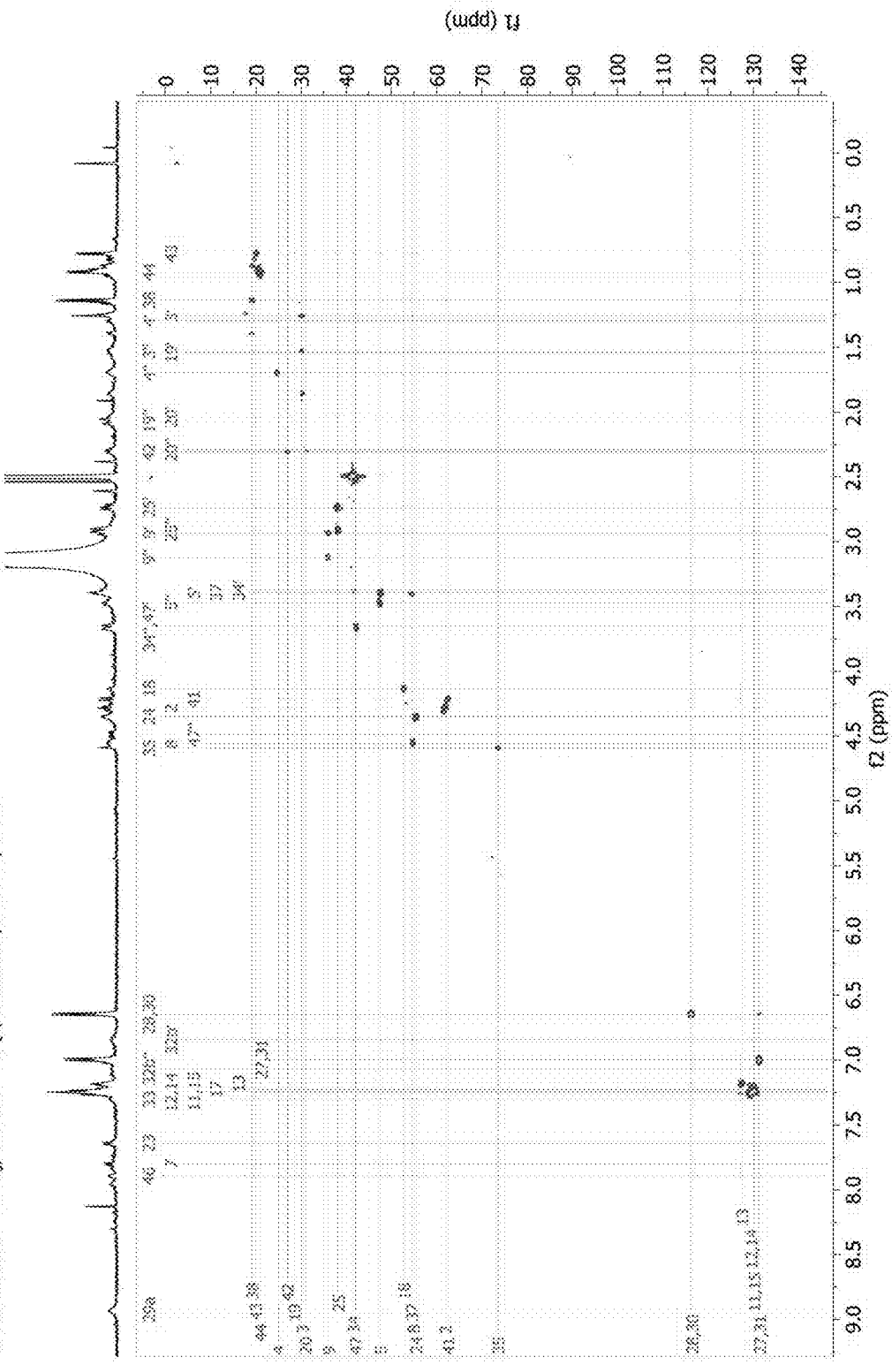

$^1$H / $^1$H COSY NMR (600 / 600 MHz, DMSO-$d_6$)

$^1$H / $^1$H TOCSY NMR (600 / 600 MHz, DMSO-$d_6$)

$^1H / ^{13}C$ HMBC NMR (600 / 151 MHz, DMSO-$d_6$)

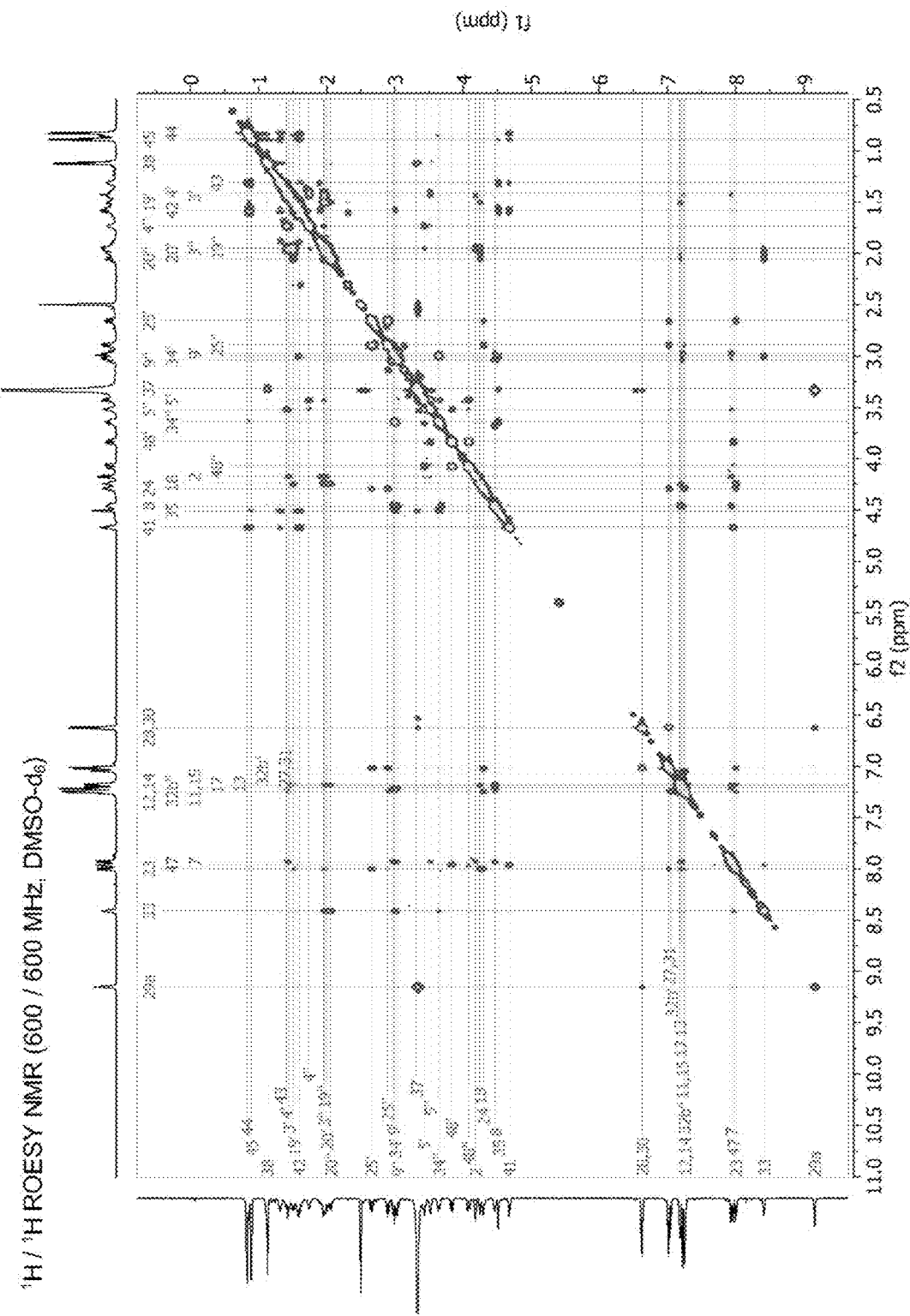

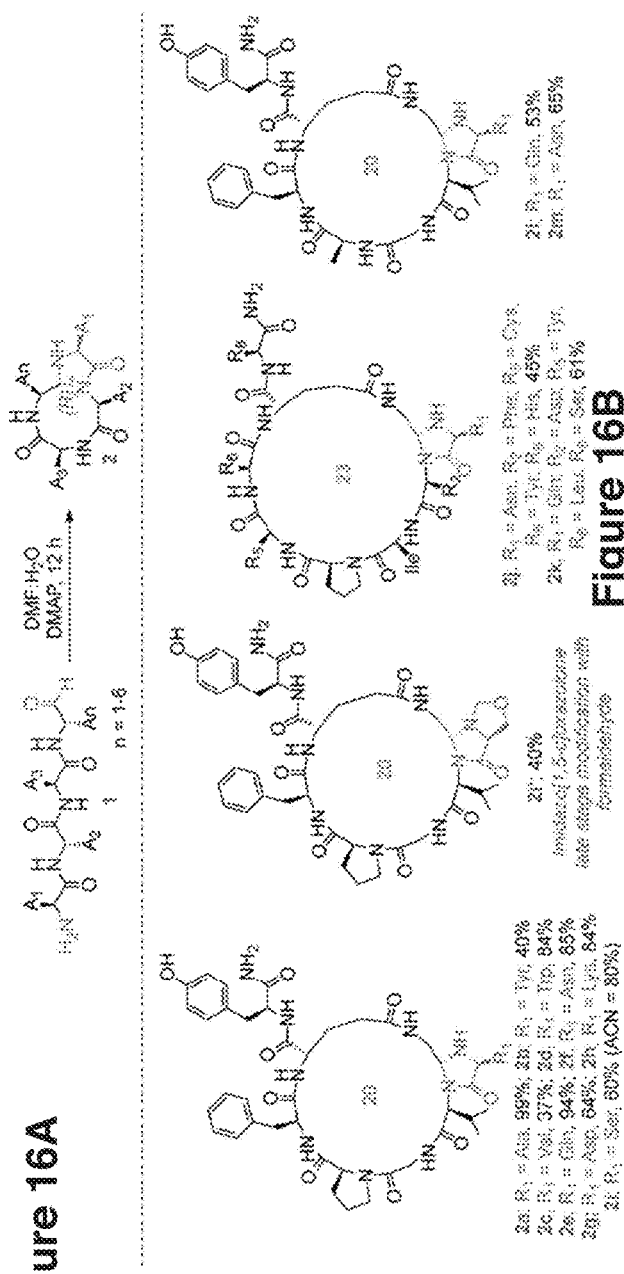
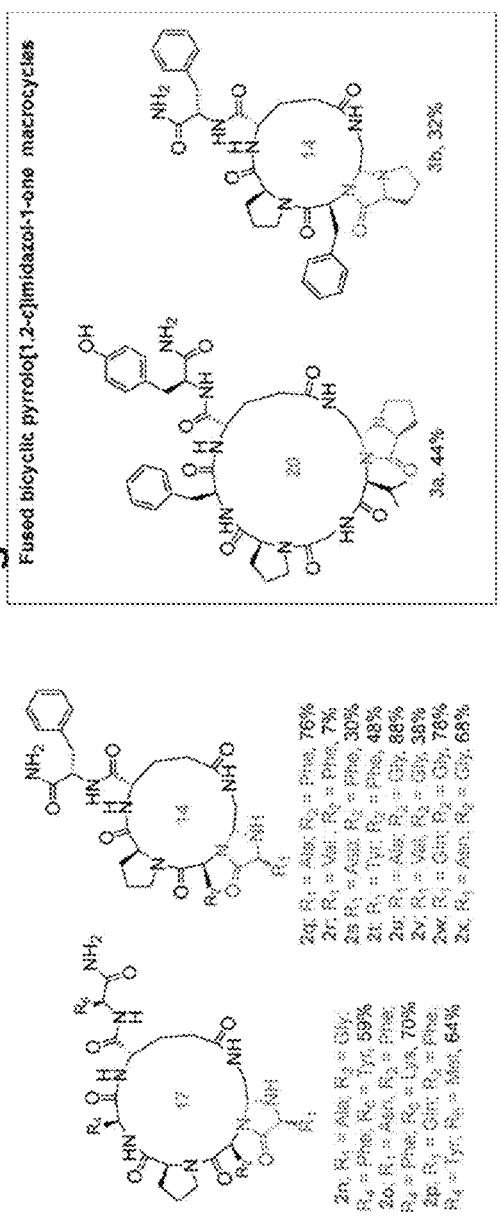
Figure 16A
Figure 16B. Fused bicyclic pyrrolo[1,2-c]imidazol-1-one macrocycles
Figure 16

Head to Tail Macrocyclization

Figure 16D *Substrate Scope of CyClick Chemistry with Internal and N-terminal Lysine*

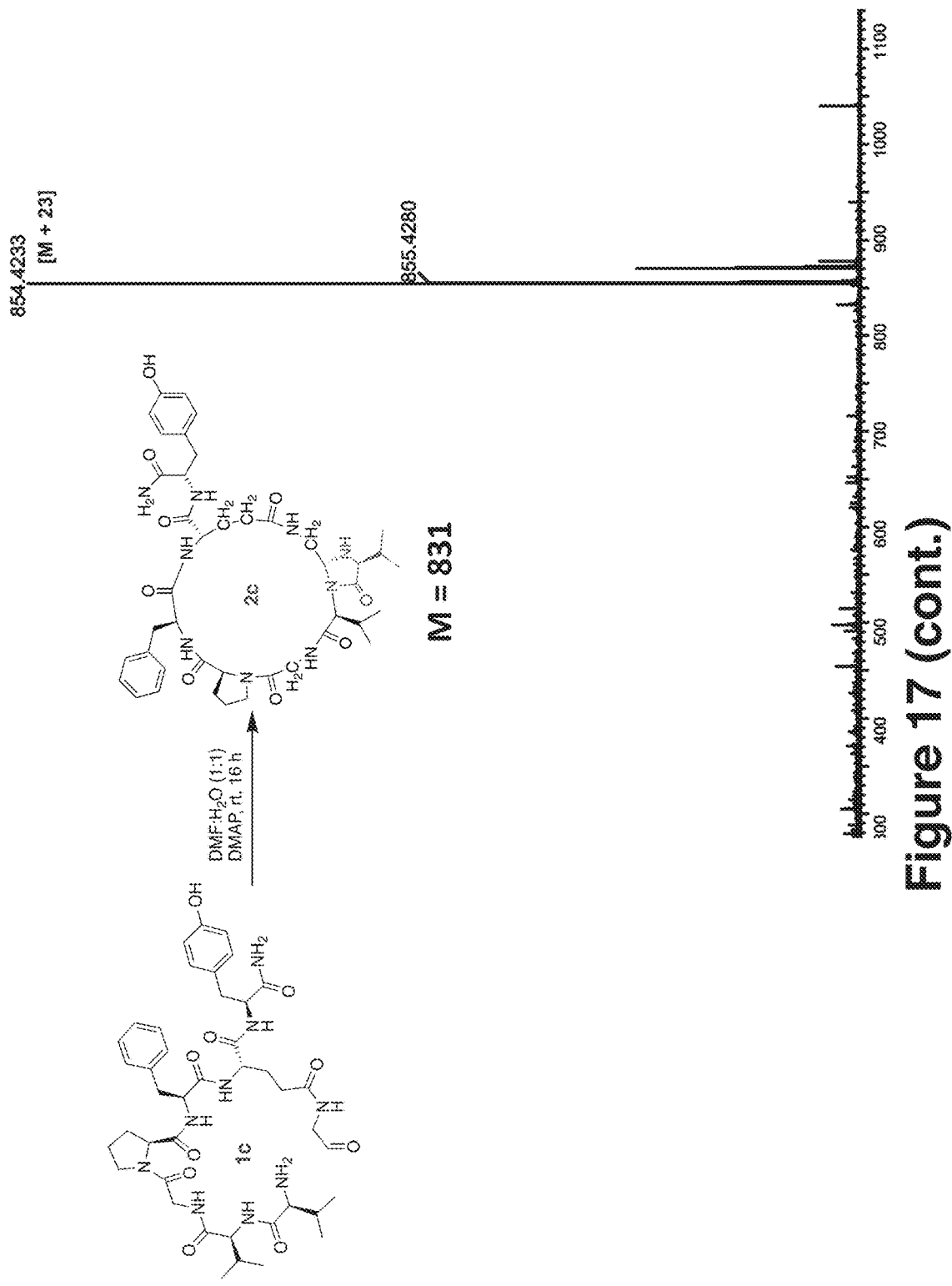

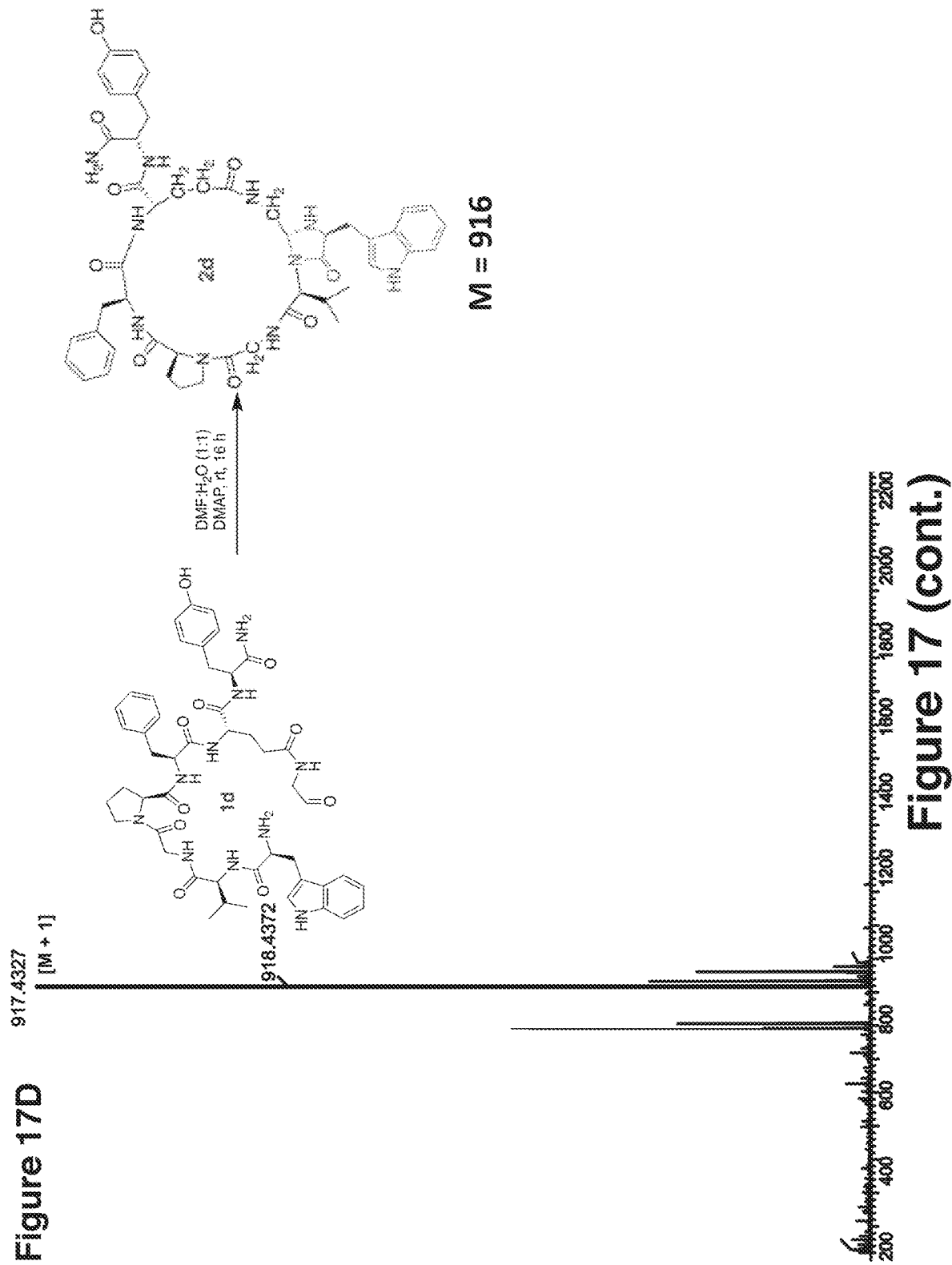

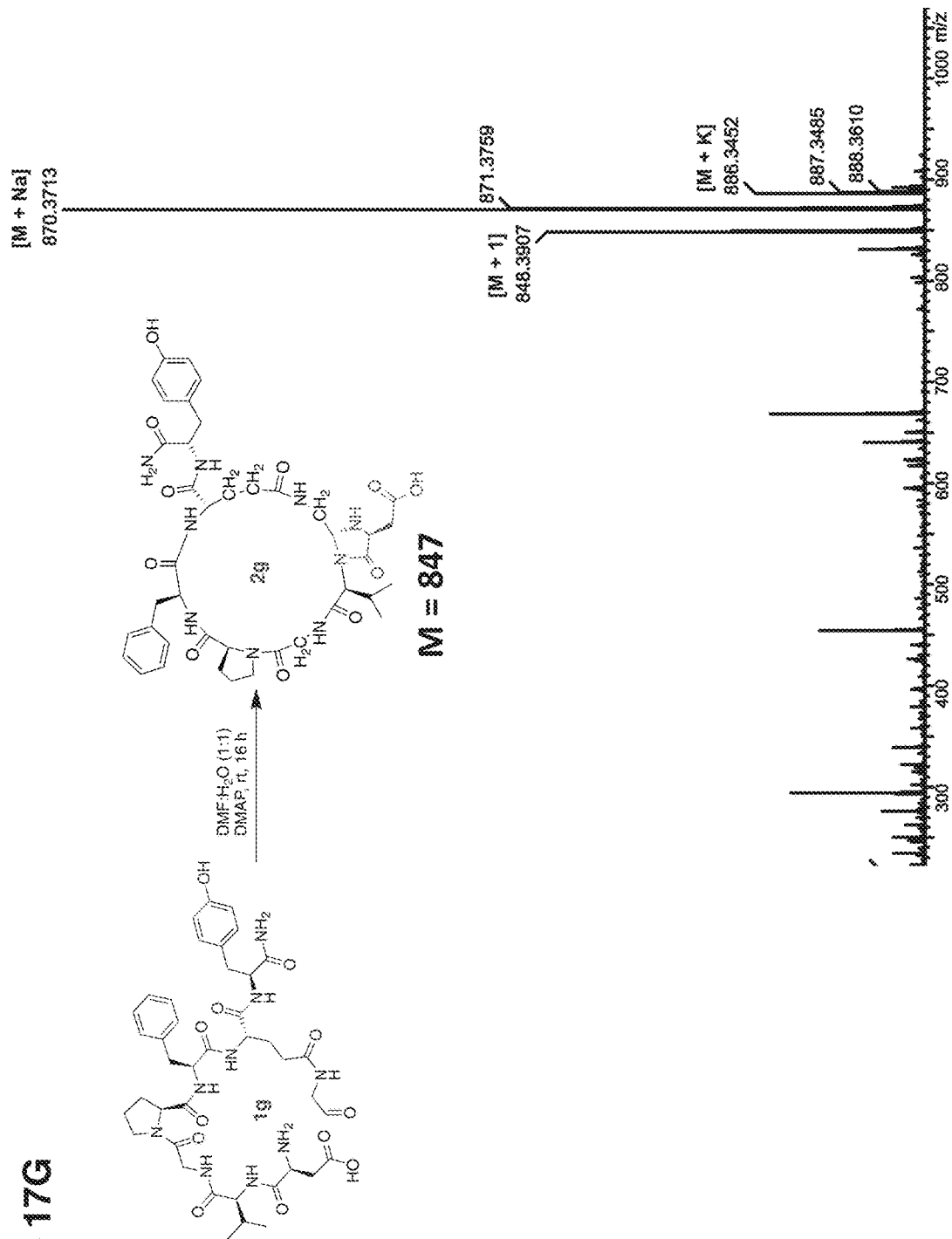

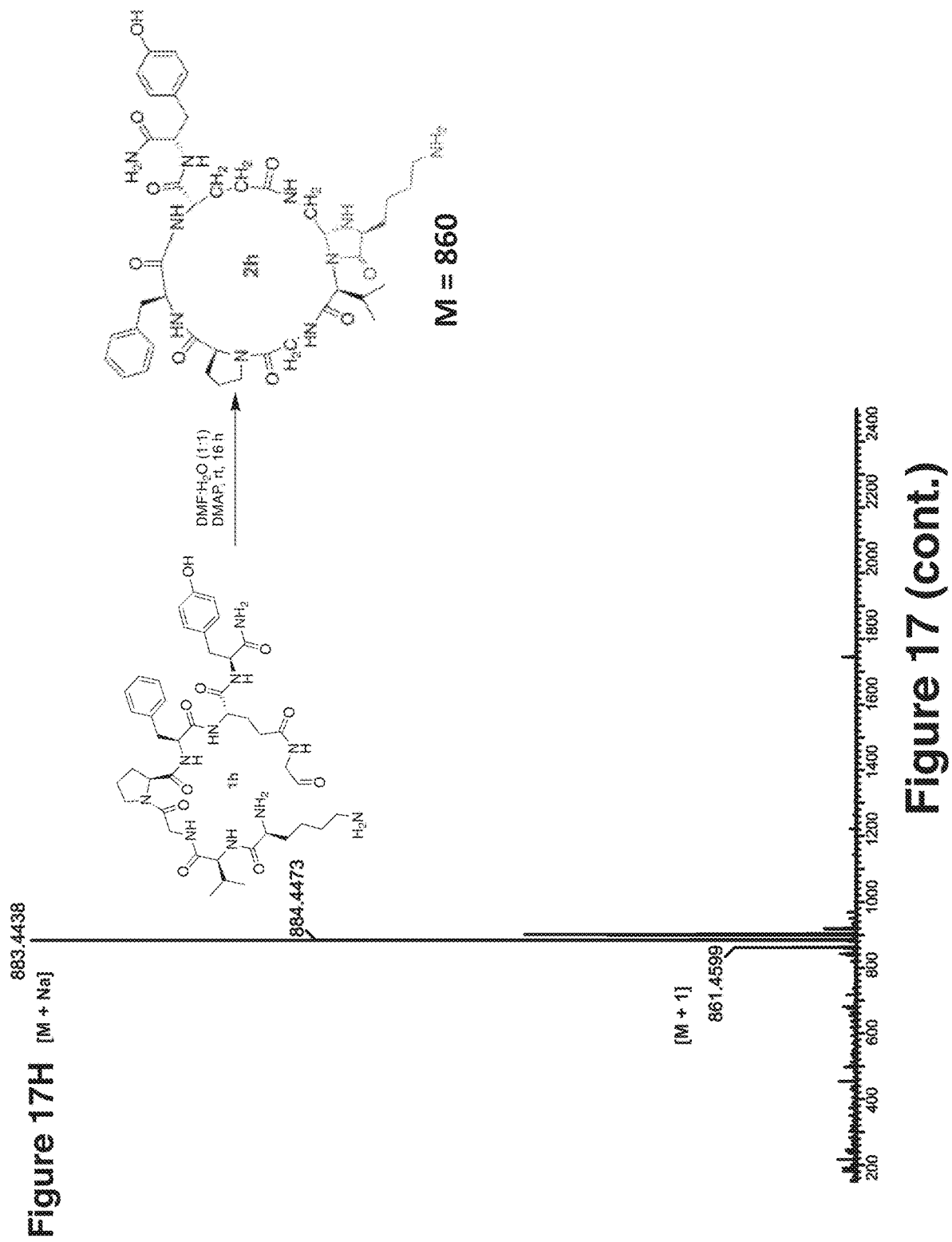

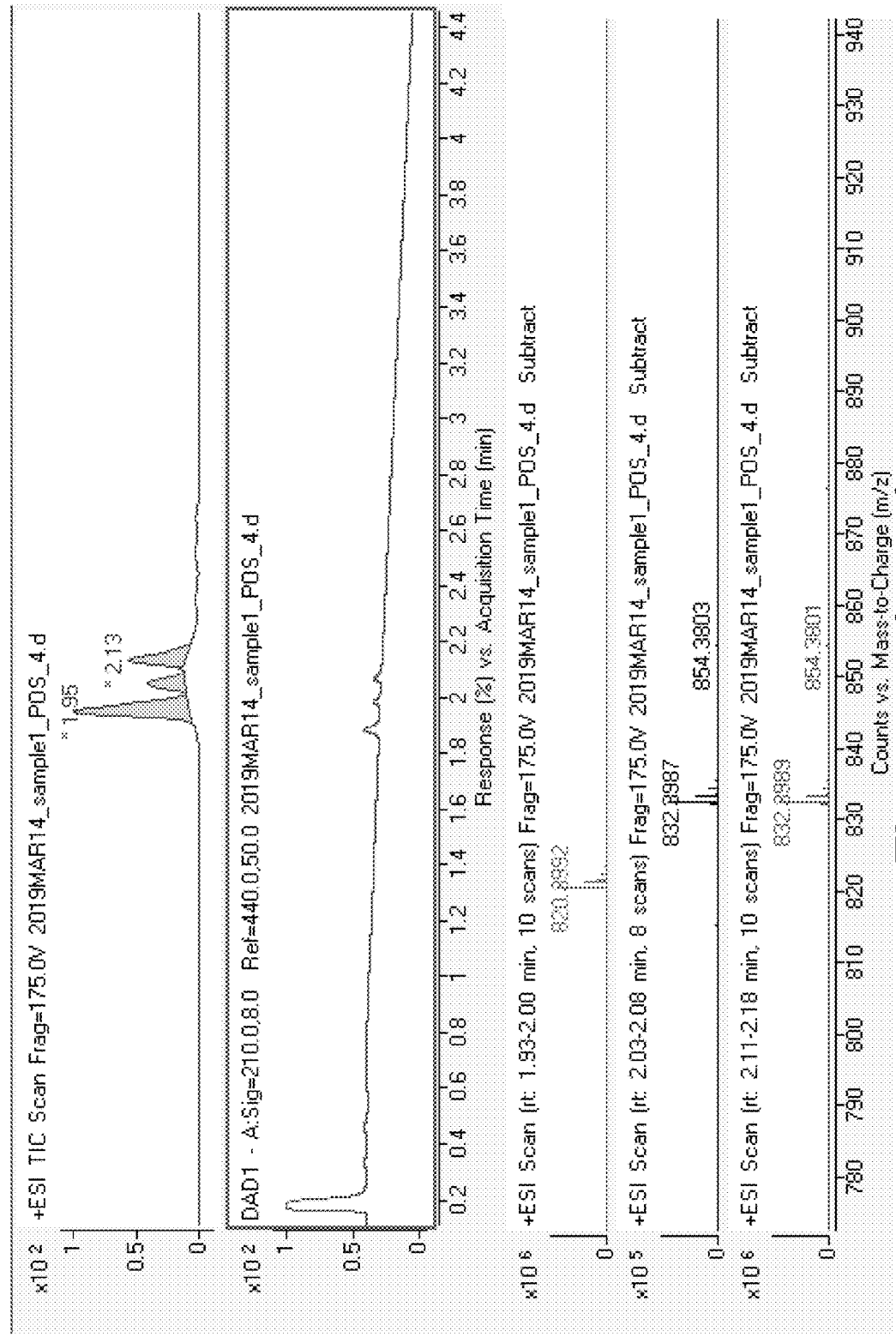

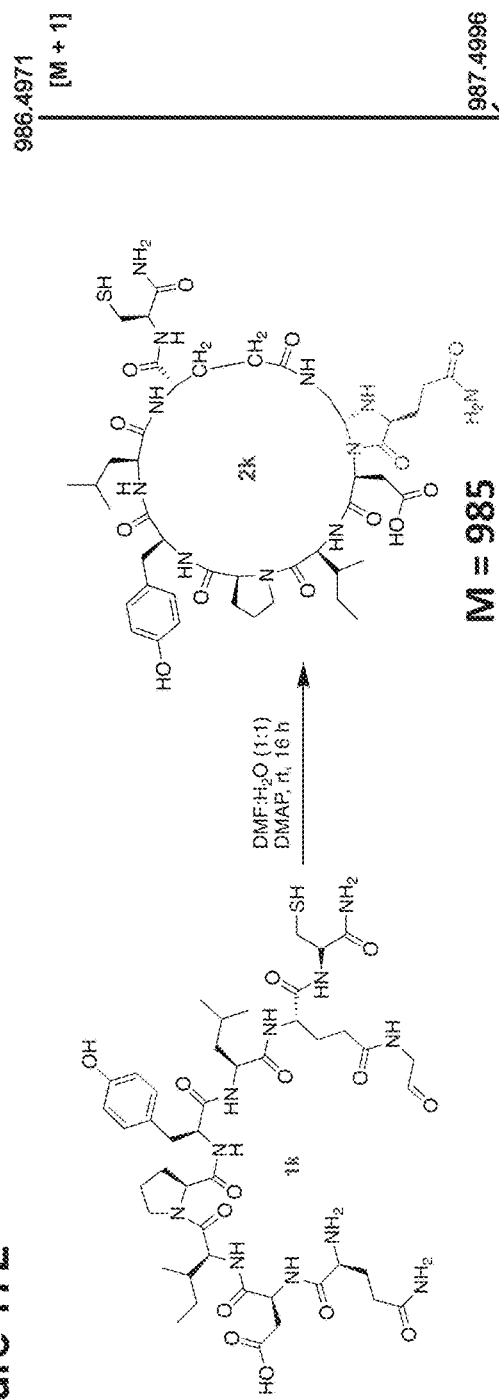
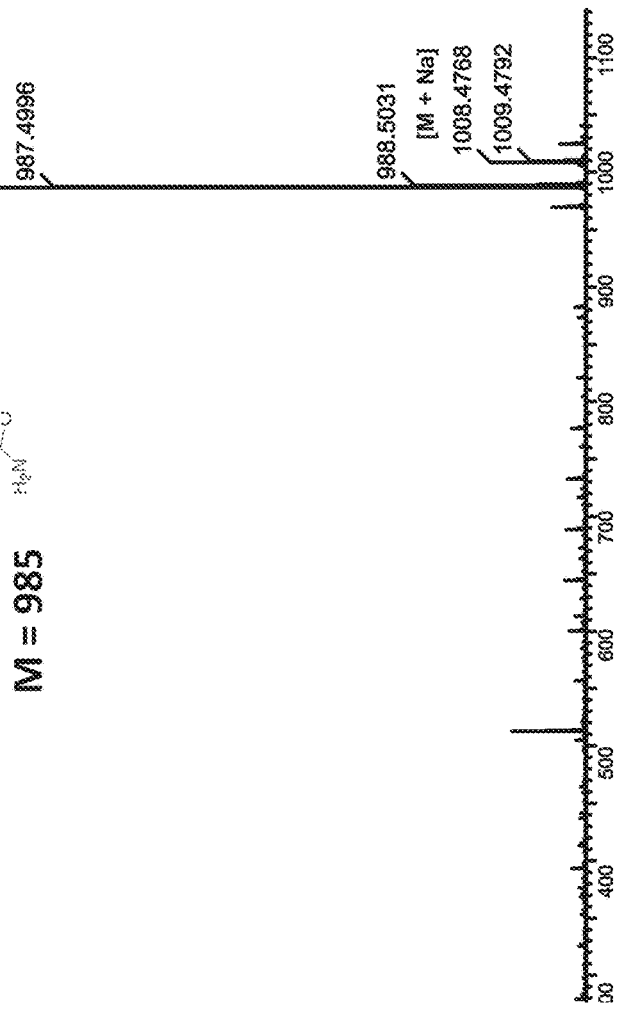
Figure 17L
Figure 17 (cont.)

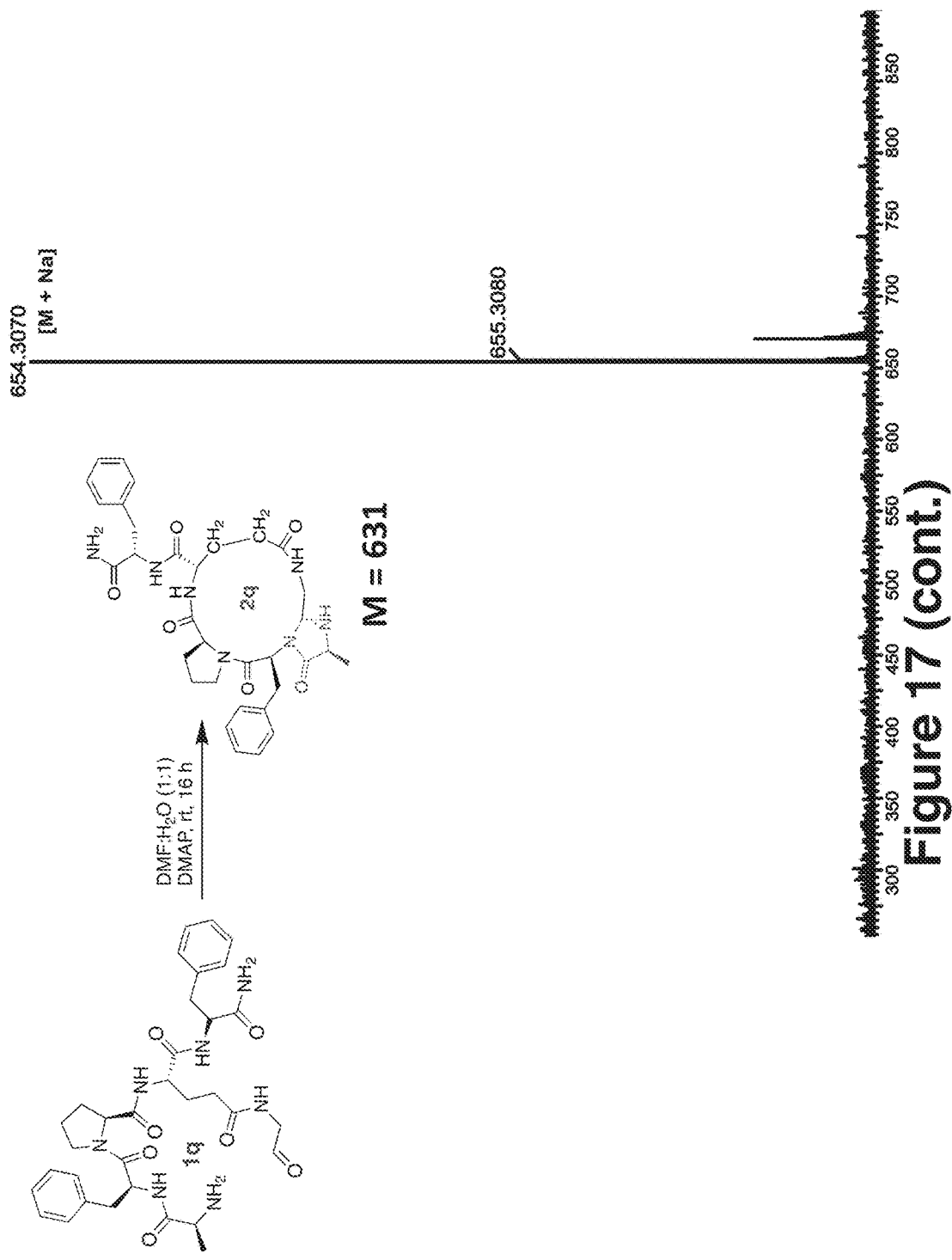

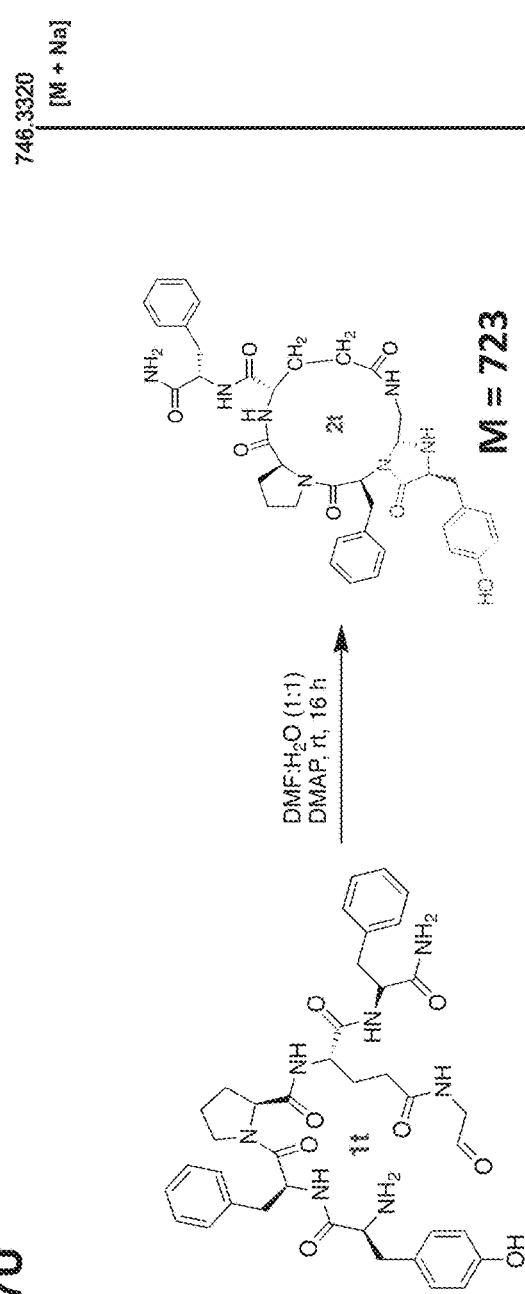
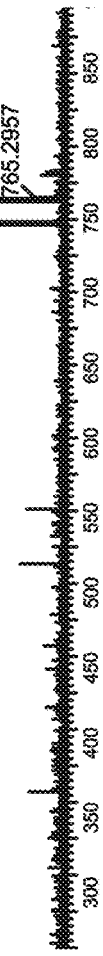
Figure 17U
Figure 17 (cont.)

Figure 17V
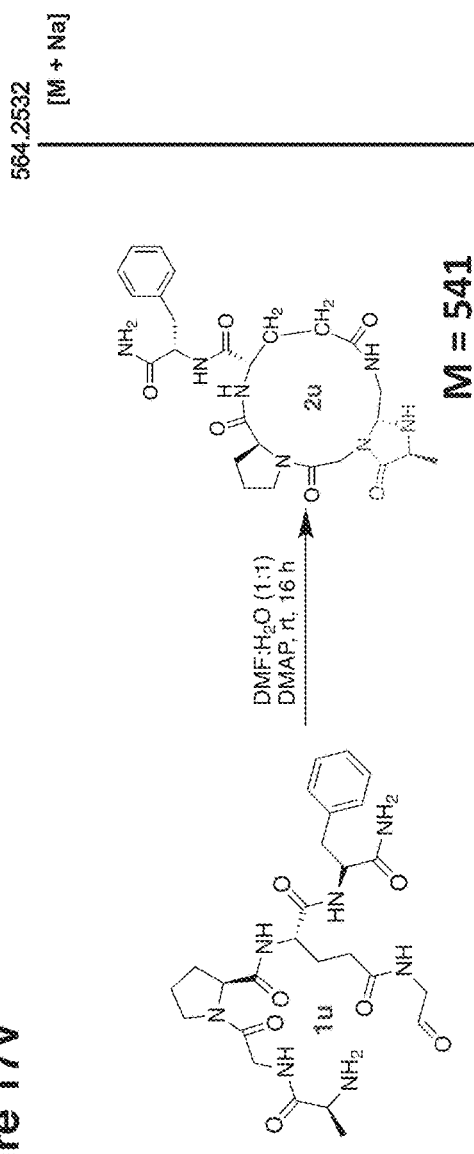
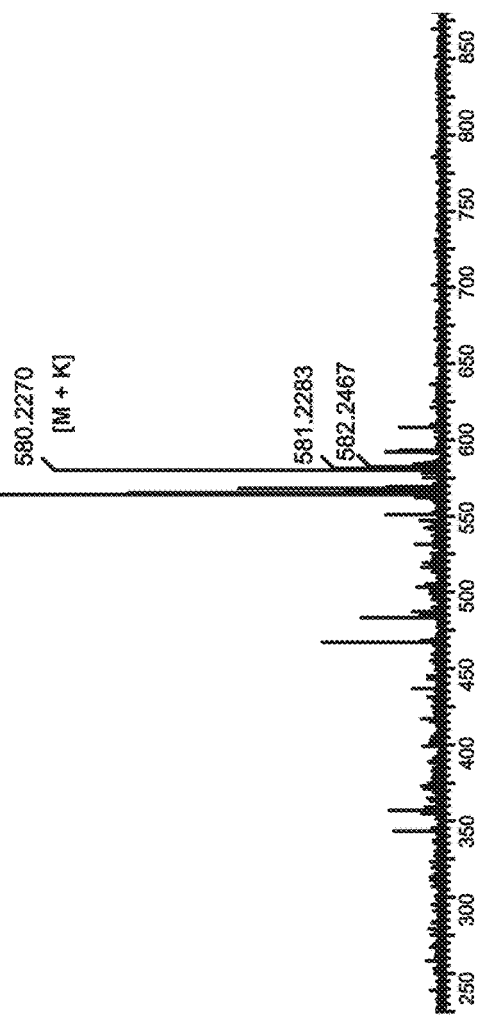
Figure 17 (cont.)

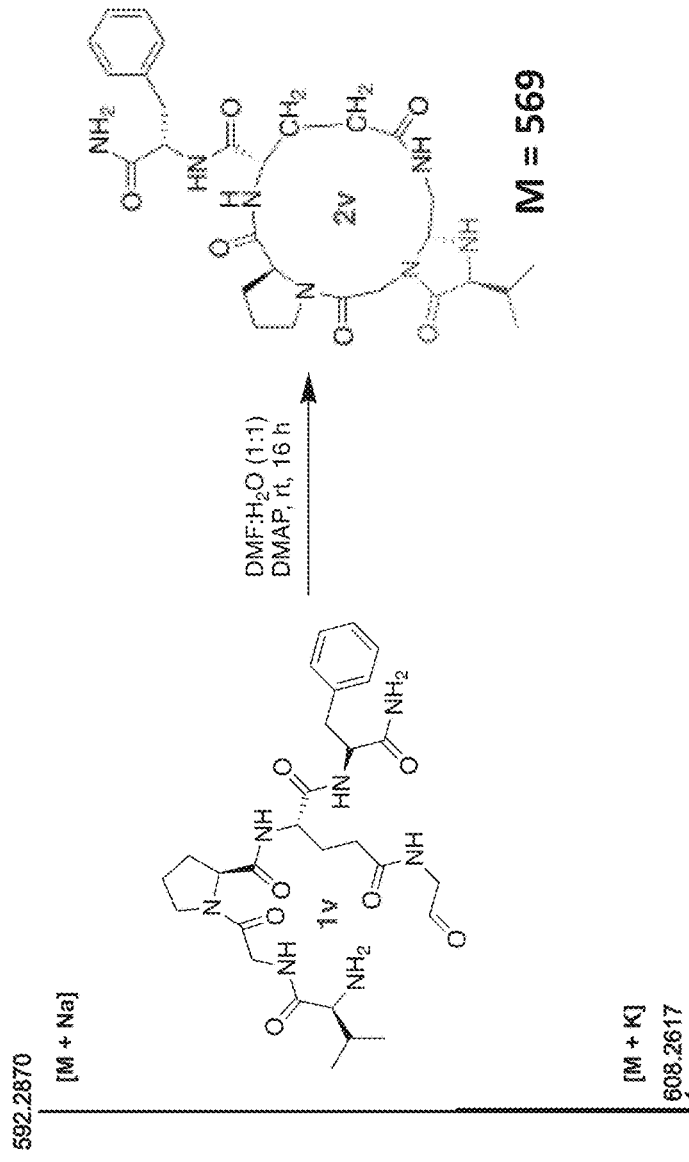
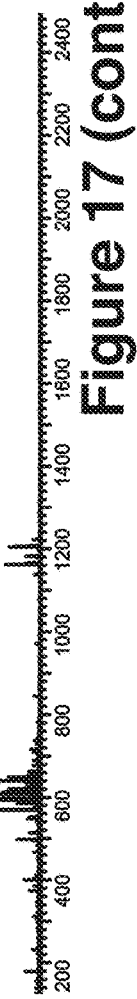
Figure 17W
Figure 17 (cont.)

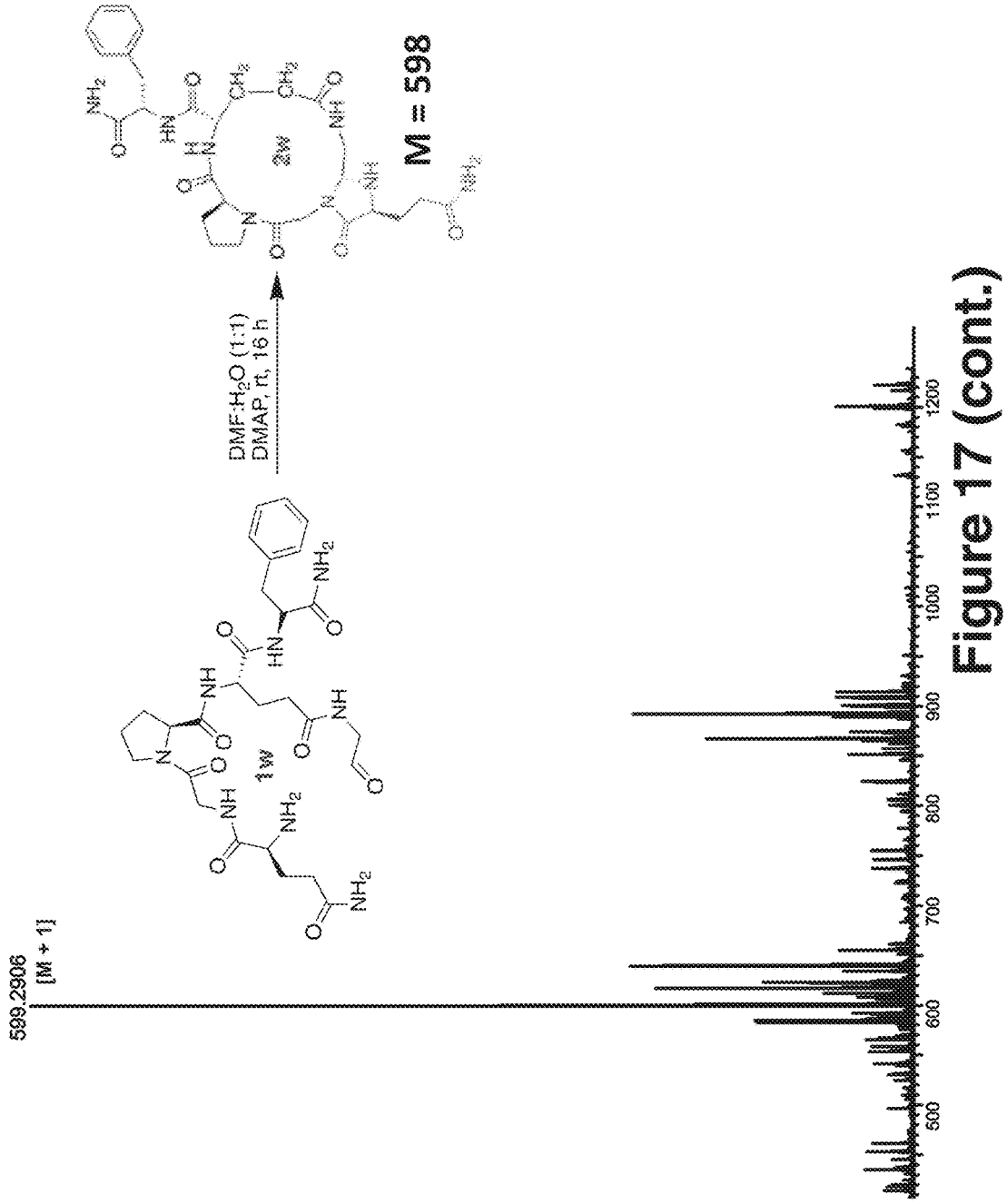

Figure 17Y
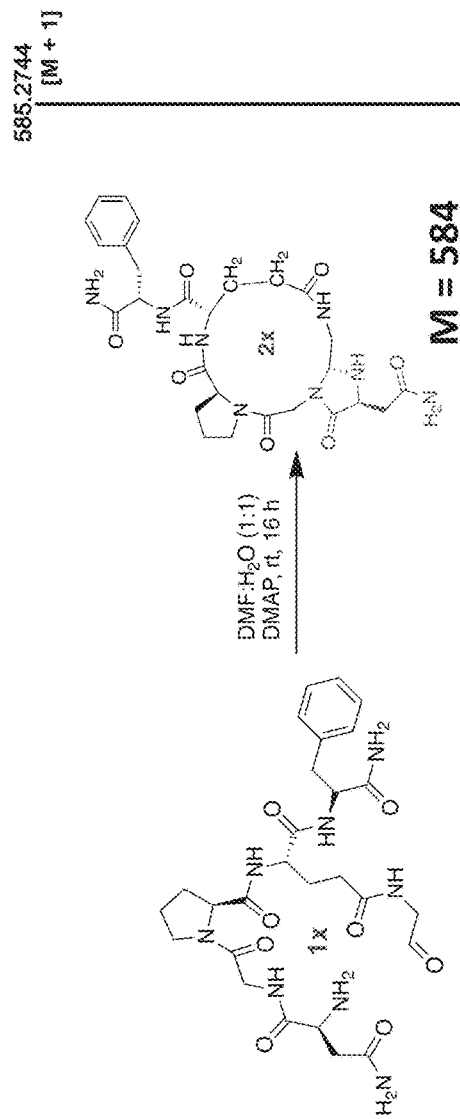
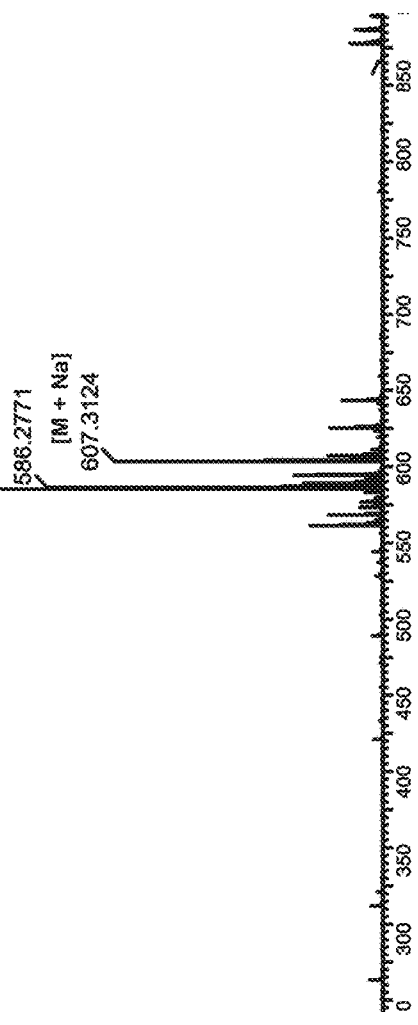
Figure 17 (cont.)

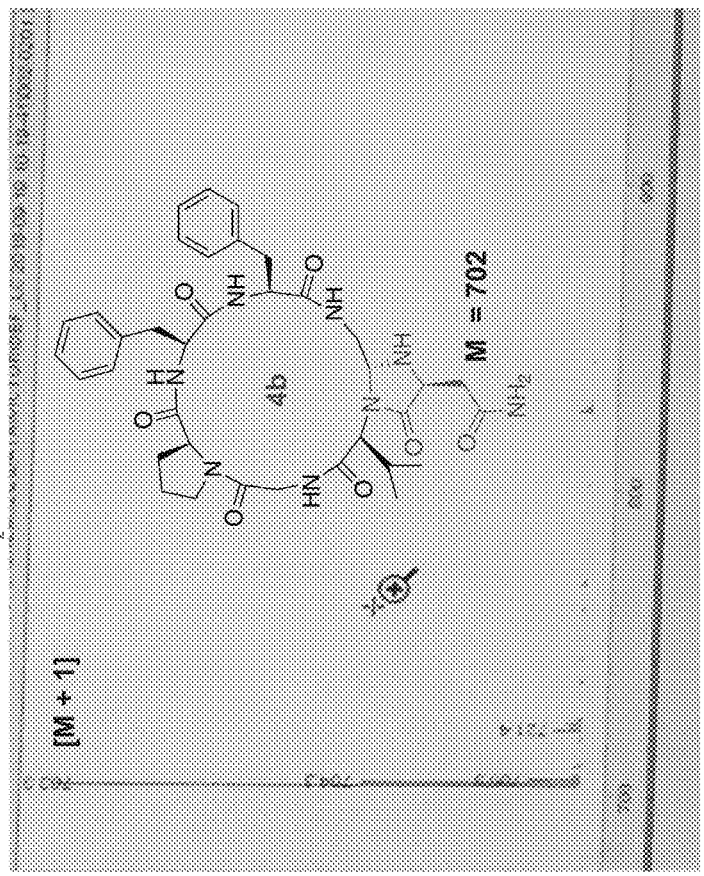
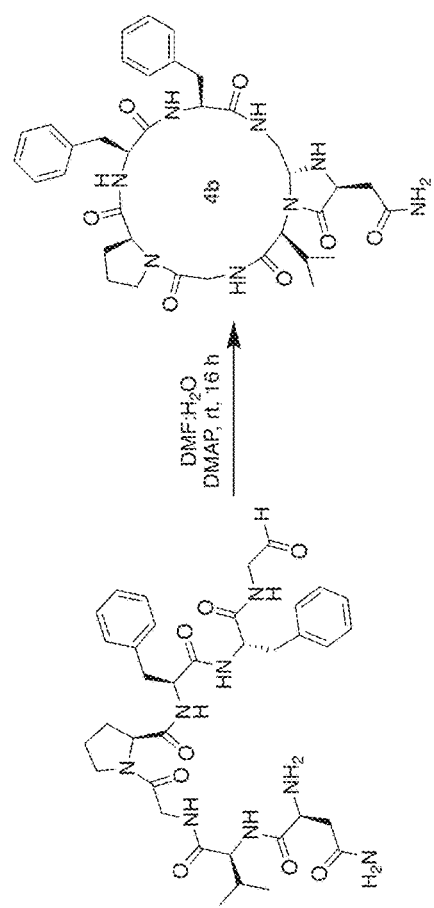
Figure 19D
Figure 19 (cont.)

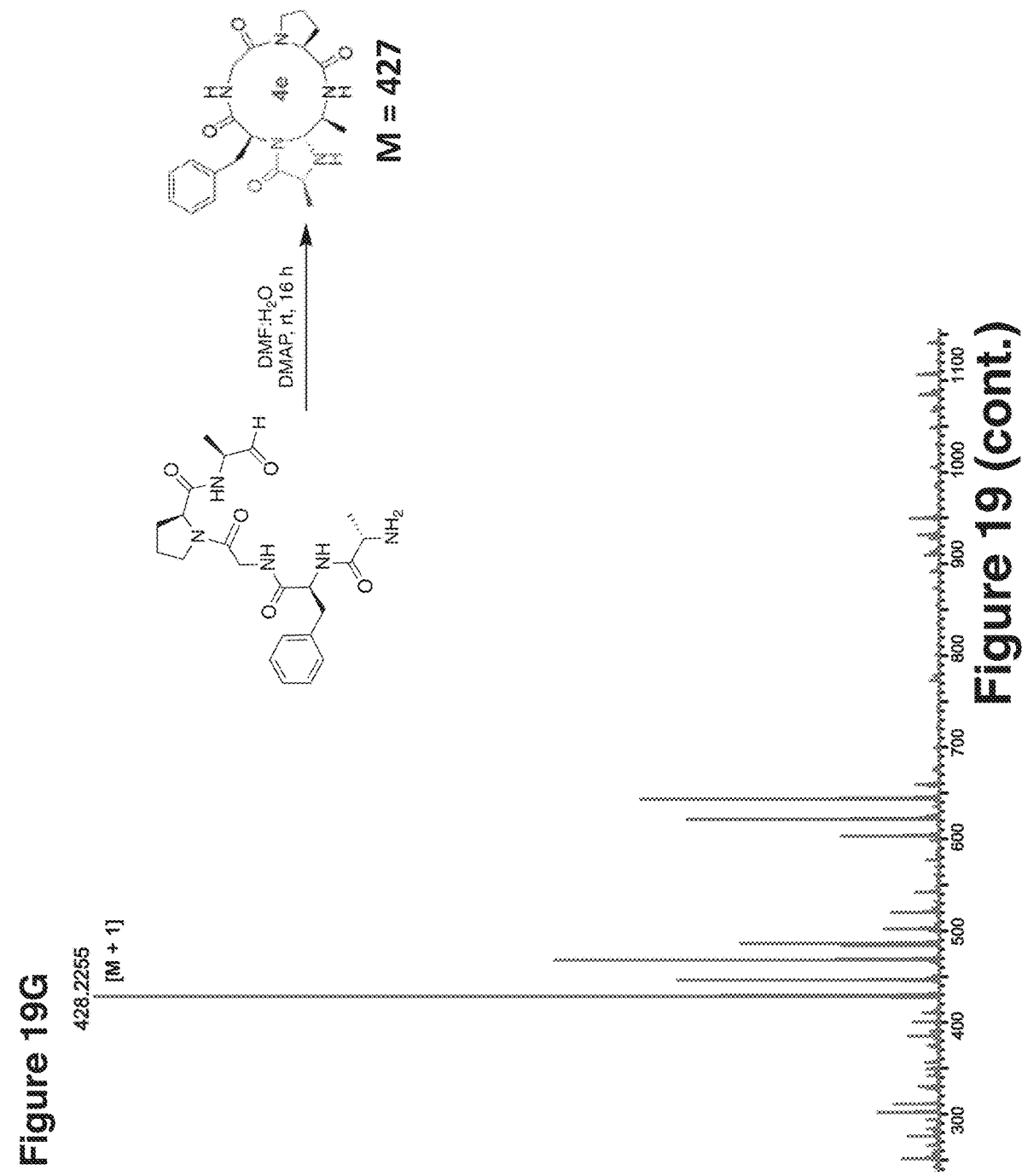

$^1$H NMR (600 MHz, DMSO-$d_6$)

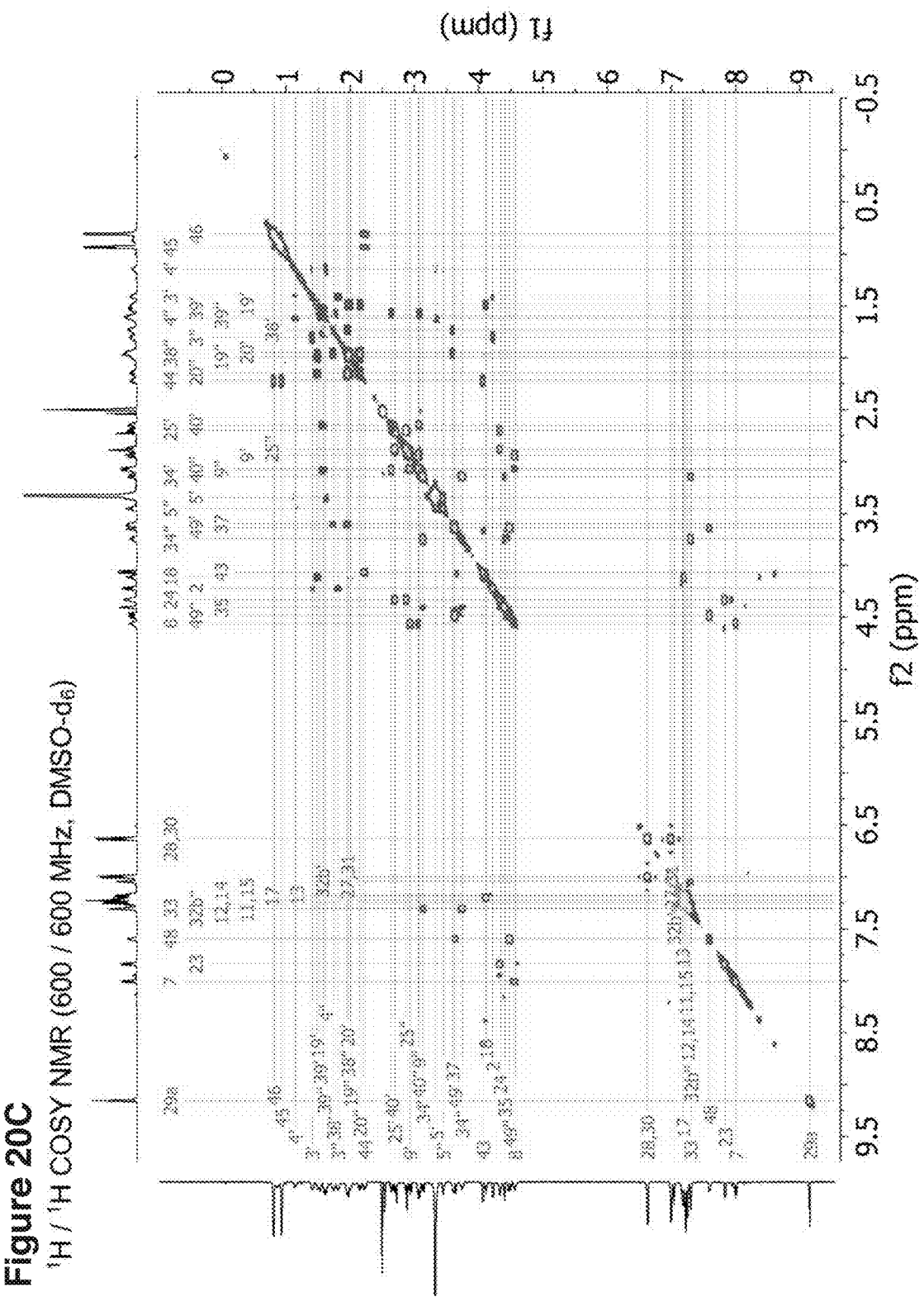

$^1$H / $^1$H TOCSY NMR (600 / 600 MHz, DMSO-$d_6$)

$^1H / ^{13}C$ HSQC NMR (600 / 151 MHz, DMSO-$d_6$)

¹H / ¹H ROESY NMR (600 / 600 MHz, DMSO-d₆)

$^1$H NMR (600 MHz, CD$_3$CN / H$_2$O, 7:3, v/v, 298 K)

$^1$H / $^1$H TOCSY NMR (600 / 600 MHz, CD$_3$CN / H$_2$O, 7:3, v/v, 298 K)

$^1H / ^{13}C$ HSQC NMR (600 / 151 MHz, $CD_3CN / H_2O$, 7:3, v/v, 298 K)

$^1H / ^{13}C$ HMBC NMR (600 / 151 MHz, $CD_3CN / H_2O$, 7:3, v/v, 298 K $^1H / ^{13}C$ band selective HMBC NMR (600 / 151 MHz, $CD_3CN / H_2O$, 7:3, v/v, 298 K)

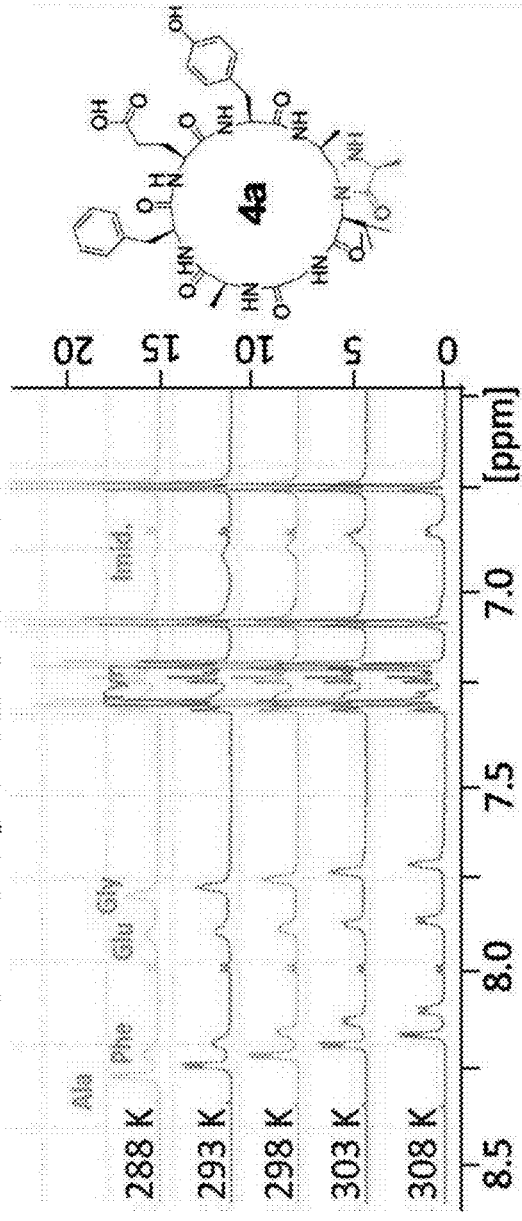
Figure 22A
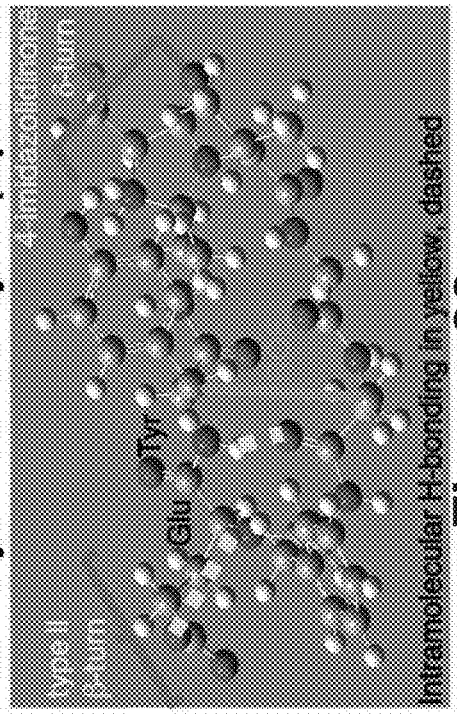
Figure 22B
Figure 22

Figure 21D  Enzyme stability studies

Figure 22C  pH stability studies

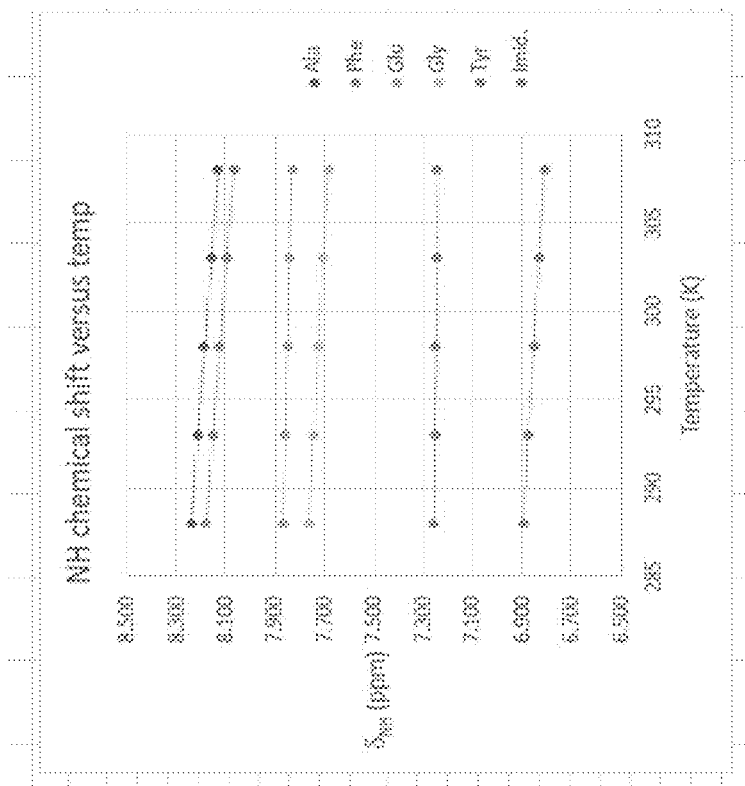
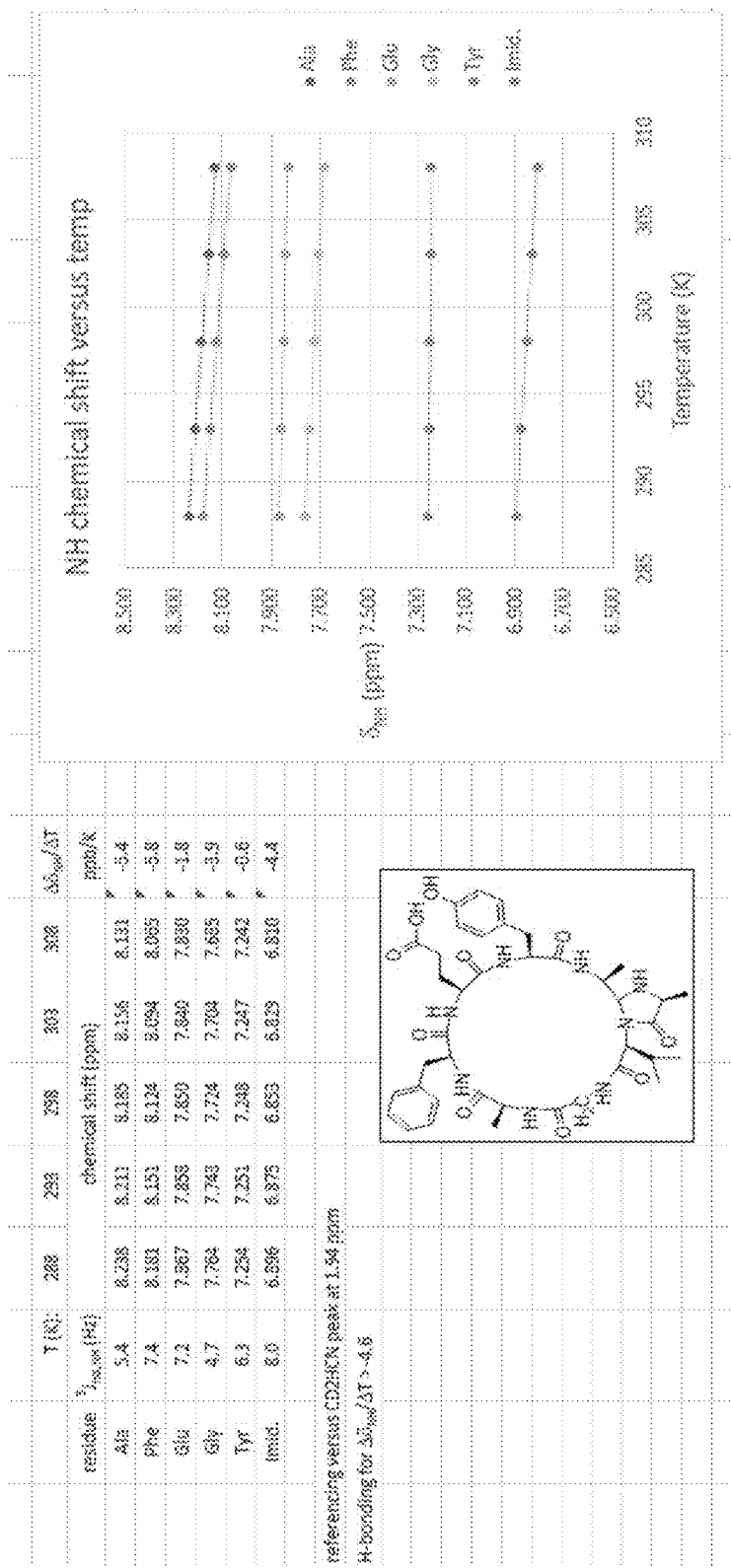
Figure 23A
Figure 23

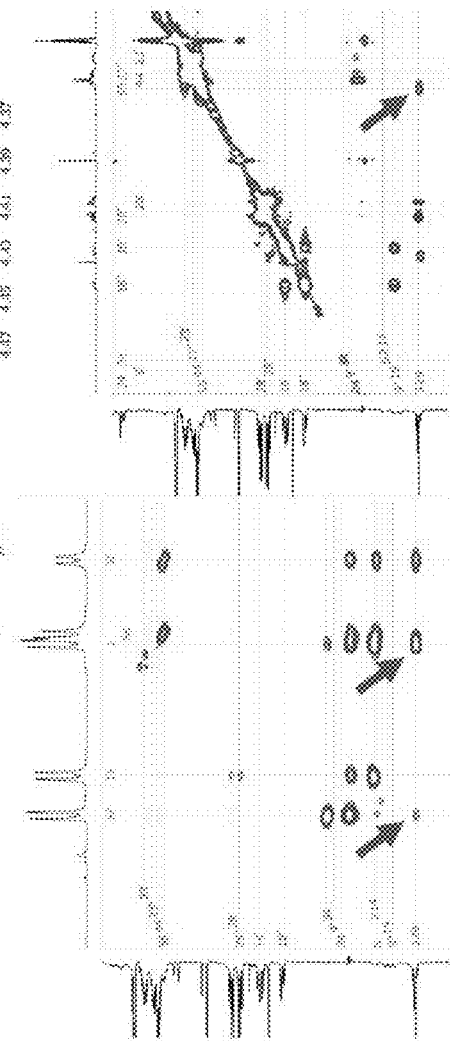
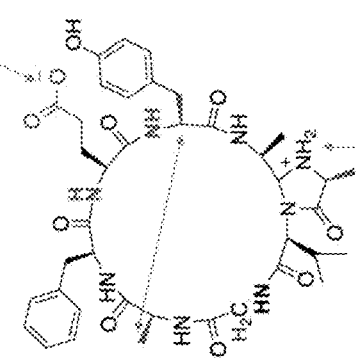
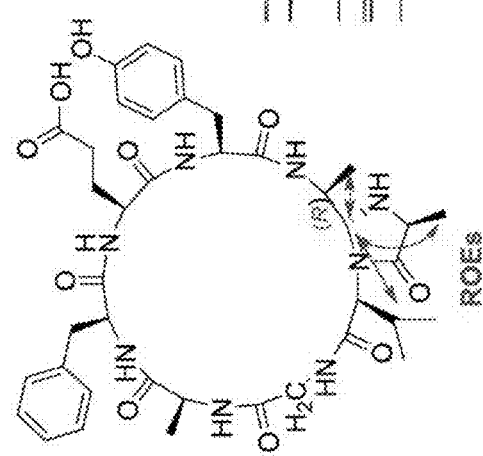
Figure 23B
Figure 23 (cont.)

Figure 24A

Running forcegen with NMR restraints

Run the program using the command:
sf-tools.exe --molconstraint nmr-cons -pquant testprep macro-ex.mol2 macgeom where:
- nmr-cons is a text file containing the NMR distance and dihedral restraints
- All other parameters are the same as in the previous slide (without NMR data)

Distance Restraints

```
# Type Pen  Dist Wiggle  a1  a2
nmr   1.0  4.24 0.5      39  134
nmr   1.0  3.87 0.5      39  98
...
# Type Pen  Dist Wgt  a1N a2N  a1list   a2list
qnmr  1.0  2.86 0.5   1   3    98       15 16 17
qnmr  1.0  2.78 0.5   1   3    98       15 16 17
...
```

-Note that # is a comment line; tabs can be used between parameters
-Pen is a penalty value (kcal/mol/Å²)
-Dist is in Å
-Wiggle (or Wgt) allows for free movement (in this case, ±0.5 Å) up to which a quadratic penalty is applied
-qNMR type restraint is to centroid of symmetry-related group of protons
-a1N and a2N are the number of atoms in the list (e.g., 1 to 6)

Dihedral Restraints

```
# Type    Pen  L_Bound  U_Bound  a1  a2  a3  a4
torsion   0.3  -150     -90      36  38  40  56
torsion   0.3  -160     -80      93  95  97  112
...
```

-L_Bound and U_Bound are the lower and upper bounds for dihedral angles, which are generated from Karplus-type curves using coupling constants

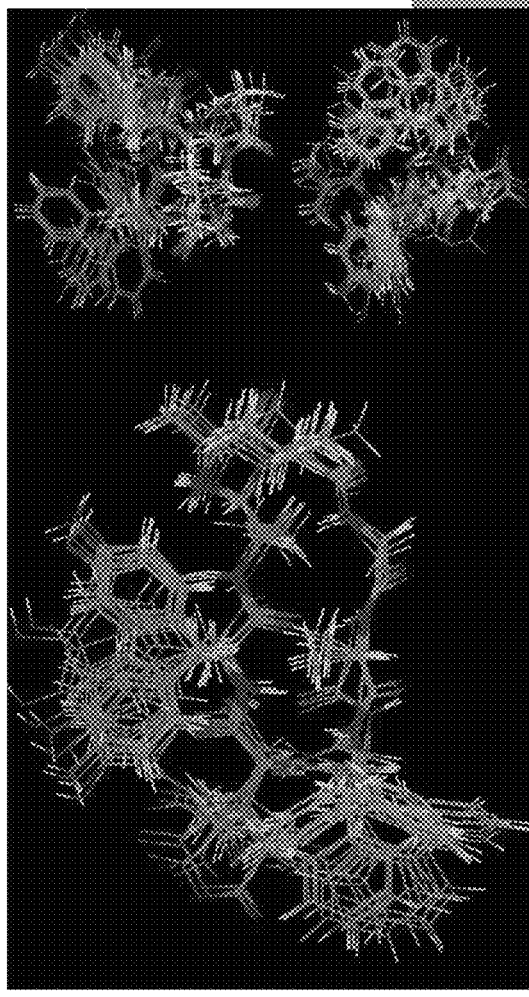
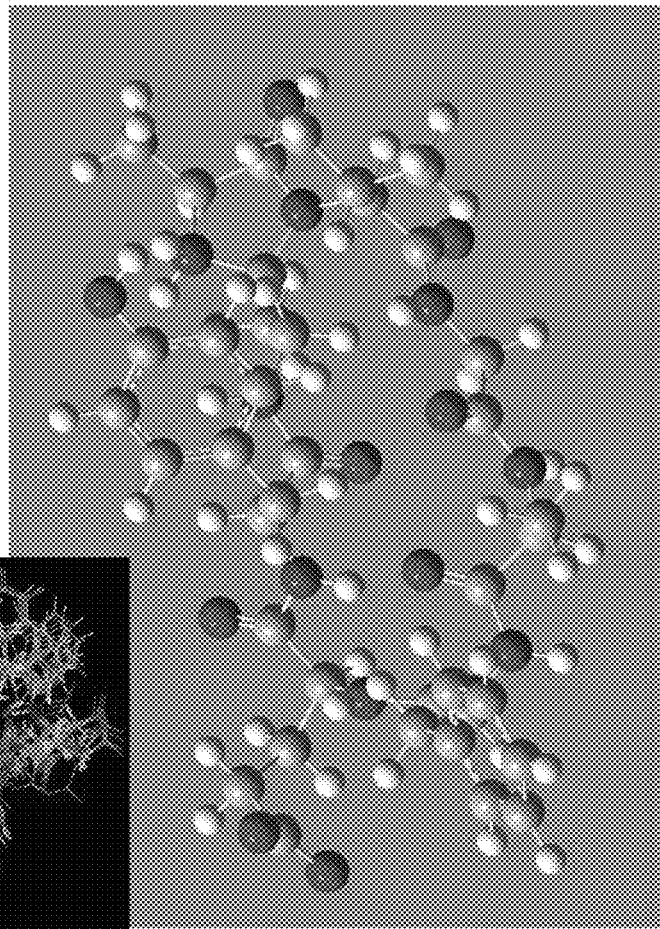
Figure 24E
Figure 24F
Figure 24 (cont.)

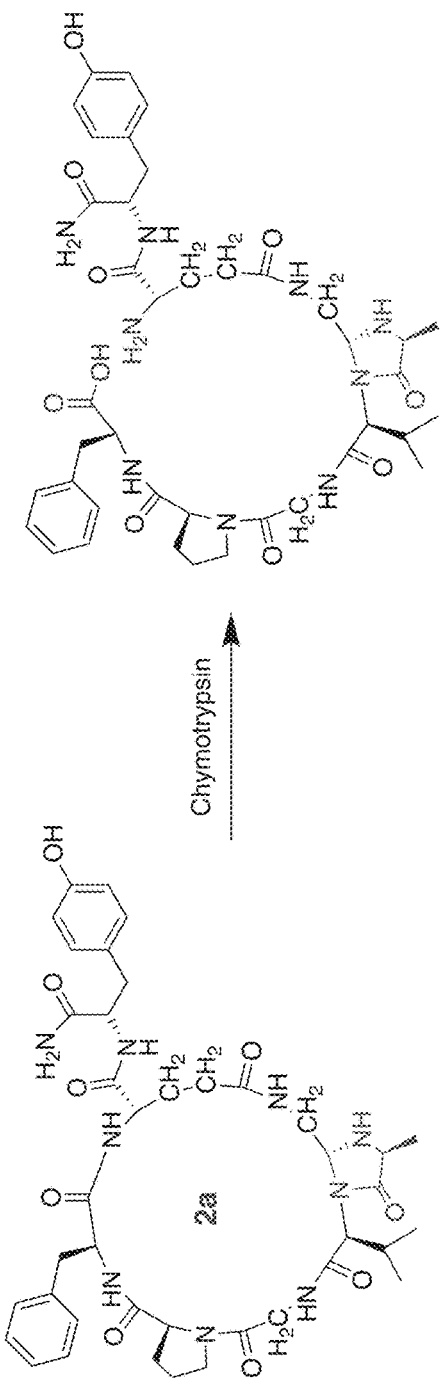
Figure 25A
Figure 25B
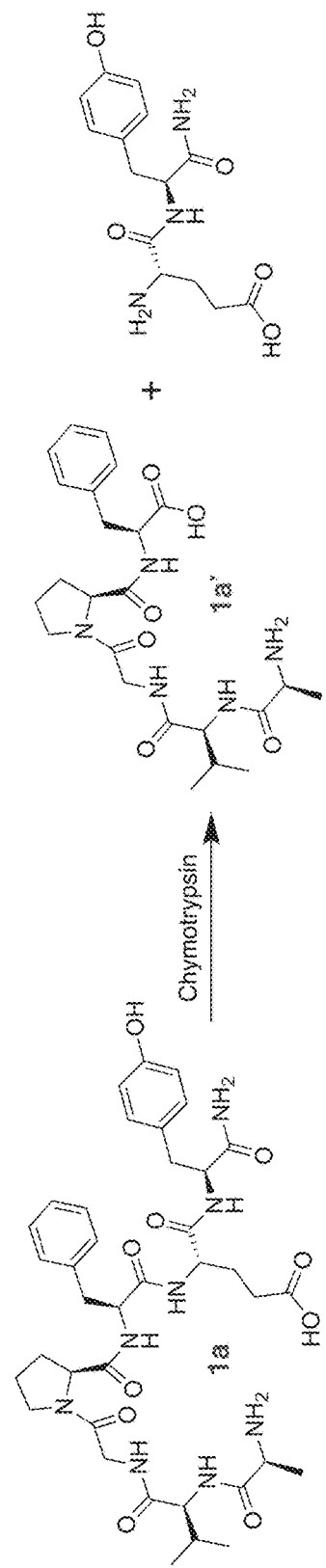
Figure 25

SEQUENCE LISTING

```
<160> NUMBER OF SEQ ID NOS: 53

<210> SEQ ID NO 1
<211> LENGTH: 3
<212> TYPE: PRT
<213> ORGANISM: Artificial Sequence
<220> FEATURE:
<223> OTHER INFORMATION: core amino acid sequence of 2a through 2i, 3a,
      and 4c

<400> SEQUENCE: 1

Gly Pro Phe
1

<210> SEQ ID NO 2
<211> LENGTH: 4
<212> TYPE: PRT
<213> ORGANISM: Artificial Sequence
<220> FEATURE:
<223> OTHER INFORMATION: core amino acid sequence of 2j

<400> SEQUENCE: 2

Ile Pro Cys Tyr
1

<210> SEQ ID NO 3
<211> LENGTH: 4
<212> TYPE: PRT
<213> ORGANISM: Artificial Sequence
<220> FEATURE:
<223> OTHER INFORMATION: core amino acid sequence of 2k

<400> SEQUENCE: 3

Ile Pro Tyr Leu
1
```

```
<210> SEQ ID NO 4
<211> LENGTH: 3
<212> TYPE: PRT
<213> ORGANISM: Artificial Sequence
<220> FEATURE:
<223> OTHER INFORMATION: core amino acid sequence of 2l and 2m

<400> SEQUENCE: 4

Gly Ala Phe
1

<210> SEQ ID NO 5
<211> LENGTH: 2
<212> TYPE: PRT
<213> ORGANISM: Artificial Sequence
<220> FEATURE:
<223> OTHER INFORMATION: core amino acid sequence of 2n and 2o

<400> SEQUENCE: 5

Pro Phe
1

<210> SEQ ID NO 6
<211> LENGTH: 2
<212> TYPE: PRT
<213> ORGANISM: Artificial Sequence
<220> FEATURE:
<223> OTHER INFORMATION: core amino acid sequence of 2p

<400> SEQUENCE: 6

Pro Tyr
1

<210> SEQ ID NO 7
<211> LENGTH: 1
<212> TYPE: PRT
<213> ORGANISM: Artificial Sequence
<220> FEATURE:
<223> OTHER INFORMATION: core amino acid sequence of 2q through 2x and
      3b

<400> SEQUENCE: 7

Pro
1

<210> SEQ ID NO 8
<211> LENGTH: 5
<212> TYPE: PRT
<213> ORGANISM: Artificial Sequence
<220> FEATURE:
<223> OTHER INFORMATION: core amino acid sequence of 4a

<400> SEQUENCE: 8

Gly Ala Phe Glu Tyr
1               5

<210> SEQ ID NO 9
<211> LENGTH: 4
<212> TYPE: PRT
<213> ORGANISM: Artificial Sequence
<220> FEATURE:
<223> OTHER INFORMATION: core amino acid sequence of 4b
```

```
<400> SEQUENCE: 9

Gly Pro Phe Phe
1

<210> SEQ ID NO 10
<211> LENGTH: 5
<212> TYPE: PRT
<213> ORGANISM: Artificial Sequence
<220> FEATURE:
<223> OTHER INFORMATION: core amino acid sequence of 4d

<400> SEQUENCE: 10

Gly Pro Asp Gly Arg
1               5

<210> SEQ ID NO 11
<211> LENGTH: 2
<212> TYPE: PRT
<213> ORGANISM: Artificial Sequence
<220> FEATURE:
<223> OTHER INFORMATION: core amino acid sequence of 4e

<400> SEQUENCE: 11

Gly Pro
1

<210> SEQ ID NO 12
<211> LENGTH: 4
<212> TYPE: PRT
<213> ORGANISM: Artificial Sequence
<220> FEATURE:
<223> OTHER INFORMATION: core amino acid sequence of 4f

<400> SEQUENCE: 12

Gly Pro Phe Lys
1

<210> SEQ ID NO 13
<211> LENGTH: 7
<212> TYPE: PRT
<213> ORGANISM: Artificial Sequence
<220> FEATURE:
<223> OTHER INFORMATION: 1a and 2a

<400> SEQUENCE: 13

Ala Val Gly Pro Phe Glu Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: 1A linear

<400> SEQUENCE: 14

Ala Pro Gly Ala Phe Glu Tyr
1               5
```

<210> SEQ ID NO 15
<211> LENGTH: 7
<212> TYPE: PRT
<213> ORGANISM: Artificial Sequence
<220> FEATURE:
<223> OTHER INFORMATION: 1b and 2b

<400> SEQUENCE: 15

Tyr Val Gly Pro Phe Glu Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: 1c and 2c

<400> SEQUENCE: 16

Val Val Gly Pro Phe Glu Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: 1d and 2d

<400> SEQUENCE: 17

Trp Val Gly Pro Phe Glu Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: 1e and 2e

<400> SEQUENCE: 18

Gln Val Gly Pro Phe Glu Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: 1f and 2f

<400> SEQUENCE: 19

Asn Val Gly Pro Phe Glu Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: 1g and 2g

<400> SEQUENCE: 20

Asp Val Gly Pro Phe Glu Tyr
1               5

```
<210> SEQ ID NO 21
<211> LENGTH: 7
<212> TYPE: PRT
<213> ORGANISM: Artificial Sequence
<220> FEATURE:
<223> OTHER INFORMATION: 1h and 2h

<400> SEQUENCE: 21

Lys Val Gly Pro Phe Glu Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: 1i and 2i

<400> SEQUENCE: 22

Ser Val Gly Pro Phe Glu Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: 1j and 2j

<400> SEQUENCE: 23

Asn Phe Ile Pro Cys Tyr Glu His
1               5

<210> SEQ ID NO 24
<211> LENGTH: 8
<212> TYPE: PRT
<213> ORGANISM: Artificial Sequence
<220> FEATURE:
<223> OTHER INFORMATION: 1k and 2k

<400> SEQUENCE: 24

Gln Asp Ile Pro Tyr Leu Glu Ser
1               5

<210> SEQ ID NO 25
<211> LENGTH: 7
<212> TYPE: PRT
<213> ORGANISM: Artificial Sequence
<220> FEATURE:
<223> OTHER INFORMATION: 1l and 2l

<400> SEQUENCE: 25

Gln Val Gly Ala Phe Glu Tyr
1               5

<210> SEQ ID NO 26
<211> LENGTH: 7
<212> TYPE: PRT
<213> ORGANISM: Artificial Sequence
<220> FEATURE:
<223> OTHER INFORMATION: 1m and 2m

<400> SEQUENCE: 26

Asn Val Gly Ala Phe Glu Tyr
1               5
```

```
<210> SEQ ID NO 27
<211> LENGTH: 6
<212> TYPE: PRT
<213> ORGANISM: Artificial Sequence
<220> FEATURE:
<223> OTHER INFORMATION: 1n and 2n

<400> SEQUENCE: 27

Ala Gly Pro Phe Glu Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: 1o and 2o

<400> SEQUENCE: 28

Asn Phe Pro Phe Glu Lys
1               5

<210> SEQ ID NO 29
<211> LENGTH: 6
<212> TYPE: PRT
<213> ORGANISM: Artificial Sequence
<220> FEATURE:
<223> OTHER INFORMATION: 1p and 2p

<400> SEQUENCE: 29

Gln Phe Pro Tyr Glu Met
1               5

<210> SEQ ID NO 30
<211> LENGTH: 5
<212> TYPE: PRT
<213> ORGANISM: Artificial Sequence
<220> FEATURE:
<223> OTHER INFORMATION: 1q and 2q

<400> SEQUENCE: 30

Ala Phe Pro Glu Phe
1               5

<210> SEQ ID NO 31
<211> LENGTH: 5
<212> TYPE: PRT
<213> ORGANISM: Artificial Sequence
<220> FEATURE:
<223> OTHER INFORMATION: 1r and 2r

<400> SEQUENCE: 31

Val Phe Pro Glu Phe
1               5

<210> SEQ ID NO 32
<211> LENGTH: 5
<212> TYPE: PRT
<213> ORGANISM: Artificial Sequence
<220> FEATURE:
<223> OTHER INFORMATION: 1s and 2s

<400> SEQUENCE: 32

Asp Phe Pro Glu Phe
1               5

<210> SEQ ID NO 33
```

```
<211> LENGTH: 5
<212> TYPE: PRT
<213> ORGANISM: Artificial Sequence
<220> FEATURE:
<223> OTHER INFORMATION: 1t and 2t

<400> SEQUENCE: 33

Tyr Phe Pro Glu Phe
1               5

<210> SEQ ID NO 34
<211> LENGTH: 5
<212> TYPE: PRT
<213> ORGANISM: Artificial Sequence
<220> FEATURE:
<223> OTHER INFORMATION: 1u and 2u

<400> SEQUENCE: 34

Ala Gly Pro Glu Phe
1               5

<210> SEQ ID NO 35
<211> LENGTH: 5
<212> TYPE: PRT
<213> ORGANISM: Artificial Sequence
<220> FEATURE:
<223> OTHER INFORMATION: 1v and 2v

<400> SEQUENCE: 35

Val Gly Pro Glu Phe
1               5

<210> SEQ ID NO 36
<211> LENGTH: 5
<212> TYPE: PRT
<213> ORGANISM: Artificial Sequence
<220> FEATURE:
<223> OTHER INFORMATION: 1w and 2w

<400> SEQUENCE: 36

Gln Gly Pro Glu Phe
1               5

<210> SEQ ID NO 37
<211> LENGTH: 5
<212> TYPE: PRT
<213> ORGANISM: Artificial Sequence
<220> FEATURE:
<223> OTHER INFORMATION: 1x and 2x

<400> SEQUENCE: 37

Asn Gly Pro Glu Phe
1               5

<210> SEQ ID NO 38
<211> LENGTH: 7
<212> TYPE: PRT
<213> ORGANISM: Artificial Sequence
<220> FEATURE:
<223> OTHER INFORMATION: 3a

<400> SEQUENCE: 38

Pro Val Gly Pro Phe Glu Tyr
1               5

<210> SEQ ID NO 39
<211> LENGTH: 5
```

```
<212> TYPE: PRT
<213> ORGANISM: Artificial Sequence
<220> FEATURE:
<223> OTHER INFORMATION: 3b

<400> SEQUENCE: 39

Pro Phe Pro Glu Phe
1               5

<210> SEQ ID NO 40
<211> LENGTH: 8
<212> TYPE: PRT
<213> ORGANISM: Artificial Sequence
<220> FEATURE:
<223> OTHER INFORMATION: 4a

<400> SEQUENCE: 40

Ala Val Gly Ala Phe Glu Tyr Ala
1               5

<210> SEQ ID NO 41
<211> LENGTH: 7
<212> TYPE: PRT
<213> ORGANISM: Artificial Sequence
<220> FEATURE:
<223> OTHER INFORMATION: 4b

<400> SEQUENCE: 41

Gln Val Gly Pro Phe Phe Gly
1               5

<210> SEQ ID NO 42
<211> LENGTH: 6
<212> TYPE: PRT
<213> ORGANISM: Artificial Sequence
<220> FEATURE:
<223> OTHER INFORMATION: 4c

<400> SEQUENCE: 42

Ala Ile Gly Pro Phe Ala
1               5

<210> SEQ ID NO 43
<211> LENGTH: 8
<212> TYPE: PRT
<213> ORGANISM: Artificial Sequence
<220> FEATURE:
<223> OTHER INFORMATION: 4d

<400> SEQUENCE: 43

Ala Lys Gly Pro Asp Gly Arg Ala
1               5

<210> SEQ ID NO 44
<211> LENGTH: 5
<212> TYPE: PRT
<213> ORGANISM: Artificial Sequence
<220> FEATURE:
<223> OTHER INFORMATION: 4e

<400> SEQUENCE: 44

Ala Phe Gly Pro Ala
1               5

<210> SEQ ID NO 45
<211> LENGTH: 7
<212> TYPE: PRT
```

```
<213> ORGANISM: Artificial Sequence
<220> FEATURE:
<223> OTHER INFORMATION: 4f

<400> SEQUENCE: 45

Ala Val Gly Pro Phe Lys Tyr
1               5

<210> SEQ ID NO 46
<211> LENGTH: 7
<212> TYPE: PRT
<213> ORGANISM: Artificial Sequence
<220> FEATURE:
<223> OTHER INFORMATION: cyc(AiGPFEY)

<400> SEQUENCE: 46

Ala Ile Gly Pro Phe Glu Tyr
1               5

<210> SEQ ID NO 47
<211> LENGTH: 10
<212> TYPE: PRT
<213> ORGANISM: Artificial Sequence
<220> FEATURE:
<223> OTHER INFORMATION: 30-membered ring Figure 16C

<400> SEQUENCE: 47

Ala Tyr Ala Trp Ala Asn Ser Ala Gly Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: 33-membered ring Figure 16C

<400> SEQUENCE: 48

Ala Tyr Ala Trp Ala Ala Asn Ser Ala Gly Val
1               5                   10

<210> SEQ ID NO 49
<211> LENGTH: 4
<212> TYPE: PRT
<213> ORGANISM: Artificial Sequence
<220> FEATURE:
<223> OTHER INFORMATION: Figure 30 monomer unit

<400> SEQUENCE: 49

Phe Gly Pro Ala
1

<210> SEQ ID NO 50
<211> LENGTH: 4
<212> TYPE: PRT
<213> ORGANISM: Artificial Sequence
<220> FEATURE:
<223> OTHER INFORMATION: Head-to-Tail Peptide Cyclization - Figure 7

<400> SEQUENCE: 50

Ala Pro Cys Ala
1

<210> SEQ ID NO 51
<211> LENGTH: 3
<212> TYPE: PRT
<213> ORGANISM: Artificial Sequence
```

```
<220> FEATURE:
<223> OTHER INFORMATION: Figure 8 top

<400> SEQUENCE: 51

Phe Val Ala
1

<210> SEQ ID NO 52
<211> LENGTH: 2
<212> TYPE: PRT
<213> ORGANISM: Artificial Sequence
<220> FEATURE:
<223> OTHER INFORMATION: Figure 8 bottom - reagant 1

<400> SEQUENCE: 52

Val Phe
1

<210> SEQ ID NO 53
<211> LENGTH: 4
<212> TYPE: PRT
<213> ORGANISM: Artificial Sequence
<220> FEATURE:
<223> OTHER INFORMATION: Figure 8 bottom - reagant 2

<400> SEQUENCE: 53

Ala Ser Val Phe
1
```

SYNTHETIC CYCLIC PEPTIDES AND METHODS OF PREPARATION AND USE THEREOF

CROSS-REFERENCE TO RELATED APPLICATION

This application claims priority to U.S. Provisional Application Ser. No. 63/092,343, filed Oct. 15, 2020, the disclosure of which Is hereby incorporated by reference herein in its entirety.

STATEMENT REGARDING FEDERALLY SPONSORED RESEARCH OR DEVELOPMENT

This invention was made with government support under CHE-1752654 awarded by the National Science Foundation. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206300_0002_00US_SequenceListing_ST25.txt" in ASCII format. The text file containing the Sequence Listing of the present application was created on Oct. 13, 2021 and is 9 KB in size.

BACKGROUND OF THE INVENTION

Cyclic peptides have recently received considerable attention in the pharmaceutical industry because of their high stability, cell permeability, and enhanced potency as compared to their linear counterparts (Zhang X et al., 2018, Nat. Chem., 10:540; Driggers E M et al., 2008, Nat. Rev. Drag Discovery, 7:608; Frost J R et al., 2016, Nat. Chem., 8:1105; Adessi C et al., 2002, Curr. Med. Chem., 9:963; Craik D J et al., 2013, Chem. Biol. Drug Des., 81:136). Currently, more than forty cyclic peptides are used as pharmaceuticals, and most of them are obtained from nature (Albericio F et al., 2012, Future Med. Chem., 4:1527; Vinogradov A A et al., 2019, J. Am. Chem. Soc., 141:4167; Schilling N et al., 2019, Angew. Chem. Int. Ed., 58:9234). The major driving force for the growing interest in cyclic peptides is due to their ability to interrupt protein-protein interactions (PPIs) in a highly specific manner (Cardote T A F et al., 2016, Chem Med Chem, 11:787; Hill T A et al., 2014, Angew. Chem. Int. Ed., 53:13020; Heinis C et al., 2014, Nat. Chem. Biol., 10:696).

Despite their importance, laboratory synthesis of cyclic peptides can be challenging. Among the most challenging cyclizations are those attempted on linear peptides containing less than seven amino acid residues (White C J et al., 2011, Nat. Chem., 3:509; Lambert J N et al., 2001, J. Chem. Soc. Perkin Trans. 1, 471; Puentes A R et al., 2017, Org, Lett., 19:4022; Meutermans W D F et al., 2003, Org. Lett., 5:2711; Wong C T T et al., 2013, Angew. Chem. Int. Ed., 52:10212). The chain/ring conformational equilibrium (Bielawski C W et al., 2002, Science, 297:2041) is the central obstacle in the synthesis of cyclic peptides from acyclic precursors. This process is characterized by an unfavorable entropy change when moving from a linear precursor to a cyclic product. The major problems associated with current cyclization strategies are C-terminal epimerization, cyclo-oligomerization, and formation of linear dimers and trimers (Lawson K V et al., 2013, Proc. Natl, Acad. Sci. USA, 110:E3753; Royo-Gracia, S et al., 2009, Future Med. Chem., 1:1289; Skropeta D et al., 2004, J. Org. Chem., 69:8804; Ehrlich A et al., 1996, J. Org. Chem., 61:8831; Chow H et al, 2019, Chem. Rev., 119:9971).

Thus, there is a need in the art for methods for generation of synthetic cyclic peptides hat can circumvent the aforementioned limitations and provide an efficient strategy for easy access to a variety of cyclic peptides as well as methods that use said synthetic cyclic peptides in treating or preventing various diseases or disorders (e.g., diseases or disorders associated with PPIs). The present invention addresses this unmet need in the art.

SUMMARY OF THE INVENTION

In one aspect, the present invention provides a compound comprising 4-imidazolidinone-fused cyclic peptide, or a derivative, prodrug, pharmaceutically acceptable salt, solvate, isomer, or tautomer thereof. In various aspects, the compound of the present invention is a compound having the structure of

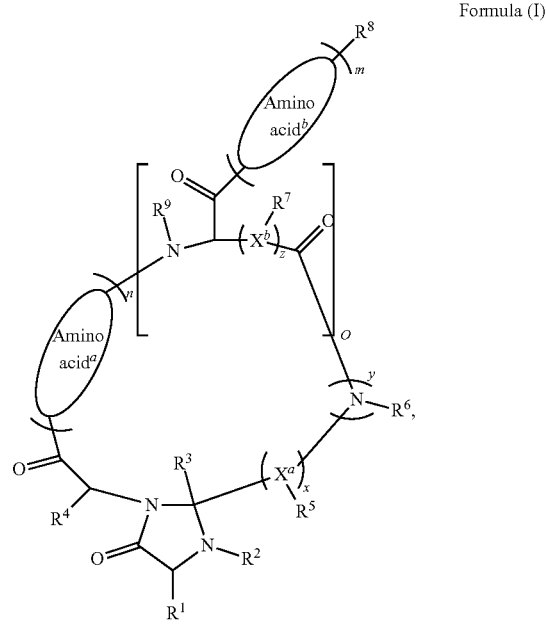

Formula (I)

or a derivative, prodrug, pharmaceutically acceptable salt, solvate, isomer, or tautomer thereof.

In some embodiments, each occurrence of $R^1$, $R^2$, $R^3$, $R^4$, $R^5$, $R^6$, $R^7$, $R^8$, and $R^9$ is independently selected from hydrogen, deuterium, halogen, hydroxyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, aryl alkyl, heteroaryl, heteroarylalkyl, acyl, ester, urea, thiourea, thiol, thioalkyl, thioxo, sulfanyl, sulfinyl, sulfonyl, phosphino, =O, nitrile, isonitrile, cyano, carbamate, guanidine, guanidine alkyl, amino acid, or any combination thereof. In some embodiments, each occurrence of $R^1$, $R^2$, $R^4$, $R^6$, and $R^9$ is independently selected hydrogen, deuterium, halogen, hydroxyl, amino,

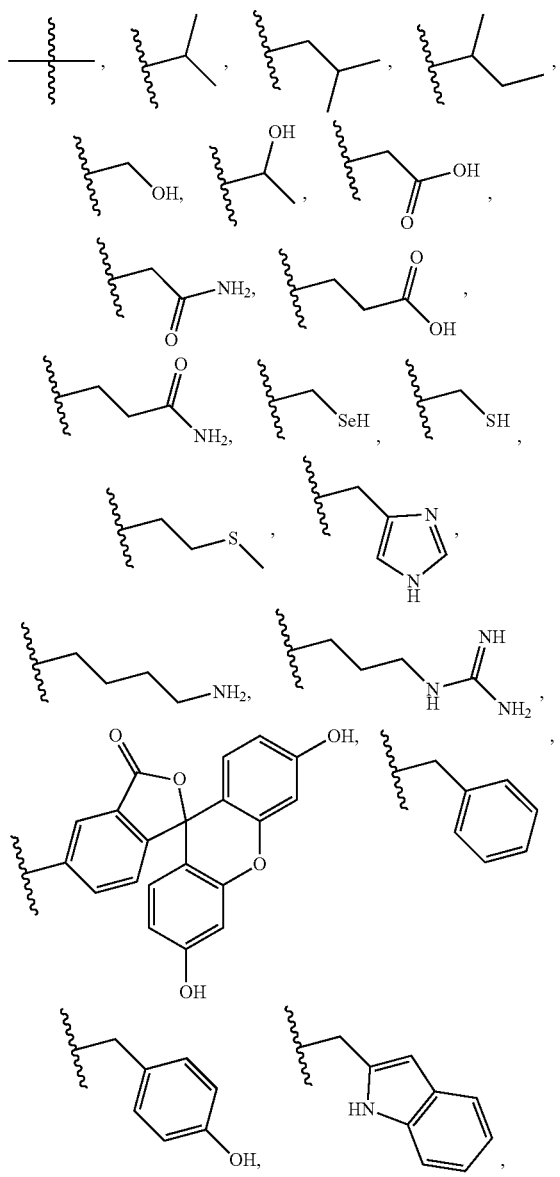

amino acid, or any combination thereof. In one embodiment, $R_2$ is hydrogen. In some embodiments, $R_3$ is hydrogen, deuterium, alkyl, or any combination thereof. In some embodiments, each occurrence of $R^5$ and $R^7$ is independently selected from hydrogen or deuterium. In one embodiment, $R^8$ is amino.

In some embodiments, $R_1$ and $R_2$ are optionally fused or joined to form a ring. In another embodiment, $R_1$ and $R_2$ are fused or joined to form a ring.

In some embodiments, each occurrence of $X^a$ and $X^b$ is independently selected from C, —$CR^{10}$, N, P, P=O, S=O, or any combination thereof. In some embodiments, each occurrence of $X^a$ and $X^b$ is independently selected from C or —$CR^{10}$.

In some embodiments, each occurrence of each occurrence of $R^{10}$ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, or any combination thereof. In some embodiments, each occurrence of $R^{10}$ is independently selected from hydrogen or deuterium.

In some embodiments, m is an integer from 1 to 100. In some embodiments, m is an integer from 1 to 5.

In some embodiments, n is an integer from 1 to 100. In some embodiments, n is an integer from 1 to 10.

In some embodiments, o is an integer from 0 to 10. In some embodiments, o is an integer 0 or 1. In one embodiment, o is an integer 0.

In some embodiments, x is an integer from 0 to 10. In some embodiments, x is an integer 0 or 1.

In some embodiments, y is an integer from 0 to 10. In some embodiments, y is an integer 0 or 1. In one embodiment, y is an integer 0. In one embodiment, y is an integer 1.

In some embodiments, z is an integer from 0 to 10. In some embodiments, z is an integer from 0, 1, or 2.

In some embodiments, each occurrence of amino acid$^a$ and amino acid$^b$ is independently selected from a natural amino acid, unnatural amino acid, D-amino acid, L-amino acid, functionalized natural amino acid, functionalized unnatural amino acid, functionalized D-amino acid, functionalized L-amino acid, or any combination thereof. In some embodiments, (Amino Acid$^a$)$_n$ is an amino acid sequence as set forth in SEQ ID NOs: 1-12.

In some embodiments, the compound having the structure of Formula (I) is a compound having the structure of Formula (Ia)

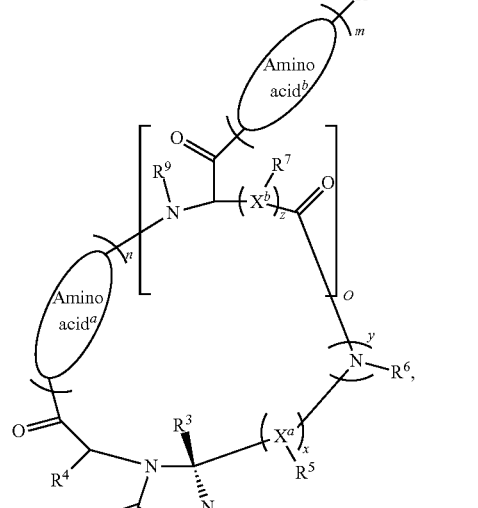

or a derivative, prodrug, pharmaceutically acceptable salt, solvate, isomer, or tautomer thereof, or Formula (Ib)

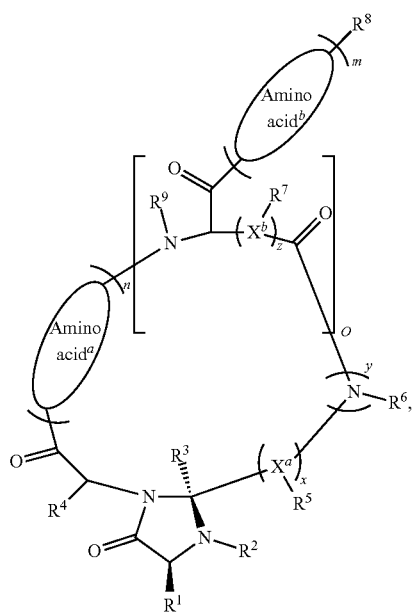

or a derivative, prodrug, pharmaceutically acceptable salt, solvate, isomer, or tautomer thereof.

In one embodiment, the compound having the structure of Formula (I) is a compound having the structure of Formula (II)

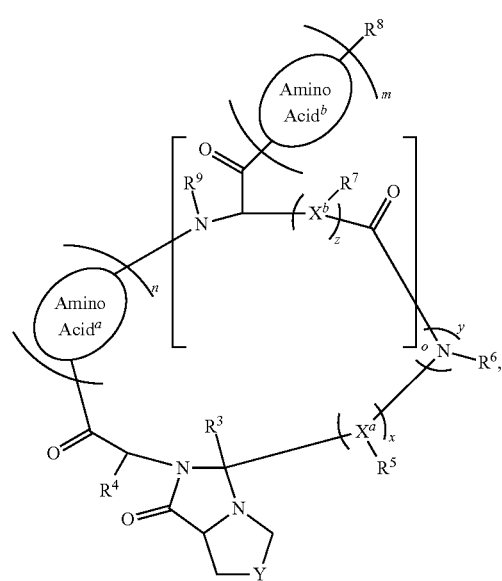

or a derivative, prodrug, pharmaceutically acceptable salt, solvate, isomer, or tautomer thereof.

In some embodiments, Y is O, S, NH, C=O, or $CH_2$.

In some embodiments, the compound having the structure of Formula (II) is a compound having the structure of Formula (IIa)

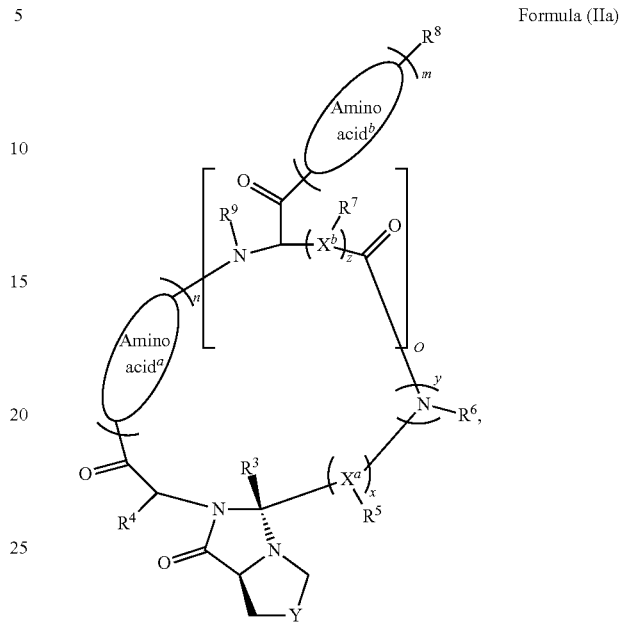

or a derivative, prodrug, pharmaceutically acceptable salt, solvate, isomer, or tautomer thereof, or Formula (IIb)

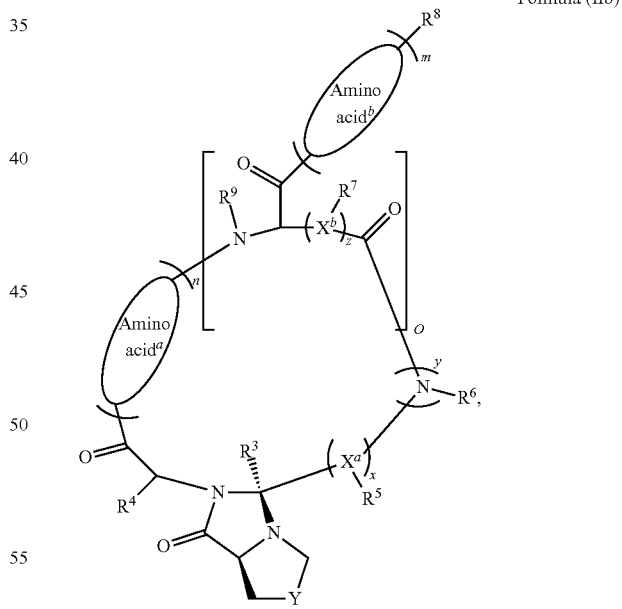

or a derivative, prodrug, pharmaceutically acceptable salt, solvate, isomer, or tautomer thereof.

In various aspects, the compound of the present invention inhibits at least one protein-protein interaction.

In one aspect, the present invention provides a composition comprising at least one compound of the present invention.

In one aspect, the present invention provides a method of reducing or inhibiting at least one protein-protein interaction in a subject in need thereof. In one aspect, the present invention pro vides a method of treating or preventing a disease or disorder in a subject in need thereof. In some embodiments, the method comprises administering a therapeutically effective amount of at least one compound of the present invent or a composition thereof to the subject.

In one embodiment, the disease or disorder is a disease or disorder associated with a protein-protein interaction. In some embodiments, the disease or disorder is cancer, Huntington's disease, cystic fibrosis, seizure, or Alzheimer's disease.

In one aspect, the present invention provides a method of preparing the compound of the present invention. In some embodiments, the method comprises the steps of: a) obtaining a linear peptide; b) adding an aldehyde group to the linear peptide to generate an aldehyde functionalized linear peptide; e) incubating the aldehyde functionalized linear peptide in a solvent in the presence of a nucleophilic catalyst; d) covalently cyclizing the aldehyde functionalized linear peptide to generate at least one compound of the present invention; and e) isolating the compound of the present invention.

In one aspect, the present invention provides a method of generating a library of 4-imidazolidinone-fused cyclic peptides. In some embodiments, the method comprises the steps of: a) obtaining a mixture of linear peptides; b) adding an aldehyde group to the linear peptides to generate aldehyde functionalized linear peptides; e) incubating the aldehyde functionalized linear peptides in a solvent in the presence of a nucleophilic catalyst; d) covalently cyclizing the aldehyde functionalized linear peptides to generate 4-imidazolidinone-fused cyclic peptides, or derivatives, prodrugs, pharmaceutically acceptable salts, solvates, isomers, or tautomers thereof; and e) isolating the 4-imidazolidinone-fused cyclic peptides, or derivatives, prodrugs, pharmaceutically acceptable salts, solvates, isomers, or tautomers thereof.

In some embodiments, the linear peptide comprises at least three amino acids. In some embodiments, each occurrence of amino acid is independently selected from a natural amino acid, unnatural amino acid, D-amino acid, L-amino acid, functionalized natural amino acid, functionalized unnatural amino acid, functionalized D-amino acid, functionalized L-amino acid, or any combination thereof.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 1A through FIG. 1C, depicts a schematic representation of the CyClick approach based, on the conformationally induced, activation of the amide backbone for peptide macrocyclization. FIG. 1A depicts a schematic representation of exemplary limitations of current peptide macrocyclization strategies. FIG. 1B depicts a schematic representation of the synthesis of cyclic peptides via CyClick chemistry. FIG. 1C depicts a schematic representation of exemplary 4-imidazolidinone-containing bioactive compounds.

FIG. 2A through FIG. 2D, depicts representative structural characterization of cyclic peptide 2a identified by NMR spectroscopy. FIG. 2A depicts representative $^{13}$C NMR spectrum with the diagnostic aminal chemical shift highlighted (*) and HMBC correlations confirming the 4-imidazolidinone ring structure of 2a (SEQ ID NO: 13). FIG. 2B depicts a representative control reaction using APGAFE(CHO)Y (SEQ ID NO: 14) 1A, which contains Pro in the second position, validating that no macrocyclization occurred. FIG. 2C depicts a representative key rotating frame overhause (ROEs) of 2a to assign the (R)-configuration of the new chiral center. FIG. 2D depicts a representative proposed mechanistic pathway for observed the stereo-selectivity in the cyclic peptide.

FIG. 4A through FIG. 4K, depicts representative NMR data of cyc(AVGPFE(CHO)Y) (SEQ ID NO: 13) 2a. FIG. 4A depicts a schematic representation of the synthesis of cyc(AVGPFE(CHQ)Y) (SEQ ID NO: 13) 2a. FIG. 4B depicts a representative $^{13}$C NMR chemical shift for validation of 4-imidazolidinone structure of cyclic peptide cyc(AVGPFE(CHO)Y) (SEQ ID NO: 13) 2a, FIG. 4C depict representative results demonstrating HMBC correlations for validation of 4-imidazolidinone structure of cyc(AVGPFE(CHQ)Y) (SEQ ID NO: 13) 2a. FIG. 4D depict representative results demonstrating HMBC correlations from Val (41), 37, and 38 to the carbonyl carbon C39. FIG. 4E depicts a representative $^1$H NMR spectrum of cyc (AVGPFE(CHO)Y) (SEQ ID NO: 13) 2a. FIG. 4F depicts a representative $^{13}$C NMR spectrum of cyc(AVGPFE(CHO) Y) (SEQ ID NO: 13) 2a. FIG. 4G depicts a representative $^1$H/$^1$H DQF-COSY NMR spectrum of cyc(AVGPFE(CHO) Y) (SEQ ID NO: 1) 2a. FIG. 4H depicts a representative $^1$H/$^1$H TCOSY NMR spectrum of cyc(AVGPFE(CHO)Y) (SEQ ID NO: 13) 2a. FIG. 4I depicts a representative $^1$H/$^{13}$C HSQC NMR spectrum of cyc(AVGPFE(CHO)Y) (SEQ ID NO: 13) 2a. FIG. 4J depicts a representative $^1$H/$^{13}$C HMBC NMR spectrum of cyc(AVGPFE(CHO)Y) (SEQ ID NO: 13) 2a. FIG. 4K depicts a representative $^1$H/$^1$H ROESY NMR spectrum of cyc(AVGPFE(CHO)Y) (SEQ ID NO: 13) 2a.

FIG. 5, comprising FIG. 5A through FIG. 5J, depicts representative NMR data of cyc(QVGPFE(CHO)Y) (SEQ ID NO: 18) 2e. FIG. 5A depicts a schematic representation of the synthesis of cyc(QVGPFE(CHO)Y) (SEQ ID NO: 18) 2e. FIG. 5B depicts a representative $^{13}$C NMR chemical shifts for 5- and 7-membered ring structures. FIG. 5C depicts a representative $^1$H NMR spectrum of cyc(QVGPFE (CHO)Y) (SEQ ID NO: 18) 2e. FIG. 5D depicts a representative $^{13}$C NMR spectrum of cyc(QVGPFE(CHO)Y) (SEQ ID NO: 18) 2e. FIG. 5E depicts a representative $^1$H/$^1$H DQF-COSY NMR spectrum of cyc(QVGPFE(CHO)Y) (SEQ ID NO: 18) 2e. FIG. 5F depicts a representative $^1$H/$^1$H TCOSY NMR spectrum of cyc(QVGPFE(CHO)Y) (SEQ ID NO: 18) 2e. FIG. 5G depicts a representative $^1$H/$^{13}$C HSQC NMR spectrum of cyc(QVGPFE(CHO)Y) (SEQ ID NO: 18) 2e. FIG. 5H depicts a representative $^1$H/$^{13}$C HMBC NMR spectrum of cyc(QVGPFE(CHO)Y) (SEQ ID NO: 18) 2e, FIG. 5I depicts a representative $^1$H/$^1$H ROESY NMR spectrum of cyc(QVGPFE(CHO)Y) (SEQ ID NO: 18) 2e. FIG. 5J depicts a representative $^1$H/$^{15}$N HSQC NMR spectrum of cyc(QVGPFE(CHO)Y) (SEQ ID NO: 18) 2e.

FIG. 6A through FIG. 6I, depicts representative NMR data of cyc(NVGPFE(CHO)Y) (SEQ ID NO: 19) 2f. FIG. 6A depicts a schematic representation of cyc(NVGPFE(CHO)Y) (SEQ ID NO: 19) 2f and representative $^1$H NMR spectrum of cyc(NVGPFE(CHO)Y) (SEQ ID NO: 19) 2f. FIG. 6B depicts a representative $^{13}$C NMR spectrum of cyc(NVGPFE(CHO)Y) (SEQ ID NO: 19) 2f. FIG. 6C depicts a representative $^1$H/$^1$H DQF-COSY NMR spectrum of cyc(NVGPFE(CHO)Y) (SEQ ID NO: 19) 2f. FIG. 6D depicts a representative $^1$H/$^{13}$H TCOSY NMR spectrum of cyc(NVGPFE(CHO)Y) (SEQ ID NO: 19) 2f. FIG. 6E depicts a representative $^1$H/$^{13}$C HSQC NMR spectrum of cyc(NVGPFE(CHO)Y) (SEQ ID NO: 19) 2f. FIG. 6F depicts a representative $^1$H/$^{13}$C HSQC-TOCSY NMR spectrum of cyc(NVGPFE(CHO)Y) (SEQ ID NO: 19) 2f. FIG. 6G depicts a representative HMBC NMR spectrum of eye(NVGPFE(CHO)Y) (SEQ ID NO: 19) 2f. FIG. 6H depicts a representative $^1$H/$^1$H ROESY NMR spectrum of cyc(NVGPFE(CHO)Y) (SEQ ID NO: 19) 2f. FIG. 6I depicts a representative $^1$H/$^{15}$N HSQC NMR spectrum of cyc (NVGPFE(CHO)Y) (SEQ ID NO: 19) 2f.

FIG. 9, comprising FIG. 9A through FIG. 9C, depicts representative stereoconfiguration of cyclic peptide cyc (AVGPFE(CHO)Y) (SEQ ID NO: 13) 2a via NMR. FIG. 9A depicts a schematic representation of synthesis of cyclic peptide cyc(AVGPFE(CHO)Y) (SEQ ID NO: 13) 2a and the corresponding TI NMR results of high concentration reaction (100 mM). FIG. 9B depicts representative $^1$H/$^1$H ROESY NMR of cyclic peptide cyc(AVGPFE(CHO)Y) (SEQ ID NO: 13) 2a demonstrating ROEs from 35 to 42, 43, 44, and 38; weak ROE that determines stereoconfiguration. FIG. 9C depicts representative zoomed in section of $^1$H/$^1$H ROESY NMR of cyclic peptide cyc(AVGPFE(CHO)Y) (SEQ ID NO: 13) 2a demonstrating ROEs from 35 to 42, 43, 44, and 38; weak ROE that determines stereoconfiguration.

FIG. 10, comprising FIG. 10A through FIG. 10E, depicts a schematic representation of the synthesis of cyc (aVGPFEY) (SEQ ID NO: 13) 2a' and corresponding representative NMR results. FIG. 10A depicts a schematic representation of the synthesis of cyc(aVGPFEY) (SEQ ID NO: 13) 2a'. FIG. 10B depicts a representative NMR spectrum of cyc(aVGPFEY) (SEQ ID NO: 13) 2a'. FIG. 10C depicts a representative HSQC NMR spectrum of cyc (aVGPFEY) (SEQ ID NO: 13) 2a'. FIG. 10D depicts a representative ROESY NMR spectrum of cyc(aVGPFEY) (SEQ ID NO: 13) 2a'. FIG. 10E depicts a representative TOCSY NMR spectrum of cyc(aVGPFEY) (SEQ ID NO: 13) 2a'.

FIG. 11, comprising FIG. 11A through FIG. 11I, depicts a schematic representation of the synthesis of cyclic peptide cyc(AiGPFEY) (SEQ ID NO: 46) and representative NMR and HUMS results. FIG. 11A depicts a schematic representation of the synthesis of cyclic peptide cyc(AiGPFEY) (SEQ ID NO: 46). FIG. 11B depicts a representative $^1$H NMR spectrum of cyc(AiGPFE(CHO)Y (SEQ ID NO: 46). FIG. 11C depicts a representative $^{13}$C NMR spectrum of eye(AiGPFEY) (SEQ ID NO: 46). FIG. 11D depicts a representative $^1$H/$^1$H COSY NMR spectrum of cyc (AiGPFEY) (SEQ ID NO: 46). FIG. 11E depicts a representative $^1$H/$^1$H TOCSY NMR spectrum of cyc(AiGPFEY) (SEQ ID NO: 46). FIG. 11F depicts a representative $^1$H/$^{13}$C HSQC NMR spectrum of cyc(AiGPFEY) (SEQ ID NO: 46). FIG. 11G depicts a representative $^1$H/$^{13}$C HMBC NMR spectrum of cyc(AiGPFEY) (SEQ ID NO: 46). FIG. 11H depicts a representative $^1$H/$^1$H ROESY NMR spectrum of cyc(AiGPFEY) (SEQ ID NO: 46). FIG. 11I depicts a representative HRMS results for cyc(AiGPFE(CHO)Y (SEQ ID NO: 46) from Agilent 6560 Q-TOF. Observed m/z: 818.4208. Theoretical m/z: 818.4196; Mass accuracy: 1.5 ppm.

FIG. 16A through FIG. 16D, depicts a representative substrate scope of CyClick chemistry. FIG. 16A depicts representative high conversion results of cyclic peptides (12- to 23-membered) with various amino acid residues and lengths of peptide chains (SEQ ID NOs: 13 and 15-37). FIG. 16B depicts representative fused bicyclic pyrrolo[1,2-c]imidazolone macrocycles formed at the site of macrocyclization (SEQ ID NOs: 38 and 39). FIG. 16C depicts representative results demonstrating head-to-tail macrocyclization of cyclic peptides by CyClick chemistry (SEQ ID NOs: 40-45, 47, and 48). Number in the middle of the rings denotes ring size. Macrocyclic peptide 4f with quaternary chiral center (*) was generated by reaction with peptide ketone. FIG. 16D depicts representative substrate scope of CyClick chemistry demonstrated with internal and N-terminal lysine.

FIG. 17A through FIG. 17Y, depicts schematic representations of the syntheses of cyclic peptides 2a through 2x and the corresponding HRMS traces. FIG.

17A depicts a schematic representation of the synthesis of cyclic peptide 2a and the corresponding HRMS trace. cyc(Ala-Val-Gly-Pro-Phe-Glu)Tyr (SEQ ID NO: 13) (2a). LCMS: m/z 804.4 (calcd [M+H]+=804.3), m/z 826.4 (calcd [M+Na]+=826.3), Purity: >95% (HPLC analysis at 220 nm), Retention time: 12.8. FIG. 17C depicts a schematic representation of the synthesis of cyclic peptide 2c and the corresponding HRMS trace. cyc(Val-Val-Gly-Pro-Phe-Glu)Tyr) (SEQ ID NO: 16) (2c), LCMS: m/z 832.4 (calcd [M+H]+=832.4), m/z 854.4 (calcd [M+Na]+=854.4, Purity: >95% (HPLC analysis at 220 nm). Retention time: 14.7. FIG. 17D depicts a schematic representation of the synthesis of cyclic peptide 2d and the corresponding HRMS trace. cyc(Trp-Val-Gly-Pro-Phe-Glu)-Tyr (SEQ ID NO: 17) (2d), LCMS: m/z 917.4 (calcd [M+H]+=917.4), Purity: >95% (HPLC analysis at 220 nm). Retention time: 16.5. FIG. 17G depicts a schematic representation of the synthesis of cyclic peptide 2g and the corresponding HRMS trace. cyc(Asp-Val-Gly-Pro-Phe-Glu)-Tyr (SEQ ID NO: 20) (2g). LCMS: m/z 848.4 (calcd [M+H]+=848.3), m/z 870.4 (calcd [M+Na]+=870.3), m/z 886.4 (calcd [M+H]+=886.3), Purity: >95% (HPLC analysis at 220 nm). Retention time: 14.9. FIG. 17H depicts a schematic representation of the synthesis of cyclic peptide 2h and the corresponding HRMS trace. cyc(Lys-Val-Gly-Pro-Phe-Glu)-Tyr (SEQ ID NO: 21) (2h). LCMS: m/z 861.5 (calcd [M+H]+=861.4), m/z 883.4 (calcd [M+Na]+=883.4), Purity: >95% (HPLC analysis at 220 nm). Retention time: 11.3. FIG. 17I depicts a schematic representation of the synthesis of cyclic peptide 2i and the corresponding HRMS trace. cyc(Ser-Val-Gly-Pro-Phe-Glu)-Tyr (SEQ ID NO: 22) (2i). LCMS: m/z 820.4 (calcd [M+H]+=820.3), Purity: >95% (HPLC analysis at 220 nm). Retention time: 1.95. FIG. 17J depicts a schematic representation of the synthesis of cyclic peptide 2f and the corresponding HRMS trace. cyc(Ser(CO)-Val-Gly-Pro-Phe-Glu)-Tyr (SEQ ID NO: 22) (2i'). LCMS: m/z 832.4 (calcd [M+H]+=832.3), Purity: >95% (HPLC analysis at 220 nm). Retention time: 2.13. FIG. 17L depicts a schematic representation of the synthesis of cyclic peptide 2k and the corresponding HRMS trace. cyc(Gln-Asp-Ile-Pro-Tyr-Leu-Glu)-Ser (SEQ ID NO: 24) (2k). LCMS: m/z 986.5 (calcd [M+H]+=986.4), m/z 1008.5 (calcd [M+Na]+=1008.4), Purity: >95% (HPLC analysis at 220 nm). Retention time: 14.2. FIG. 17R depicts a schematic representation of the synthesis of cyclic peptide 2q and the corresponding HRMS trace. cyc(Ala-Phe-Pro-Glu)-Phe (SEQ ID NO: 30) (2q). LCMS: m/z 654.3 (calcd [M+Na]+=654.4), Purity: >95% (HPLC analysis at 220 nm). Retention time: 12.0. FIG. 17T depicts a schematic representation of the synthesis of cyclic peptide 2s and the corresponding HRMS trace. cyc(Asp-Phe-Pro-Glu)-Phe (SEQ ID NO: 32) (2s). LCMS: m/z 676.3 (calcd [M+H]+=676.3), m/z 698.3 (calcd [M+Na]+=698.3), m/z 714.2 (calcd [M+H]+=714.3), m/z 1351.5 (calcd [2M+H]+=1351.6), m/z 1373.5 (calcd [2M+Na]+=1373.6), Purity: >95% (HPLC analysis at 220 nm). Retention time: 14.6. FIG. 17U depicts a schematic representation of the synthesis of cyclic peptide 2t and the corresponding HRMS trace. cyc(Tyr-Phe-Pro-Glu)-Phe (SEQ ID NO: 33) (2t). LCMS: m/z 746.3 (calcd [M+Na]+=746.4), m/z 762.3 (calcd [M+K]+=762.4), Purity: >95% (HPLC analysis at 220 nm). Retention time: 14.4, FIG. 17V depicts a schematic representation of the synthesis of cyclic peptide 2u and the corresponding HRMS trace. cyc(Ala-Gly-Pro-Glu)-Phe (SEQ ID NO: 34) (2u). LCMS: m/z 564.2 (calcd [M+Na]+=564.4), m/z 580.2 (calcd [M+K]+=580.4), Purity: >95% (HPLC analysis at 220 nm). Retention time: 9.26. FIG. 17W depicts a schematic representation of the synthesis of cyclic peptide 2v and the corresponding HRMS trace. cyc(Val-Gly-Pro-Glu)-Phe (SEQ ID NO: 35) (2v). LCMS: m/z 592.3 (calcd [M+Na]+=592.4), m/z 608.3 (calcd [M+H]+608.4), Purity: >95% (HPLC analysis at 220 nm). Retention time: 12.7. FIG. 17X depicts a schematic representation of the synthesis of cyclic peptide 2w and the corresponding HRMS trace, cyc(Gln-Gly-Pro-Glu)-Phe (SEQ ID NO: 36) (2w). LCMS: m/z 599.3 (calcd [M+H]+=599.3), Purity: >95% (HPLC analysis at 220 nm). Retention time: 10.0. FIG. 17Y depicts a schematic representation of the synthesis of cyclic peptide 2x and the corresponding HRMS trace. cyc(Asn-Gly-Pro-Glu-Phe) (SEQ ID NO: 37) (2x), LCMS: m/z 585.3

(calcd [M+H]+=585.3), m/z 607.3 (calcd [M+Na]+=607.3), Purity: >95% (HPLC analysis at 220 nm). Retention time: 10.1.

FIG. 19A through FIG. 19H, depicts schematic representations of the syntheses of cyclic peptides 3a, 3b, and 4a through 4f and the corresponding HRMS traces. FIG. 19A depicts a schematic representation of the synthesis of cyclic peptide 3a. cyc(Pro-Val-Gly-Pro-Phe-Glu)-Tyr (SEQ ID NO: 38) (3a). Purity: >95% (HPLC analysis at 220 nm). Retention time: 12.8. FIG. 19B depicts a schematic representation of the synthesis of cyclic peptide 3b and the corresponding HRMS trace. cyc(Pro-Phe-Pro-Glu)-Phe (SEQ ID NO: 39) (3b). LCMS: m/z 658.3 (calcd [M+H]+=658.5), m/z 680.3 (calcd [M+Na]+=680.5), m/z 698.3 (calcd [M+K]+=698.5), Purity: >95% (HPLC analysis at 220 nm). Retention time: 13.0. FIG. 19C depicts a schematic representation of the synthesis of cyclic peptide 4a and the corresponding HRMS trace. cyc(Ala-Val-Gly-Ala-Phe-Glu-Tyr)-Ala) (SEQ ID NO: 40) (4a). LCMS: m/z 793.4 (calcd [M+H]+=793.4), Purity: >95% (HPLC analysis at 220 nm). Retention time: 1.7. FIG. 19D depicts a schematic representation of the synthesis of cyclic peptide 4b and the corresponding HRMS trace. cyc(Gln-Val-Gly-Pro-Phe-Phe-Gly) (SEQ ID NO: 41) (4b). LCMS: m/z 703.3 (calcd [M+H]+=703.3), Purity: >95% (HPLC analysis at 220 nm). Retention time: 16.8. FIG. 19E depicts a schematic representation of the synthesis of cyclic peptide 4c and the corresponding HRMS trace. cyc(Ala-Ile-Gly-Pro-Phe-Ala) (SEQ ID NO: 42) (4c). LCMS: m/z 562.4 (calcd [M+Na]+= 563.5), Purity: >95% (HPLC analysis at 220 nm). Retention time: 11.3-12.3. FIG. 19F depicts a schematic representation of the synthesis of cyclic peptide 4d and the corresponding HRMS trace. cyc(Ala-Lys-Gly-Pro-Asp-Gly-Arg-Ala)-Fluorescein isothiocyanate (FITC) (SEQ ID NO: 43) (4d). LCMS: m/z 1126.4 (calcd [M+H]+=1126.5), m/z 563.7 (calcd. [(M+2)/2]=563.7), Purity: >95% (HPLC analysis at 220 nm). Retention time: 13.5. FIG. 19G depicts a schematic representation of the synthesis of cyclic peptide 4e and the corresponding HRMS trace. cyc(Ala-Phe-Gly-Pro-Ala) (SEQ ID NO: 44) (4e). LCMS: m/z 428.2 (calcd [M+H]+= 428.2), Purity: >95% (HPLC analysis at 220 nm). Retention time: 8.2-9.7. FIG. 19H depicts a schematic representation of the synthesis of cyclic peptide 4f and the corresponding HRMS trace. cyc(Ala-Val-Gly-Pro-Phe-Lys(CO)-Tyr (SEQ ID NO: 45) (4f). LCMS: m/z 884.4 (calcd [M+Na]+=884.5), m/z 900.4 (calcd [M+K]+=900.5), Purity: >95% (HPLC analysis at 220 nm). Retention time: 10.7.

FIG. 20A through FIG. 20G, depicts representative NMR data of fused bicyclic five membered pyrrolo[1,2-c]imidazolone cyclic peptide 3a. FIG. 20A depicts a representative $^1$H NMR data of fused bicyclic five membered pyrrolo[1,2-c]imidazolone cyclic peptide 3a. FIG. 20B depicts a representative $^{13}$C NMR data effused bicyclic five membered pyrrolo[1,2-c]imidazolone cyclic peptide 3a. FIG. 20C depicts a representative $^1$H/$^1$H COSY NMR data of fused bicyclic five membered pyrrolo[1,2-c] imidazolone cyclic peptide 3a. FIG. 20D depicts a representative $^1$H/$^1$H TOCSY NMR data of fused bicyclic five membered pyrrolo[1,2-c]imidazolone cyclic peptide 3a, FIG. 20E depicts a representative $^1$H/$^1$H HSQC NMR data of fused bicyclic five membered pyrrolo[1,2-c]imidazolone cyclic peptide 3a. FIG. 20F depicts a representative $^1$H/$^{13}$C HMBC NMR data of fused bicyclic five membered pyrrolo [1,2~c]imidazolone cyclic peptide 3a. FIG. 20G depicts a representative $^1$H/$^1$H ROESY NMR data of fused bicyclic five membered pyrrolo[1,2-c]imidazolone cyclic peptide 3a.

FIG. 21A through FIG. 21G, depicts representative NMR data of head-to-tail 4-imidazolidinone cyclic peptide 4a. FIG. 21A depicts a representative $^1$H NMR data of head-to-tail 4-imidazolidinone cyclic peptide 4a. FIG. 21B depicts a representative $^{13}$C NMR data of head-to-tail 4-imidazolidinone cyclic peptide 4a. FIG. 21C depicts a representative $^1$H/$^1$H DQF-COSY NMR data of head-to-tail 4-imidazolidinone cyclic peptide 4a. FIG. 21D depicts a representative $^1$H/$^1$H TOCSY NMR data of head-to-tail 4-imidazolidinone cyclic peptide 4a. FIG. 21E depicts a representative $^1$H/$^{13}$C HSQC NMR data of head-to-tail 4-imidazolidinone cyclic peptide 4a. FIG. 21F depicts a representative $^1$H/$^{13}$C HMBC NMR data of head-to-tail 4-imidazolidinone cyclic peptide 4a. FIG. 21G depicts a representative $^1$H/$^{13}$C band selective HMBC NMR data of head-to-tail 4-imidazolidinone cyclic peptide 4a. FIG. 21H depicts a representative $^1$H/$^1$H ROESY NMR data of head-to-tail 4-imidazolidinone cyclic peptide 4a.

FIG. 22A through FIG. 22D, depicts representative effects of 4-imidazolidinone in cyclic peptides. FIG. 22A depicts representative VT-NMR spectra of head-to-tail 4-imidazolidinone cyclic peptide 4a in aqueous solutions. FIG. 22B depicts representative turn structure of 4-imidazolidinone cyclic peptide 4a obtained by running ForceGen (Jain A N et al., 2019, J. Comput.-Aided Mol. Des., 33:531) with NMR constraints. FIG. 22C depicts representative 4-imidazolidinone cyclic peptide 2f exhibiting enhanced resistance towards hydrolysis under different pH conditions. Cyclic peptide cyc(NVGPFEY) (SEQ ID NO: 19) 2f (2.5 mg) was dissolved in $H_2O$ to form a stock solution (500 μL, conc. 7 mM). 100 μL of the stock was added to 400 μL of sodium phosphate buffer (10 mM) at the following pH values: 3.5, 5.5, 7.5, 8.5, 10.5 (total conc. 1.4 mM). The reactions were shaken at room temperature. Samples were analyzed by injecting them in HPLC after regular intervals of time. No degradation of cyc(NVGPFEY) (SEQ ID NO: 19) 2f was observed even after 24 h at different pH values. FIG. 22D depicts representative proteolytic stability of 4-imidazolidinone cyclic peptide 2a as compared to its linear counterpart.

FIG. 23A through FIG. 23C, depicts representative variable temperature VT-NMR of head-to-tail cyclic peptide 4a. FIG. 23A depicts representative temperature coefficients that were used to determine H-bonding, Temperature coefficients >−4.6 ppb/DT may show H-bonding. Tyr and Glu appeared to be H-bound, while Gly and the Imidazoline residues were borderline. FIG. 23B depicts representative stereochemical determination of newly formed stereocenter. Weak ROEs were observed between Imid methyl and Glu methylene protons. This indicated dimerization. However, to minimize dimerization, the sample required to be diluted, which has a negative effect on NMR sensitivity. Thus, these ROEs were ignored. In contrast, two long ROEs were observed between Ala methyl and both Ty methylenes. This was consisted, along with hydrogen bonding for Tyr, with Phe or Glu involved in a turn. FIG. 23C depicts representative ROE distance restrains. Volume integrals from ROESY spectrum were converted into distance restrains by bracketing them into strong, medium, and weak ROEs.

FIG. 24, comprising FIG. 24A through FIG. 24F, depicts representative secondary structure determination of 4a by NMR coupling constants and ForceGen (Jain A N et al., 2019, J. Comput. Aided Mol. Des., 33:531). FIG. 24A depicts representative instructions for performing ForceGen with NMR restraints. FIG. 24B depicts representative example of the restraint file used for the herein-described peptides. The "#" column represents comments, ForceGen was run with and without using dihedral angle restraints (torsions). In the present example, distance restraints (ROEs) were used and J-couplings were then calculated using DFT as a way to eliminate incorrect structures. FIG. 24C depicts representative procedure after running Force-Gen where violations of distance restraints were used as a way to ensure that these were correctly assigned ROEs and should be used in the model. If there were too many violations, then these were removed. FIG. 24D depicts representative filter by J-couplings approach applied to the herein-described peptides. A python script was written to filed conformers with J-couplings that fit the observed. The set with total absolute error <10 Hz was then used to generate an accurate ensemble. FIG. 24E depicts representative results from post J-coupling constant filtering, which showed a turn at Glu and Phe. The H-bond was also observed for Tyr. The imidazoline group was conformationally constrained with limited flexibility. FIG. 24F depicts a representative, more accurate structure that was produced by rerunning ForceGen with the Tyr NH to Ala C=O hydrogen bond as a restraint. This structure showed that the Ala NH hydrogen bond is not present.

FIG. 25A through FIG. 25C, depicts representative enzymatic Degradation Studies. Linear peptide AVGPFEY (SEQ ID NO: 13) and cyclic peptide cyc (AVGPFEY) (SEQ ID NO: 13) 2a were individually dissolved in 10 mM Tris buffer pH 7.5 (final conc. 1.5 mM). A chymotrypsin stock solution was created by the addition of 1 mg chymotrypsin in 100 μL $CaCl_2$ (0.01 M), 100 μL tris buffer (0.1 M pH 7.5), 100 μL HCl (1 mM). 10 μL of the chymotrypsin stock solution was added to both linear peptide AVGPFEY (SEQ ID NO: 13) and cyclic peptide cyc (AVGPFEY) (SEQ ID NO: 13) 2a solutions. Samples (100 μL) were taken after regular intervals of time from both linear and cyclic peptide solutions. 100 μL of each sample was quenched with 400 μL of frozen water and solutions were frozen at −80° C. at the following time intervals: 0 min, 5 min, 15 min, 30 min, 45 min, 60 min, 90 min, 120 min, and 480 min. Each sample was lyophilized and analyzed using HPLC and LCMS. FIG. 25A depicts a schematic representation of the enzyme degradation of cyclic peptide cyc (AVGPFEY) (SEQ ID NO: 13) 2a. FIG. 25B depicts a schematic representation of the enzyme degradation of linear peptide 1a. FIG. 25C depicts representative HPLC data of various time aliquots of the enzyme degradation of linear peptide 1a.

FIG. 30A through FIG. 30C, depicts representative reaction with tetrapeptide FGPA(CHO) (SEQ ID NO: 49) and the corresponding HRMS results. FIG. 30A depicts schematic representations of reaction with tetrapeptide FGPA(CHO) (SEQ ID NO: 49). FIG. 30B depicts representative HRMS results of the tetrapeptide reaction before reduction. FIG. 30C depicts representative HRMS results of the tetrapeptide reaction after reduction.

DETAILED DESCRIPTION

Figure 1:
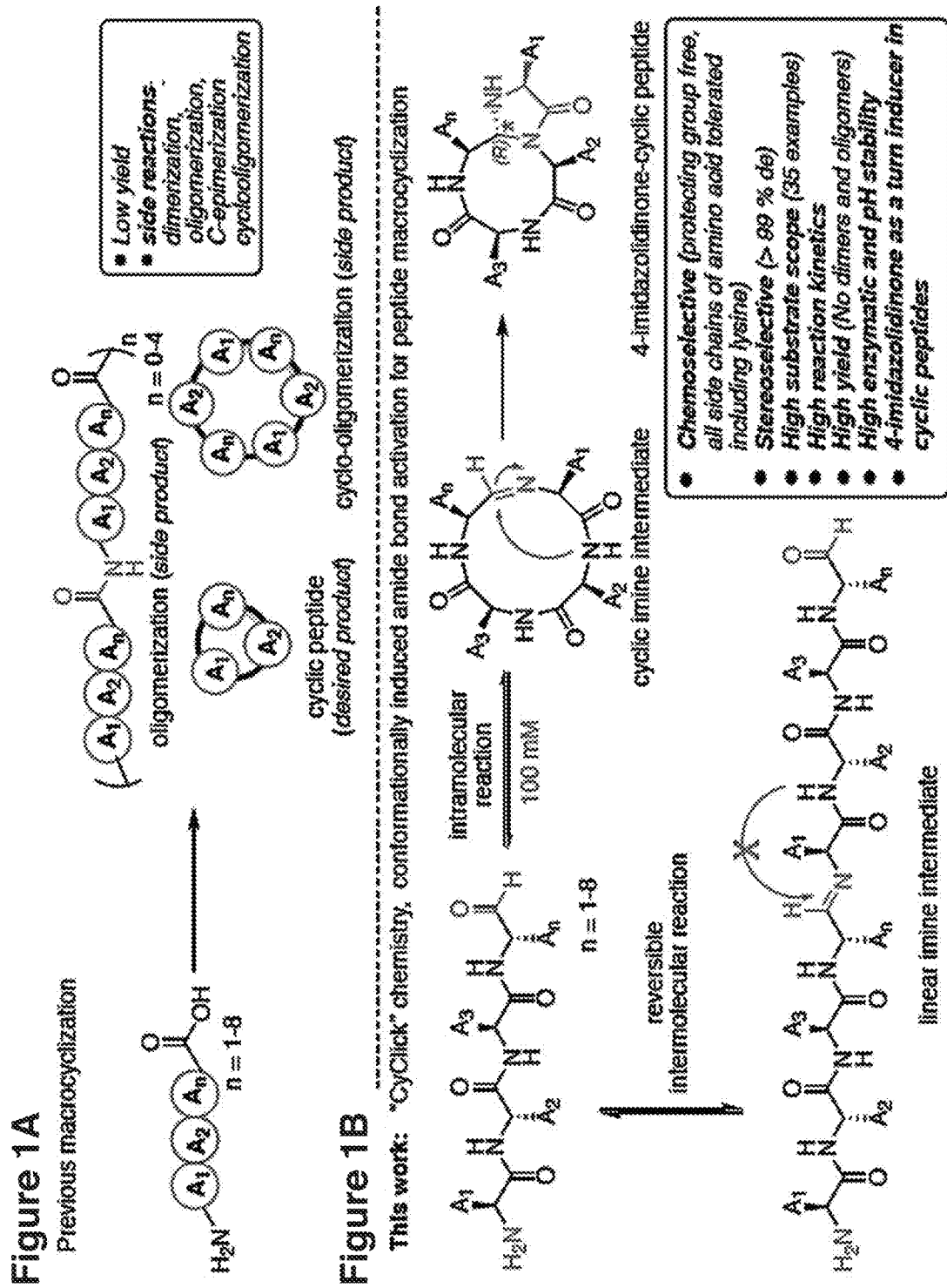
FIG. 1, comprising
Figure 1:
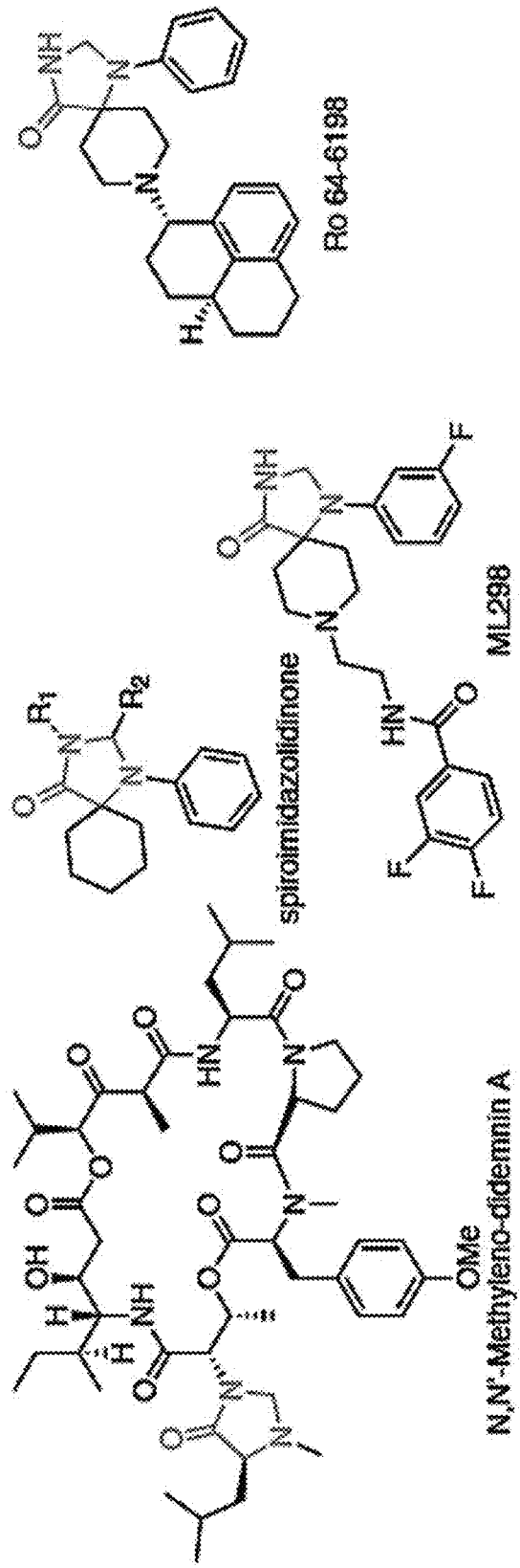

The present invention relates, in part, to novel compounds comprising 4-imidazolidinone-fused cyclic peptides and compositions thereof. In various aspects, the compounds of the present invention comprise at least one natural amino acid, at least one unnatural amino acid, or any combination thereof. The present invention also relates, in part, to methods of generating said compounds comprising 4-imidazolidinone-fused cyclic peptides and compositions thereof. In one aspect, the present invention also relates, in part, to methods of using said compounds or compositions thereof. In one aspect, the present invention also relates, in part, to methods of inhibiting protein-protein interaction using said compounds or compositions thereof. In another aspect, the present invention relates, in part, to methods of treating or preventing a various diseases or disorders using said compounds or compositions thereof.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value, for example numerical values and/or ranges, such as an amount, a temporal duration, and the like, is meant to encompass variations of ±20%, ±10%, ±5%, ±1%, or ±0.1% from the specified value, as such variations are appropriate to perform the disclosed methods. For example, "about 40 [units]" may mean within ±25% of 40 (e.g., from 30 to 50), within ±20%, ±1.5%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein.

The term "derivative" refers to a small molecule that differs in structure from the reference molecule, but retains the essential properties of the reference molecule, A derivative may change its interaction with certain other molecules relative to the reference molecule. A derivative molecule may also include a salt, an adduct, tautomer, isomer, prodrug, or other variant of the reference molecule.

As used herein, the term "prodrug" refers to an agent that is converted into the parent drug in vivo. For example, the term "prodrug" refers to a derivative of a known direct acting drug, which derivative has enhanced delivery characteristics and therapeutic value as compared to the drug, and is transformed, into the active drug by an enzymatic or chemical process. In some embodiments, "prodrug" refers to an Inactive or relatively less active form of an active agent that becomes active by undergoing a chemical conversion through one or more metabolic processes. In one embodiment, upon in vivo administration, a prodrug Is chemically converted to the biologically, pharmaceutically, or therapeutically active form of the compound. In another embodiment, a prodrug is enzymatically metabolized by one or more steps or processes to the biologically, pharmaceutically, or therapeutically active form of the compound. For example, the present compounds can be administered to a subject as a prodrug that includes an initiator bound to an active agent, and, by virtue of being degraded by a metabolic process, the active agent is released in its active form.

The term "tautomers" are constitutional isomers of organic compounds that readily interconvert by a chemical process (tautomerization).

The term "isomers" or "stereoisomers" refers to compounds, which have identical chemical constitution, but differ with regard to the arrangement of the atoms or groups in space.

As used herein, the term "alkyl," or "alkyl group" by itself or as part of another substituent means, unless otherwise stated, a straight or branched chain hydrocarbon having from 1 to 12 carbon atoms. In some embodiments, the alkyl is a $C_1$-$C_{12}$ alkyl, a $C_1$-$C_{10}$ alkyl, a $C_1$-$C_8$ alkyl, a $C_1$-$C_6$ alkyl, a $C_1$-$C_4$ alkyl, or a $C_1$-$C_3$ alkyl. For example, an alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples include methyl, ethyl, n-propyl, isopropyl, n-butyl, isobutyl, sec-butyl, tert-butyl, n-pentyl, neopentyl, n-hexyl, n-heptyl, n-octyl, n-nonyl, n-decyl, n-undecyl, n-dodecyl, and cyclopropylmethyl. Unless stated otherwise specifically in the specification, an alkyl group can be optionally substituted.

"Alkylene" or "alkylene chain" refers to a fully saturated, straight or branched divalent hydrocarbon, and having from one to twelve carbon atoms, and which has two points of attachment to the rest of the molecule. In some embodiments, the alkylene is a $C_1$-$C_{12}$ alkylene, a $C_1$-$C_{10}$ alkylene, a $C_1$-$C_5$ alkylene, a $C_1$-$C_6$ alkylene, a $C_1$-$C_4$ alkylene, or a $C_1$-$C_3$ alkylene. Non-limiting examples of $C_1$-$C_{12}$ alkylene include methylene, ethylene, propylene, n-butylene, ethenylene, propenylene, n-butenylene, propynylene, n-butynylene, and the like. The points of attachment of the alkylene chain to the rest of the molecule can be through one carbon or any two carbons within the chain. Unless stated otherwise specifically in the specification, an alkylene chain can be optionally substituted.

"Alkenyl" or "alkenyl group" refers to a straight or branched hydrocarbon chain having from two to twelve carbon atoms, and having one or more carbon-carbon double bonds. Each alkenyl group is attached to the rest of the molecule by a single bond. Alkenyl group comprising any number of carbon atoms from 2 to 12 are included, in some embodiments, the alkenyl is a $C_2$-$C_{12}$ alkenyl, a $C_2$-$C_{10}$ alkenyl, a $C_2$-$C_8$ alkenyl, a $C_2$-$C_6$ alkenyl, a $C_2$-$C_4$ alkenyl, or a $C_2$-$C_3$ alkenyl. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes Ce alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkynyl" or "alkynyl group" refers to a straight or branched hydrocarbon chain having from two to twelve carbon atoms, and having one or more carbon-carbon triple bonds. Each alkynyl group is attached to the rest of the molecule by a single bond. In some embodiments, the alkynyl is a $C_2$-$C_{12}$ alkynyl, a $C_2$-$C_{10}$ alkynyl, a $C_2$-$C_8$ alkynyl, a $C_2$-$C_6$ alkynyl, a $C_2$-$C_4$ arynyl, or a $C_2$-$C_3$ alkynyl. Alkynyl group comprising arty number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

The term "hydroxy" or "hydroxy l" refers to a group of the formula —OH group.

As used herein, the term "alkoxy" employed alone or in combination with other terms means, unless otherwise stated, refers to a group of the formula —$OR_a$ where $R_a$ is an alkyl, alkenyl or alknyl group having from 1 to 12 carbon atoms, as defined above, connected to the rest of the molecule via an oxygen atom, such as, for example, methoxy, ethoxy, 1-propoxy, 2-propoxy (isopropoxy) and the higher homologs and isomers. Unless stated otherwise specifically in the specification, an alkoxy group can be optionally substituted.

As used herein, the term "halo" or "halogen" alone or as part of another substituent means, unless otherwise stated, a fluorine, chlorine, bromine, or iodine group.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

As used herein, the term "heteroalkyl" by itself or in combination with another term means, unless otherwise stated, a stable straight or branched chain alkyl group consisting of from 1 to 12 carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$. Unless slated otherwise specifically in the specification, an heteroalkyl group can be optionally substituted.

The term "amino" refers to a group of the formula —NR$_a$R$_a$, —NHR$_a$, or —NH$_2$, where each R$_a$ is, independently, an alkyl, alkenyl or alkynyl group as defined above containing one to twelve carbon atoms. Unless stated otherwise specifically in the specification, an alkylamino group can be optionally substituted.

"Alkylamino" refers to a group of the formula —NHR$_a$ or —NR$_a$R$_a$ where each R$_a$ is, independently, an alkyl, alkenyl or alkynyl group as defined above containing one to twelve carbon atoms. Unless stated otherwise specifically in the specification, an alkylamino group can be optionally substituted.

The term "cyano" refers to a group of the formula —CN group.

The term "imino" refers to a group of the formula =NH group.

The term "nitro" refers to a group of the formula —NO$_2$ group.

The term "oxo" refers to a group of the formula the =O group.

"Alkylcarbonyl" refers to the —C(=O)R$_a$ moiety, wherein R$_a$ is an alkyl, alkenyl or alkynyl group as defined above. A non-limiting example of an alkyl carbonyl is the methyl carbonyl ("acetal") moiety. Alkylcarbonyl groups can also be referred to as "C$_w$-C$_z$ acyl" where w and z depicts the range of the number of carbon in R$_a$, as defined above. For example, "C$_1$-C$_{10}$ acyl" refers to alkylcarbonyl group as defined above, where R$_a$ is C$_1$-C$_{10}$ alkyl, C$_1$-C$_{10}$ alkenyl, or C$_1$-C$_{10}$ alkynyl group as defined above. Unless stated otherwise specifically in the specification, an alkyl carbonyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

As used herein, the term "cycloalkyl" refers to a stable mono cyclic or polycyclic non-aromatic group, wherein each of the atoms forming the ring (i.e. skeletal atoms) is a carbon atom, which can include fused or bridged ring systems, having from three to twenty carbon atoms (e.g., having from three to ten carbon atoms) and which is attached to the rest of the molecule by a single bond. In one embodiment, the cycloalkyl group is saturated or partially unsaturated. In another embodiment, the cycloalkyl group is fused with an aromatic ring. Cycloalkyl groups include groups having from 3 to 20 carbon ring atoms. Illustrative examples of cycloalkyl groups include, but are not limited to, the following moieties:

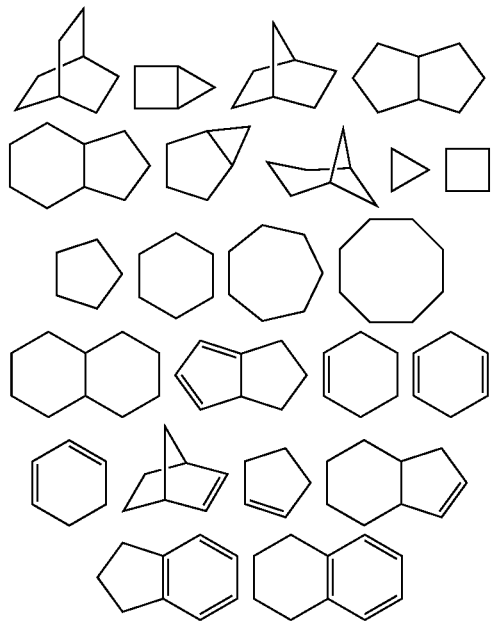

wherein any hydrogen atom in the above groups may be replaced by a bond to the molecule.

Monocyclic cycloalkyls include, but are not limited to, cyclopropyl, cyclobutyl, cyclopentyl, cyclohexyl, cycloheptyl, and cyclooctyl, Dicyclic or polycyclic cycloalkyls include, but are not limited to, tetrahydronaphthyl, indanyl, and tetrahydropentalenyl, adamantyl and norbornyl. The term cycloalkyl includes "unsaturated nonaromatic carbocyclyl," "carbocyclyl," "carbocylic ring," "carbocycle," or "nonaromatic unsaturated carbocyclyl" groups, both of which refer to a nonaromatic carbocycle as defined herein, which contains at least one carbon double bond or one carbon triple bond.

"Cycloalkenyl" refers to a stable non aromatic monocyclic or polycyclic hydrocarbon consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyls include, for example, cyclopentenyl, cyclohexenyl, cycloheptenyl, cycloctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non aromatic monocyclic or polycyclic hydrocarbon consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyls include, for example, cycloheptynyl, cyclooctynyl, and the like. Unless otherwise stated specifically in the specification, a cycloalkynyl group can be optionally substituted.

"Cycloalkylalkyl" refers to a radical of the formula —R$_b$-R$_d$ where R$_b$ is an alkylene, alkenylene, or alkynylene group as defined above and R$_d$ is a cycloalkyl, cycloalkenyl, cycloalkynyl radical as defined above. Unless stated otherwise specifically in the specification, a cycloalkylalkyl group can be optionally substituted.

The terms "heterocyclic ring", "heterocycle" and "heterocyclyl" are used interchangeably herein to refer to a 3- to 20-membered containing one to six heteroatoms each independently selected from the group consisting of O, S and N. In one embodiment, each heterocyclyl group has from 4- to 10-atoms in its ring system, and from one to three heteroatoms each independently selected from the group consisting of O, S and N. Unless stated otherwise specifically in the specification, the heterocyclyl can be a monocyclic, bicyclic, tricyclic or tetracyclic ring system, which can include fused or bridged ring systems. In one embodiment, the nitrogen, carbon, or sulfur heteroatoms may be optionally oxidized, and the nitrogen atom may be optionally quaternized. The heterocyclic system may be attached, unless otherwise stated, at any heteroatom or carbon atom that affords a stable structure. The heterocyclyl can be partially or fully saturated, A heterocycle may be polycyclic, wherein the polycyclic ring may be non-aromatic or contain both aromatic and non-aromatic rings. Unless stated otherwise specifically in the specification, a heterocyclyl group can be optionally substituted.

Examples of such heterocyclyls include, but are not limited to, aziridinyl, azetidinyl, beta lactamyl, dioxolanyl, oxazolidinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrrolinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, oxiranyl, thiiranyl, oxetanyl, thietanyl, sulfolanyl, 2,3-dihydrofuranyl, 2,5-dihydrofuranyl, thiophanyl, 1,2,3,6-tetrahydropyridinyl, 1,4-dihydropyridinyl, piperazinyl, thiomorpholinyl, pyranyl, 2,3-dihydropyranyl, tetrahydropyranyl, 1,4-dioxanyl, 1,3-dioxanyl, homopiperazinyl, homopiperidinyl, 1,3-dioxepanyl, 4,7-dihydro-1,3-dioxepinyl, and hexamethyleneoxidyl.

Other non-limiting examples of heterocyclyl groups are:

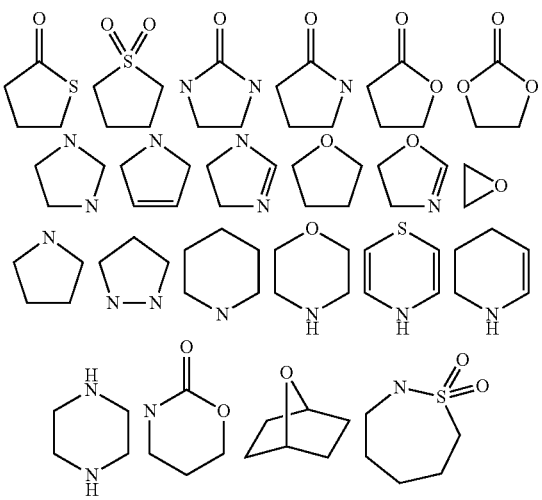

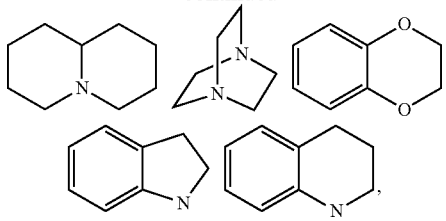

wherein any hydrogen atom in the above groups may be replaced by a bond to the molecule.

"Heterocycloalkyl" refers to a radical of the formula —R$_b$-R$_c$ where R$_b$ is an alkylene, alkenylene, or alkynylene group as defined above and R$_e$ is a heterocyclyl radical as defined above. Unless stated otherwise specifically in the specification, a heterocycloalkylalkyl group can be optionally substituted.

"Thioalkyl" refers to a formula —SR$_a$ where R$_a$ is an alkyl, alkenyl, or alkynyl as defined above containing one to twelve carbon atoms. Unless stated otherwise specifically in the specification, a thioalkyl group can be optionally substituted.

The term "thioxo" refers to a group of the formula the =S group.

As used herein, the term "aromatic" refers to a carbocyclyl or heterocyclyl with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a hydrocarbon ring system, comprising hydrogen, 6 to 18 carbon atoms and at least one aromatic ring. For purposes of this disclosure, the aryl can be a monocyclic, bicyclic, tricyclic or tetracyclic ring system, which can include fused or bridged ring systems. For example, aryls include, but are not limited to, a biphenyl, or may be fused, such as naphthalene. Examples of aryl groups include benzyl, indacenyl, pyrenyl, triphenyl, phenyl, anthracyl, and naphthyl. Unless stated otherwise specifically in the specification, the term "aryl" is meant to include aryl groups that are optionally substituted.

As used herein, the term "heteroaryl" or "heteroaromatic" refers to a 5 to 20 membered ring system comprising hydrogen atoms, one to fourteen carbon atoms, one to six heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems: and the nitrogen, carbon or sulfur atoms in the heteroaryl can be optionally oxidized; the nitrogen atom can be optionally quaternized. A polycyclic heteroaryl may include one or more rings that are partially saturated. Examples include the following moieties:

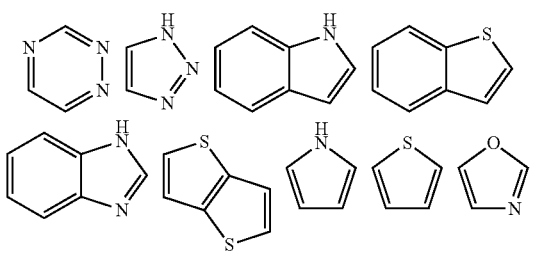

-continued

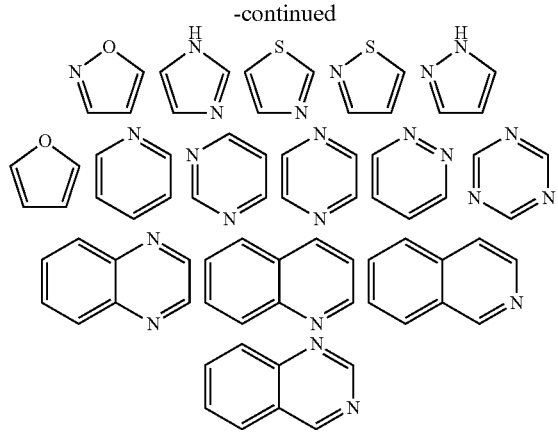

wherein any hydrogen atom in the above groups may be replaced by a bond to the molecule.

Examples of heteroaryl groups include, but are not limited to, pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, 1,3,4-oxadiazolyl, indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3~, 4-, 5-, 6~, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl. Unless stated otherwise specifically in the specification, a heteroaryl group can be optionally substituted.

"Aralkyl" or "arylalkyl" refers to a radical of the formula —$R_b$-$R_c$ where $R_b$ is an alkylene group as defined above and $R_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —$R_b$-$R_c$ where $R_b$ is an alkenylene o group as defined above and $R_c$ is one or more aryl radicals as defined above. Unless stated otherwise specifically in the specification, an aralkenyl group can be optionally substituted.

"Aralkynyl" or "arylalkynyl" refers to a radical of the formula —$R_b$-$R_c$ where $R_b$ is an alkynylene group as defined above and $R_c$ is one or more aryl radicals as defined above. Unless stated otherwise specifically in the specification, an aralkynyl group can be optionally-substituted.

"Heteroarylalkyl" refers to a radical of the formula —$R_b$-$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$-$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$-$R_f$ where $R_b$ is an alkynylene chain as defined above and $R_f$ is a heteroaryl radical as defined above. Unless stated otherwise specifically in the specification, a heteroaryl alkynyl group can be optionally substituted.

As used herein, the term "substituted" means any of the above groups (i.e., alkyl, alkylene, alkenyl, alkynyl, alkoxy, aryl, carbocyclyl, cycloalkyl, cycloalkenyl, cycloalkynyl, heterocyclyl, and/or heteroaryl) wherein at least hydrogen atom is replaced by a bond to a non-hydrogen atom or group of atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, aryl amines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. "Substituted" also means any of the above groups in which one or more hydrogen atoms are replaced by a higher-order bond (e.g., a double- or triple-bond) to a heteroatom such as oxygen in oxo, carbonyl, carboxyl, carboxylic acid and ester groups; and nitrogen in groups such as imines, oximes, hydrazones, and nitriles. For example, "substituted" includes any of the above groups in which one or more hydrogen atoms are replaced with, for example, —$NR_gR_h$, ~$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and –$SO_2NR_gR_h$. "Substituted" also means any of the above groups in which one or more hydrogen atoms are replaced with, for example, —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently selected from any of the above groups, including but not limited to: hydrogen, alkyl, alkenyl, alkynyl, alkoxy, akylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocycylalkyl, heteroaryl, N-heteroaryl and/or heteroarylalkyl. "Substituted" further means any of the above groups in which one or more hydrogen atoms are replaced by a bond to any of the above groups, including but not limited to amino, cyano, hydroxyl, imino, nitro, oxo, thioxo, halo, alkyl, alkenyl, alkynyl, alkoxy, akylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, IV-heteroaryl and/or heteroarylalkyl group.

In addition, each of the foregoing substituents can also be optionally substituted with one or more of the above substituents.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "binding" refers to a direct association between at least two molecules, due to, for example, covalent, electrostatic, hydrophobic, ionic and/or hydrogen-bond interactions.

"Contacting" refers to a process in which two or more molecules or two or more components of the same molecule or different molecules are brought into physical proximity such that they are able undergo an interaction. Molecules or components thereof may be contacted by combining two or more different components containing molecules, for example by mixing two or more solution components, preparing a solution comprising two or more molecules such as target, candidate or competitive binding reference molecules, and/or combining two or more flowing components. Alternatively, molecules or components thereof may be contacted combining a fluid component with molecules immobilized on or in a cell or on or in a substrate, such as a polymer bead, a membrane, a polymeric glass substrate or substrate surface derivatized to provide immobilization of target molecules, candidate molecules, competitive binding reference molecules or any combination of these, Molecules or components thereof may be contacted by selectively adjusting solution conditions such as, the composition of the solution, ion strength, pH or temperature. Molecules or components thereof may be contacted in a static vessel, such as a microwell of a microarray system, or a flow-through system, such as a micro fluidic or nano fluidic system. Molecules or components thereof may be contacted in or on a variety of ceils, media, liquids, solutions, colloids, suspensions, emulsions, gels, solids, membrane surfaces, glass surfaces, polymer surfaces, vesicle samples, bilayer samples, micelle samples and other types of cellular models or any combination of these. As used herein, the term "contacting" includes, but is not limited to, impregnating, compounding, mixing, integrating, coating, rubbing, painting, spraying, immersing, rolling, smearing and dipping.

A "disease" is a state of health of a subject wherein the subject cannot maintain homeostasis, and wherein if the disease is not ameliorated then the subject's health continues to deteriorate.

In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

The term "cancer," as used herein, refers to the abnormal growth or division of cells, Generally, the growth and/or life span of a cancer cell exceeds, and is not coordinated with, that of the normal cells and tissues around it. Cancers may be benign, pre-malignant or malignant, Cancer occurs in a variety of cells and tissues, including the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human or a non-human mammal. Non-human mammals include, for example, livestock and pets, such as ovine, bovine, porcine, canine, feline and murine mammals.

As used herein, the term "treatment" or "treating," is defined as one or more of relieving, alleviating, delaying, reducing, reversing, improving, or managing at least one symptom of a condition in a subject. The term "treating" may also mean one or more of arresting, delaying the onset (i.e., the period prior to clinical manifestation of the condition) or reducing the risk of developing or worsening a condition. In one embodiment, "treatment" or "treating," is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated, herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of medicine or pharmacology.

As used herein, "treating a disease or disorder" means reducing the frequency with which a sign or symptom of the disease or disorder is experienced by a subject.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

A disease or disorder is "alleviated" if the severity of a symptom of the disease or disorder, the frequency with which such a symptom is experienced by a subject, or both, is reduced.

A "therapeutic" treatment is a treatment administered, to a subject who exhibits signs or symptoms of pathology, for the purpose of diminishing or eliminating those signs or symptoms.

As used herein, the term "pharmaceutical composition" refers to a mixture of at least one compound useful within the disclosure with a pharmaceutically acceptable carrier. The pharmaceutical composition facilitates administration of the compound to a patient or subject, or use of the compound within the methods of the disclosure. Multiple techniques of administering a compound exist in the art including, but not limited to, intravenous, oral, aerosol, parenteral, ophthalmic, pulmonary and topical administration.

The phrase "effective amount", "pharmaceutically effective amount", or "therapeutically effective amount," as used herein, refers to an amount that is sufficient or effective to provide the desired biological and/or clinical result (e.g., prevent, treat, delay the onset of, prevent the onset of, prevent the progression of, inhibit, decrease, or reverse a disease or disorder). That result may be reduction and/or alleviation of the signs, symptoms, or causes of a disease, or any other desired alteration of a biological system. An appropriate therapeutic amount in any individual case may be determined by one of ordinary skill in the art using routine experimentation. An "effective amount" or "therapeutically effective amount" of a compound is that amount of a compound which is sufficient to provide a beneficial effect to the subject to which the compound is administered. An "effective amount" will vary depending on the active ingredient, the state, disorder, or condition to be treated and its severity, and the age, weight, physical condition and responsiveness of the mammal to be treated.

As used herein, an "inhibitory-effective amount" is an amount that results in a detectable (e.g., measurable) amount of inhibition of an activity. In some instance, the activity is its ability to bind with another component.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

As used herein, the term "PPI" or "protein-protein interaction" refers to refers to the binding of two or more proteins together. PPIs may be binary (two protein binding partners; a dimer) or tertiary (three or more protein binding partners, e.g., a trimer). Proteins within a PPI (i.e., binding partners) may be the same protein (such as a homodimer or homotrimer) or different proteins (such as a heterodimer or heterotrimer). Proteins within a tertiary interaction may be bound to one or more proteins within the PPI. In some embodiments, the PPI comprises a tyrosine kinase, such as the human tyrosine kinases listed in Tables 3 and 4. The PPI may comprise an interaction between the binding partners listed in Table 5 (human tyrosine kinase interactions The term "interact" or "interaction" refers to a measurable chemical or physical interaction between two components, such as a target molecule and a candidate molecule, that is capable of affecting the structure and/or composition of at least one of the components, such as a target molecule, a candidate molecule or both such that the biological activity of at least one of the components, such as the target molecule, the candidate molecule or both, is affected. Interactions capable of affecting the structure and/or composition of a component include, but are not limited to, reactions resulting in the formation of one or more covalent bonds, resulting in the breaking of one or more covalent bonds, electrostatic associations and repulsions, formation and/or disruption of hydrogen bonds, formation and/or disruption of electrostatic forces such as dipole-dipole Interactions, formation and/or disruption of van der Waals Interactions or processes comprising combinations of these.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" embraces addition salts of free acids or free bases. Suitable acid addition salts may be prepared from an inorganic acid or from an organic acid. Examples of inorganic acids include hydrochloric, hydrobromic, hydriodic, nitric, carbonic, sulfuric, phosphoric, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxy ethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the disclosure include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. Supplementary active compounds may also be incorporated into the compositions. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the term "organic solvent" refers to solvents including, but not limited to, alcohols (e.g., methanol and ethanol), ketones (e.g., acetone and methylethy Ike tone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the terms "amino acid", "amino acidic monomer", or "amino acid residue" refer to any of the twenty naturally occurring amino acids including synthetic amino acids with unnatural side chains and including both D and L optical isomers.

As used herein, the terms "natural amino acid", "naturally encoded amino acid", "naturally occurring amino acid", and "genetically encoded amino acid" refer to an amino acid that is one of the twenty common amino acids or pyrolysine or selenocysteine. The term "natural amino acid" includes, but is not limited to, proteinogenic amino acids.

As used herein, the term "non-naturally encoded amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," "nongenetically-encoded amino acid", and variously hyphenated and non-hyphenated versions thereof. The term "non-natural amino acid" includes, but is not limited to, amino acids which occur naturally by modification of a naturally encoded amino acid (including but not limited to, the common amino acids or pyrrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, nonproteinogenic amino acids and amino acids, which do not occur naturally and may be obtained synthetically (e.g., Q-proline-based amino acids) or may be obtained by modification of non-natural amino acids.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 0.5, 5.3, and 6. This applies regardless of the breadth of the range.

DESCRIPTION

The present invention relates, in part, to novel compounds comprising 4-imidazolidinone-fused cyclic peptides and compositions thereof. In various aspects, the compounds of the present invention comprise at least one natural amino acid, at least one unnatural amino acid, or any combination thereof. The present invention also relates, in part, to methods of generating said compounds comprising 4-imidazolidinone-fused cyclic peptides and compositions thereof. In one aspect, the present invention also relates, in part, to methods of using said compounds or compositions thereof. In one aspect, the present invention also relates, in part, to methods of inhibiting protein-protein interaction using said compounds or compositions thereof. In another aspect, the present invention relates, in part, to methods of treating or pre venting a various diseases or disorders using said compounds or compositions thereof.

Compounds

In various aspects, the present invention provides, in part, a compound comprising 4-imidazolidinone-fused cyclic peptides. In one embodiment, the compound comprises at least one amino acid. Thus, in various aspects, the compound of the present invention is a compound having the structure of

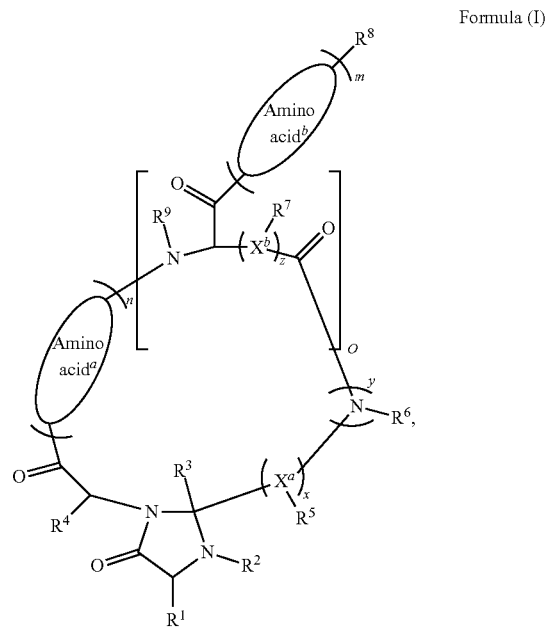

Formula (I)

or a derivative, prodrug, pharmaceutically acceptable salt, solvate, isomer, or tautomer thereof.

In various embodiments, each occurrence of amino acid is independently selected from any amino acid known to the skilled artisan. Such amino acid includes, but are not limited to a natural amino acid, unnatural amino acid, D-amino acid, L-amino acid, functionalized natural amino acid, functionalized unnatural amino acid, functionalized D-amino acid, functionalized L-amino acid, or any combination thereof.

In some embodiments, each occurrence of amino acid$^a$ and amino acid$^b$ is independently-selected from alanine, glycine, isoleucine, leucine, proline, valine, phenylalanine, tryptophan, tyrosine, aspartic acid, glutamic acid, arginine, histidine, lysine, serine, threonine, cysteine, methionine, asparagine, glutamine, hydroxyglycine, hydroxyproline, hypusine, ornithine, citrulline, cystine, cystathionine, lanthionine, djenkolic acid, diaminopimelic acid, norvaline, norleucine, leucine, isoleucine, alloisoleucine, t-leucine, aminoheptanoic acid, pipecolic acid, diaminopropionic acid, diamino butyric acid, ornithine, allothreonine, methionine, homocysteine, homoserine, homoalanine, homonorleucine, isovaline, sarcosine, methyl-homoserine, ethyl-homoserine, N-ethyl glycine, N-propyl glycine, N-isopropyl glycine, N-methyl alanine, N-ethyl alanine, isoserine, hydroxyaminobutyric acid, pyroglutamic acid, carboxyglutamic acid, dehydroalanine, pyrolysine, selenocysteine, selenomethionine, selenoethionine, aminomalonic acid, aminobutyric acid, aminoisobutyric acid, aminolevulinic acid, aminobezoic acid, thialysine, quisqualic acid, canavanine, azetidine-2-carboxylic acid, cepthalosporin C, penicillamine, microcystin, nodularin, taurine, sarcosine, or glycine betaine. For example, in some embodiments, each occurrence of amino acid$^a$ and amino acid$^b$ is independently selected from D-alanine, D-glycine, D-isoleucine, D-leucine, D-proline, D-valine, D-phenylalanine, D-tryptophan, D-tyrosine, D-aspartic acid, D-glutamic acid, D-arginine, D-histidine, D-lysine, D-serine, D-threonine, D-cysteine, D-methionine, D-asparagine, D-glutamine, L-alanine, L-glycine, L-isoleucine, L-leucine, L-proline, L-valine, L-phenylalanine, L-tryptophan, L-tyrosine, L-aspartic acid, L-glutamic acid, L-arginine, L-histidine, L-lysine, L-serine, L-threonine, L-cysteine, L-methionine, L-asparagine, or L-glutamine.

For example, in some embodiments, the (Amino Acid$^a$)$_n$ is selected from an amino acid sequence as set forth in SEQ ID NOs: 1-53, or any combination thereof. In some embodiments, the (Amino Acid$^a$)$_n$ is selected from an amino acid sequence as set forth in SEQ ID NOs: 1-12, or any combination thereof. In some embodiments, each occurrence of (Amino Acid$^b$)$_m$ is independently selected from alanine, glycine, isoleucine, leucine, proline, valine, phenylalanine, tryptophan, tyrosine, aspartic acid, glutamic acid, arginine, histidine, lysine, serine, threonine, cysteine, methionine, asparagine, glutamine, or any combination thereof. In some embodiments, each occurrence of (Amino Acid$^b$)$_m$ is tyrosine, histidine, serine, lysine, methionine, or phenylalanine.

In various embodiments, each occurrence of m is an integer from 1 to 1000. In some embodiments, each occurrence of m is an integer from 1 to 100. In some embodiments, each occurrence of m is an integer from 1 to 50. In some embodiments, each occurrence of m is an integer from 1 to 30. In some embodiments, each occurrence of m is an integer from 1 to 20. In some embodiments, each occurrence of m is an integer from 8 to 30. In some embodiments, each occurrence of m is an integer front 12 to 30. In some embodiments, each occurrence of m is an integer from 1 to 11. In some embodiments, each occurrence of m is an integer from 1 to 5, For example, in one embodiment, each occurrence of m is an integer of 1. In one embodiment, each occurrence of m is an integer of 2. In one embodiment, each occurrence of m is an integer of 3. In one embodiment, each occurrence of m is an integer of 4. In one embodiment, each occurrence of m is an integer of 5. In one embodiment, each occurrence of m is an integer of 6.

In one embodiment, each occurrence of m is an integer of 7. In one embodiment, each occurrence of m is an integer of 8. In one embodiment, each occurrence of m is an integer of 9. In one embodiment, each occurrence of m is an integer of 10. In one embodiment, each occurrence of m is an integer of 11. In one embodiment, each occurrence of m is an integer of 12. In one embodiment, each occurrence of m is an integer of 15. In one embodiment, each occurrence of m is an integer of 20. In one embodiment, each occurrence of m is an integer of 50.

In various embodiments, n is an integer from 1 to 1000. In some embodiments, n is an integer from 1 to 100. In some embodiments, n is an integer from 1 to 50. In some embodiments, n is an integer from 8 to 50. In some embodiments, n is an integer from 12 to 50. In some embodiments, n is an integer from 1 to 30. In some embodiments, n is an integer from 1 to 20. In some embodiments, n is an integer from 1 to 11. For example, in one embodiment, n is an integer of 1. In one embodiment, n is an integer of 2. In one embodiment, n is an integer of 3. In one embodiment, n is an integer of 4. In one embodiment, n is an integer of 5. In one embodiment, n is an integer of 6. In one embodiment, n is an integer of 7. In one embodiment, n is an Integer of 8. In one embodiment, n is an integer of 9. In one embodiment, n is an integer of 10. In one embodiment, n is an integer of 11. In one embodiment, n is an integer of 12. In one embodiment, n is an integer of 15. In one embodiment, n is an integer of 20. In one embodiment, n is an integer of 50.

In various embodiments, $R^1$ is selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, and, arylalkyl, heteroaryl, heteroarylalkyl, aryl alkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, $R^1$ is selected from hydrogen, deuterium, halogen, hydroxyl, amino,

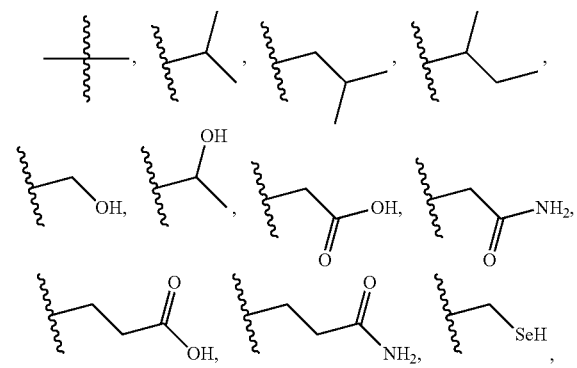

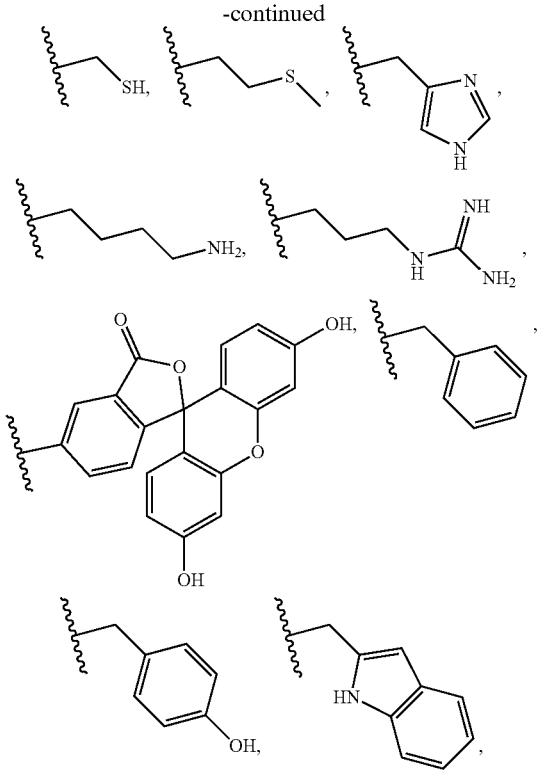

amino acid, or any combination thereof.

In various embodiments, R² is selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, R² is selected from hydrogen, deuterium, alkyl, carbonyl, or any combination thereof. In one embodiment, R² is hydrogen. In one embodiment, R² is deuterium. In one embodiment, R² is carbonyl.

In various embodiments, R³ is selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, R³ is selected from hydrogen, deuterium, alkyl, or any combination thereof. In one embodiment, R³ is hydrogen. In one embodiment, R³ is deuterium. In one embodiment, R³ is methyl.

In various embodiments, R⁴ is selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, R⁴ is selected from hydrogen, deuterium, halogen, hydroxyl, amino,

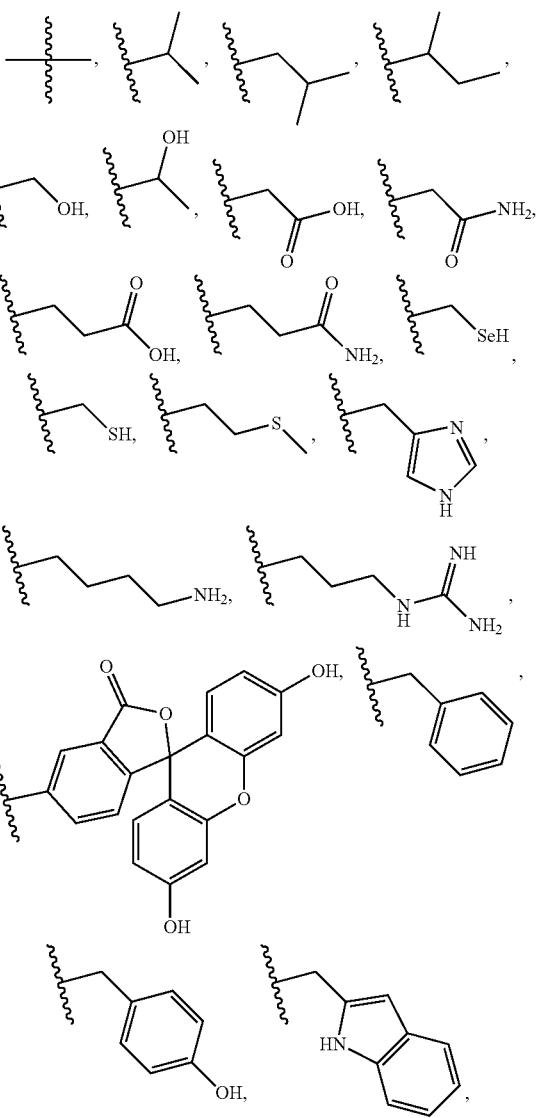

amino acid, or any combination thereof.

In various embodiments, each occurrence of $X^a$ is independently selected from C, —CR¹⁰, N, P, P=O, S=O, and any combination thereof. For example, in some embodiments, each occurrence of $X^a$ is independently selected from C or —CR¹⁰. In one embodiment, each occurrence of $X^a$ is —CR¹⁰.

In various embodiments, each occurrence of R⁵ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroaryl alkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, each occurrence of $R^5$ is independently selected from hydrogen, deuterium, alkyl, or any combination thereof. In one embodiment, each occurrence of $R^5$ is hydrogen.

In various embodiments, x is an integer from 0 to 50. In some embodiments, x is independently an integer from 11 to 50. In some embodiments, x is independently an integer from 0 to 40. In some embodiments, x is independently an integer from 0 to 30. In some embodiments, x is independently an integer from 0 to 20. In some embodiments, x is independently an integer from 0 to 10. In some embodiments, x is independently an integer from 1 to 10. In some embodiments, x is independently an Integer from 0 to 5. In some embodiments, x is independently an integer from 0 to 2. For example, in one embodiment, x is an integer of 0. In one embodiment, x is an integer of 1. In one embodiment, x is an integer of 2. In one embodiment, x is an integer of 3. In one embodiment, x is an integer of 4. In one embodiment, x is an integer of 5. In one embodiment, x is an integer of 6. In one embodiment, x is an integer of 7. In one embodiment, x is an integer of 8. In one embodiment, x is an integer of 9. In one embodiment, x is an integer of 10. In one embodiment, x is an integer of 11. In one embodiment, x is an integer of 15. In one embodiment, x is an integer of 20. In one embodiment, x is an integer of 50.

In various embodiments, each occurrence of $R^6$ is selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or arty combination thereof. For example, in some embodiments, each occurrence of $R^6$ is selected from hydrogen, deuterium, alkyl, or any combination thereof. In one embodiment, $R^6$ is hydrogen.

In various embodiments, y is an integer from 0 to 50. In some embodiments, y is independently an integer from 11 to 50. In some embodiments, y is independently an integer from 0 to 40. In some embodiments, y is independently an integer from 0 to 30. In some embodiments, y is independently an integer from 0 to 20. In some embodiments, y is an integer from 0 to 10. In some embodiments, y is independently an integer from 1 to 10. In some embodiments, y is independently an integer from 0 to 5. In some embodiments, y is independently an integer from 0 to 2, For example, in one embodiment, y is an integer of 0. In one embodiment, y is an integer of 1. In one embodiment, y is an integer of 2. In one embodiment, y is an integer of 3. In one embodiment, y is an integer of 4. In one embodiment, y is an integer of 5. In one embodiment, y is an integer of 6. In one embodiment, y is an integer of 7. In one embodiment, y is an integer of 8. In one embodiment, v is an integer of 9. In one embodiment, y is an integer of 10. In one embodiment, y is an integer of 11. In one embodiment, y is an integer of 15. In one embodiment, y is an integer of 20. In one embodiment, y is an integer of 50.

In various embodiments, each occurrence of $X^b$ is independently selected from C, —$CR^{10}$, N, P, P=O, S=O, and any combination thereof. For example, in some embodiments, each occurrence of $X^b$ is independently selected from C or —$CR^{10}$. In one embodiment, each occurrence of $X^b$ is —$CR^{10}$.

In various embodiments, each occurrence of $R^7$ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, each occurrence of $R^7$ is independently selected from hydrogen, deuterium, alkyl, or any combination thereof. In one embodiment, each occurrence of $R^7$ is hydrogen.

In various embodiments, each occurrence of z is an integer from 0 to 50. In some embodiments, each occurrence of z is independently an integer from 11 to 50. In some embodiments, each occurrence of z is independently an integer from 0 to 40. In some embodiments, each occurrence of z is independently an integer from 0 to 30. In some embodiments, each occurrence of z is independently an integer from 0 to 20. In some embodiments, each occurrence of z is an integer from 0 to 10. In some embodiments, each occurrence of z is independently an integer from 1 to 10. In some embodiments, each occurrence of z is independently an integer from 0 to 5. In some embodiments, each occurrence of z is independently an integer from 0 to 2. For example, in one embodiment, each occurrence of z is an integer of 0. In one embodiment, each occurrence of z is an integer of 1. In one embodiment, each occurrence of z is an integer of 2. In one embodiment, each occurrence of z is an integer of 3. In one embodiment, each occurrence of z is an integer of 4. In one embodiment, each occurrence of z is an integer of 5. In one embodiment, each occurrence of z is an integer of 6. In one embodiment, each occurrence of z is an integer of 7. In one embodiment, each occurrence of z is an integer of 8. In one embodiment, each occurrence of z is an integer of 9. In one embodiment, each occurrence of z is an integer of 10. In one embodiment, each occurrence of z is an integer of 11. In one embodiment, each occurrence of z is an integer of 15. In one embodiment, each occurrence of z is an integer of 20. In one embodiment, each occurrence of z is an integer of 50.

In various embodiments, each occurrence of $R^8$ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in one embodiments, each occurrence of $R^8$ is independently selected from hydroxyl, amino, alkyl, or any combination thereof. In one embodiment, each occurrence of $R^8$ is amino.

In various embodiments, each occurrence of $R^9$ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, and, arylalkyl, heteroaryl, heteroarylalkyl, arylalkenyl, heteroarylalkenyl, arylalkynyl, heteroarylalkynyl, acyl, ester, urea, thiourea, thiol, thin alkyl, thioxo, sulfanyl, sulfinyl, sulfonyl, phosphino, oxo, nitrile, isonitrile, cyano, carbamate, guanidine, guanidine alkyl, amino acid, or any combination thereof. For example, in some embodiments, each occurrence of $R^9$ is independently selected from hydrogen, deuterium, alkyl, or any combination thereof. In one embodiment, each occurrence of $R^9$ is hydrogen.

In various embodiments, o is an integer from 0 to 50. In some embodiments, o Is independently an integer from 11 to 50. In some embodiments, o is independently an integer from 0 to 40. In some embodiments, o is independently an integer from 0 to 30. In some embodiments, o is independently an integer from 0 to 20. In some embodiments, o is an integer from 0 to 10. In some embodiments, o is independently an integer from 1 to 10. In some embodiments, o is independently an integer from 0 to 5. In some embodiments, a is independently an integer from 0 to 2. For example, in one embodiment, o is an integer of 0. In one embodiment, o is an integer of 1. In one embodiment, a is an integer of 2. In one embodiment, o is an integer of 3. In one embodiment, o is an integer of 4. In one embodiment, o is an integer of 5. In one embodiment, o is an integer of 6. In one embodiment, o is an integer of 7. In one embodiment, o is an integer of 8. In one embodiment, o is an integer of 9. In one embodiment, o is an integer of 10. In one embodiment, o is an integer of 11. In one embodiment, o is an integer of 15. In one embodiment, o is an integer of 20. In one embodiment, o is an integer of 50.

In some embodiments, each occurrence of each occurrence of $R^{10}$ is independently hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, aryl alkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, or any combination thereof. For example, in one embodiment, each occurrence of $R^{10}$ is hydrogen.

In various embodiments, alkyl is $C_{1-20}$ alkyl, in one embodiment, alkyl is $C_1$ alkyl, in one embodiment, alkyl is $C_2$ alkyl. In one embodiment, alkyl is $C_3$ alkyl. In one embodiment, alkyl is $C_4$ alkyl. In one embodiment, alkyl is $C_8$ alkyl. In one embodiment, alkyl is $C_6$ alkyl. In one embodiment, alkyl is $C_7$ alkyl. In one embodiment, alkyl is $C_8$ alkyl. In one embodiment, alkyl is $C_9$ alkyl. In one embodiment, alkyl is $C_{10}$ alkyl. In one embodiment, alkyl is $C_{11}$ alkyl. In one embodiment, alkyl is $C_{12}$ alkyl. In one embodiment, alkyl is $C_{13}$ alkyl. In one embodiment, alkyl is $C_{14}$ alkyl. In one embodiment, alkyl is $C_{15}$ alkyl. In one embodiment, alkyl is $C_{16}$ alkyl. In one embodiment, alkyl is $C_{17}$ alkyl. In one embodiment, alkyl is $C_{18}$ alkyl. In one embodiment, alkyl is $C_{119}$ alkyl. In one embodiment, alkyl is $C_{20}$ alkyl.

In one embodiment, alkyl is methyl. In one embodiment, alkyl is ethyl. In one embodiment, alkyl is propyl. In one embodiment, alkyl is butyl. In one embodiment, alkyl is pentyl. In one embodiment, alkyl is hexyl. In one embodiment, alkyl is isopropyl. In one embodiment, alkyl is isobutyl. In one embodiment, alkyl is isopentyl. In one embodiment, alkyl is isohexyl. In one embodiment, alkyl is secbutyl. In one embodiment, alkyl is secpentyl. In one embodiment, alkyl is sechexyl. In one embodiment, alkyl is tertbutyl.

In some embodiments, alkenyl is $C_{2-20}$ alkenyl. In one embodiment, alkenyl is $C_2$ alkenyl. In one embodiment, alkenyl is $C_3$ alkenyl. In one embodiment, alkenyl is $C_4$ alkenyl, in one embodiment, alkenyl is $C_5$ alkenyl. In one embodiment, alkenyl is $C_6$ alkenyl. In one embodiment, alkenyl is $C_7$ alkenyl. In one embodiment, alkenyl is $C_8$ alkenyl. In one embodiment, alkenyl is $C_9$ alkenyl. In one embodiment, alkenyl is $C_{10}$ alkenyl. In one embodiment, alkenyl is $C_{11}$ alkenyl. In one embodiment, alkenyl is $C_{12}$ alkenyl. In one embodiment, alkenyl is $C_{13}$ alkenyl. In one embodiment, alkenyl is $C_{14}$ alkenyl. In one embodiment, alkenyl is $C_{15}$ alkenyl. In one embodiment, alkenyl is $C_{16}$ alkenyl. In one embodiment, alkenyl is $C_{17}$ alkenyl. In one embodiment, alkenyl is $C_{18}$ alkenyl. In one embodiment, alkenyl is $C_{19}$ alkenyl. In one embodiment, alkenyl is $C_{20}$ alkenyl.

In some embodiments, alkynyl is $C_{2-20}$ alkynyl. In one embodiment, alkynyl is $C_2$ alkynyl. In one embodiment, alkynyl is $C_3$ alkynyl. In one embodiment, alkynyl is $C_4$ alkynyl. In one embodiment, alkynyl is $C_5$ alkynyl. In one embodiment, alkynyl is $C_6$ alkynyl. In one embodiment, alkynyl is $C_7$ alkynyl. In one embodiment, alkynyl is $C_8$ alkynyl. In one embodiment, alkynyl is $C_9$ alkynyl. In one embodiment, alkynyl is $C_{10}$ alkynyl. In one embodiment, alkynyl is $C_{11}$ alkynyl. In one embodiment, alkynyl is $C_{12}$ alkynyl. In one embodiment, alkynyl is $C_{13}$ alkynyl. In one embodiment, alkynyl is $C_{14}$ alkynyl. In one embodiment, alkynyl is $C_{15}$ alkynyl. In one embodiment, alkynyl is $C_{16}$ alkynyl. In one embodiment, alkynyl is $C_{17}$ alkynyl. In one embodiment, alkynyl is $C_{18}$ alkynyl. In one embodiment, alkynyl is $C_{19}$ alkynyl. In one embodiment, alkynyl is $C_{20}$ alkynyl.

In some embodiments, the cycloalkyl is a $C_{3-10}$ cycloalkyl. In some embodiments, the cycloalkenyl is a $C_{3-10}$ cycloalkenyl. In some embodiments, the cycloalkynyl is a $C_{3-10}$ cycloalkynyl. In some embodiments, the heterocyclyl is a 3-10 membered heterocyclyl having 1, 2, or 3 heteroatoms selected from the group consisting of nitrogen, oxygen, sulfur, and any combination thereof.

In one embodiment, and is $C_{6-14}$ aryl. For example, in some embodiments, the arylalkyl is a $C_{1-6}$ alkyl-$C_{6-14}$ aryl.

In one embodiment, heteroaryl is a 5- to 24-membered heteroaryl ring having 1, 2, 3, 4, or 5 heteroatoms selected from the group consisting of nitrogen, oxygen, sulfur, and any combination thereof.

In some embodiments, the arylalkenyl is a $C_{2-6}$ alkenylene-$C_{6-14}$ aryl. In some embodiments, the arylalkynyl is a $C_{2-6}$ alkynylene-$C_{6-14}$ aryl. In some embodiments, the heteroaryl alkyl is a $C_{1-6}$ alkyl-5 to 14 membered heteroaryl ring having 1, 2, 3, 4, or 5 heteroatoms selected from the group consisting of nitrogen, oxygen, sulfur, and any combination thereof. In some embodiments, the heteroaryl alkenyl is a $C_{2-6}$ alkenyl-5 to 14 membered heteroaryl ring having 1, 2, 3, 4, or 5 heteroatoms selected from the group consisting of nitrogen, oxygen, sulfur, and arty combination thereof. In some embodiments, the heteroarylalkynyl is a $C_{2-6}$ alkynyl-5 to 14 membered heteroaryl ring having 1, 2, 3, 4, or 5 heteroatoms selected from the group consisting of nitrogen, oxygen, sulfur, and any combination thereof.

In one embodiment, alkoxy is —$OR^{11}$.

In one embodiment, amino is —$N(R^{11})(R^{11})$.

In various embodiments, each occurrence of $R^{11}$ is independently selected from hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, oxo, nitrile, isonitrile, cyano, carbamate, guanidine, guanidine alkyl, amino acid, or any combination thereof.

In one embodiment, each occurrence of each occurrence of $R^1$, $R^2$, $R^3$, $R^4$, $R^5$, $R^6$, $R^7$, $R^8$, $R^9$, $R^{10}$, and $R^{11}$ is optionally substituted.

It is understood that, for a compound of Formula (I), $R^1$, $R^2$, $R^3$, $R^4$, $R^5$, $R^6$, $R^7$, $R^8$, $R^9$, $R^{10}$, and $R^{11}$ can each be, where applicable, selected from the groups described herein, and any group described herein for any of $R^1$, $R^2$, $R^3$, $R^4$, $R^5$, $R^6$, $R^7$, $R^8$, $R^9$, $R^{10}$, and $R^{11}$ can be combined, where applicable, with any group described herein for one or more of the remainder of $R^1$, $R^2$, $R^3$, $R^4$, $R^5$, $R^6$, $R^7$, $R^8$, $R^9$, $R^{10}$, and $R^{11}$.

For example, in some embodiments, each occurrence of $R^1$, $R^2$, $R^3$, $R^4$, $R^5$, $R^6$, $R^7$, $R^8$, $R^9$, $R^{10}$, and $R^{11}$ is independently selected from

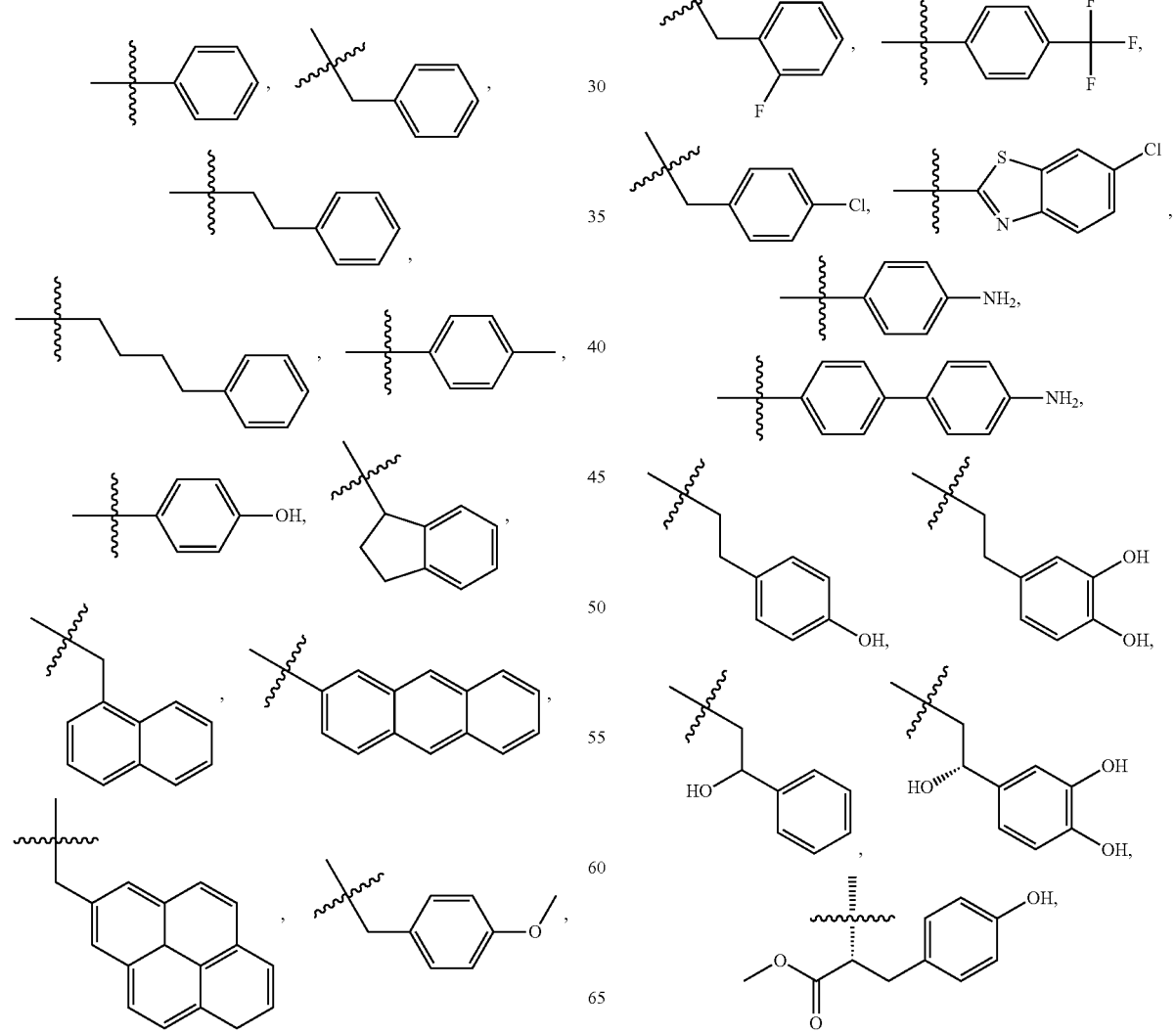

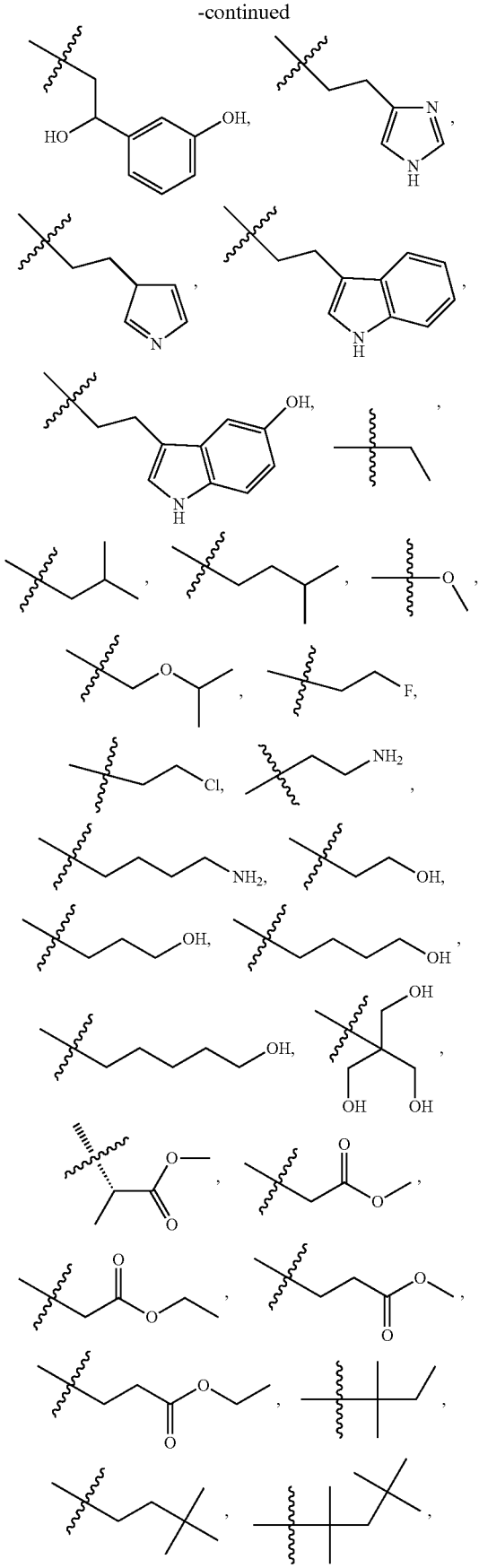
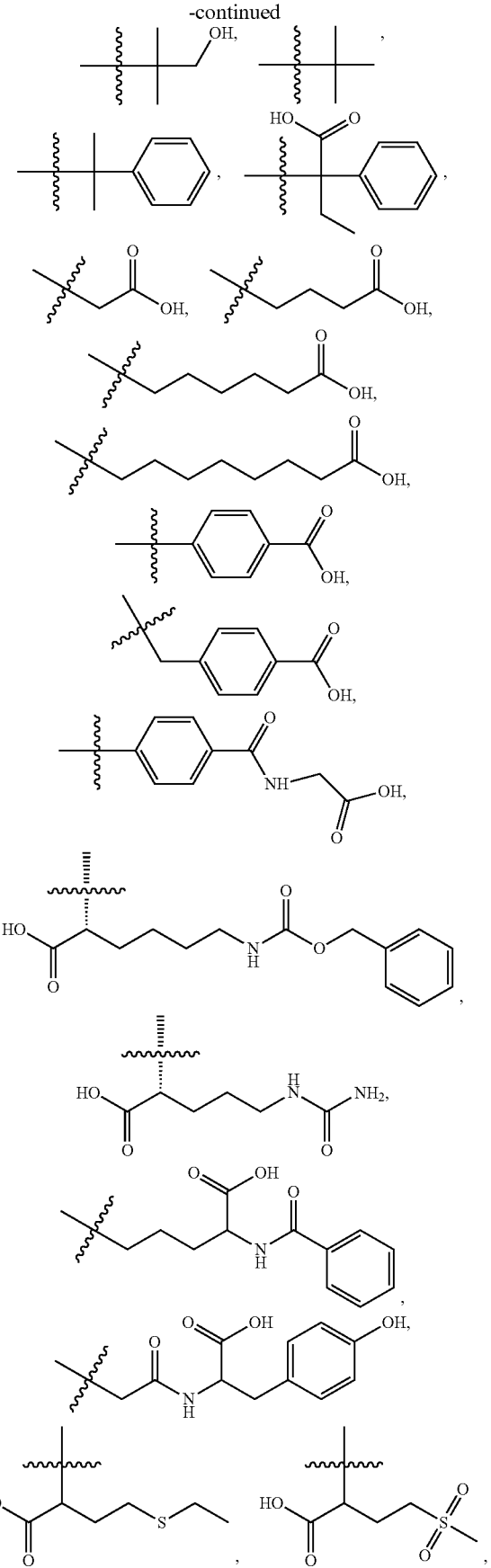

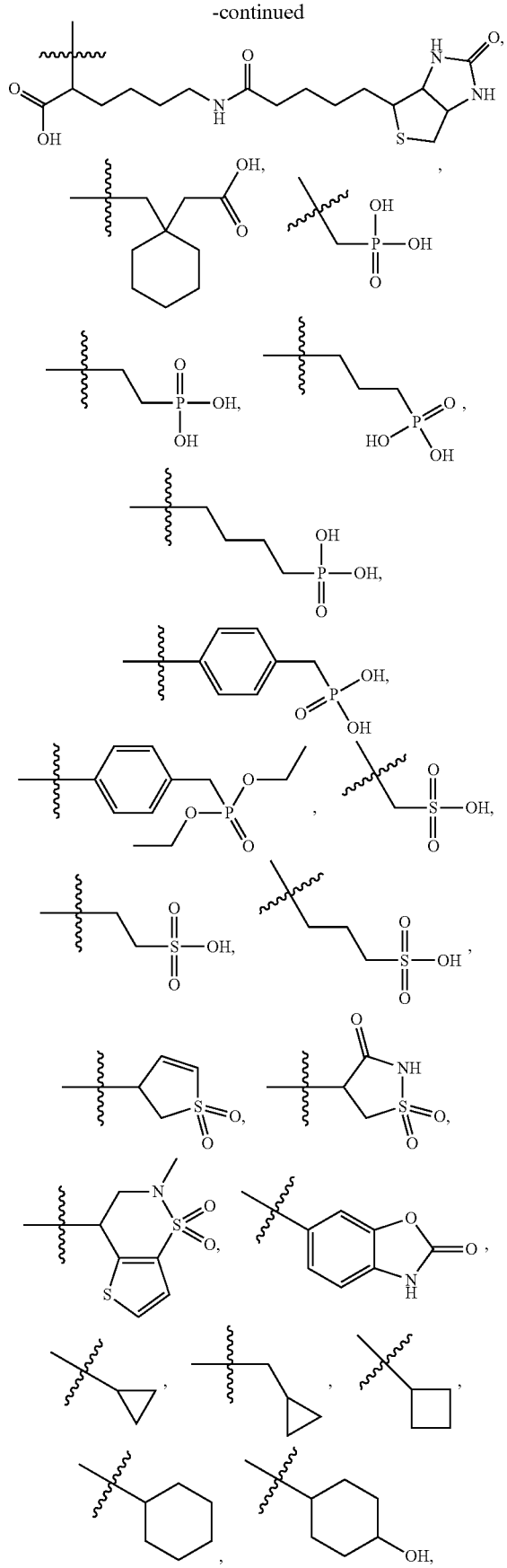
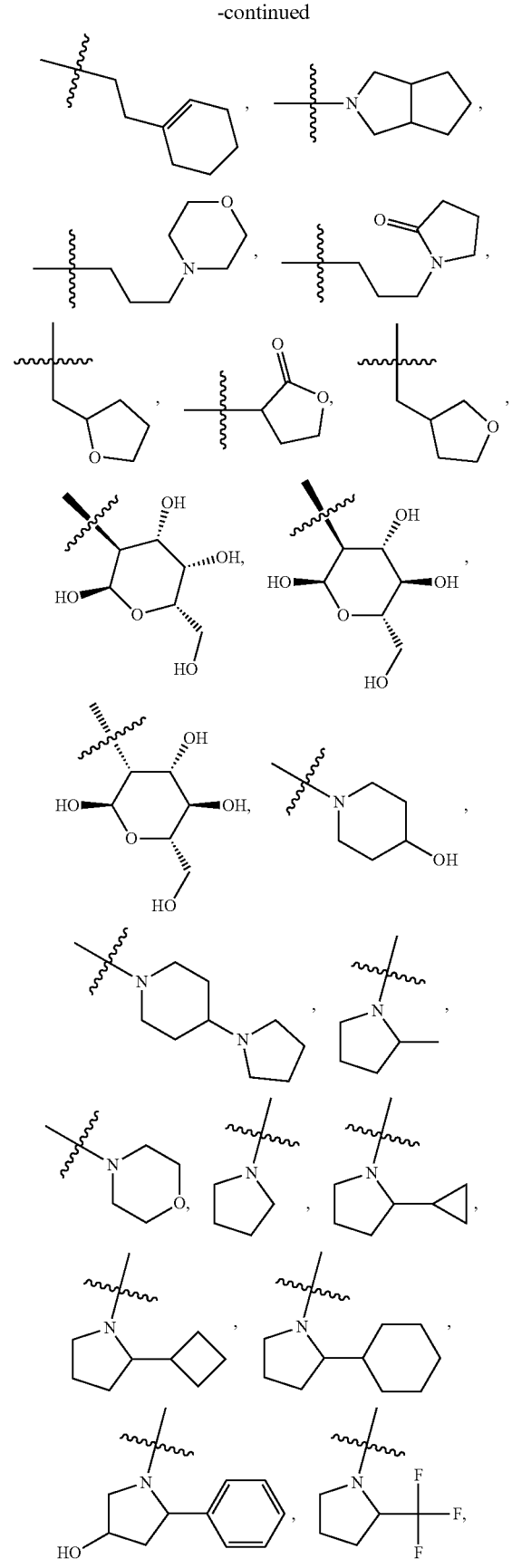

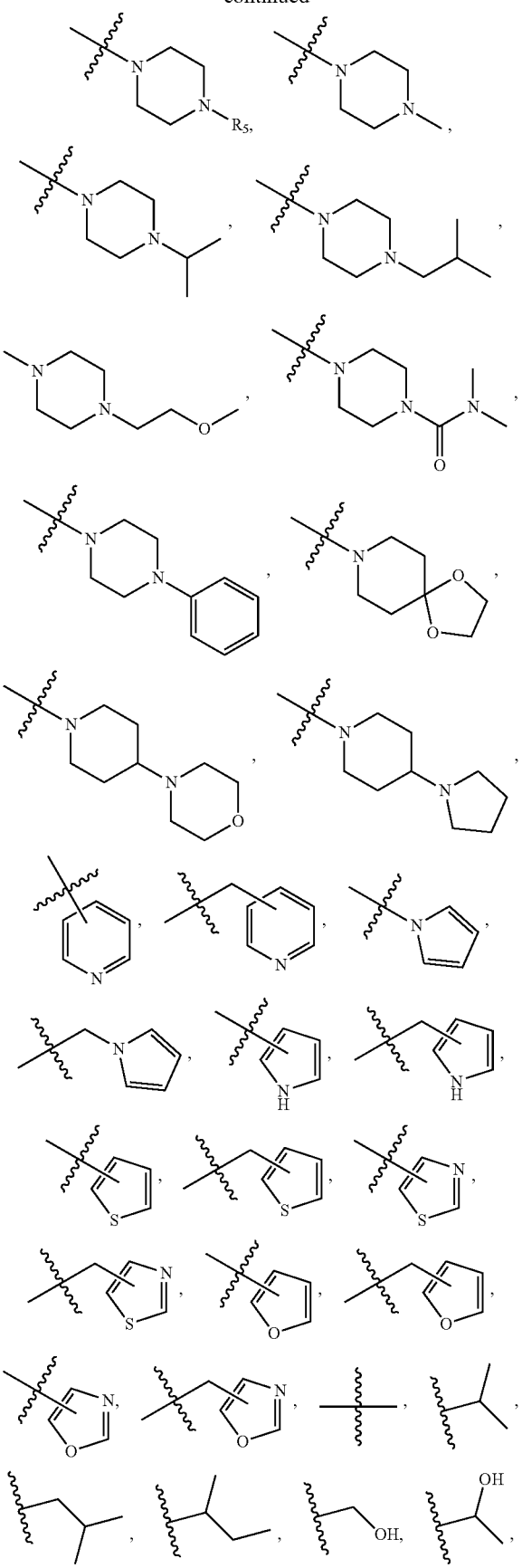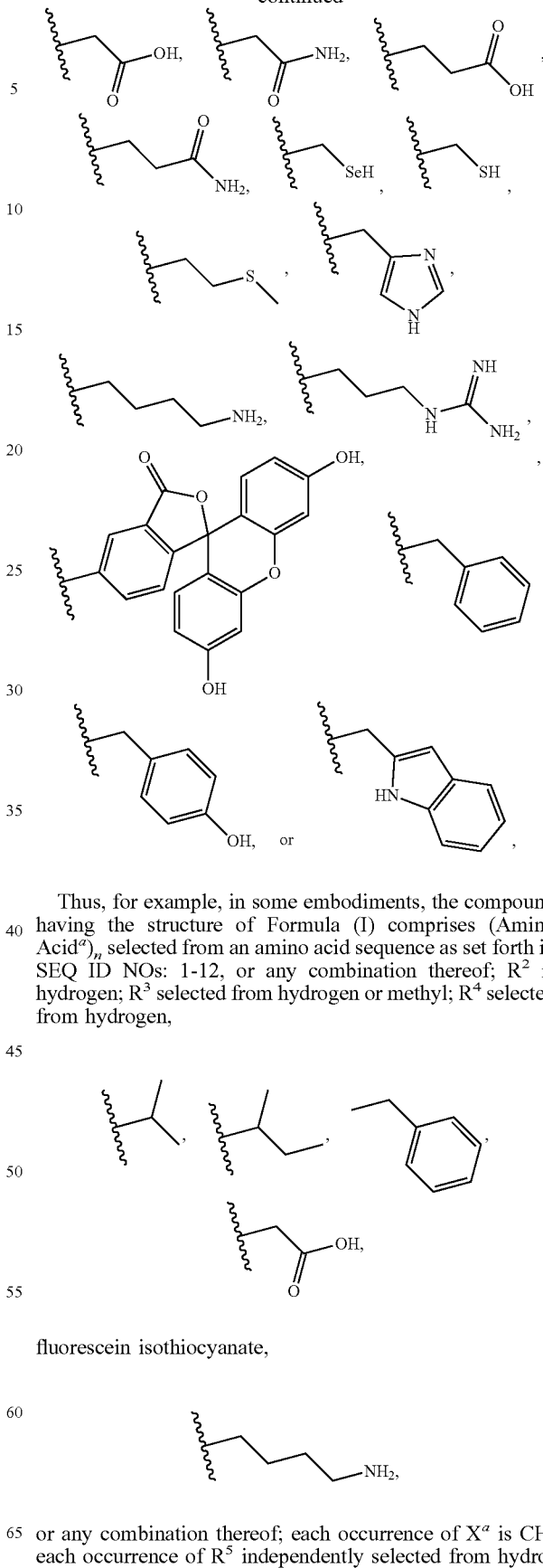

Thus, for example, in some embodiments, the compound having the structure of Formula (I) comprises (Amino Acid$^a$)$_n$ selected from an amino acid sequence as set forth in SEQ ID NOs: 1-12, or any combination thereof; $R^2$ is hydrogen; $R^3$ selected from hydrogen or methyl; $R^4$ selected from hydrogen, fluorescein isothiocyanate, or any combination thereof; each occurrence of $X^a$ is CH; each occurrence of $R^5$ independently selected from hydrogen or methyl; x selected from 1 or 2; $R^6$ is hydrogen; y is selected from 0 or 1; each occurrence of $X^b$ independently selected from CH or N; each occurrence of $R^7$ is hydrogen; each occurrence of z independently selected from 2 or 5; each occurrence $(Amino\ Acid^b)_m$ independently selected from tyrosine, histidine, serine, lysine, methionine, or phenylalanine; $R^1$ selected from

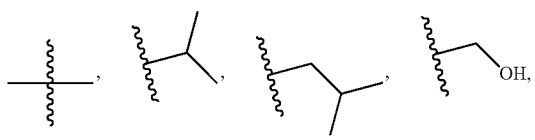

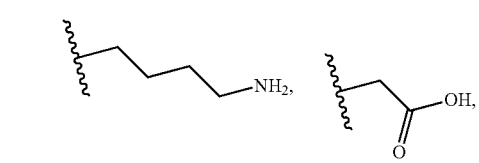

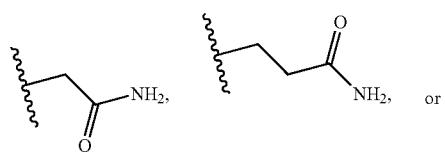

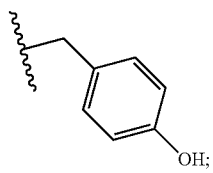

$R^8$ is amino; $R^9$ is hydrogen; and o selected from 0 or 1.

In various embodiments, $R_1$ and $R_2$ are optionally fused or joined to form a ring. In some embodiments, $R_1$ and $R_2$ are fused or joined to form a 5- to 24-membered cycloalkyl ring. In some embodiments, $R_1$ and $R_2$ are fused or joined to form a 5- to 24-membered heterocycloalkyl ring having 1, 2, 3, 4, or 5 heteroatoms selected from the group consisting of nitrogen, oxygen, sulfur, and any combination thereof. For example, in some embodiments, $R_1$ and $R_2$ are fused or joined to form a 5-membered cycloalkyl ring or 5-membered heterocycloalkyl ring having 1, 2, 3, 4, or 5 heteroatoms selected from the group consisting of nitrogen, oxygen, sulfur, and any combination thereof.

Thus, for example, in some embodiments, the compound having the structure of Formula (I) is a compound having the structure of

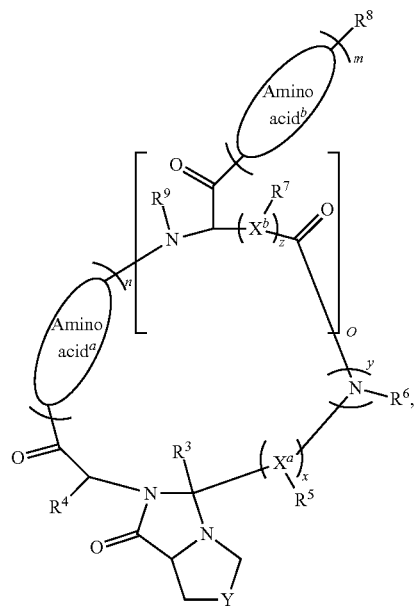

Formula (II)

or a derivative, prodrug, pharmaceutically acceptable salt, solvate, isomer, or tautomer thereof.

In some embodiments, Y is O, S, S(=O)$_2$, NH, C=O, or CH$_2$.

In various embodiments, o is an integer 0, Thus, for example, in some embodiments, the compound having the structure of Formula (I) is a compound having the structure of

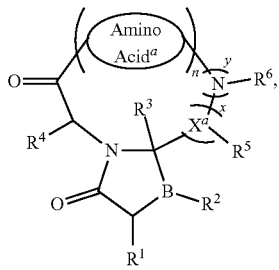

Formula (III)

or a derivative, prodrug, pharmaceutically acceptable salt, solvate, isomer, or tautomer thereof.

In some embodiments, the compound having the structure of Formula (III) is a compound having the structure of

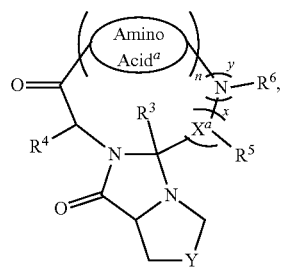

Formula (IV)

or a derivative, prodrug, pharmaceutically acceptable salt, solvate, isomer, or tautomer thereof.

In various embodiments, the compounds of the present invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or any combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase.

Thus, in some embodiments, the compound having the structure of Formula (I) is a compound having the structure of

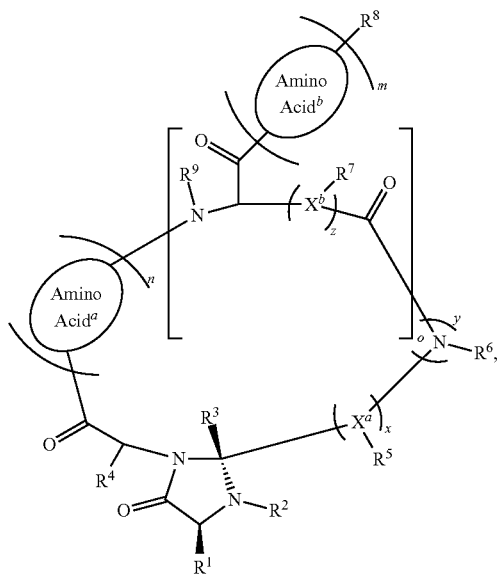

Formula (Ia)

or a derivative, prodrug, pharmaceutically acceptable salt, solvate, isomer, or tautomer thereof, or

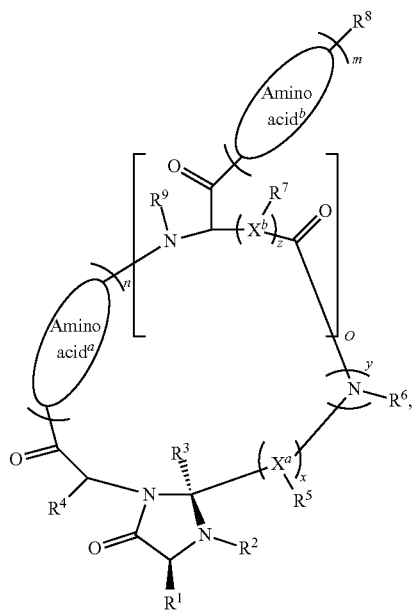

Formula (Ib)

or a derivative, prodrug, pharmaceutically acceptable salt, solvate, isomer, or tautomer thereof.

In some embodiments, the compound having the structure of Formula (II) is a compound having the structure of

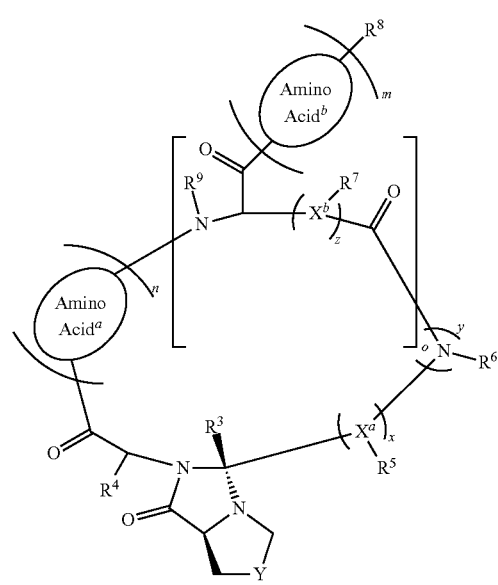

Formula (IIa)

or a derivative, prodrug, pharmaceutically acceptable salt, solvate, isomer, or tautomer thereof, or Formula (IIb)

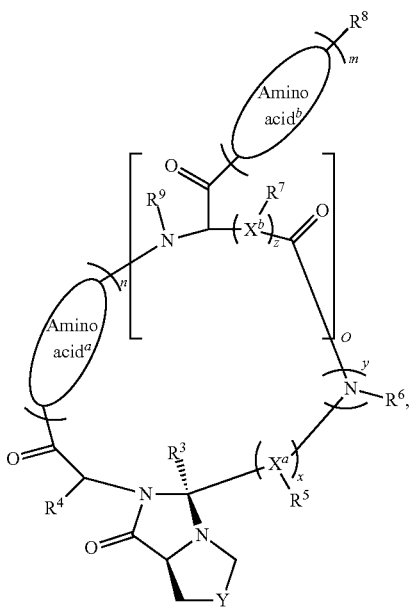

or a derivative, prodrug, pharmaceutically acceptable salt, solvate, isomer, or tautomer thereof.

In some embodiments, the compound having the structure of Formula (III) is a compound having the structure of Formula (IIIa)

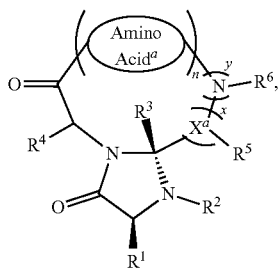

or a derivative, prodrug, pharmaceutically acceptable salt, solvate, isomer, or tautomer thereof, or Formula (IIIb)

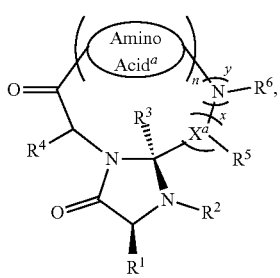

or a derivative, prodrug, pharmaceutically acceptable salt, solvate, isomer, or tautomer thereof.

In some embodiments, the compound having the structure of Formula (IV) is a compound having the structure of Formula (IVa)

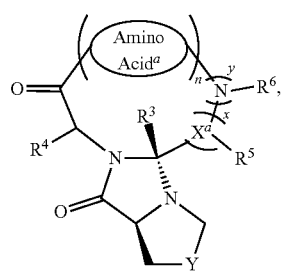

or a derivative, prodrug, pharmaceutically acceptable salt, solvate, isomer, or tautomer thereof, or Formula (IVb)

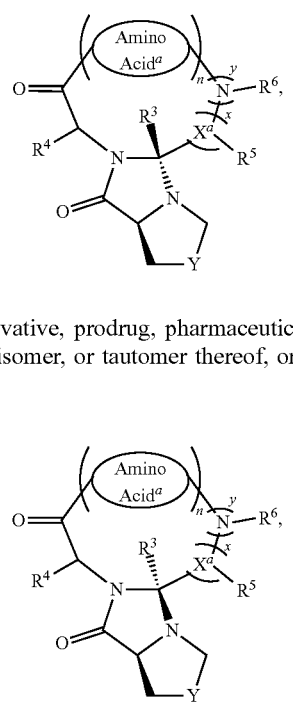

or a derivative, prodrug, pharmaceutically acceptable salt, solvate, isomer, or tautomer thereof.

In one embodiment, the compounds of the disclosure may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels. For example, in some embodiments, the compounds of Formula (I) are labelled by functionalizing $R^4$ with fluorescein isothiocyanate.

In various embodiments, the compound of the present invention modulates at least one protein-protein interaction. In some embodiments, the compound of the present invention reduces or inhibits at least one protein-protein interaction. For example, in one embodiment, the compound having the structure of Formula (I) inhibits at least one protein-protein interaction.

In some embodiments, the compound results in reduced protein-protein interaction that is reduced or decreased by at least about 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 9001%, by at least 1000%, by at least 1500%, by at least 2000%, by at least 2500%, by at least 3000%, by at least 4000%, or by at least 5000%, when compared with a comparator.

In some embodiments, the compound results in reduced protein-protein interaction that is at least about 0.01 fold less than the comparator (e.g., control), e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 0.500 fold, about 550 fold, about 600 fold, about 650 fold, about 700 fold, about 750 fold, about 800 fold, about 850 fold, about 900 fold, about 950 fold, about 1000 fold or more, including all values and ranges in-between.

In various embodiments, the compound of the present invention has an anticonvulsant activity. In various embodiments, the compound of the present invention is an anticonvulsant compound. In various embodiments, the compound of the present invention modulates the severity or frequency of at least one convulsion (e.g., epileptic fit). In some embodiments, the compound of the present invention prevents or reduces the severity or frequency of at least one convulsion (e.g., epileptic fit). For example, in one embodiment, the compound having the structure of Formula (I) prevents at least one convulsion (e.g., epileptic fit). In one embodiment, the compound having the structure of Formula (I) reduces the severity or frequency of at least one convulsion (e.g., epileptic fit).

In some embodiments, the compound results in reduced severity or frequency of at least one convulsion (e.g., epileptic fit) that are reduced or decreased by at least about 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 4001%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator.

In some embodiments, the compound results in reduced severity of at least one convulsion (e.g., epileptic fit) that are at least about 0.01 fold less than the comparator (e.g., control), e.g., about 0.01 fold, about 0.05 fold, about 0.10 fold, about 0.25 fold, about 0.50 fold, about 0.75 fold, about 1.0 fold, about 1.25 fold, 1.5 fold, about 2 fold, about 2.5 fold, about 3 fold, about 3.5 fold, about 4 fold, about 4.5 fold, about 5 fold, about 5.5 fold, about 6 fold, about 6.5 fold, about 7 fold, about 7.5 fold, about 8 fold, about 8.5 fold, about 9 fold, about 9.5 fold, about 10 fold, about 11 fold, about 12 fold, about 13 fold, about 14 fold, about 15 fold, about 16 fold, about 17 fold, about 18 fold, about 19 fold, about 20 fold, about 25 fold, about 30 fold, about 35 fold, about 40 fold, about 45 fold, about 50 fold, about 55 fold, about 60 fold, about 65 fold, about 70 fold, about 75 fold, about 80 fold, about 85 fold, about 90 fold, about 95 fold, about 100 fold, about 150 fold, about 200 fold, about 250 fold, about 300 fold, about 350 fold, about 400 fold, about 450 fold, about 500 fold, about 550 fold, about 600 fold, about 650 fold, about 700 fold, about 750 fold, about 800 fold, about 850 fold, about 900 fold, about 950 fold, about 1000 fold or more, including all values and ranges in-between.

In various aspects, the present invention also relates, in part, to compositions comprising at least one compound of the present invention. In one embodiment, the invention provides a therapeutic composition comprising at least one compound having the structure of Formula (I), In one embodiment, a mixture of one or more isomer is utilized as the therapeutic compound described herein.

Methods of Preparation and Screening of 4-Imidazolidinone-Fused Cyclic Peptides

In some aspects, the present invention also provides methods of preparing, screening, and/or identifying compounds of the present invention. In one aspect, the present invention provides a method of preparing the 4-imidazolidinone-fused cyclic peptides of the present invention. In one aspect, the present invention provides a method of generating a library of 4-imidazolidinone-fused cyclic peptides. In some aspects, the present invention provides a method of screening the 4-imidazolidinone-fused cyclic peptides of the present invention and identifying the 4-imidazolidinone-fused cyclic peptides displaying the activity of interest (e.g., anticonvulsant activity, anticancer activity, anti-inflammatory activity, antiseptic activity, antiviral activity, antibacterial activity, reduced protein-protein interaction, or a combination thereof).

In one aspect, the present invention provides a method of preparing the compound of the present invention. In some embodiments, the method comprises the steps of: a) obtaining a linear peptide; b) adding an aldehyde group to the linear peptide to generate an aldehyde functionalized linear peptide; c) incubating the aldehyde functionalized linear peptide in a solvent in the presence of a nucleophilic catalyst; d) covalently cyclizing the aldehyde functionalized linear peptide to generate at least one compound of the present invention; and e) isolating the compound of the present invention.

In one aspect, the present invention provides a method of generating a library of 4-imidazolidinone-fused cyclic peptides. In some embodiments, the method comprises the steps of: a) obtaining a mixture of linear peptides; b) adding an aldehyde group to the linear peptides to generate aldehyde functionalized linear peptides; c) incubating the aldehyde functionalized linear peptides in a solvent in the presence of a nucleophilic catalyst; d) covalently cyclizing the aldehyde functionalized linear peptides to generate 4-imidazolidinone-fused cyclic peptides, or derivatives, prodrugs, pharmaceutically acceptable salts, solvates, isomers, or tautomers thereof; and e) isolating the 4-imidazolidinone-fused cyclic peptides, or derivatives, prodrugs, pharmaceutically acceptable salts, solvates, isomers, or tautomers thereof.

In various embodiments, the linear peptides are synthesized using techniques and materials described. In various embodiments, the linear peptides are synthesized using any suitable procedures starting from compounds that are available from commercial sources, or are prepared using procedures described herein.

In various embodiments, the linear peptide comprises any amino acid described herein. In some embodiments, the linear peptide comprises at least three amino acids. For example, in some embodiments, the linear peptide comprises an amino acid sequence as set forth in SEQ ID NOs: 13-53, or any combination thereof.

In various embodiments, the aldehyde group is —C═O or —$(X^aR^5)_x$—C═O. For example, in one embodiment, the aldehyde group is —C═O. In another embodiment, the aldehyde group is —$CH_2$—C═O.

In one embodiment, the aldehyde group is added to the c terminus of the linear peptide to generate an aldehyde functionalized linear peptide. In one embodiment, the aldehyde group is added to between the n and c termini of the linear peptide to generate an aldehyde functionalized linear peptide.

In various embodiments, the aldehyde functionalized linear peptides are synthesized using techniques and materials described. In various embodiments, the aldehyde functionalized linear peptides are synthesized using any suitable procedures starting from compounds that are available from commercial sources, or are prepared using procedures described herein.

In some embodiments, the solvent is an aqueous solvent or a mixture thereof. In one embodiment, the solvent is a 5:95 mixture. In one embodiment, the solvent is a 10:90 mixture. In one embodiment, the solvent is a 20:80 mixture. In one embodiment, the solvent is a 30:70 mixture. In one embodiment, the solvent is a 40:60 mixture. In one embodiment, the solvent is a 45:55 mixture. In one embodiment, the solvent is a 50:50 mixture.

In some embodiments, the solvent is an organic solvent, water, or any combination thereof, Examples of such solvents include, but are not limited to: methanol (MeOH), ethanol, dimethylformamide (DMF), dimethyl sulfoxide (DMSO), acetonitrile (ACN), tetrahydrofuran (THF), ethylacetate, hexane, chloroform, or any combination thereof. For example, in one embodiment, the solvent is a 50:50 mixture of water:DMF.

In various embodiments, the aldehyde functionalized linear peptide is incubated, in a solvent in the presence of excess nucleophilic catalyst. In some embodiments, the aldehyde functionalized linear peptide is incubated in a solvent in the presence of between about 1 equiv. to about 1000 equiv. of nucleophilic catalyst. In some embodiments, the aldehyde functionalized linear peptide is incubated in a solvent in the presence of between about 1.5 equiv. to about 1000 equiv. of nucleophilic catalyst. In some embodiments, the aldehyde functionalized linear peptide is incubated in a solvent in the presence of between about 1.5 equiv. to about 100 equiv. of nucleophilic catalyst. In some embodiments, the aldehyde functionalized linear peptide is incubated in a solvent in the presence of between about 1.5 equiv. to about 30 equiv. of nucleophilic catalyst. In some embodiments, the aldehyde functionalized linear peptide is incubated in a solvent in the presence of between about 3 equiv. to about 20 equiv. of nucleophilic catalyst. In some embodiments, the aldehyde functionalized linear peptide is incubated in a solvent in the presence of between about 5 equiv. to about 10 equiv. of nucleophilic catalyst. For example, in one embodiment, the aldehyde functionalized linear peptide is incubated in a solvent in the presence of about 7 equiv. of nucleophilic catalyst.

In one embodiment, the nucleophilic catalyst is a base. Examples of such bases include, but are not limited to, pyridine, 4-dimethylaminopyridine (DMAP), 4-pyrrolidinylpyridine, 2,6-dimethylpyridine, 8-diazabicyclo[5.4.0]undec-7-ene (DBU), histidine, arginine, aromatic amines, aliphatic amines, primary amines, secondary amines, tertiary amines, or any combination thereof. For example, in one embodiment, the nucleophilic catalyst is DMAP.

In some embodiments, the aldehyde functionalized linear peptide is incubated in a solvent at a concentration between about 0.1 mM to about 1000 M. In some embodiments, the aldehyde functionalized linear peptide is incubated in a solvent at a concentration between about 10 M to about 1000 M. In some embodiments, the aldehyde functionalized linear peptide is incubated in a solvent at a concentration between about 0.1 mM to about 100 M. In some embodiments, the aldehyde functionalized linear peptide is incubated in a solvent at a concentration between about 0.1 mM to about 10 M. In some embodiments, the aldehyde functionalized linear peptide is incubated in a solvent at a concentration between about 0.1 mM to about 1 M. In some embodiments, the aldehyde functionalized linear peptide is incubated in a solvent at a concentration between about 1 mM to about 1 M. In some embodiments, the aldehyde functionalized linear peptide is incubated in a solvent at a concentration between about 1 mM to about 100 mM. In some embodiments, the aldehyde functionalized linear peptide is incubated in a solvent at a concentration between about 1 mM to about 10 mM. For example, in some embodiments, the aldehyde functionalized linear peptide is incubated in a solvent at a concentration above about 1 mM.

In some embodiments, the aldehyde functionalized linear peptide is incubated in a solvent in the presence of a nucleophilic catalyst at temperature between about 10° C. to about 200° C. In some embodiments, the aldehyde functionalized linear peptide is incubated in a solvent in the presence of a nucleophilic catalyst at temperature between about 20° C. to about 35° C. In some embodiments, the aldehyde functionalized linear peptide is incubated in a solvent in the presence of a nucleophilic catalyst at temperature between about 20° C. to about 25° C.

In some embodiments, the aldehyde functionalized linear peptide is incubated in a solvent in the presence of a nucleophilic catalyst to intramolecularly cyclize to generate the 4-imidazolidinone-fused cyclic peptide of the present invention.

In various embodiments, the compounds of the present invention are isolated using any suitable procedures, techniques, and materials known to the skilled artisan.

In some aspects, the present invention provides a method of screening the 4-imidazolidinone-fused cyclic peptides of the present invention and identifying the 4-imidazolidinone-fused cyclic peptides displaying the activity of interest (e.g., anticonvulsant activity, anticancer activity, anti-inflammatory activity, antiseptic activity, antiviral activity, antibacterial activity, reduced protein-protein interaction, or a combination thereof). Thus, in some embodiments, the method comprises a) exposing the 4-imidazolidinone-fused cyclic peptide to at least one component associated with the activity of interest (e.g., anticonvulsant activity, anticancer activity, anti-inflammatory activity, antiseptic activity, antiviral activity, antibacterial activity, reduced protein-protein interaction, or a combination thereof); and b) identifying the 4-imidazolidinone-fused cyclic peptide that modulate the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof).

In various embodiments of the methods of the invention, the 4-imidazolidinone-fused cyclic peptide displays the activity of interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be decreased or reduced when compared to a comparator.

In various embodiments of the methods of the invention, the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be decreased or reduced when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is decreased by at least 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator.

In various embodiments of the methods of the invention, the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be decreased or reduced when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be decreased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, or at least 10000 fold, when compared with a comparator.

In one embodiment, the 4-imidazolidinone-fused cyclic peptide displays the activity of interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is decreased or reduced in the biological sample as compared to a comparator. For example, in one embodiment, the 4-imidazolidinone-fused cyclic peptide displays the activity of Interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is decreased by at least 1 fold, at least 1.1 fold, at least 1.2 fold, at least 1.3 fold, at least 1.4 fold, or at least 1.5 fold.

In various embodiments of the methods of the invention, the 4-imidazolidinone-fused cyclic peptide displays the activity of interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be increased when compared to a comparator.

In various embodiments of the methods of the invention, the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be increased when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is increased by at least 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500°%, by at least 3000%, by at least 4000%, or by at least 5000%, when compared with a comparator.

In various embodiments of the methods of the invention, the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be increased when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is determined to be increased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, or at least 10000 fold, when compared with a comparator.

In one embodiment, the 4-imidazolidinone-fused cyclic peptide displays the activity of interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is increased in the biological sample as compared to a comparator. For example, in one embodiment, the 4-imidazolidinone-fused cyclic peptide displays the activity of interest (e.g., anticonvulsant activity, anticancer activity, anti-inflammatory activity, antiseptic activity, antiviral activity, antibacterial activity, reduced protein-protein interaction, or a combination thereof) when the level or activity of at least one component associated with the activity of interest (e.g., anticonvulsant activity, anticancer activity, anti-inflammatory activity, antiseptic activity, antiviral activity, antibacterial activity, reduced protein-protein interaction, or a combination thereof) is increased by at least 1 fold, at least 1.1 fold, at least 1.2 fold, at least 1.3 fold, at least 1.4 fold, or at least 1.5 fold.

For example, in some embodiments, the method comprises a) exposing the 4-imidazolidinone-fused cyclic peptide to at least one protein-protein interaction or to proteins that form a protein-protein interaction; and b) identifying the 4-imidazolidinone-fused cyclic peptide that reduces the level or activity of at least one protein-protein interaction.

In various embodiments of the methods of the invention, the 4-imidazolidinone-fused cyclic peptide reduces at least one protein-protein interaction when at least one protein-protein interaction is determined to be decreased or reduced when compared to a comparator.

In various embodiments of the methods of the invention, the level (e.g., activity, expression, concentration, level, etc.) of protein-protein interaction is determined to be decreased or reduced when the level (e.g., activity, expression, concentration, level, etc.) of protein-protein interaction is decreased by at least 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator.

In various embodiments of the methods of the invention, the level (e.g., activity, expression, concentration, level, etc.) of protein-protein interaction is determined to be decreased or reduced when the level (e.g., activity, expression, concentration, level, etc.) of protein-protein interaction is determined to be decreased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, or at least 10000 fold, when compared with a comparator.

In one embodiment, the 4-imidazolidinone-fused cyclic peptide reduces at least one protein-protein interaction when at least one protein-protein interaction is decreased or reduced in the biological sample as compared to a comparator. For example, in one embodiment, the 4-imidazolidinone-fused cyclic peptide reduces at least one protein-protein interaction when at least one protein-protein interaction is decreased by at least 1 fold, at least 1.1 fold, at least 1.2 fold, at least 1.3 fold, at least 1.4 fold, or at least 1.5 fold.

In some embodiments, the method comprises a) exposing the 4-imidazolidinone-fused cyclic peptide to a ceil, tissue or subject to evaluate the anticonvulsant activity of the peptide; and b) identifying the 4-imidazolidinone-fused cyclic peptide that reduces the severity or frequency of convulsion. In various embodiments of the methods of the invention, the 4-imidazolidinone-fused cyclic peptide is an anticonvulsant compound when the severity or frequency of at least one convulsion (e.g., epileptic fit) is determined to be decreased or reduced when compared to a comparator.

In various embodiments of the methods of the invention, the severity or frequency of at least one convulsion (e.g., epileptic fit) is determined to be decreased or reduced when the severity or frequency (of at least one convulsion (e.g., epileptic fit) is decreased by at least 0.1%, by at least 1%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared with a comparator.

In various embodiments of the methods of the invention, the severity or frequency of at least one convulsion (e.g., epileptic fit) is determined to be decreased or reduced when the severity or frequency of at least one convulsion (e.g., epileptic fit) is determined to be decreased by at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 20 fold, at least 25 fold, at least 30 fold, at least 40 fold, at least 50 fold, at least 75 fold, at least 100 fold, at least 200 fold, at least 250 fold, at least 500 fold, or at least 1000 fold, or at least 10000 fold, when compared with a comparator.

In one embodiment, the 4-imidazolidinone-fused cyclic peptide is an anticonvulsant compound when the severity or frequency of at least one convulsion (e.g., epileptic fit) is decreased or reduced as compared to a comparator. For example, in one embodiment, the 4-imidazolidinone-fused cyclic peptide is an anticonvulsant compound when the severity or frequency of at least one convulsion (e.g., epileptic fit) is decreased by at least 1 fold, at least 1.1 fold, at least 1.2 fold, at least 1.3 fold, at least 1.4 fold, or at least 1.5 fold.

In one embodiment, the method comprises using a multi-dimensional non-linear algorithm to determine if the protein-protein interaction or the severity or frequency of at least one convulsion (e.g., epileptic fit) is statistically different than the level in a comparator sample. In some embodiments, the algorithm is drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; a plurality of algorithms arranged in a committee network; and forward floating search or backward floating search algorithms.

Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of.

In one embodiment, the comparator is a level of the at least one protein-protein interaction in a sample obtained from a subject not having a disease or disorder associated with protein-protein interaction. In one embodiment, the comparator is a level of the one or more biomarker in a sample obtained from a subject known not to have a disease or disorder associated with protein-protein interaction.

In one embodiment, the comparator is a level of the at least one convulsion in a subject not having a disease or disorder, such as seizure. In one embodiment, the comparator is a level of the one or more biomarker in a sample obtained from a subject known not to have a disease or disorder, such as seizure.

In certain embodiments, the biological sample obtained from the subject comprises gastrointestinal tissue of the subject, including gastrointestinal tissue excised during biopsy. Biological samples may be of any biological tissue or fluid. Frequently the sample will be a "clinical sample" which is a sample derived from a patient. The biological sample may contain any biological material suitable for detecting the desired protein-protein interaction or convulsion, and may comprise cellular and/or non-cellular material obtained from the individual. A biological sample can be obtained by appropriate methods, such as, by way of examples, blood draw, fluid draw, biopsy, or surgical resection, Examples of such samples include but are not limited to blood, lymph, urine, gastrointestinal fluid, semen, and biopsies. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient, Such samples include, but are not limited to, bodily fluids which may or may not contain cells, e.g., blood (e.g., whole blood, serum or plasma), urine, saliva, tissue or fine needle biopsy-samples, tissue sample obtained during surgical resection, and archival samples with known diagnosis, treatment and/or outcome history. In certain embodiments, the biological sample comprises gastrointestinal tissue.

In some embodiments, the methods of the invention use live cells, tissues, or subjects to perform experiments as the basis for the identification of an anticonvulsant compounds.

Various methods are known in the art for identifying an unknown compound in a complex mixture. Individual components may be separated, analyzed, and characterized using methods known to those skilled in the art. In a non-limiting embodiment, the individual components may be partially or completely purified using, for example, chromatographic methods (such as, but not limited to, high performance liquid chromatography (HPLC), silica gel chromatography or alumina chromatography), selective crystallization or precipitation, or selective solvent extraction. In another non-limiting embodiment, the partially or completely-purified components of the library may be analyzed or characterized using methods such as, but not limited to, nuclear magnetic resonance (NMR), mass spectrometry (MS), liquid chromatography-mass spectrometry (LC-MS), ultraviolet-visible (UV-vis) spectroscopy, and infrared (IR) spectroscopy. The information derived from these methods may be used to establish the structure of the specific components of the library.

In one embodiment, the methods of the invention relate to high throughput screening methods and automated screening of large quantities of test compounds (i.e., 4-imidazolidinone-fused cyclic peptides) to identify with the function of the compounds of the present invention. In some embodiments, the assays and methods comprise high content screening (HCS) of suitable compounds. Typically, HCS is an automated system to enhance the throughput of the screening process. However, the present invention is not limited to the speed or automation of the screening process.

In one embodiment, the assay of the invention may also be used to test delivery vehicles. These may be of any form, from conventional pharmaceutical formulations, to gene delivery vehicles. For example, the assay may be used to compare the effects of the same compound administered by two or more different delivery systems (e.g. a depot formulation and a controlled release formulation). Thus, the test compound may be delivered by a delivery vehicle of any appropriate type with or without any associated therapeutic agent.

In one embodiment, compounds are evaluated alone. In another embodiment, compounds are evaluated when delivered along with a deli very vehicle. Non-limiting examples of delivery vehicles include polymersomes, vesicles, micelles, plasmid vectors, viral vectors, and the like. As described elsewhere herein, the test compounds are evaluated for their ability to inhibit or reduce at least one protein-protein interaction or prevent or reduce the severity or frequency of at least one convulsion. In one embodiment, the methods of the invention comprise selecting a test compound that inhibits or reduces at least one protein-protein interaction or prevents or reduces the severity or frequency of at least one convulsion. In one embodiment, the test compound is delivered along with other known agents to determine whether the test compounds exhibit interference or synergy with other agents.

The test compound may be added to the assay method to be tested by any suitable means. For example, the test compound may be injected into the cells of the assay, or it can be added to the nutrient medium and allowed to diffuse into the cells.

In one embodiment, the screening methods involve providing a library containing a large number of test compounds, at least one of which potentially having an activity through its interaction with at least one at least one protein-protein interaction or convulsion. Such a library is then screened in one or more assays, as described herein, to identify those library members (particular chemical species or subclasses) that display a desired characteristic activity. The compounds thus identified can serve as conventional "hit compounds" or can themselves be used as potential or actual therapeutics. It is typical to that new chemical entities with useful properties are generated by identifying a chemical compound (called a "hit compound") with some desirable property or activity, and evaluating the property of those compounds. The invention includes such hit compounds, as well as compounds derived from such hit compounds.

Thus, the present invention also relates to methods of screening and identifying test compounds to identify compounds that reduce or inhibit at least one protein-protein interaction or prevent or reduce the severity or frequency of at least one convulsion. In one embodiment, the invention comprises assessing whether the test compound reduces or inhibits at least one protein-protein interaction or prevents or reduces the severity or frequency of at least one convulsion.

In various embodiments, the methods of screening and identifying anticonvulsant compounds to identify drug compounds that prevent or reduce the severity or frequency of at least one convulsion are any of the methods described herein.

In various aspects, the present invention also relates, in part, to methods of preparing compositions comprising at least one compound of the present invention. In one embodiment, the invention provides methods of preparing a therapeutic composition comprising at least one compound having the structure of Formula (I). In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one aspect of the invention, the therapeutic composition is used to prevent or treat a disease or disorder in a subject in need thereof. In various embodiments, the disease or disorder is associated with at least one protein-protein interaction.

Methods of Treating or Preventing Diseases or Disorders

The present invention relates, in part, to a method of reducing or inhibits at least one protein-protein interaction. For example, in one embodiment, the present invention provides a method, of reducing or inhibiting at least one protein-protein interaction in a subject in need thereof, in one aspect, the present invention provides a method of preventing or treating a disease or disorder associated with at least one protein-protein interaction in a subject in need thereof.

The present invention relates, in part, to a method of preventing or reducing the severity or frequency of at least one convulsion (e.g., epileptic fit). For example, in one embodiment, the present invention provides a method of preventing or reducing the severity or frequency of at least one convulsion (e.g., epileptic fit) in a subject in need thereof. In one aspect, the present invention provides a method of preventing or treating a disease or disorder associated with at least one convulsion (e.g., epileptic fit) in a subject in need thereof.

In various embodiments, the methods of invention comprise administering a therapeutically effective amount of at least one compound or a composition thereof described herein to the subject.

In various embodiments, the disease or disorder is associated with at least one protein-protein interaction, at least one convulsion, or a combination thereof. In various embodiments, the disease or disorder is cancer, Huntington's disease, seizure, cystic fibrosis, or Alzheimer's disease, or any combination thereof.

The following are non-limiting examples of cancers that can be treated by the disclosed methods and compositions: acute lymphoblastic; acute myeloid leukemia; adrenocortical carcinoma; adrenocortical carcinoma, childhood; appendix cancer; basal cell carcinoma; bile duct cancer, extrahepatic; bladder cancer; bone cancer; osteosarcoma and malignant fibrous histiocytoma; brain stem glioma, childhood; brain tumor, adult; brain tumor, brain stem glioma, childhood; brain tumor, central nervous system atypical teratoid/rhabdoid tumor, childhood; central nervous system embryonal tumors; cerebellar astrocytoma; cerebral astrocytotna/malignant glioma; craniopharyngioma; ependymoblastoma; ependymoma; medulloblastoma; medulloepithelioma; pineal parenchymal tumors of intermediate differentiation; supratentorial primitive neuroectodermal tumors and pineoblastoma; visual pathway and hypothalamic glioma; brain and spinal cord tumors; breast cancer; bronchial tumors; Burkitt lymphoma; carcinoid tumor; carcinoid tumor, gastrointestinal; central nervous system atypical teratoid/rhabdoid tumor; central nervous system embryonal tumors; central nervous system lymphoma; cerebellar astrocytoma cerebral astrocytoma/malignant glioma, childhood; cervical cancer; chordoma, childhood; chronic lymphocytic leukemia; chronic myelogenous leukemia; chronic myeloproliferative disorders; colon cancer; colorectal cancer; craniopharyngioma; cutaneous T-cell lymphoma; esophageal cancer; Ewing family of tumors; extragonadal germ cell tumor; extrahepatic bile duct cancer; eye cancer, intraocular melanoma; eye cancer, retinoblastoma; gallbladder cancer; gastric (stomach) cancer; gastrointestinal carcinoid tumor; gastrointestinal stromal tumor (gist); germ cell tumor, extracranial; germ cell tumor, extragonadal; germ cell tumor, ovarian; gestational trophoblastic tumor; glioma; glioma, childhood brain stem; glioma, childhood cerebral astrocytoma; glioma, childhood visual pathway and hypothalamic; hairy cell leukemia; head and neck cancer; hepatocellular (liver) cancer; histiocytosis, langerhans cell; Hodgkin lymphoma; hypopharyngeal cancer; hypothalamic and visual pathway glioma; intraocular melanoma; islet cell tumors; kidney (renal cell) cancer; Langerhans cell histiocytosis; laryngeal cancer; leukemia, acute lymphoblastic; leukemia, acute myeloid; leukemia, chronic lymphocytic; leukemia, chronic myelogenous; leukemia, hairy cell; lip and oral cavity cancer; liver cancer; lung cancer, non-small cell; lung cancer, small cell; lymphoma, aids-related; lymphoma, burkitt; lymphoma, cutaneous T-cell; lymphoma, non-Hodgkin lymphoma; lymphoma, primary central nervous system; macroglobulinemia, Waldenstrom; malignant fibrous histiocytoma of bone and osteosarcoma; medulloblastoma; melanoma; melanoma, intraocular (eye); Merkel cell carcinoma; mesothelioma; metastatic squamous neck cancer with occult primary; mouth cancer; multiple endocrine neoplasia syndrome, (childhood); multiple myeloma/plasma cell neoplasm; mycosis; fungoides; myelodysplastic syndromes; myelodysplastic/myeloproliferative diseases; myelogenous leukemia, chronic; myeloid leukemia, adult acute; myeloid leukemia, childhood acute; myeloma, multiple; myeloproliferative disorders, chronic; nasal cavity and paranasal sinus cancer; nasopharyngeal cancer; neuroblastoma; non-small cell lung cancer; oral cancer; oral cavity cancer; oropharyngeal cancer; osteosarcoma and malignant fibrous histiocytoma of bone; ovarian cancer; ovarian epithelial cancer; ovarian germ cell tumor; ovarian low malignant potential tumor; pancreatic cancer; pancreatic cancer, islet cell tumors; papillomatosis; parathyroid cancer; penile cancer; pharyngeal cancer; pheochromocytoma; pineal parenchymal tumors of intermediate differentiation; pineoblastoma and supratentorial primitive neuroectodermal tumors; pituitary tumor; plasma celt neoplasm/multiple myeloma; pleuropulmonary blastoma; primary central nervous system lymphoma; prostate cancer; rectal cancer; renal cell (kidney) cancer; renal pelvis and ureter, transitional cell cancer; respiratory tract carcinoma involving the nut gene on chromosome 15; retinoblastoma; rhabdomyosarcoma; salivary gland cancer; sarcoma, ewing family of tumors; sarcoma, Kaposi; sarcoma, soft tissue; sarcoma, uterine; sezary syndrome; skin cancer (nonmelanoma); skin cancer (melanoma); skin carcinoma, Merkel cell; small cell lung cancer; small intestine cancer; soft tissue sarcoma; squamous cell carcinoma, squamous neck cancer with occult primary, metastatic; stomach (gastric) cancer; supratentorial primitive neuroectodermal tumors; T-cell lymphoma, cutaneous; testicular cancer; throat cancer; thymoma and thymic carcinoma; thyroid cancer; transitional cell cancer of the renal pelvis and ureter; trophoblastic tumor, gestational; urethral cancer; uterine cancer, endometrial; uterine sarcoma; vaginal cancer; vulvar cancer; Waldenstrom macroglobulinemia; and Wilms tumor.

In some aspects of the invention, the methods of the present invention modulate the level (e.g., activity, expression, level, etc.) of at least one protein-protein interaction, severity or frequency of at least one convulsion, or any combination thereof by administering at least one compound of the present invention to a subject in need thereof. In some embodiments, the methods of the present invention reduce or eliminate the level (e.g., activity, expression, level, etc.) of at least one protein-protein interaction, severity or frequency of at least one convulsion, or any combination thereof by administering at least one compound of the present invention to a subject in need thereof.

In some embodiments, the method of treatment comprises monitoring the level (e.g., activity, expression, level, etc.) of at least one protein-protein interaction, severity or frequency of at least one convulsion, or any combination thereof during the course of treatment of a disease or disorder. In some embodiments, the method of treatment comprises an assessment of the effectiveness of the treatment regimen for a disease or disorder, such as seizure or cancer, by detecting at least one biomarker in an effective amount from samples obtained from a subject over time and comparing the amount of biomarker or biomarkers detected. In some embodiments, a first sample is obtained prior to the subject receiving treatment and one or more subsequent samples are taken after or during treatment of the subject. In some embodiments, changes in the level of at least one biomarker over time provide an indication of effectiveness of the therapy.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic agents suitable for administration to a particular subject can be identified by detecting one or more biomarkers in an effective amount from a sample obtained from a subject and exposing the subject-derived sample to a test compound that determines the amount of the biomarker(s) in the subject-derived sample. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

In various exemplary embodiments, effecting a therapy comprises administering a disease-modulating drug to the subject. The subject may be treated with one or more drugs until altered levels of the measured biomarkers return closer to the baseline value measured in a population not having a disease or disorder, or showing improvements in disease biomarkers as a result of treatment with a drag. Additionally, improvements related to a changed level of a biomarker or clinical parameter may be the result of treatment with a disease-modulating drug.

Any drug or any combination of drags disclosed herein may be administered to a subject to treat a disease. The drugs herein can be formulated in any number of ways, often according to various known formulations in the art or as disclosed or referenced herein.

In various embodiments, any drug or any combination of drugs disclosed herein is not administered to a subject to treat a disease, in these embodiments, the practitioner may refrain from administering the drag or any combination of drags, may recommend that the subject not be administered the drug or any combination of drugs or may prevent the subject from being administered the drug or any combination of drugs.

In various embodiments, one or more additional drugs may be optionally administered in addition to those that are recommended, or have been administered.

Compositions

The invention also includes compositions comprising at least one compound of the present invention. The disclosure also encompasses a pharmaceutical composition comprising a compound of the disclosure. For example, in one embodiment, the pharmaceutical composition is useful for reducing or inhibiting at least one protein-protein interaction. In another embodiment, the pharmaceutical composition is useful for preventing or reducing the severity or frequency of at least one convulsion (e.g. epileptic fit). Such a pharmaceutical composition may consist of a compound of the disclosure in a form suitable for administration to a subject. The compound of the disclosure may be present in the pharmaceutical composition in the form of a physiologically acceptable salt, such as in combination with a physiologically acceptable cation, as is well known in the art.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. For example, the therapeutic agent may be directly injected into the tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

In an embodiment, the pharmaceutical compositions useful for practicing the method of the disclosure may be administered to deliver a dose of between 1 ng/kg/day and 100 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, inclusive of all value sand ranges therebetween). In another embodiment, the pharmaceutical compositions useful for practicing the disclosure may be administered to deliver a dose of between 1 ng/kg/day and 500 mg/kg/day (e.g., about 1 ng/kg/day, about 10 ng/kg/day, 100 ng/kg/day, about 500 ng/kg/day, about 1000 ng/kg/day, about 5000 ng/kg/day, about 10000 ng/kg/day, about 50000 ng/kg/day, about 1 mg/kg/day, about 10 mg/kg/day, about 100 mg/kg/day, about 200 mg/kg/day, about 300 mg/kg/day, about 400 mg/kg/day, or about 500 mg/kg/day inclusive of all value sand ranges therebetween).

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient (e.g., about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, inclusive of all values and subranges therebetween).

Pharmaceutical compositions of the disclosure may be formulated for any suitable route of administration, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit. The methods and formulations described herein include the use of N-oxides (if appropriate), crystalline forms (also known as polymorphs), solvates, amorphous phases, and/or pharmaceutically acceptable salts of compounds having the structure of any compound of the disclosure, as well as metabolites and active metabolites of these compounds having the same type of activity, Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In one embodiment, the compositions of the disclosure are formulated using one or more pharmaceutically acceptable excipients or carriers. In one embodiment, the pharmaceutical compositions of the disclosure comprise a therapeutically effective amount of a compound of the disclosure and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the disclosure are known in the art and described, for example in Genaro, ed. (1985, Remington's Pharmaceutical Sciences, Mack Publishing Co., Easton, PA), which is incorporated herein by reference.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure include but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition optionally includes an antioxidant and a chelating agent which inhibit the degradation of the compound. Preferred antioxidants for some compounds are BHT, BHA, alpha-tocopherol and ascorbic acid in the preferred range of about 0,01% to 0.3% and more preferably BHT in the range of 0.03% to 0.1% by weight by total weight of the composition. Preferably, the chelating agent is present in an amount of from 0.01% to 0,5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

In some embodiments, the pharmaceutical compositions of the present disclosure (e.g., containing therapeutically effective amounts of one or more compounds of Formula (I) may be formulated as immediate release formulation, a delayed release formulation, or a sustained release formulation, and may comprise at least one pharmaceutically acceptable carrier, diluent, and/or excipient. Pharmaceutically acceptable carriers, diluents or excipients include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier.

In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, aqueous and non-aqueous solutions. Pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. Liquid carriers suitable for use in the present application include, but are not limited to, water (partially containing additives, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the disclosure may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

The compositions useful within the disclosure comprise at least one compound of Formula (I). The compositions of the disclosure may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In one embodiment, the composition is an anticonvulsant composition.

Solid carriers suitable for use in the present application include, but are not limited to, inactive substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets may contain up to 99% of the active compound. Suitable solid carriers include, for example, calcium phosphate, magnesium stearate, talc, sugars, lactose, dextrin, starch, gelatin, cellulose, polyvinylpyrrolidone, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated, or scored and may be formulated, so as to provide delayed or controlled release of the active ingredient therein using, for example, hydroxypropyl methylcellulose in varying proportions to provide the desired release profile. Tablets may optionally be provided with an enteric coating, to provide release in parts of the gut other than the stomach.

Carriers suitable for use in the present application can be mixed as needed with disintegrates, diluents, granulating agents, lubricants, binders and the like using conventional techniques known in the art. The carriers can also be sterilized using methods that do not deleteriously react with the compounds, as is generally known in the art.

Diluents may be added to the formulations described herein. Diluents increase the bulk of a solid pharmaceutical composition and/or combination, and may make a pharmaceutical dosage form containing the composition and/or combination easier for the patient and care giver to handle. In various embodiments, diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc, and/or mixtures of any of the foregoing, Specific examples of: microcrystalline cellulose include those sold under the Trademark Avicel (FMC Corp., Philadelphia, Pa.), for example, Avicel™ pH101, Avicel™ pH102 and Avicel™ pH112; lactose include lactose monohydrate, lactose anhydrous and Pharmatose DCL21; dibasic calcium phosphate includes Emcompress.

Lubricants are used to facilitate tablet manufacture, promoting powder flow and preventing particle capping (i.e., particle breakage) when pressure is relieved. Useful lubricants are magnesium stearate, calcium stearate, stearic acid, glyceryl behenate, talc, colloidal silicon dioxide such as Aerosil™ 200, mineral oil (in PEG), hydrogenated vegetable oil (e.g., comprised of hydrogenated and refined triglycerides of stearic and palmitic acids), combinations thereof.

Binders are used to impart cohesive qualities to a tablet, and thus ensure that the tablet or tablet layer remains intact after compression. Suitable binder materials include, but are not limited to, starch (including corn starch and pregelatinized starch), gelatin, sugars (including sucrose, glucose, dextrose and lactose), polyethylene glycol, polyvinyl alcohol, waxes, and natural and synthetic gums, e.g., acacia sodium alginate, polyvinylpyrrolidone, cellulosic polymers (including hydroxypropyl cellulose, hydroxy-propyl methylcellulose, methyl cellulose, microcrystalline cellulose, ethyl cellulose, hydroxyethyl cellulose, and the like), and Veegum, and combinations thereof. Examples of polyvinylpyrrolidone include povidone, copovidone and crospovidone.

Fillers include, for example, materials such as silicon dioxide, titanium dioxide, alumina, talc, kaolin, powdered cellulose, microcrystalline cellulose, urea, sodium chloride, as well as saccharides, or combinations thereof. Any suitable saccharide may be used in the composition of the present invention. As used herein, the "saccharides" used in the invention include sugar alcohols, monosaccharides, disaccharides, and oligosaccharides. Exemplary sugar alcohols include, but not limited to, xylitol, mannitol, sorbitol, erythritol, lactitol, pentitol, and hexitol. Exemplary monosaccharides include, but are not limited to, glucose, fructose, aldose and ketose. Exemplary disaccharides include, but are not limited to, sucrose, isomalt, lactose, trehalose, and maltose. Exemplary oligosaccharides include, but are not limited to, fructo-oligosaccharides, inulin, galacto-ologosaccharides, and mannan-oligosaccharides. In some embodiments, the saccharide is sorbitol, mannitol, or xylitol. In some embodiments, the saccharide is sorbitol. In some embodiments, the saccharide is sucrose.

Disintegrants are used to facilitate disintegration of the tablet, thereby increasing the erosion rate relative to the dissolution rate, and are generally starches, clays, celluloses, algins, gums, or crosslinked polymers (e.g., crosslinked polyvinyl pyrrolidone). Other non-limiting examples of suitable disintegrants include, for example, lightly crosslinked polyvinyl pyrrolidone, corn starch, potato starch, maize starch and modified starches, croscarmellose sodium, crospovidone, sodium starch glycolate, and combinations and mixtures thereof.

In some embodiments of the present disclosure, the pharmaceutical composition may be prepared in an oral formulation. For oral administration, the compounds can be formulated readily by combining the active compounds with pharmaceutically acceptable carriers known in the art. Such carriers enable the compounds disclosed herein to be formulated as tablets, pills, dragees, capsules, liquids, gels, syrups, slurries, suspensions and the like, for oral ingestion by a subject. Pharmaceutical compositions for oral use may be obtained as solid excipients, optionally grinding a resulting mixture, and processing the mixture of granules, after adding suitable adjuvants, if desired, to obtain tablets or dragee cores. Such oral pharmaceutical compositions may also be prepared by milling or melt extrusion. Suitable excipients may be any of those disclosed herein and, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Wetting agents, such as sodium dodecyl sulfate and the like, may be added.

In some embodiments, one or more of the compounds of the present invention are combined with excipients to form a core comprising an active (an active core), thereby forming a solid dosage form. In some embodiments, the active core may comprise an inert particle such as a sugar sphere with an appropriate mean particle size. In one embodiment, the inactive core may be a sugar sphere, a cellulose sphere, a spheroidal silicon dioxide bead, a buffer crystal or an encapsulated buffer crystal, such as calcium carbonate, sodium bicarbonate, fumaric acid, tartaric acid, etc. Buffer crystals are useful to alter the microenvironment. Alternatively, in accordance with other embodiments, drug-containing microgranules or pellets may be prepared by rotogranulation, high-shear granulation and extrusion-spheronization or compression of the drug (as mini-tablets, e.g., having a diameter of about 2 mm or more), a polymeric binder and optionally fillers/diluents.

In some embodiments, dragee cores may be provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds doses.

In some embodiments, pharmaceutical compositions described herein comprise one or more delayed release components. In some embodiments, delayed release is achieved by appropriately coating a drug-containing component with one or more suitable delayed-release polymers (also referred to as a controlled release polymer or rate-controlling polymer) or embedding the drug in a matrix comprising one or more suitable delayed-release polymers. Suitable delayed-release polymers include pharmaceutically acceptable water-insoluble polymers (also referred to as hydrophobic polymers), pharmaceutically acceptable water-soluble polymers (also referred to as hydrophilic polymers), pharmaceutically acceptable gastrosoluble polymers, pharmaceutically acceptable enteric polymers, and combinations thereof.

Non-limiting examples of pharmaceutically acceptable water-insoluble polymers include acrylic polymers, methacrylic acid polymers, acrylic copolymers, such as a methacrylic acid-ethyl acrylate copolymer available under the trade name of EUDRAGIT® (type L, RL, RS and NE30D), and their respective esters, zein, waxes, shellac and hydrogenated vegetable oil, cellulose derivatives, such as ethyl cellulose, cellulose acetate, cellulose acetate butyrate, and the like.

Non-limiting examples of pharmaceutically acceptable water-soluble polymers include homopolymers and copolymers of N-vinyl lactams, including homopolymers and copolymers of N-vinyl pyrrolidone, e.g. polyvinylpyrrolidone (PVP), copolymers of N-vinyl pyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, and hydroxypropylmethylcellulose, cellulose phthalates, succinates, butyrates, or trimellitates, in particular cellulose acetate phthalate, hydroxypropylmethylcellulose phthalate, hydroxypropylmethylcellulose succinate, and hydroxypropylmethylcellulose acetate succinate; high molecular polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-diimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially saponified "polyvinyl alcohol"), polyvinyl alcohol, polyethylene glycol oligo- and polysaccharides such as carrageenans, galactomannans and xanthan gum, or mixtures of one or more thereof.

Non-limiting examples of gastrosoluble polymers include maltrin, an aminoalkyl methacrylate copolymer available under the trade name of EUDRAGIT® (type E100 or EPO), polyvinylacetal diethylaminoacetate e.g., AEA® available from Sankyo Company Limited, Tokyo (Japan), and the like.

Non-limiting examples of such enteric polymers include carboxymethylethylcellulose, cellulose acetate phthalate (CAP), cellulose acetate succinate, methylcellulose phthalate, hydroxymethylethylcellulose phthalate, hydroxypropylmethylcellulose phthalate (HPMCP), hychoxypropylmethylcellulose acetate succinate (HPMCAS), polyvinyl alcohol phthalate, polyvinyl butyrate phthalate, polyvinyl acetal phthalate (PVAP), a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, cellulose acetate hexahydrophthalate, hydroxypropyl methylcellulose hexahydrophthalate, hydroxypropyl methylcellulose phthalate, cellulose propionate phthalate, cellulose acetate maleate, cellulose acetate trimellitate, cellulose acetate butyrate, cellulose acetate propionate, methacrylic acid/methacrylate polymer (acid number 300 to 330 and also known as EUDRAGIT L), methacrylic acid-methyl methacrylate copolymer, ethyl methacrylate-methylmethacrylate-chlorotrimethylammonium ethyl methacrylate copolymer, and the like, and combinations comprising one or more of the foregoing enteric polymers. Other examples include natural resins, such as shellac, SANDARAC, copal collophorium, and combinations comprising one or more of the foregoing polymers. Yet other examples of enteric polymers include synthetic resin hearing carboxyl, groups. The term "enteric polymer" as used herein is defined to mean a polymeric substance that when used in an enteric coat formulation, is substantially insoluble and/or substantially stable under acidic conditions at a pH of less than about 5 and which are substantially soluble or can decompose under conditions exhibiting a pH of about 5 or more.

Non-limiting examples of hydrophilic polymers include hydroxypropyl celluloses (HPC), hydroxypropyl methylcelluloses, methylcelluloses, polyethylene oxides, sodium carboxymethyl celluloses, and the like, or combinations thereof.

In certain embodiments, the delayed release component is a matrix. As used herein, the term "matrix" means a composition in which the drag is embedded or dispersed in water soluble, water insoluble, or hydrophilic polymers, or lipophilic maters, in order to achieve delayed, release of the drug. The mechanisms of the drug release generally involve drug diffusion through, a viscous gel layer or tortuous channels; and/or drug dissolution via gradual erosion or degradation of the polymer(s). In some embodiments, the matrix comprises swellable/erodable polymers, for example hydrophilic polymers which in contact with the water form a gel of high viscosity. In other embodiments, the matrix comprises water-insoluble polymers or lipophilic polymers.

For example, the matrix may be prepared using one or more hydrophilic polymers (e.g., hydroxypropyl cellulose, hydroxypropyl methylcellulose, polyethylene oxide), one or more lipophilic materials (e.g., carnauba wax, hardened castor oil, hardened rape seed oil, polyglycerin fatty acid ester), and/or coating tablets or granules with one or more delayed, release polymers (e.g., cellulose polymers such as ethylcellulose; acrylic acid copolymer such as aminoalkyl methacrylate copolymer RS [Eudragit RS (trade name, Degussa Co.)], ethyl acrylate-methyl methacrylate copolymer suspension [Eudragit NE (trade name, Degussa Co.)]).

The hydrophilic matrix may further contain a pH-dependent polymer. The term "pH-dependent." refers to a polymer which releases the active at a certain pH. Non-limiting examples of suitable pH-dependent polymers include hydroxypropyl methylcellulose phthalate, cellulose acetate phthalate, carboxymethyl ethyl cellulose, methyl methacrylate-methacrylic acid copolymer, methacrylic acid-ethyl acrylate copolymer, ethyl acrylate-methyl methacrylate-trimethylammoniumethyl methacrylate chloride copolymer, methyl methacrylate-ethyl acrylate copolymer, methacrylic acid-methyl acrylate-methyl methacrylate copolymer, hydroxypropyl cellulose acetate succinate, polyvinyl acetate phthalate and the like, and combinations thereof.

In some embodiments, the pharmaceutical composition is formulated as a sustained release formulations, e.g., by appropriately integrating additional polymers into the composition, or as coatings over the core (e.g., pellet or granule). The polymers useful for this purpose can be, but are not limited to, ethylcellulose; hydroxypropylmethylcellulose; hydroxypropylcellulose; hydroxyethylcellulose; carboxymethylcellulose; methylcellulose; nitrocellulose; Eudragit R; Eudragit RS; and Eudragit RL: Carbopol; polyethyleneoxide or polyethylene glycols with molecular weights in excess of 8,000 daltons. In some embodiments, these polymers are present concentrations from about 4-20 w/w % (e.g., about 4, about 5, about 6, about 7, about 8, about 9, about 10, about 11, about 12, about 13, about 14, about 15, about 16, about 17, about 18, about 19, or about 20% w/w %). The sustained release polymers may be combined with the delayed release components described above.

The compositions useful within the disclosure may further comprise at least one additional anticonvulsant agent. Non-limiting examples of the at least one additional anticonvulsant agent are phenytoin, dilantin, valproic acid, depakote, phenobarbital, lamotrigine, lamictal, carbamazepine, tegretol, topiramate, topamax, oxcarbazepine, trileptal, zonisamide, zonegran, gabapentin, neurontin, levetiracetam, keppra, pregabalin, lyrica, clonazepam, klonopin, lacosamide, vimpat, rufinamide, banzel, vigabatrin, sabril, and any combination thereof.

In one embodiment, the compound of the disclosure and the at least one additional anticonvulsant agent act synergistically in preventing, reducing, or treating at least one convulsion, A synergistic effect may be calculated, for example, using suitable methods such as, for example, the Sigmoid-$E_{max}$ equation (Holford & Schemer, 19981, Clin. Pharmacokinet. 6: 429-453), the equation of Loewe additivity (Loewe & Muisehnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated, with the equations referred to above are the concentration-effect curve, isobologram curve and combination index curve, respectively.

The pharmaceutical compositions may be prepared by any suitable method, such as mixing, dissolving, granulating, dragee-making, levigating, emulsifying, encapsulating, entrapping, or lyophilizing processes.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated, to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

The methods described herein are by no means all-inclusive, and further methods to suit the specific application wall be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed, as being limited to the following examples, but rather, should be construed to encompass any and all variations which become evident as a result of the teaching provided, herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: "CyClick" Chemistry for the Synthesis of Cyclic Peptides

To achieve new synthetic methodologies that circumvent current limitations (FIG. 1A) and provide an efficient strategy for easy access to a variety of cyclic peptides, the herein described studies focused on the development of a strategy that works in an exclusively intramolecular fashion. To develop a chemoselective reaction that works in an intramolecular fashion only, peptide aldehydes were used for macrocyclization. As a key design element, formation of a cyclic imine between an N-terminal peptide and a C-terminal aldehyde was used to promote conformational preorganization by bringing the amide at the second position in close proximity to the cyclic imine. This led to nucleophilic attack by the second amidic nitrogen on the imine to generate a stable 4-imidazolidinone-fused cyclic peptide (FIG. 1B). In contrast, the linear imine intermediate formed by intermolecular reaction between two peptides was unable to activate the amide bond and thus did not lead to formation of stable dimers (FIG. 1B). The herein-described approach was termed "CyClick" because the reaction is highly chemoselective for formation of cyclic peptides without dimerization or oligomerization.

Furthermore, the present approach represented, a rare example of conformationally induced amide bond activation that offered a general strategy for the efficient synthesis of 4-imidazolidinone-fused cyclic peptides (FIG. 1). 4-Imidazolidinone is an important structural motif found in many pharmaceuticals and biologically active compounds (Ji D et al., 2018, Org. Lett., 20:2745; Mach R H et AL., 1992, J. Med, Chem., 35:423), such as N,N'-methyleno-didemnin A, which is cytotoxic against human colon tumor cells (Molinski T F et al., 2011, J. Nat. Prod., 74:882); spiroimidazolidinone, which exhibits anticonvulsant activity (Aboul-Enein M N et al., 2015, Arch. Pharm., 348:575); Ro 64-6198, an agonist for the nociception/orphanin FQ opioid peptide (NOP) receptor (Chang S D et al., 2015, ACS Chem. Neuroscie., 6:1956); and ML298, a selective inhibitor of phospholipase D (PLD) (O'Reilly M C et al., 2013, J. Med. Chem., 56:2695) (FIG. 1C).

Among a number of advantages, it was recognized that the herein-described CyClick strategy:
1) was triggered by the N-terminus, without the need for coupling reagents and metals;
2) was chemoselective for reaction between the N-terminus of a peptide and an aldehyde rather than any other amino acid residues including lysine; and
3) utilized the cyclic imine-peptide conformation as an internal directing group, thus requiring no external ligand or removable directing group.

In addition, this macrocyclization led to the generation of a new chiral center with high stereoselectivity and introduced a nonpeptidic moiety, 4-imidazolidinone, into the macrocycle. This feature is known to generally improve the intrinsic pharmacokinetic profile while maintaining biological activity (Ji D et al., 2018, Org. Lett., 20:2745; Mach R H et al, 1992, J. Med. Chem., 35:423; Molinski T F et al., 2011, J. Nat. Prod., 74:882; Aboul-Enein M N et al., 2015, Arch. Pharm., 348:575; Chang S D et al., 2015, ACS Chem. Neurosci., 6:1956; O'Reilly M C et al., 2013, J. Med. Chem., 56:2695).

As such, the studies described herein also present a strategy that exploited the conformationally induced activation of the amide backbone for the efficient synthesis of cyclic peptides that was applicable across a wide range of peptide ring sizes with various amino acid residues. Most importantly, this reaction generated only cyclic peptides by intramolecular reaction without formation of side products due to linear and cyclic oligomerization. Since this method led to only intramolecular reactions, a high rate of macrocyclization were achieved when the reactions were carried out at high concentrations. Furthermore, NMR investigation revealed that the 4-imidazolidinone moiety induced a turn structure in cyclic peptides and increased their enzymatic stability; thus, this method was highly attractive for generating cyclic peptides for probing biological systems.

CyClick Reaction for Peptide Cyclization

Figure 2:
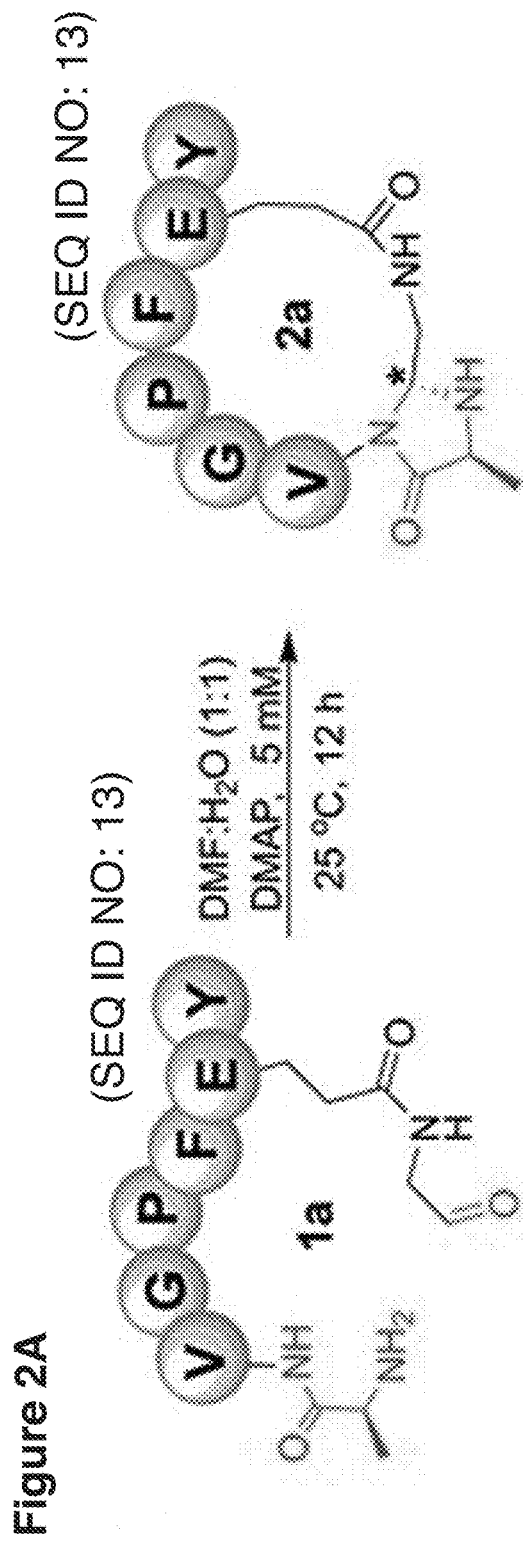
FIG. 2, comprising
Figure 2:
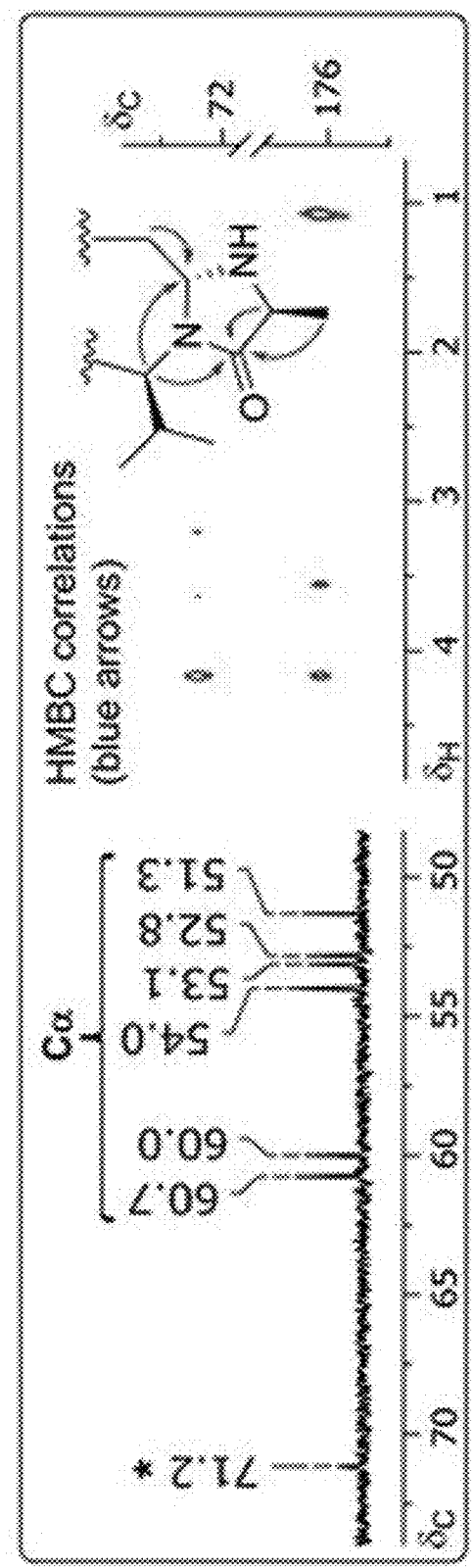
Figure 3:
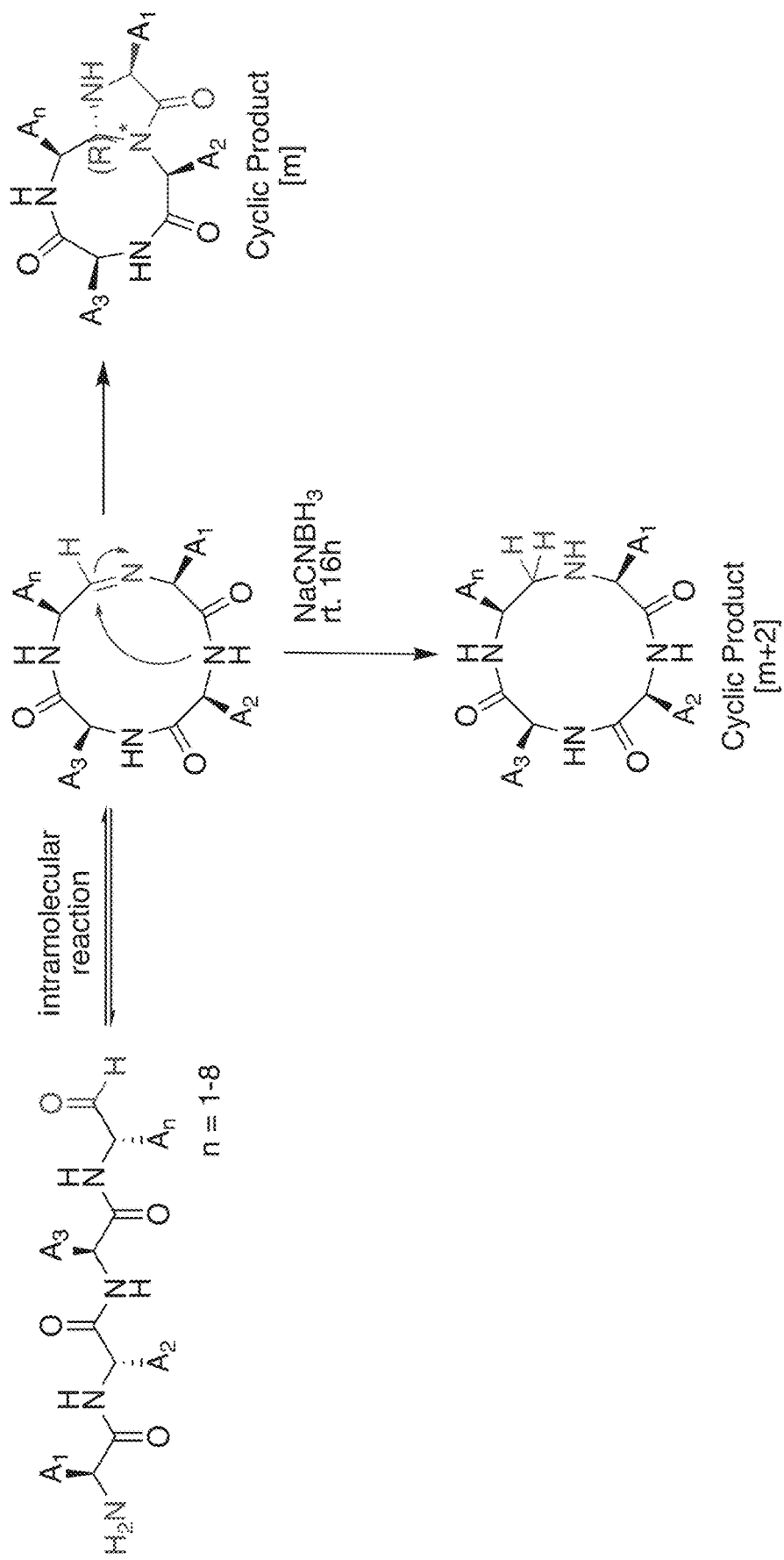
FIG. 3 depicts a schematic representation of general procedure for CyClick reaction. Lypholized peptide aldehyde (2 mg) was mixed with 7 equiv. DMAP in a 1:1 DMF:H$_2$O solution (final conc. 5 mM), The reaction was shaken at room temperature for 8-16 h. The product was analyzed with HPLC, NMR, and MS. Confirmation of cyclic product by MS. The cyclic imine intermediate exhibits mass equivalent to the cyclic product. In an effort to determine the cyclic product, sodium cyanoborohydride (50 equiv.) was added to reduce the cyclic imine intermediate FIG. 4, comprising

The initial investigation focused on a peptide with the sequence of AVGPFE(CHO)Y (SEQ ID NO: 13) 1a, where the side chain of Glu was modified to an aldehyde group (FIG. 2A and FIG. 3). Detailed optimization studies revealed that the macrocyclization between the N-terminus of a peptide and an aldehyde proceeded, most efficiently in an aqueous medium ($H_2O$/DMF (1:1)) at room temperature with addition of 4-(dimethylamino)pyridine (DMAP, 7 equiv). This resulted in the formation of a 4-imidazolidinone cyclic peptide 2a with 99% conversion (Table 1).

TABLE 1

CyClick reaction optimization.
CyClick Reaction Optimization

| Linear Peptide Sequence 1 | DMAP | Time | Concentration | Conversion to Cyclic Peptide 2 |
|---|---|---|---|---|
| AVGPFE(CHO)Y 1a (SEQ ID NO: 13) | No DMAP | 16 h | 5 mM | 2a, 11% |
| AVGPFE(CHO)Y 1a (SEQ ID NO: 13) | 7 equiv. | 8 h | 5 mM | 2a, 99% |
| NVGPFE(CHO)Y 1f (SEQ ID NO: 19) | No DMAP | 16 h | 5 mM | 2f, 10% |
| NVGPFE(CHO)Y 1f (SEQ ID NO: 19) | 7 equiv. | 16 h | 5 mM | 2f, 85% |

Linear peptide aldehydes AVGPFE(CHO)Y (SEQ ID NO: 13) 1a and NVGPFE(CHO)Y (SEQ ID NO: 19) 1f were selected for optimization and CyClick reaction was carried out in $H_2O$: DMF (1:1) under following different conditions.
Bold entries represent optimized reaction conditions.

As such, although not bound by any particular theory, it was hypothesized that DMAP facilitated macrocyclization by proton abstraction from the amidic nitrogen of the second amino acid, thereby activating the amide backbone for nucleophilic attack (Elashal H et al., 2016, Chem. Commun., 52:9699). Importantly, coupling reagents, metal catalysts, and harsh conditions (high temperature) were not required in this procedure.

Figures 4, 4C:
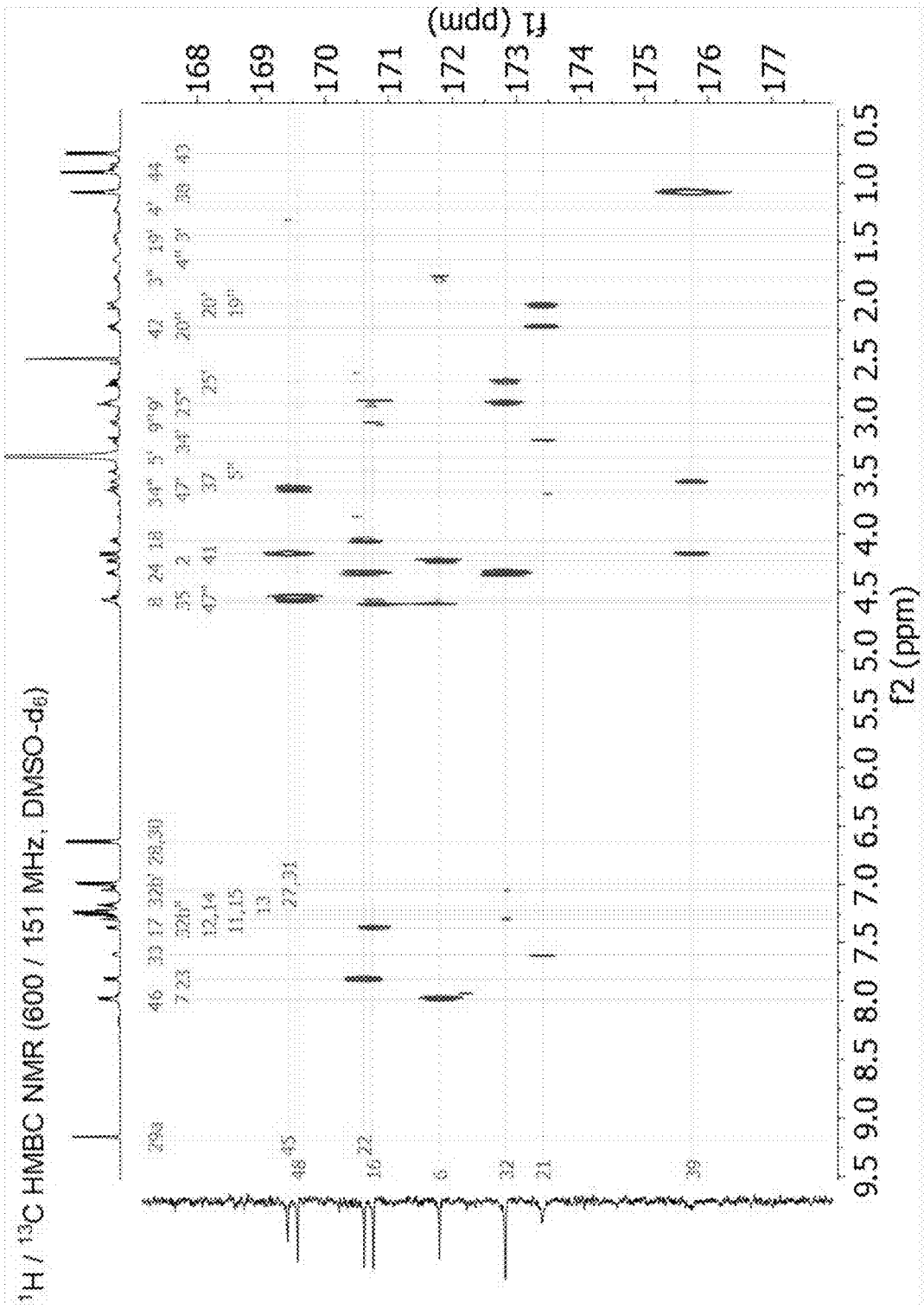

The 4-imidazolidinone cyclic peptide 2a was characterized by high-resolution mass spectrometry (HRMS) and NMR spectroscopy (FIG. 2A, FIG. 4, and Table 2).

TABLE 2

Representative NMR data for cyc(AVGPFE(CHO)Y) (SEQ ID NO: 13) 2a.

| Residue | Atom Name | Numbering | $\delta_H$ (ppm), multiplicity | $\delta_C$ (ppm) |
|---|---|---|---|---|
| Pro | N | 1 | — | — |
|  | $C_aH$ | 2 | 4.23, d (J = 9.0, 2.2 Hz) | 60.75 |
|  | $C_bH_2$ | 3 | 1.45, m; 1.81, m | 28.86 |
|  | $C_gH_2$ | 4 | 1.22, m; 1.65, m | 23.41 |
|  | $C_dH_2$ | 5 | 3.35, m; 3.46, t (J = 9.3 Hz) | 46.15 |
|  | CO | 6 | — | 171.80 |
| Phe | NH | 7 | 7.98, d (J = 8.5 Hz) | — |
|  | $C_aH$ | 8 | 4.58, m | 53.14 |
|  | $C_bH_2$ | 9 | 2.88, m; 3.05, dd (J = 14.5, 4.6 Hz) | 34.63 |
|  | $C_1$ | 10 | — | 138.16 |
|  | $C_2H, C_6H$ | 11, 15 | 7.23, m | 129.02 |
|  | $C_3H, C_5H$ | 12, 14 | 7.26, m | 128.06 |
|  | $C_4$ | 13 | 7.18, t (J = 7.1 Hz) | 126.17 |
|  | CO | 16 | — | 170.76 |
| Glu | NH | 17 | 7.37, d (J = 8.5 Hz) | — |
|  | $C_aH$ | 18 | 4.06, ddd (J = 11.1, 8.4, 3.0 Hz) | 51.32 |
|  | $C_bH_2$ | 19 | 1.49, m; 2.03, m | 26.86 |
|  | $C_gH_2$ | 20 | 2.04, m; 2.22, m | 29.45 |
|  | $C_dO$ | 21 | — | 173.41 |
|  | CO | 22 | — | 170.62 |
| Tyr | NH | 23 | 7.81, d (J = 8.4 Hz) | — |
|  | $C_aH$ | 24 | 4.33, td (J = 8.6, 4.9 Hz) | 54.01 |
|  | $C_bH_2$ | 25 | 2.70, dd (J = 13.9, 9.0 Hz); 2.87, m | 36.72 |
|  | $C_1$ | 26 | — | 127.86 |
|  | $C_2H, C_6H$ | 27, 31 | 6.99, d (J = 8.3 Hz) | 130.11 |
|  | $C_3H, C_5H$ | 28, 30 | 6.63, d (J = 8.4 Hz) | 114.81 |
|  | $C_4OH$ | 29 | 9.16, s | 155.74 |
|  | $CONH_2$ | 32 | 7.05, s; 7.30, s | 172.83 |
| Linker | NH | 33 | 7.60, dd (J = 8.1, 4.7 Hz) | — |
|  | $C_aH_2$ | 34 | 3.21, dd (J = 13.5, 4.4 Hz); 3.65, m | 41.64 |
|  | $C_bH$ | 35 | 4.57, m | 71.15 |
| Ala | NH | 36 | — | — |
|  | $C_aH$ | 37 | 3.55, q (J = 7.0 Hz) | 52.84 |
|  | $C_bH_3$ | 38 | 1.08, d (J = 6.9 Hz) | 19.62 |
|  | CO | 39 | — | 175.75 |
| Val | N | 40 | — | — |
|  | $C_aH$ | 41 | 4.17, d (J = 11.3 Hz) | 59.99 |
|  | $C_bH$ | 42 | 2.23, m | 25.25 |
|  | $C_{g1}H_3, C_{g2}H_3$ | 43, 44 | 0.74, d (J = 6.5 Hz); 0.90, d (J = 6.4 Hz) | 18.30, 19.74 |
|  | CO | 45 | — | 169.42 |
| Gly | NH | 46 | 7.99, m | — |
|  | $C_aH_2$ | 47 | 3.62, dd (J = 16.6, 3.1 Hz); 4.55, m | 40.74 |
|  | CO | 48 | — | 169.57 |

Figure 2B:
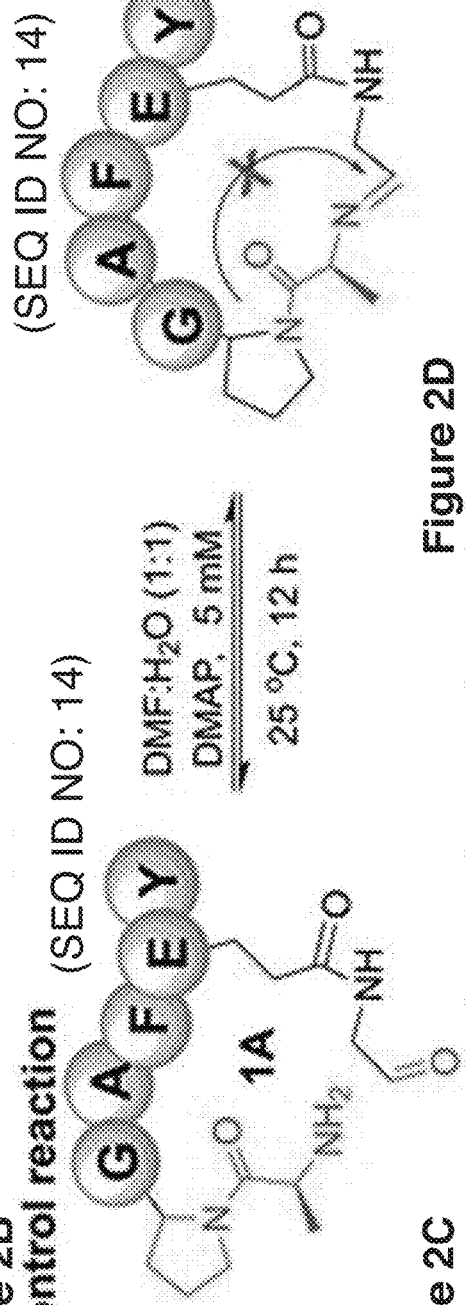
Figure 2:
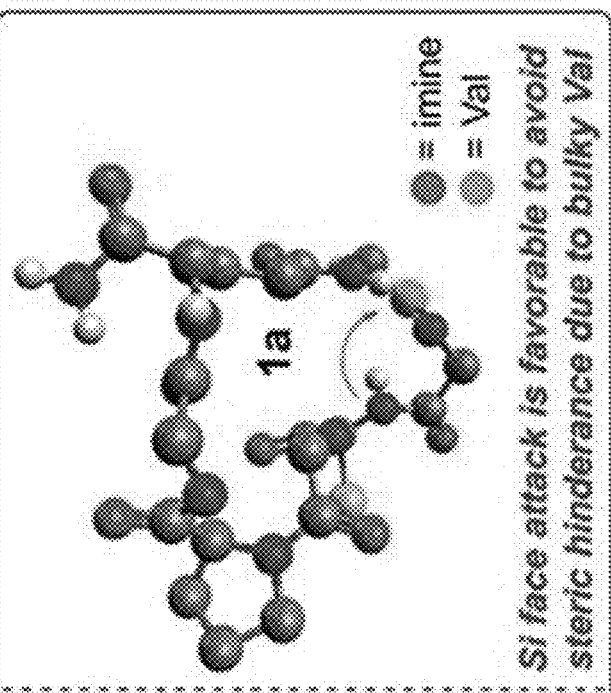
Figure 2:
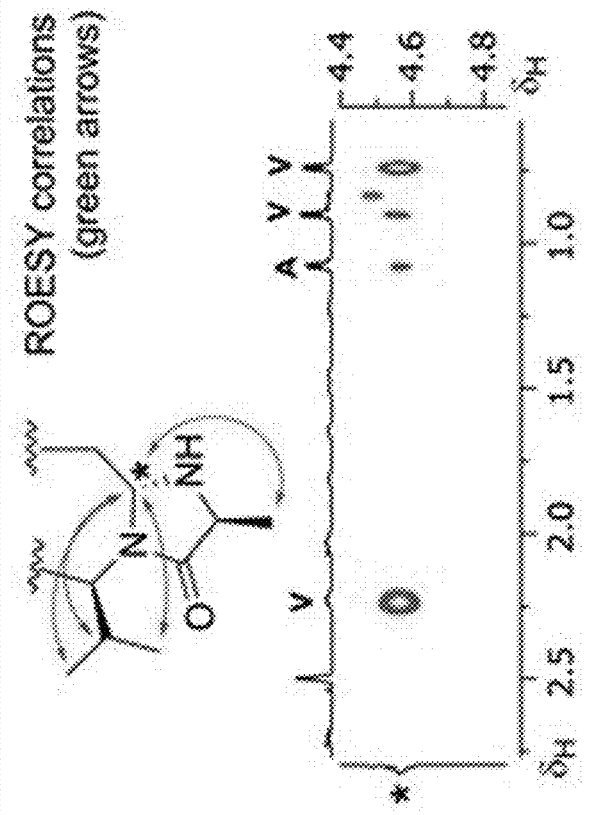
Figure 7:
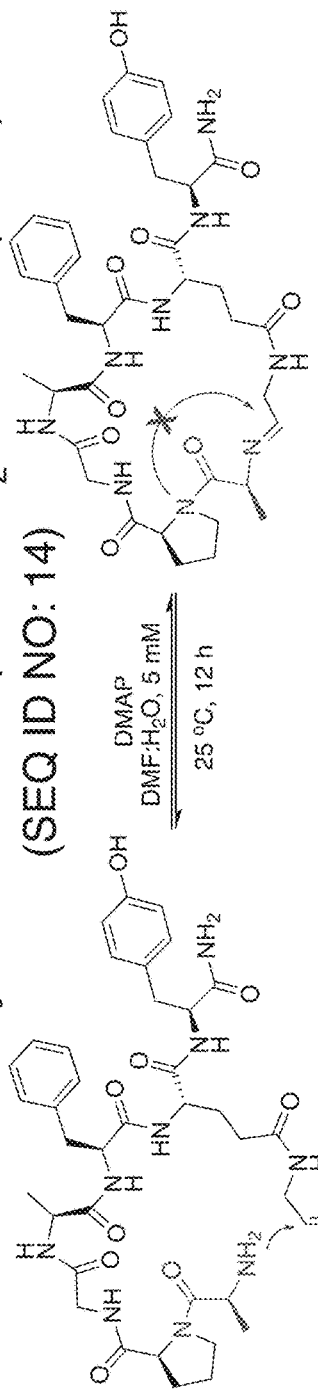
FIG. 7 depicts schematic representations of the control reactions used to determine the role of backbone amide bond at second position in macrocyclization: Two peptide aldehydes, NH$_2$-APCA-CHO (SEQ ID NO: 50) and NH$_2$-APGAFE(CHO)Y (SEQ ID NO: 14) with praline amino acid at the second position were subjected to optimized CyClick chemistry reported in FIG. 3 and FIG. 29. No product was observed under the reaction conditions.
Figure 7:
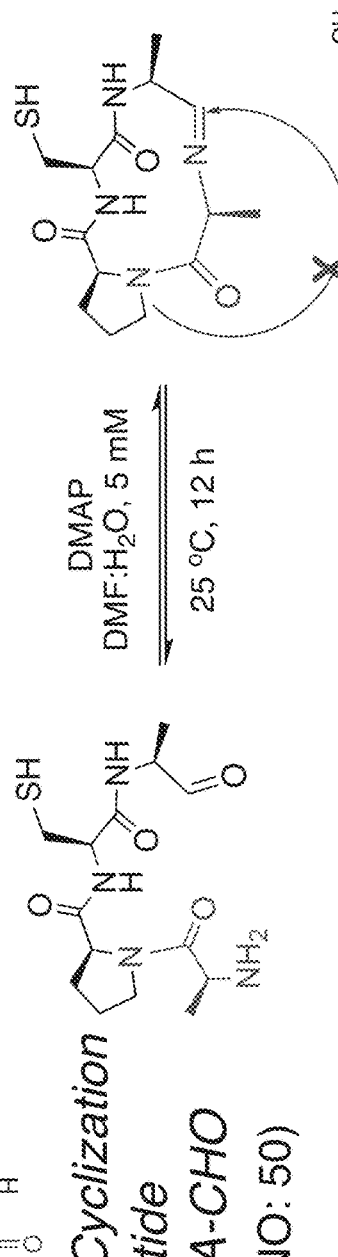
Figure 7:
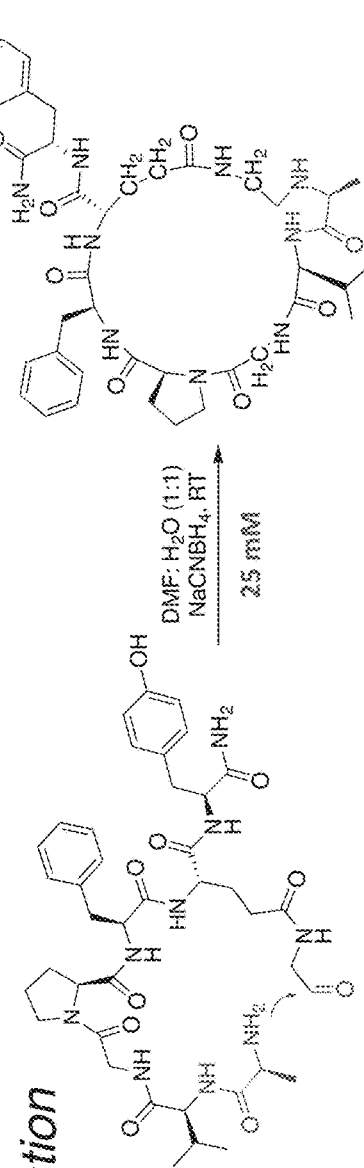

The diagnostic aminal carbon chemical shift at 71.2 ppm for 4-imidizolidinone was much further downfield than any $C\alpha$ carbon (FIG. 2A, FIG. 4 through FIG. 6, and Table 2). ACD labs' (version 2015; Pagenkopf B et al., 2005, J. Am. Chem. Soc., 127:3232) prediction for this chemical shift was 73.4 ppm. Moreover, heteronuclear multiple bond correlation (HMBC) NMR experiments confirmed the 4-imidazolidinone structure (FIG. 2A, FIG. 4 through FIG. 6, and Table 2). It is noteworthy that linear and cyclic dimerization or oligomerization products were not observed by either HPLC or MS analysis. Furthermore, replacement of the second amino acid residue with proline in linear peptide aldehydes APGAFE(CHO)Y (SEQ ID NO: 14) 1A and APCA(CHO) (SEQ ID NO: 50) completely abolished the cyclization, indicating that the amide proton at the second amino acid is essential for the formation of the 4-imidazolidinone moiety (FIG. 2B and FIG. 7).

Figure 8:
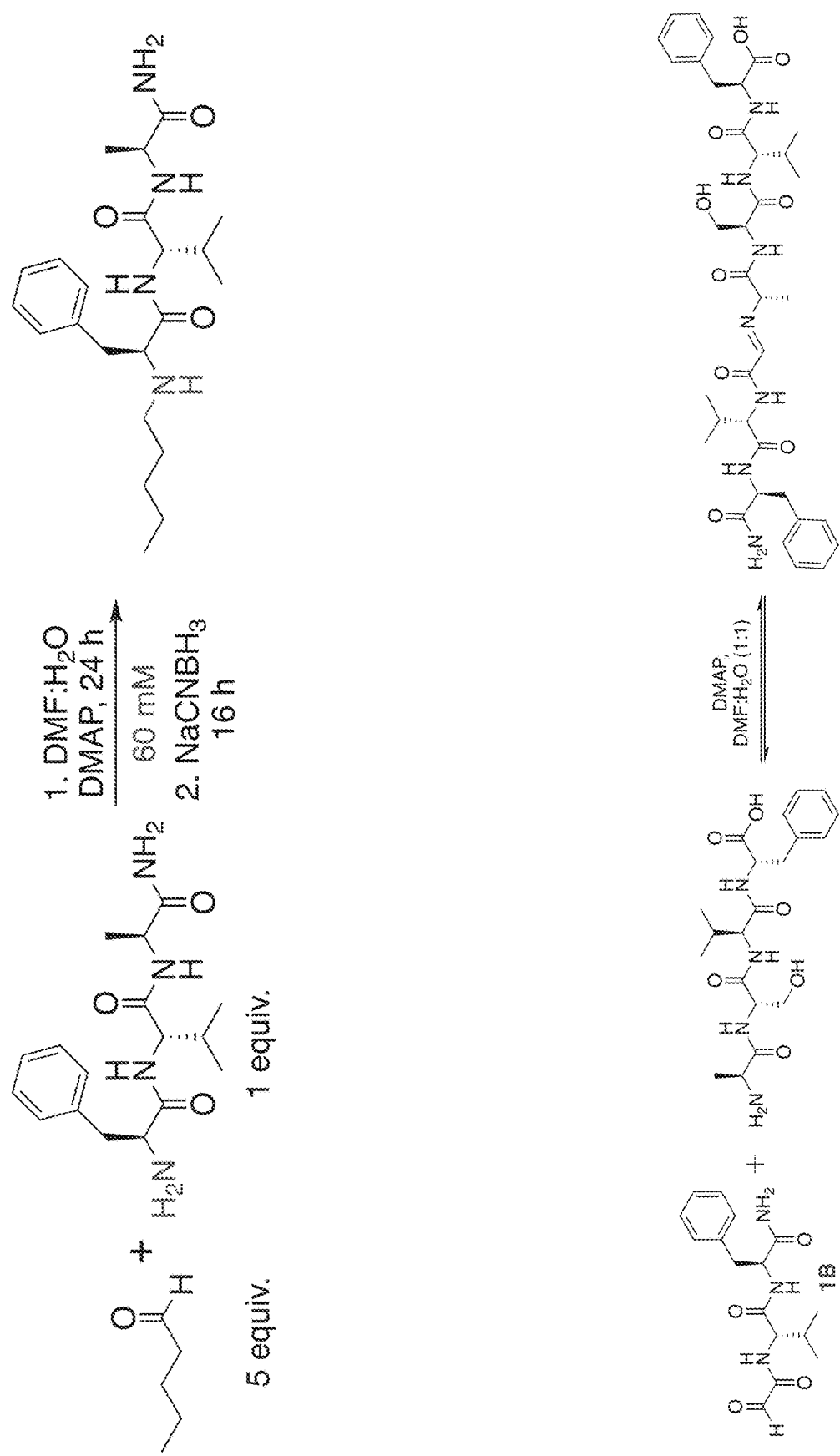
FIG. 8 depicts a schematic representation of comparison of intermolecular vs intramolecular reaction. Intramolecular macrocyclization was completed with various peptide examples. Intermolecular reaction was attempted with AVF and pentanal (top). Lypholized peptide AVF (4 mg, 60 mM) was mixed with aldehyde pentanal (5 equiv., 300 mM) and DMAP (30 equiv., 1800 mM) in a 1:1 DMF:H$_2$O solution (200 µL), The reaction was shaken at room temperature for 24 h. The linear inline intermediate exhibited mass equivalent to the desired 4-oxazolidinone products. In an effort to determine the nature of the product of intermolecular reaction, sodium cyanoborohydride (50 equiv.) was added which can reduce the linear Imine intermediate and reaction was stirred for additional 16 h. The resulting product was analyzed with LC-MS. The results indicated the formation of reduced linear imine. The formation of any 4-oxazolidinone product was not observed. Intermolecular reaction was attempted with ASVF (SEQ ID NO: 53) and keto aldehyde CHOVF (SEQ ID NO: 52) 1B (bottom). ASVF (SEQ ID NO: 53) (1 equiv.) was combined with the CHOVF (SEQ ID NO: 52) 1B (1 equiv.) and DMAP (7 equiv.) in 1:1 DMF: H$_2$O mixture (200 µL, final conc. 12 mM) and shaken at room temperature for 19 h. No product was observed under the reaction conditions.

Furthermore, the intermolecular reaction between an aldehyde, such as pentanal, and the N-terminus of a linear peptide FVA (SEQ ID NO: 51) was investigated under various reaction conditions, including longer reaction times, a great excess of aldehyde, and high amounts of DMAP. Intermolecular coupling leading to the formation of 4-imidazolidinone was not observed between the aldehyde and N-terminus of the peptide (FIG. 8). Although the intermolecular reaction led to the formation of a reversible linear imine, the synthesis of a stable 4-imidazolidinone moiety was not detected. The formation of linear imine was confirmed by reduction with NaCNBH$_3$.

Next, the studies investigated the intermolecular reaction between a highly reactive keto peptide aldehyde CHOVF (SEQ ID NO: 52) and the N-terminus of a linear peptide ASVF (SEQ ID NO: 53) under CyClick reaction conditions; however, the formation of any 4-imidazolidinone-containing product under these conditions was not observed (FIG. 8). As such, although not bound by any particular theory, it was hypothesized that this selectivity was based on the proximity of the amidic nitrogen to the cyclic imine. Together, these results confirmed that the CyClick reaction takes place in an intramolecular fashion only. Accordingly, the present studies describe the first report for such a macrocyclization where the intermolecular reaction is not possible.

Stereoselectivity of the CyClick Reaction

Figures 9, 9B:
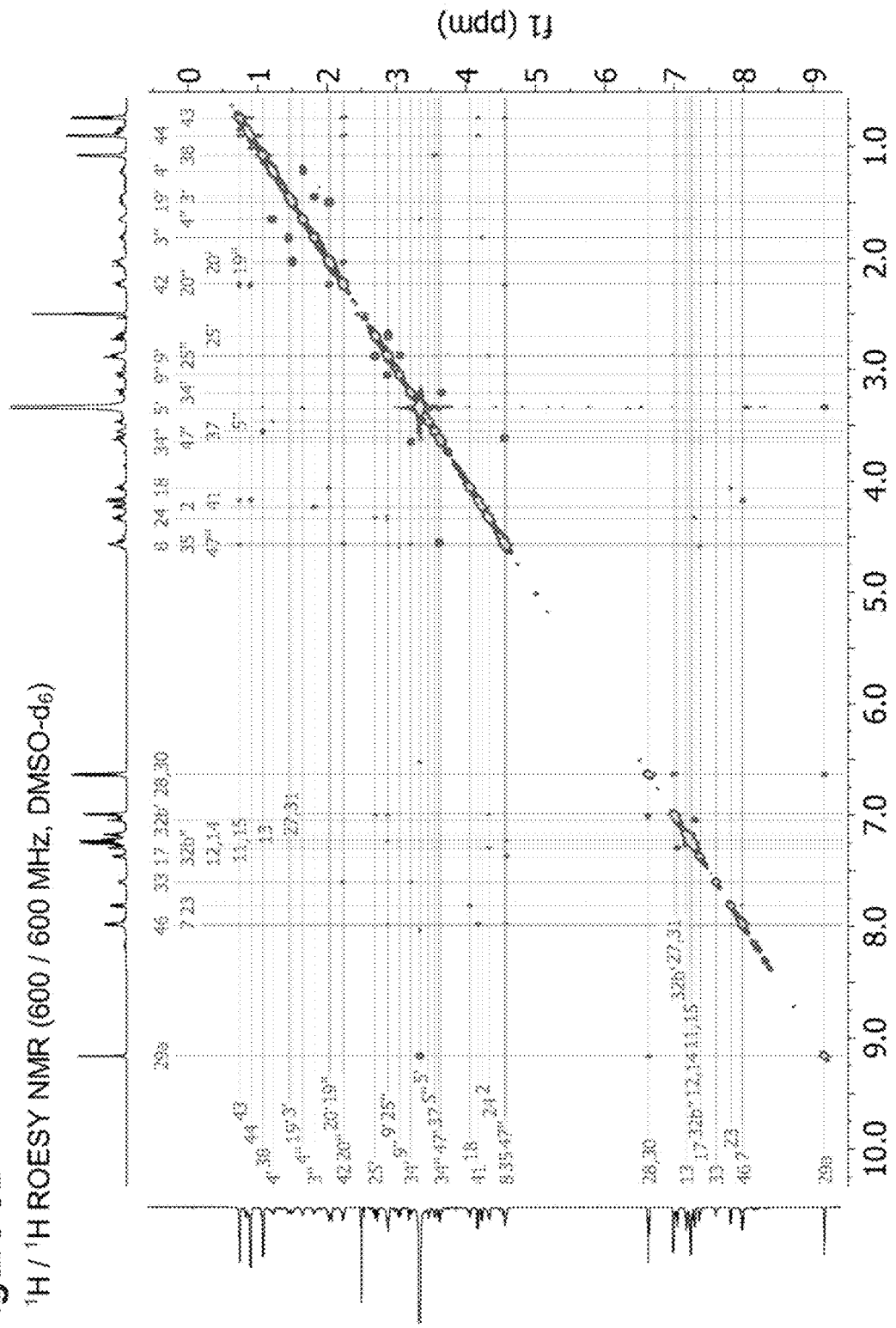

Another unique feature of this reaction is that the reaction generated a new chiral center at the site of macrocyclization with high diastereoselectivity (de>99%), which is in contrast to conventional methods of macrocyclization that lead to C-terminal epimerization (Bielawski C W et al., 2002, Science, 297:2041; Lawson K V et al., 2013, Proc. Natl. Acad. Sci. USA, 110:E3753; Royo-Gracia S et al, 2009, Future Med. Chem., 1:1289; Skropeta D et al, 2004, J, Org. Chem., 69:8804; Ehrlich A et al., 1996, J. Org. Chem., 61:8831). The absolute configuration of a new chiral center in the 4-imidazolidinone cyclic peptide cyc(AVGPFEY) (SEQ ID NO: 13) 2a was (R) and was determined by ROESY NMR spectroscopy (FIG. 2C and FIG. 9).

Figures 10, 10A:
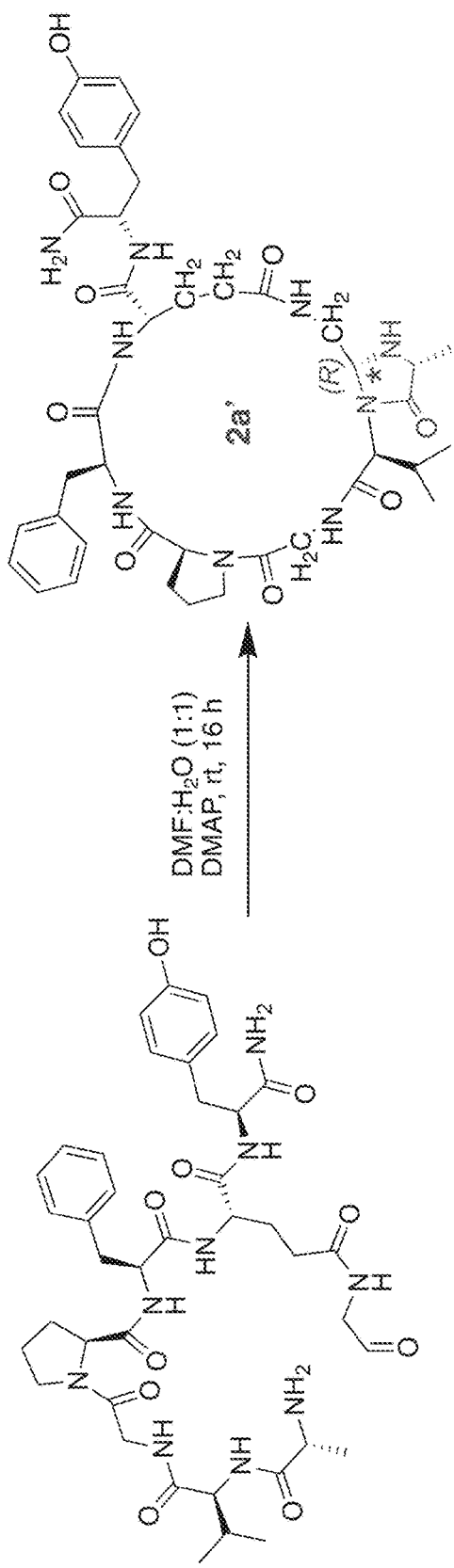
Figures 10, 10D:
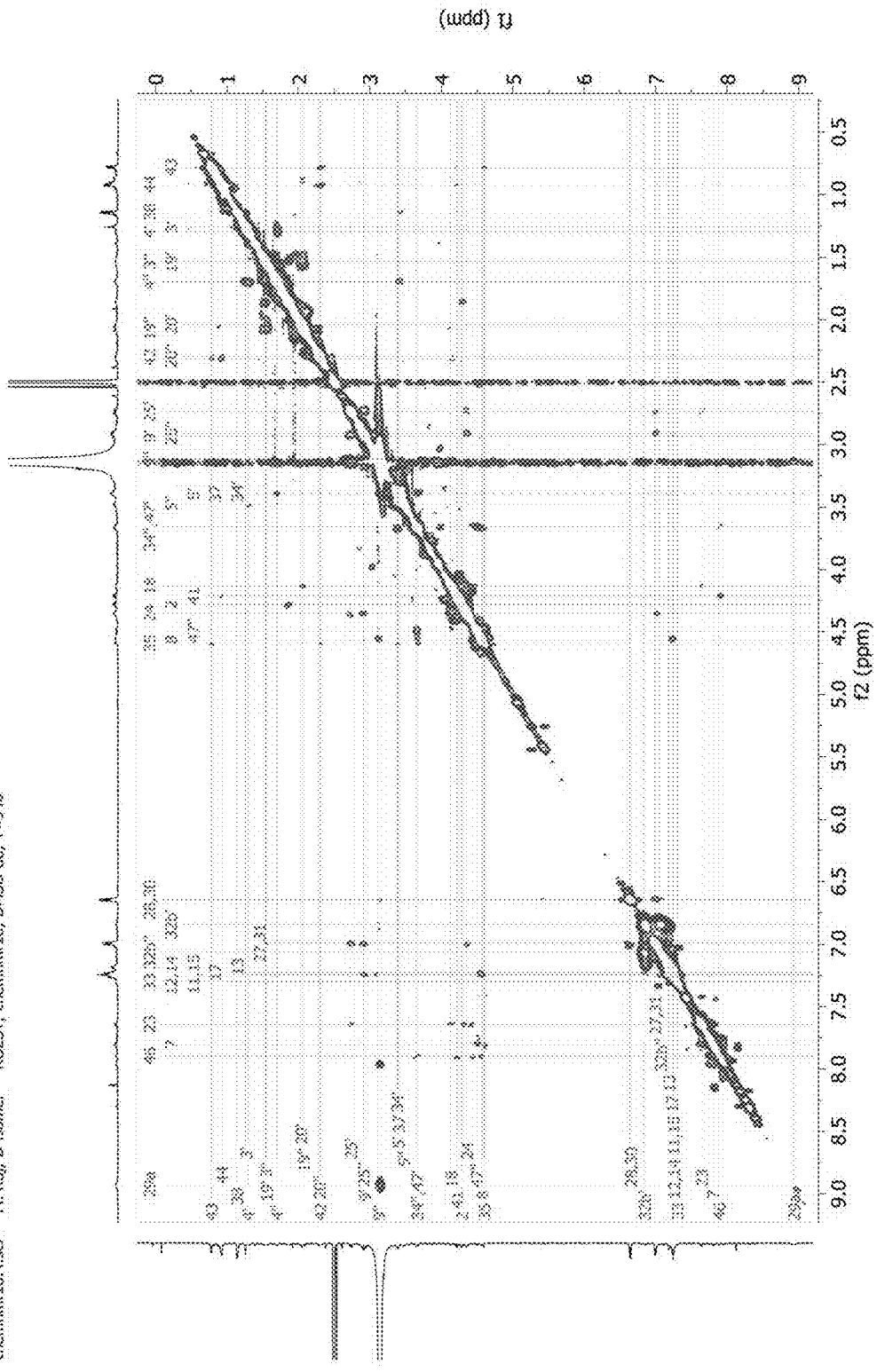
Figures 10, 10E:
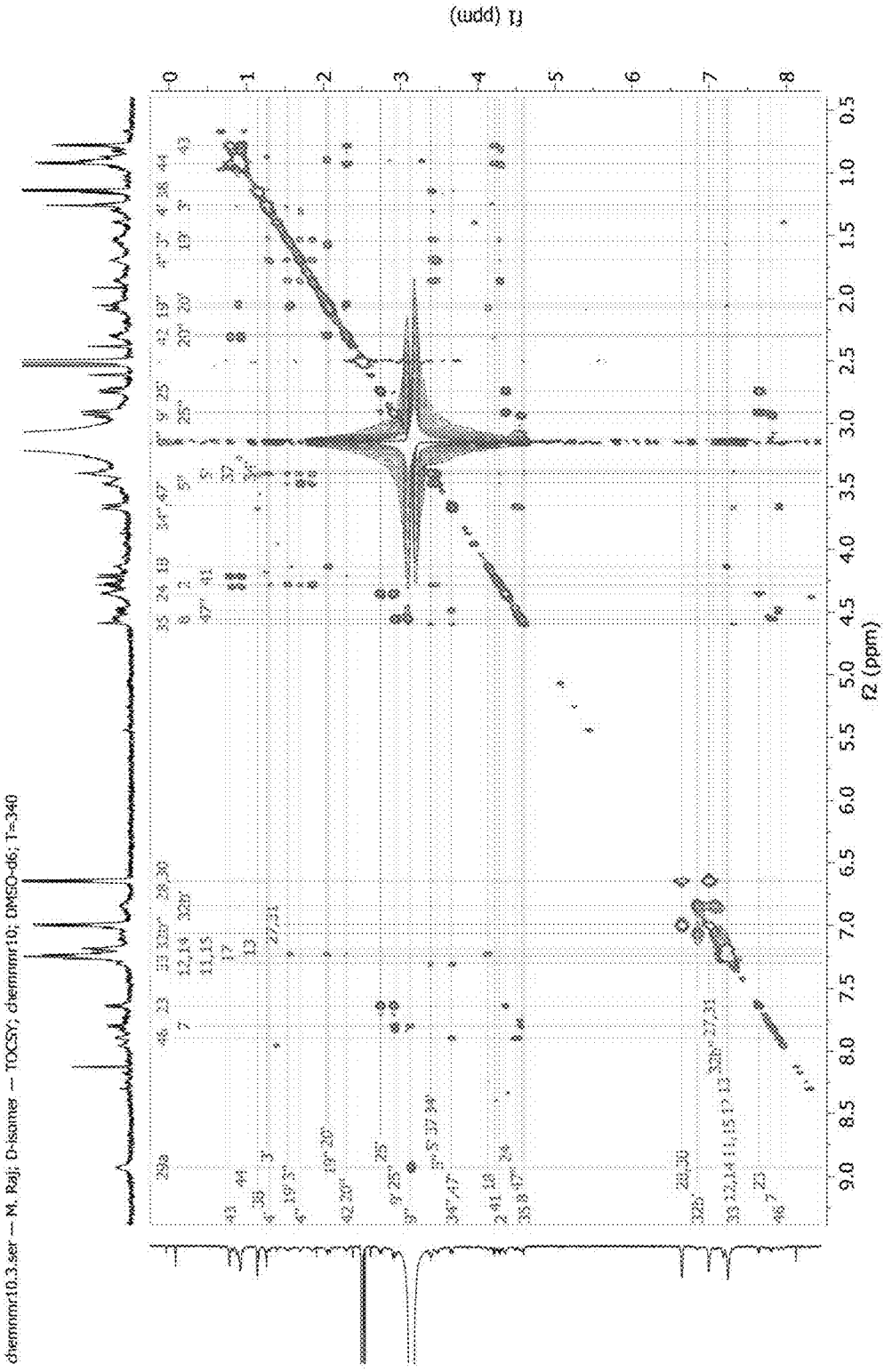
Figures 11, 11A:
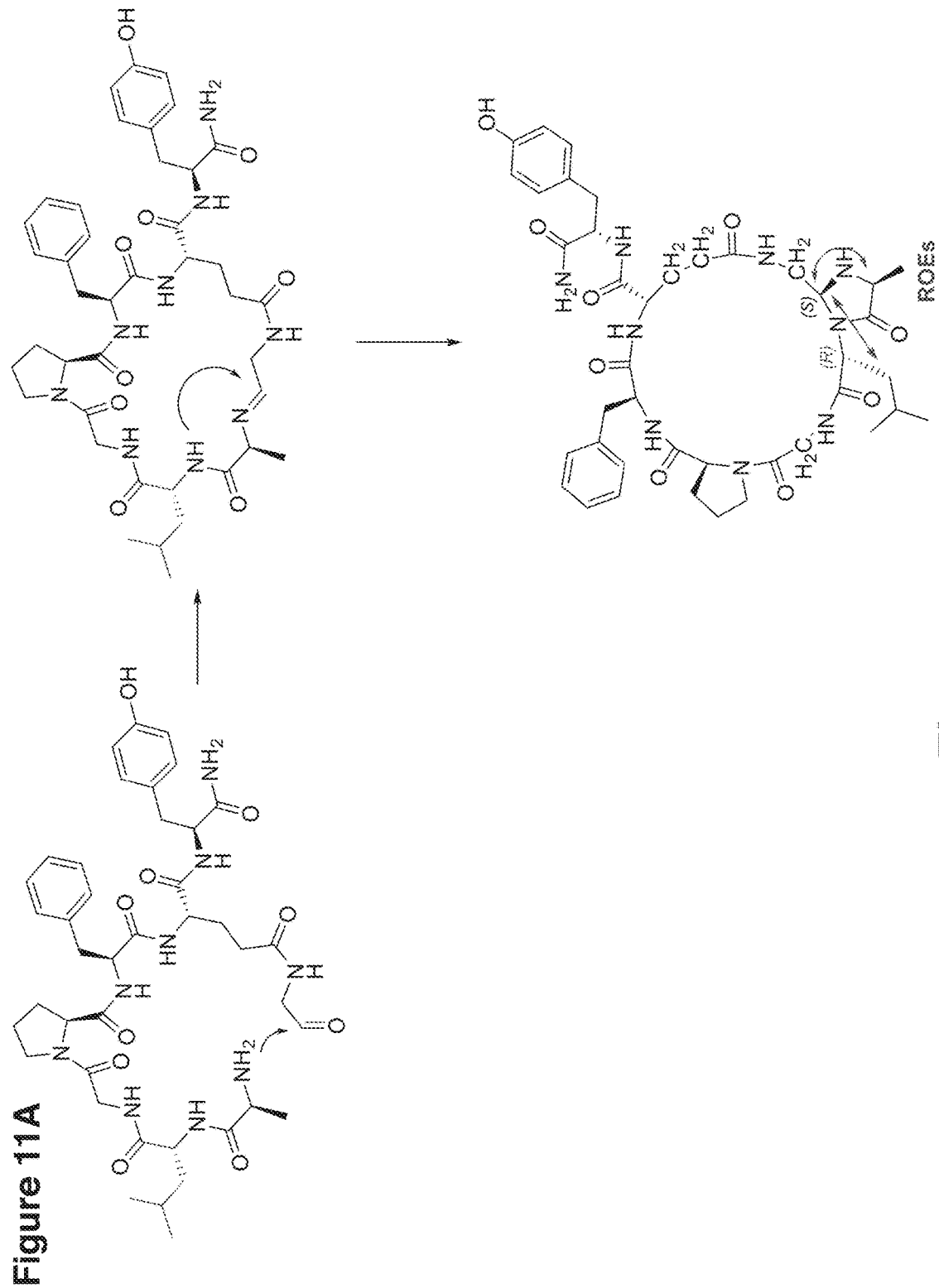
Figures 11, 11B:
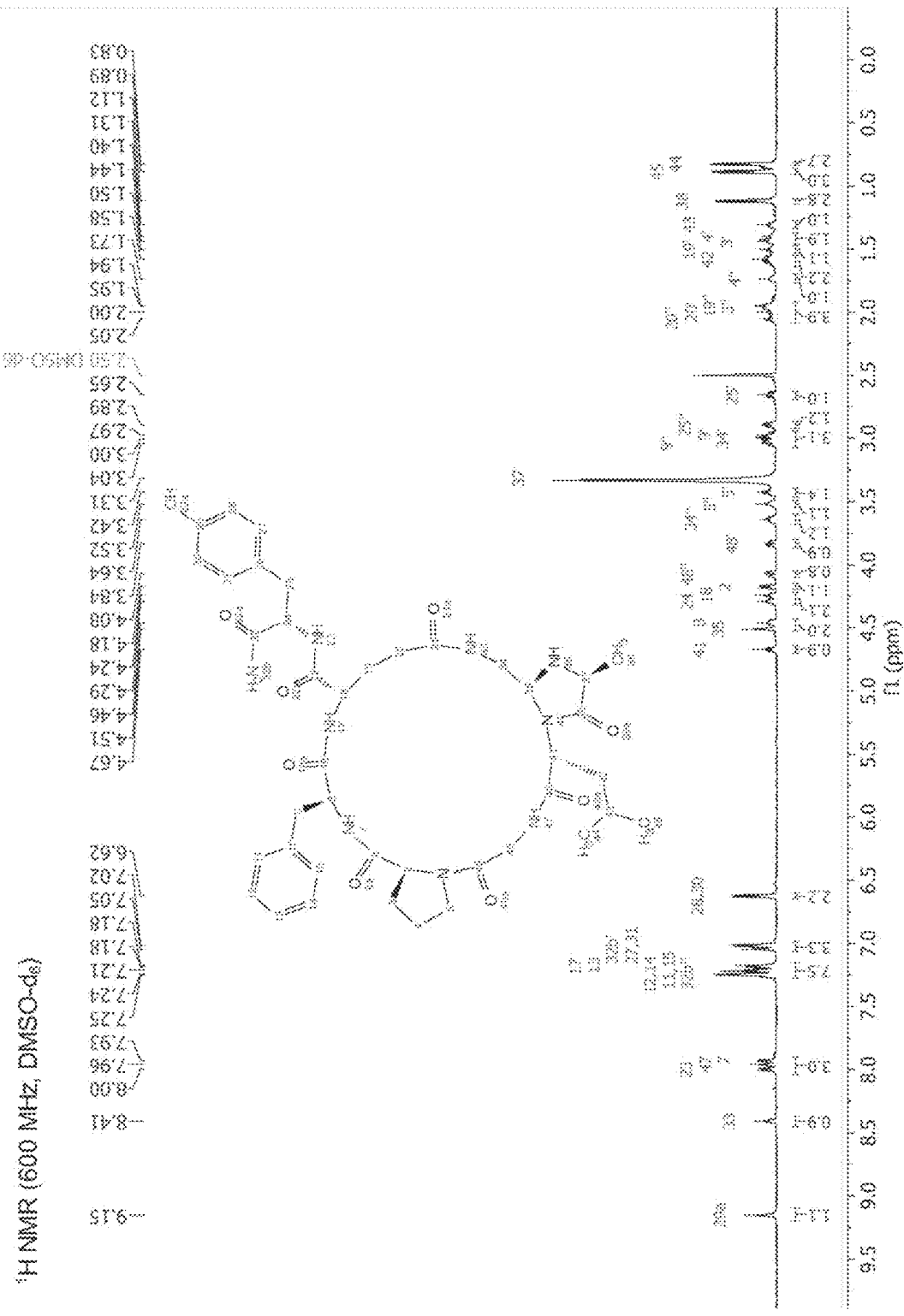
Figures 11, 11C:
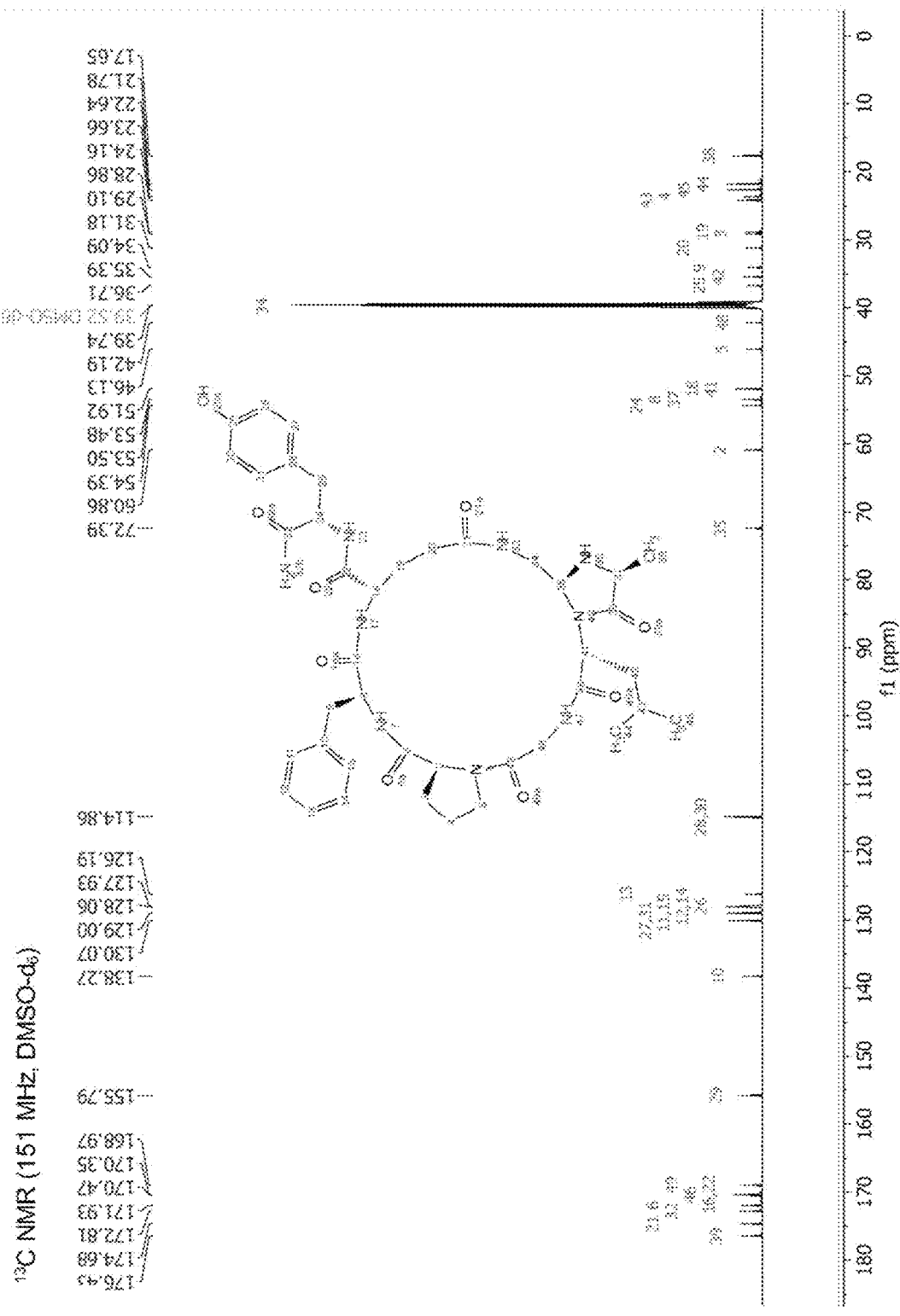
Figures 11, 11D:
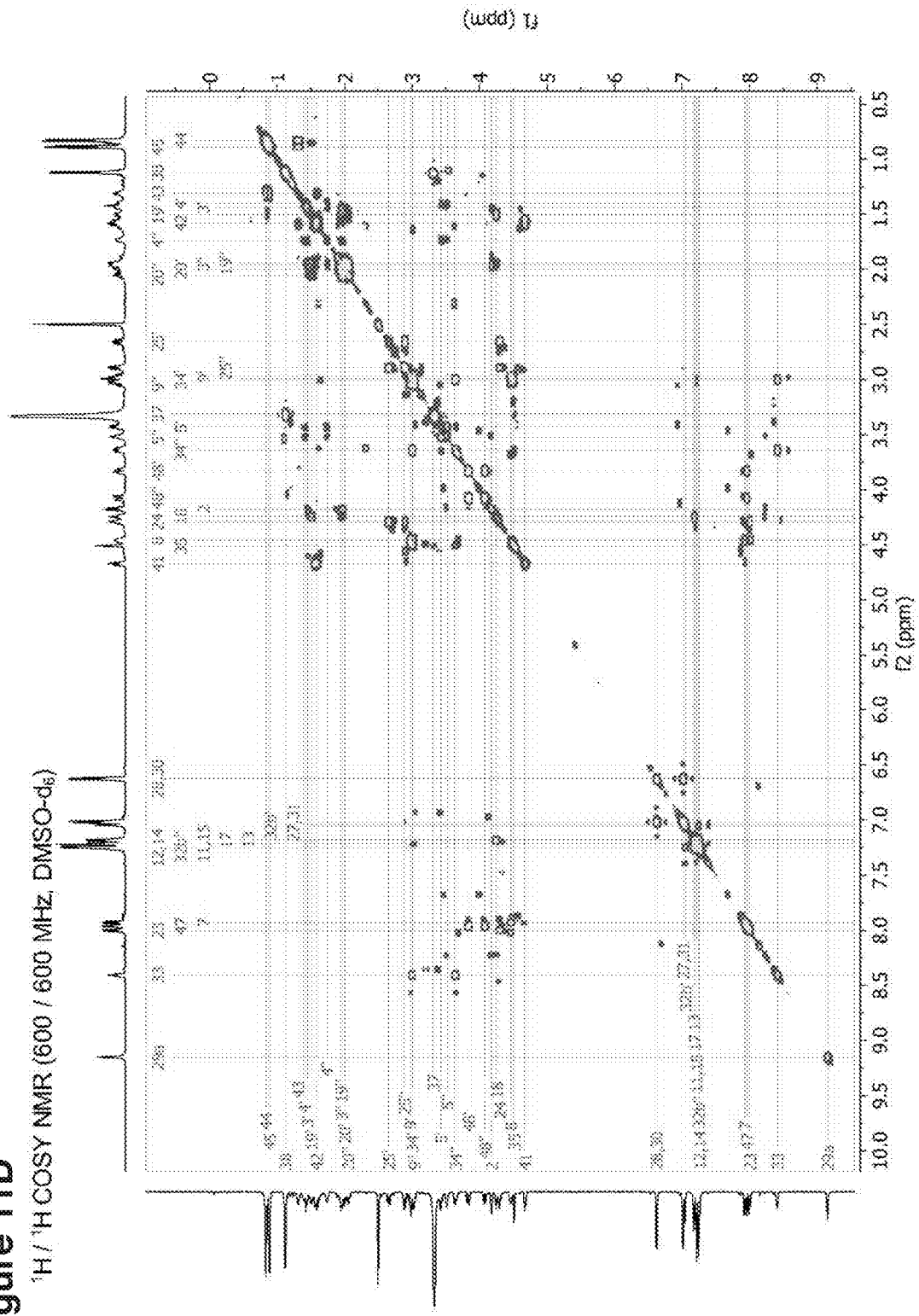
Figures 11, 11E:
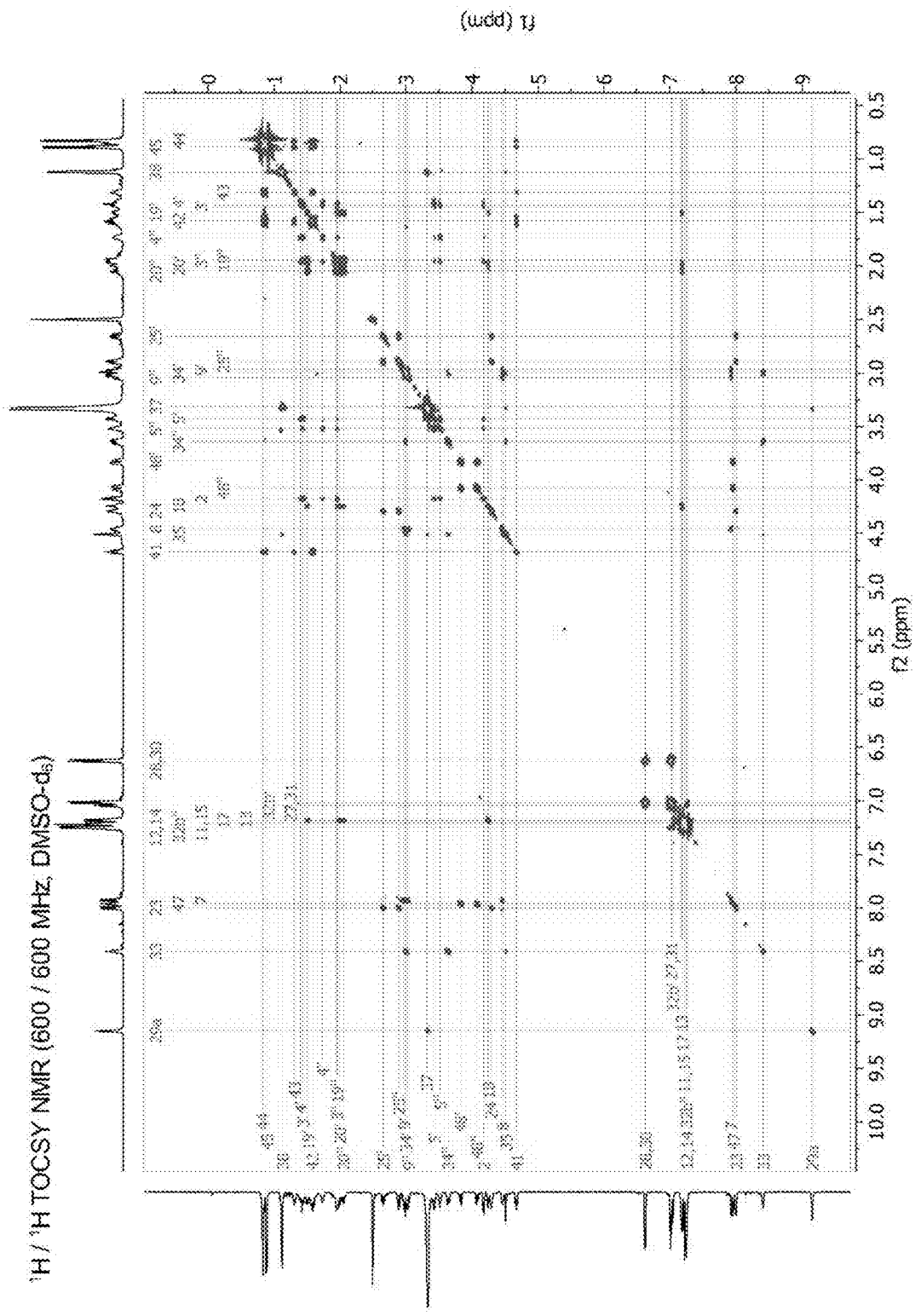
Figures 11, 11F:
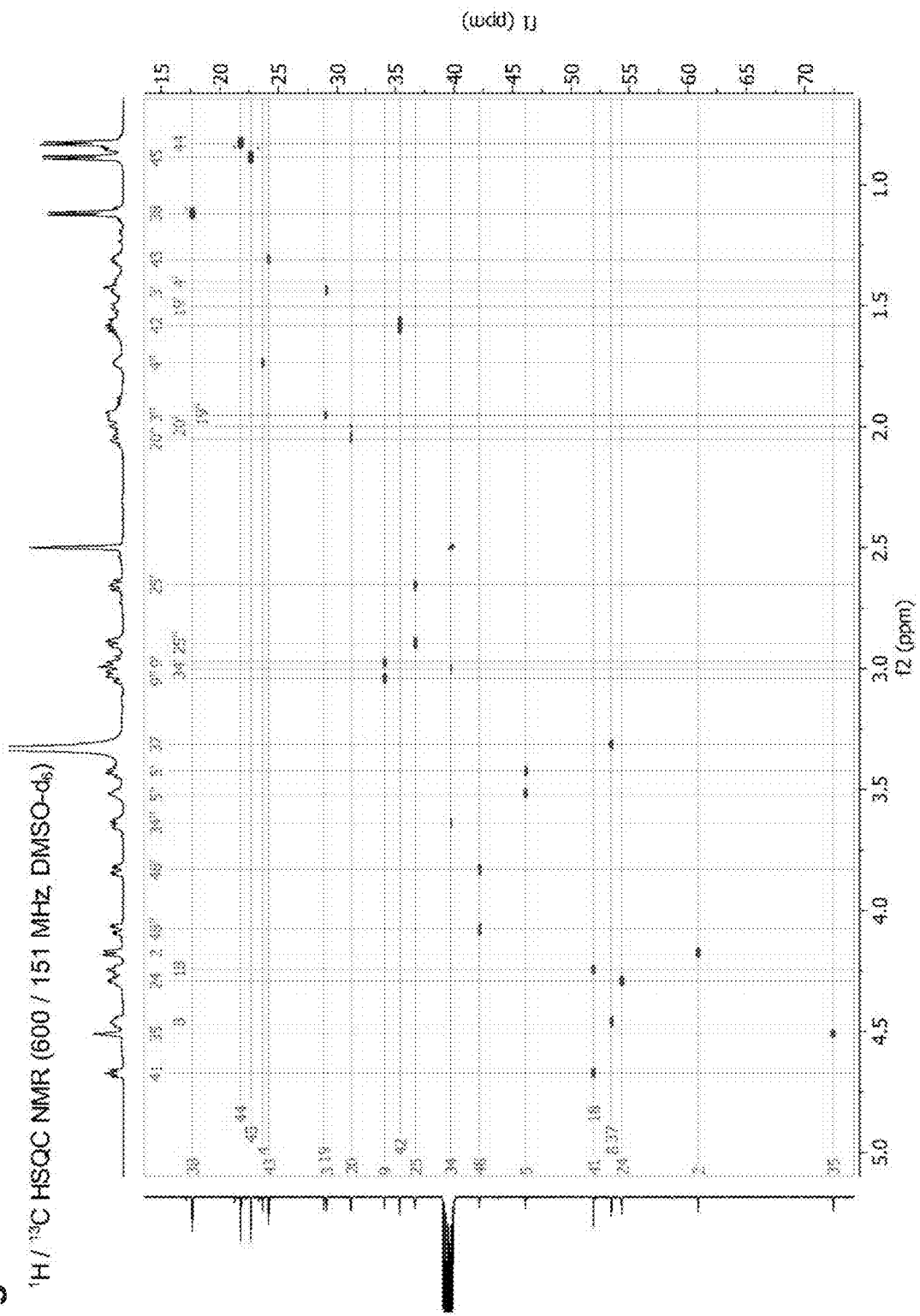
Figures 11, 11G:
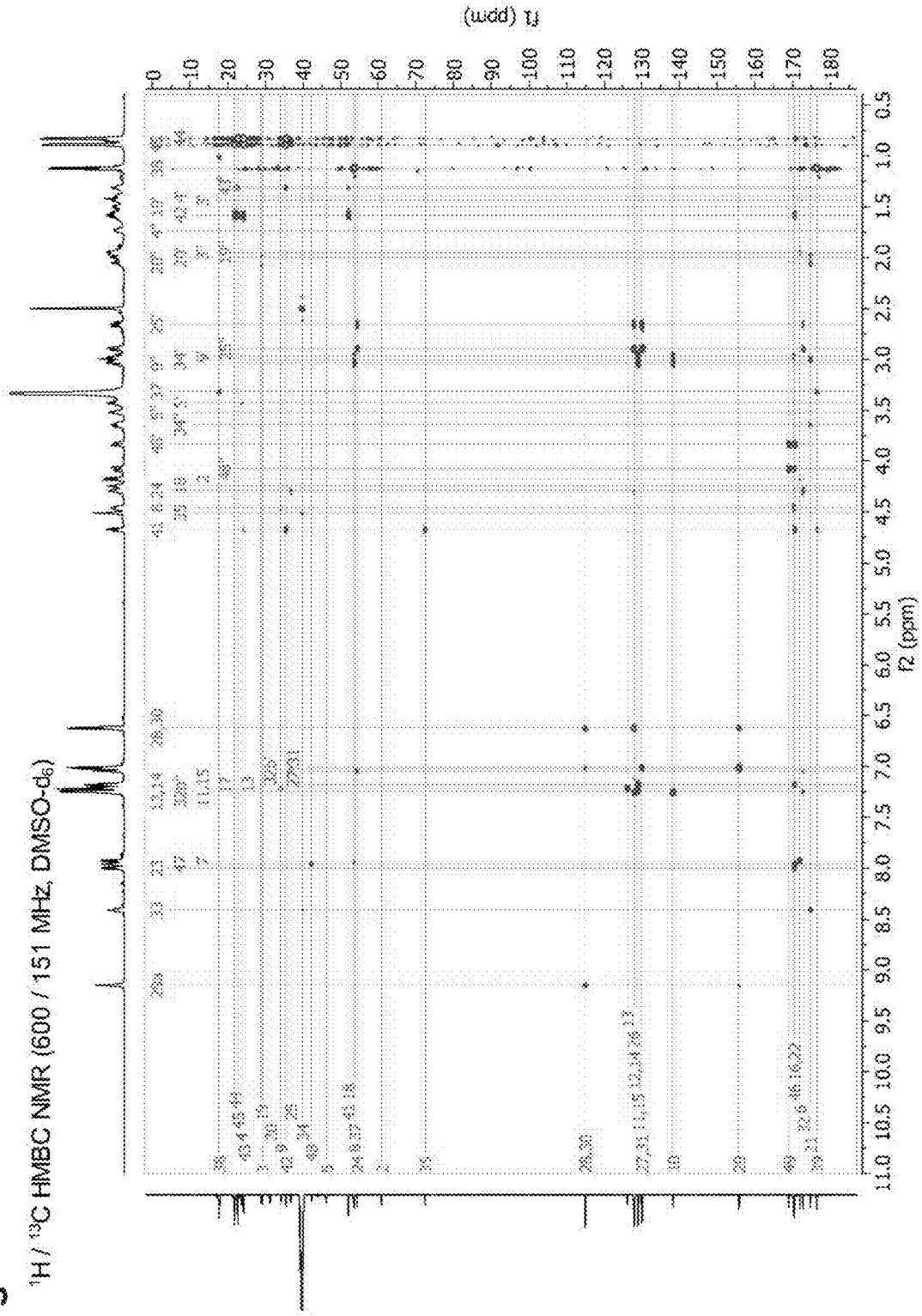
Figures 11, 11I:
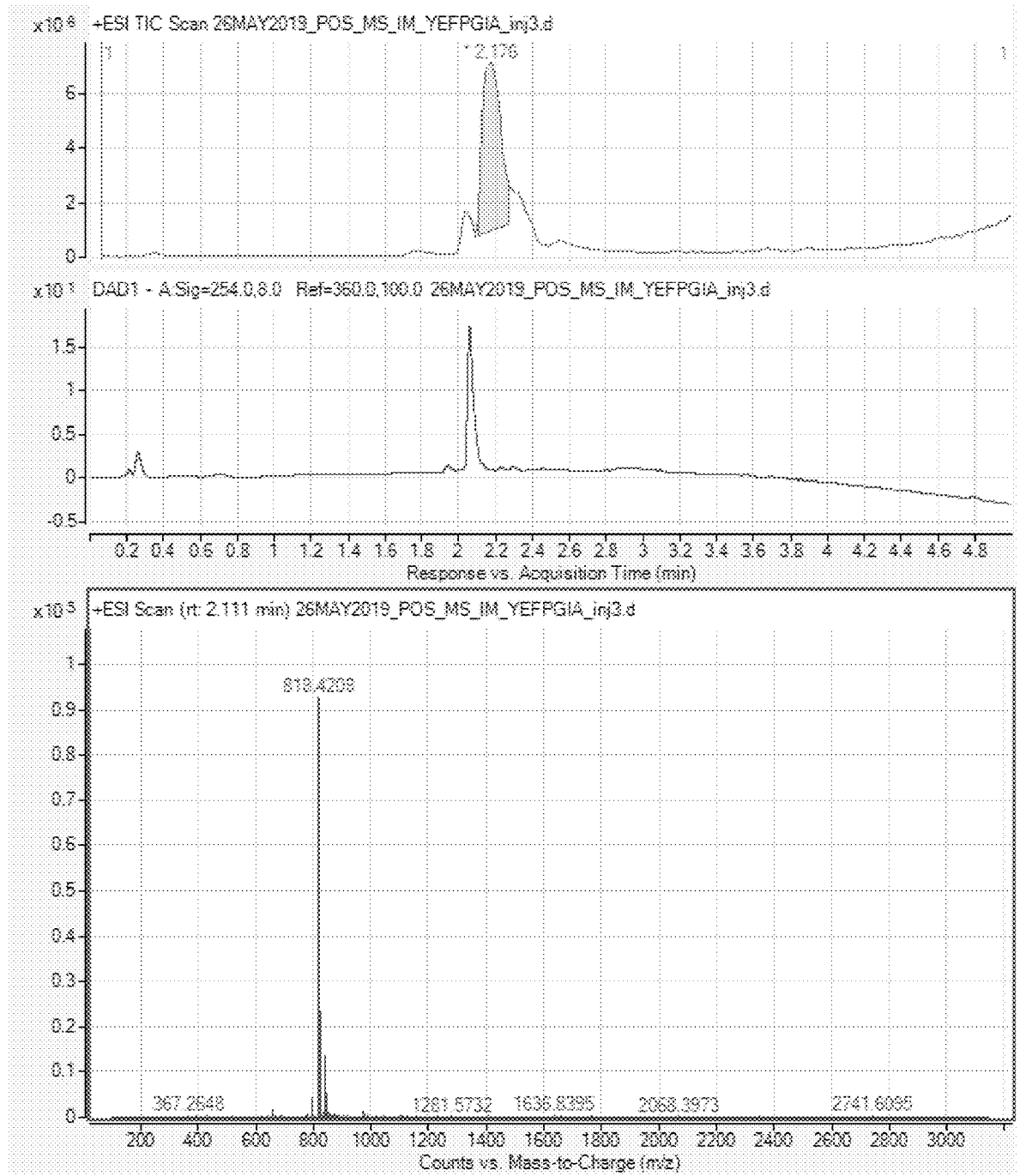

To determine the source of the high stereoselectivity of the CyClick reaction, NMR analysis of another cyclic peptide cyc(aVGPFEY) (SEQ ID NO: 13) 2a' containing D-Ala at the N-terminus was conducted. The results showed the formation of a new chiral center with (R)-configuration (de>99%) (FIG. 10), indicating that the configuration of the N-terminal amino acid was not responsible for directing the configuration of the new chiral center. Next, a cyclic peptide cyc(AiGPFEY) (SEQ ID NO: 46) with a d-Ile at the second position was synthesized and the corresponding spectroscopic data established that the configuration of the new chiral center in the cyclic peptide is (S) (FIG. 11 and Table 3).

TABLE 3

Representative NMR data for cyc(AiGPFE(CHO)Y) (SEQ ID NO: 46)

| Residue | Atom Name | Numbering | $\delta_H$ (ppm), multiplicity | $\delta_C$ (ppm) |
|---|---|---|---|---|
| Pro | N | 1 | — | — |
| | C$_\alpha$H | 2 | 4.18, d (J = 9.1 Hz) | 60.86 |
| | C$_\beta$H$_2$ | 3 | 1.44, m; 1.95, m | 29.10 |
| | C$_\gamma$H$_2$ | 4 | 1.40, m; 1.73, m | 23.66 |
| | C$_\delta$H$_2$ | 5 | 3.42, q (J = 8.5 Hz); 3.52, t (J = 8.1 Hz) | 46.13 |
| | CO | 6 | — | 171.93 |
| Phe | NH | 7 | 7.93, d (J = 8.2 Hz) | — |
| | C$_\alpha$H | 8 | 4.46, ddd (J = 13.5, 8.3, 4.9 Hz) | 53.50 |
| | C$_\beta$H$_2$ | 9 | 2.97, m; 3.04, dd (J = 14.3, 4.5 Hz) | 34.09 |
| | C$_1$ | 10 | — | 138.27 |
| | C$_2$H, C$_6$H | 11, 15 | 7.21, d (J = 7.2 Hz) | 129.00 |
| | C$_3$H, C$_5$H | 12, 14 | 7.25, t (J = 7.2 Hz) | 128.06 |
| | C$_4$ | 13 | 7.18, t (J = 6.5 Hz) | 126.19 |
| | CO | 16 | — | 170.35 |
| Glu | NH | 17 | 7.18, d (J = 7.4 Hz) | — |
| | C$_\alpha$H | 18 | 4.24, td (J = 8.3, 3.0 Hz) | 51.92 |
| | C$_\beta$H$_2$ | 19 | 1.50, m; 1.95, m | 28.86 |
| | C$_\gamma$H$_2$ | 20 | 2.00, m; 2.05, m | 31.21 |
| | C$_\delta$O | 21 | — | 174.68 |
| | CO | 22 | — | 170.35 |
| Tyr | NH | 23 | 8.00, d (J = 8.4 Hz) | — |
| | C$_\alpha$H | 24 | 4.29, td (J = 8.8, 4.9 Hz) | 54.39 |
| | C$_\beta$H$_2$ | 25 | 2.65, dd (J = 13.8, 9.4 Hz); 2.89, dd (J = 13.9, 5.0 Hz) | 36.70 |
| | C$_1$ | 26 | — | 127.93 |
| | C$_2$H, C$_6$H | 27, 31 | 7.02, d (J = 8.1 Hz) | 130.07 |
| | C$_3$H, C$_5$H | 28, 30 | 6.62, d (J = 7.9 Hz) | 114.86 |
| | C$_4$OH | 29 | 9.15, s | 155.79 |
| | CONH$_2$ | 32 | 7.05, s; 7.24, s | 172.81 |
| Linker | NH | 33 | 8.41, t (J = 6.0 Hz) | — |
| | C$_\alpha$H$_2$ | 34 | 3.00, m; 3.64 dd (J = 14.8, 7.6 Hz) | 39.74 |
| | C$_\beta$H | 35 | 4.51, s | 72.39 |
| Ala | NH | 36 | — | — |
| | C$_\alpha$H | 37 | 3.31, m | 53.48 |
| | C$_\beta$H$_3$ | 38 | 1.12, d (J = 6.8 Hz) | 17.65 |
| | CO | 39 | — | 176.43 |
| Ile | N | 40 | — | — |
| | C$_\alpha$H | 41 | 4.67, dd (J = 9.2, 6.6 Hz) | 51.92 |
| | C$_\beta$H | 42 | 1.58, m | 35.39 |
| | C$_\gamma$H | 43 | 1.31, p (J = 6.6 Hz) | 24.16 |
| | C$_{\delta 1}$H$_3$, C$_{\delta 2}$H$_3$ | 44, 45 | 0.83, d (J = 6.5 Hz); 0.89, d (J = 6.6 Hz) | 21.78, 22.64 |
| | CO | 46 | | 170.46 |

TABLE 3-continued

Representative NMR data for cyc(AiGPFE(CHO)Y) (SEQ ID NO: 46)

| Residue | Atom Name | Numbering | $\delta_H$ (ppm), multiplicity | $\delta_C$ (ppm) |
|---|---|---|---|---|
| Gly | NH | 47 | 7.96, dd (J = 5.6 Hz) | — |
| | $C_\alpha H_2$ | 48 | 3.83, dd (J = 16.6, 5.9 Hz); 4.08, dd (J =16.9, 5.3 Hz) | 42.16 |
| | CO | 49 | — | 168.95 |

This validated that high stereoselectivity and the configuration of the new chiral center in cyclic peptides was conferred by the configuration of the second amino acid, which directed nucleophilic attack of the amidic nitrogen on the cyclic inline intermediate from the Si face. Attack from the Re face were hindered due to the bulky Val residue (FIG. 2D).

Macrocyclization vs Oligomerization

One of the major limitations with current methods for peptide cyclization is their tendency to undergo intermolecular reactions to generate linear dimers, linear trimers, cyclodimers, and cyclotrimers (Bielawski C W et al., 2002, Science, 297:2041; Lawson K V et al., 2013, Proc. Natl. Acad. Sci. USA, 110:E3753; Royo-Gracia S et al., 2009, Future Med. Chem. 2009, 1, 1289; Skropeta D et al., 2004, J. Org. Chem., 69:8804; Ehrlich A et al., 1996, J. Org. Chem., 61:8831). Conventional macrocyclization reactions are carried out at high dilution, on the order of $10^{-4}$ M or greater, to limit the formation of side products such as dimers or oligomers (Malesevic M et al., 2004, J. Biotechnol., 112:73; Wessjohann L A et al., 2017, Angew. Chem. Int. Ed., 56:3501; Marti-Centelles V et al., 2015, Chem. Rev., 115:8736). Unfortunately, high dilution leads to long reaction times, which in turn promotes unwanted background processes, such as epimerization. Some strategies have been reported for the synthesis of cyclic peptides in solution at high concentrations; however, they are limited by their ability to undergo intermolecular reactions, require protected amino acids, such as Lys or Glu/Asp, to avoid side reactions, and lead to the formation of a mixture of diastereoisomers (Hili R et al., 2010, J. Am. Chem. Soc., 132: 2889; Frost J R et al., 2016, Nat, Chem., 8:1105).

In contrast, the unique feature of the herein-described approach is that the synthesis worked in intramolecular fashion only. Thus, the macrocyclization of a linear peptide AVGPFE-(CHO)Y (SEQ ID NO: 13) 1a was carried out using high concentrations (25 mM, 25 times higher than usually employed) and compared it with a conventional method of macrocyclization (reductive animation, FIG. 12 and FIG. 13; Matins L R et al., 2017, J. Am. Chem. Soc., 139:5233).

Figure 12:
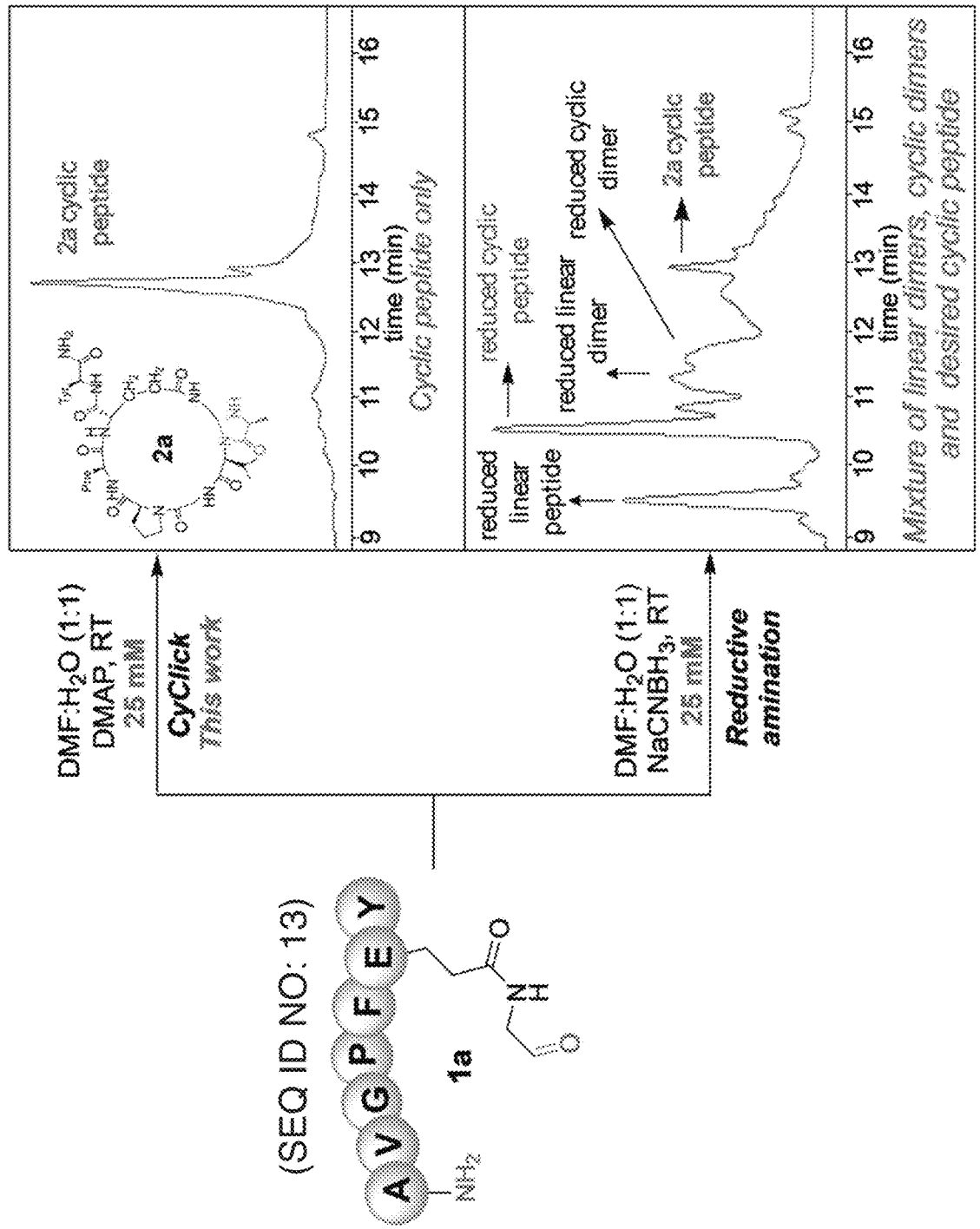
FIG. 12 depicts a schematic representation of macrocyclization vs oligomerization pathways demonstrating direct comparison of CyClick reaction and reductive animation approach for the synthesis of cyclic peptide at high concentrations (25 mm) and chromatograms of the crude reaction mixtures.
Figure 13:
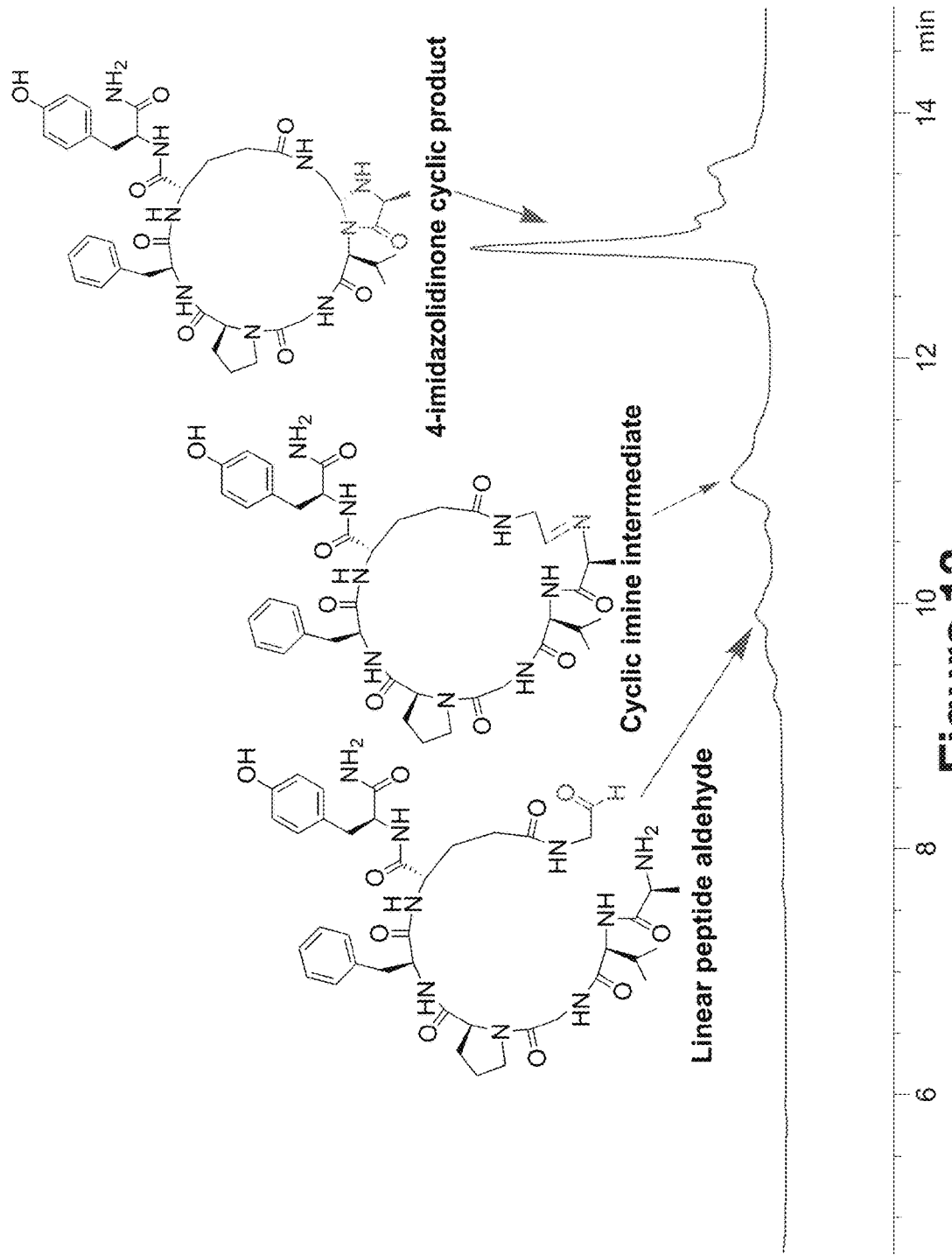
FIG. 13 depicts a representative HPLC trace of high concentration reaction by CyClick Method (100 mM).

Insights into the impact of CyClick chemistry on the efficiency of macrocyclization at high concentrations were revealed by LC-MS analysis (FIG. 12), In the conventional reductive animation approach (Frost J R et al., 2016, Nat. Chem., 8:1105) for the cyclization of linear peptide 1a at high concentration (25 mM), significant quantities of unwanted linear dimers and cyclodimers were produced (FIG. 12, bottom chromatogram). In contrast, the cyclization of the linear peptide 1a by CyClick chemistry at high concentration (25 mM) generated the desired cyclic peptide 2a with high conversion (98%) (FIG. 12, top chromatogram). The major corresponding by-products were not seen even in trace quantities (FIG. 12, top chromatogram). Thus, a significant improvement in macrocyclization was realized by using the CyClick approach. The macrocyclization of linear peptide AVGPFE(CHO)Y (SEQ ID NO: 13) 1a at 100 mM concentration with 21 equiv, of DMAP was also conducted and stirred for 8 h at room temperature. The reaction generated only the desired cyclic peptide 2a with high conversion (89%) under the reaction conditions without the formation of any side products due to dimerization and oligomerization (HPLC trace of the reaction, FIG. 13).

Figure 14:
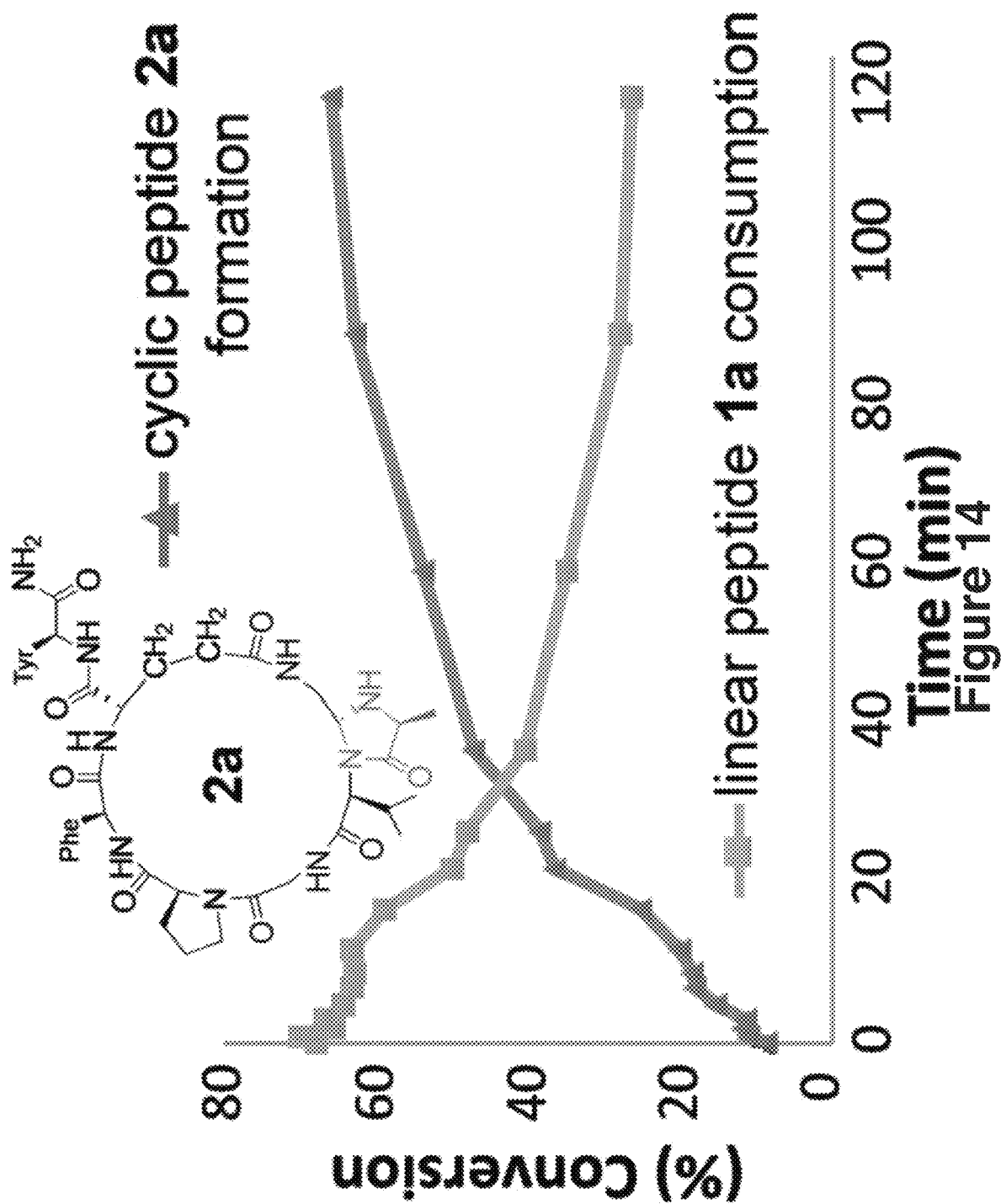
FIG. 14 depicts a representative results demonstrating rate studies for the synthesis of cyclic peptide 2a by CyClick chemistry. Peptides were quantified by HPLC.
Figure 15:
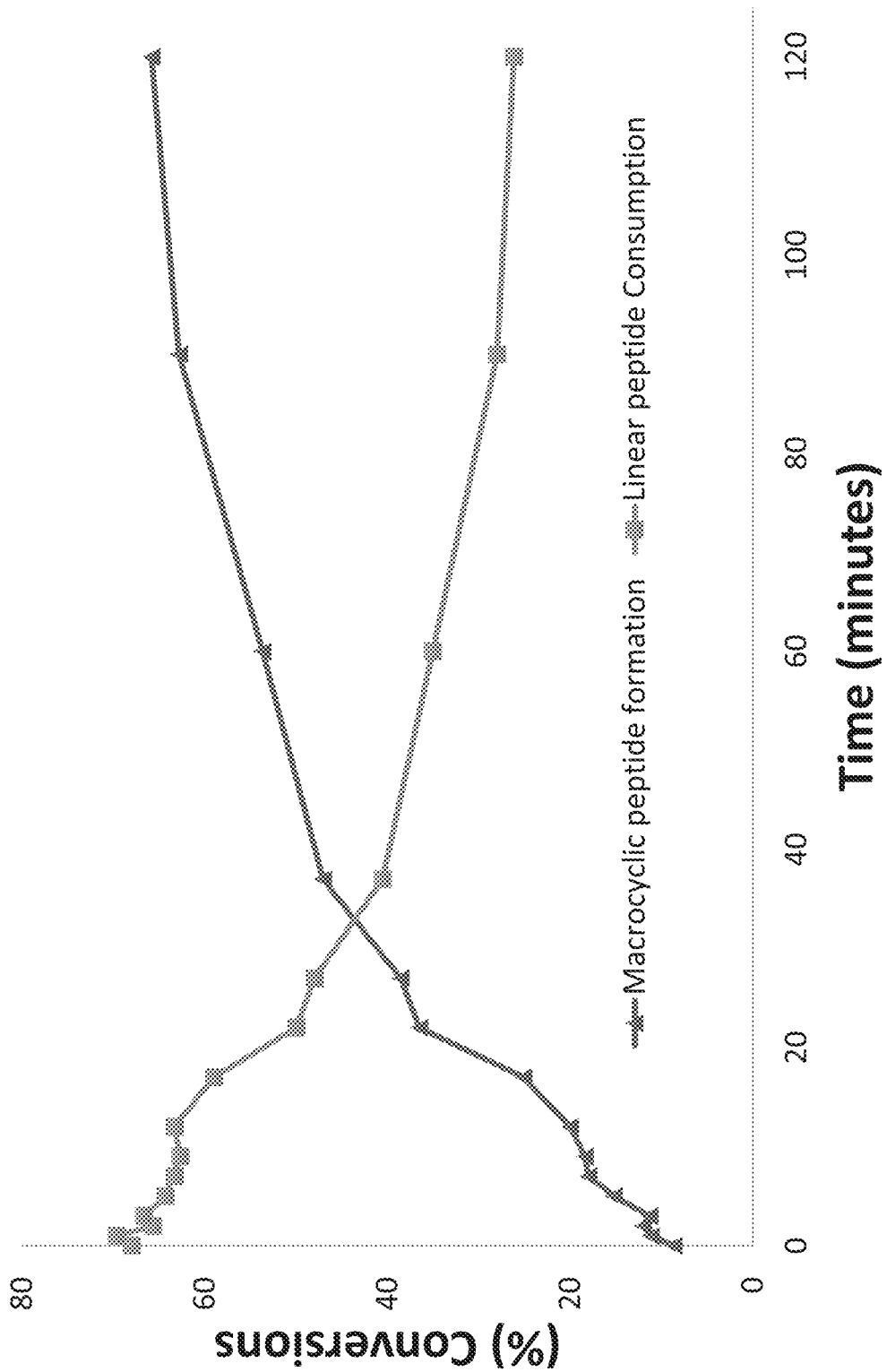
FIG. 15 depicts representative results of rate studies for macrocyclization of peptide 1a to 2a by CyClick chemistry.

To gain a deeper understanding of reaction rates and the products formed, time-course studies on linear peptide AVGPFE(CHO)Y (SEQ ID NO: 13) 1a were undertaken. For this investigation, quantitative monitoring was carried out by injecting samples for HPLC analysis at regular time intervals. The peptide AVGPFE(CHO)Y (SEQ ID NO: 13) 1a (0.67 mM) was subjected to the CyClick reaction and conversion was monitored over 4 h. From the data, it is clear that the initial rate of the formation of a cyclic peptide 2a was considerably fast with >80% conversion achieved in 4 h (FIG. 14, FIG. 15, and Table 4).

TABLE 4

Rate Studies for Macrocyclization of Peptide 1a to 2a by CyClick Chemistry.

| Time (min) | Macrocyclic peptide 2a formation Trial 1 | Macrocyclic peptide 2a formation Trial 2 | Macrocyclic peptide 2a formation Trial 3 | Macrocyclic peptide 2a formation Average of three trials |
|---|---|---|---|---|
| 0 | 9% | 8% | 9% | 8.6% |
| 1 | 11.4% | 10.5% | 11.6% | 11.1% |
| 2 | 12% | 12% | 12% | 12% |
| 3 | 12% | 11% | 11% | 11.3% |
| 5 | 14% | 14.6% | 17% | 15.2% |
| 7 | 17% | 20% | 17% | 18% |
| 9 | 18% | 19.2% | 18% | 18.4% |
| 12 | 20.6% | 19.4% | 20% | 20% |
| 17 | 24% | 24% | 27.3% | 25.1% |
| 22 | 36% | 37% | 36.5% | 36.5% |
| 27 | 38.2% | 39% | 38.5% | 38.5% |
| 37 | 44.2% | 46% | 51% | 47% |
| 60 | 54.3% | 53% | 53.7% | 53.6% |
| 90 | 63% | 62.5% | 63% | 62.8% |
| 120 | 65% | 65.4% | 67% | 65.8% |
| 250 | 83% | 84% | 83.5% | 83.5% |

Taken together, these studies established that the CyClick reaction employed mild conditions, proceeded quickly, gave higher yields and did not generate any side products, such as linear and cyclic dimers or oligomers, even at high concentrations.

Scope of CyClick Chemistry

Having established the optimal conditions, subsequent studies investigated the generality of CyClick chemistry with different amino acids at the N-terminus. As outlined in FIG. 16, substrates bearing aromatic and aliphatic amino acids at the N-terminus, including Trp, Tyr, and b-branched Val (compound 1b through compound Id) were fully tolerated in this protocol and the corresponding cyclic peptides (compound 2b through compound 2d) were generated with good conversions (37%-84%, FIG. 16A and FIG. 17), Reactions with N-terminal amino acids bearing reactive side chains, such as Gln, Asn, Asp, and Lys (compound 1e through compound 1h) did not interrupt the cyclization process, and afforded desired cyclic peptides (compound 2e through compound 2h) with good conversions(64%-94%, FIG. 16A, compound 2e and 2f NMR—FIG. 5 and FIG. 6, and HRMS—FIG. 17), Surprisingly, linear peptide 1i with serine at the N-terminus generated cyclic peptide 2i' with a fused five-membered bicyclic imidazo[1,5-c]oxazol-7-one (40% conversion) along with the expected 4-imidazolidinone cyclic peptide 2i (60% conversion) under the reaction conditions (H$_2$O/DMF (1:1), DMAP (7 equiv), 25° C., FIG. 16A).

Figures 16, 16C:
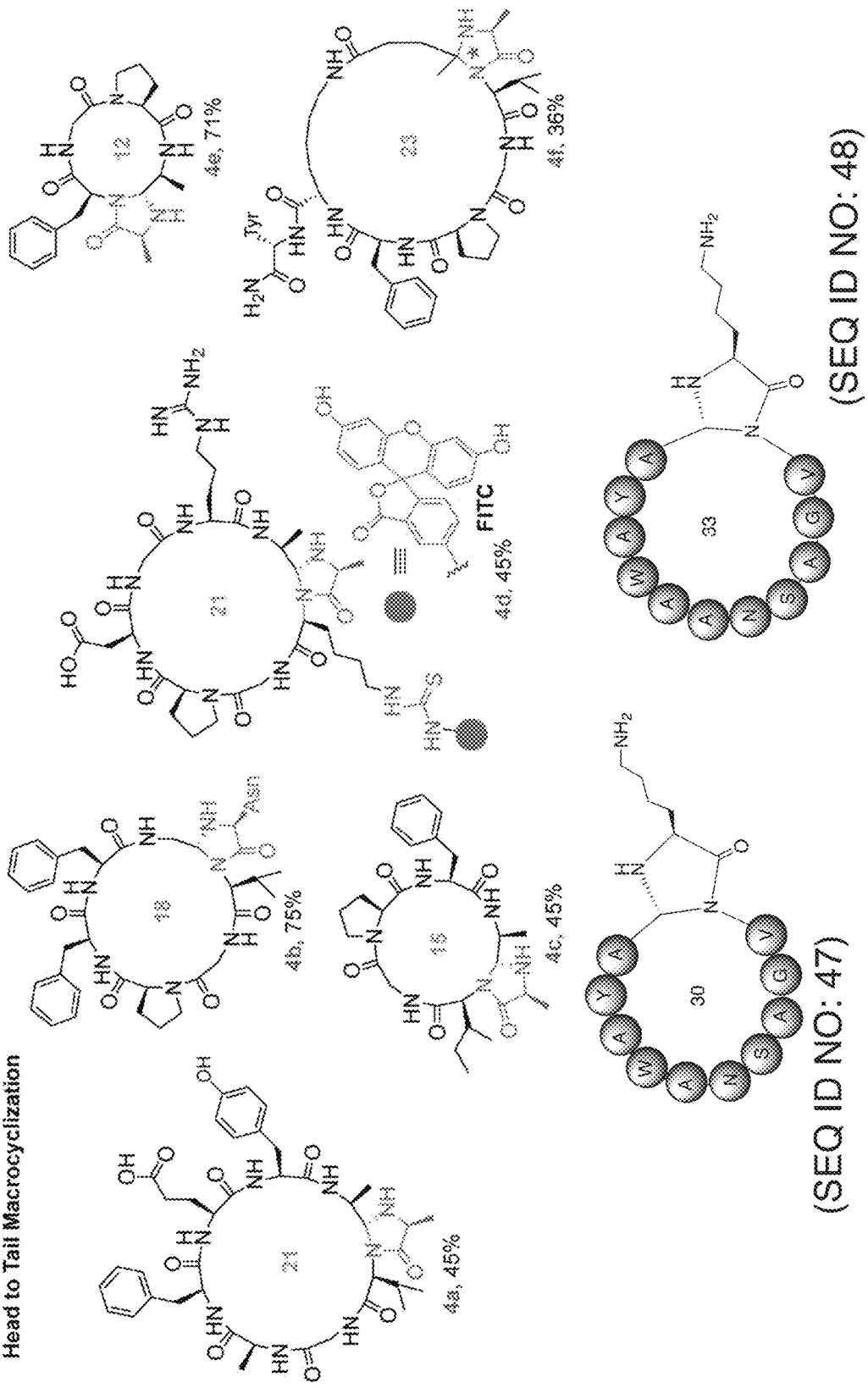
Figure 16:
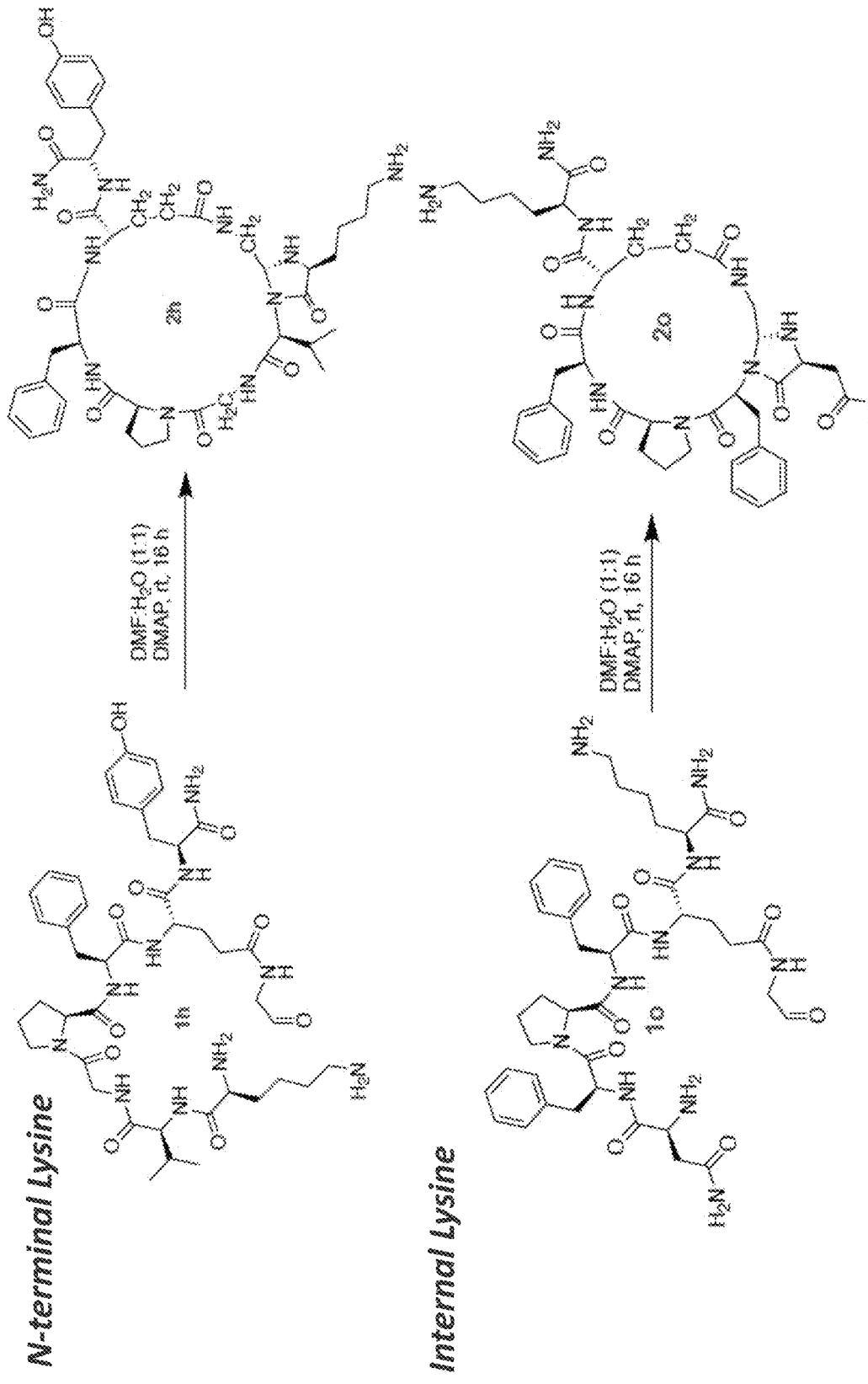
FIG. 16, comprising
Figures 17, 17A:
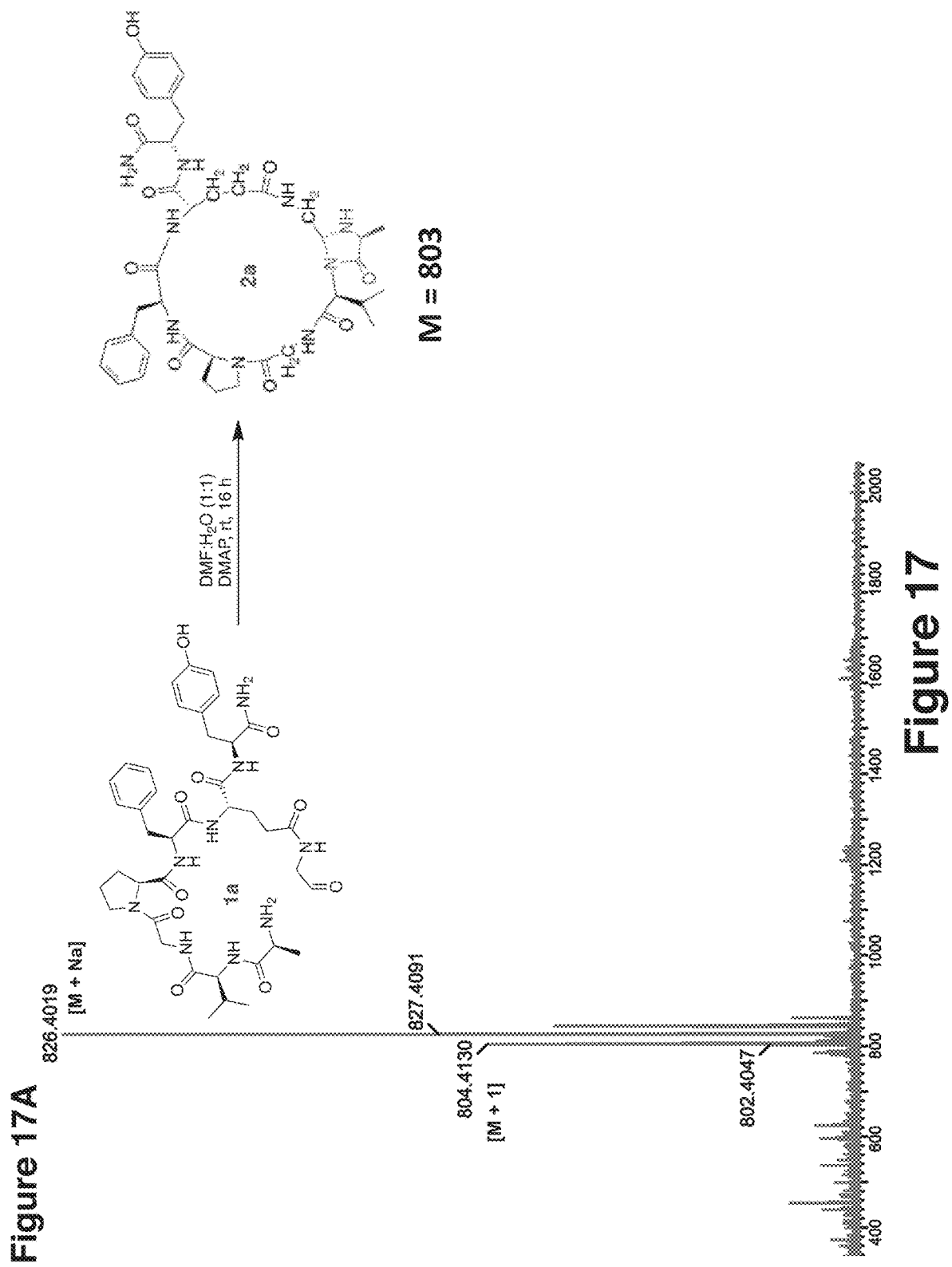
Figures 17, 17B:
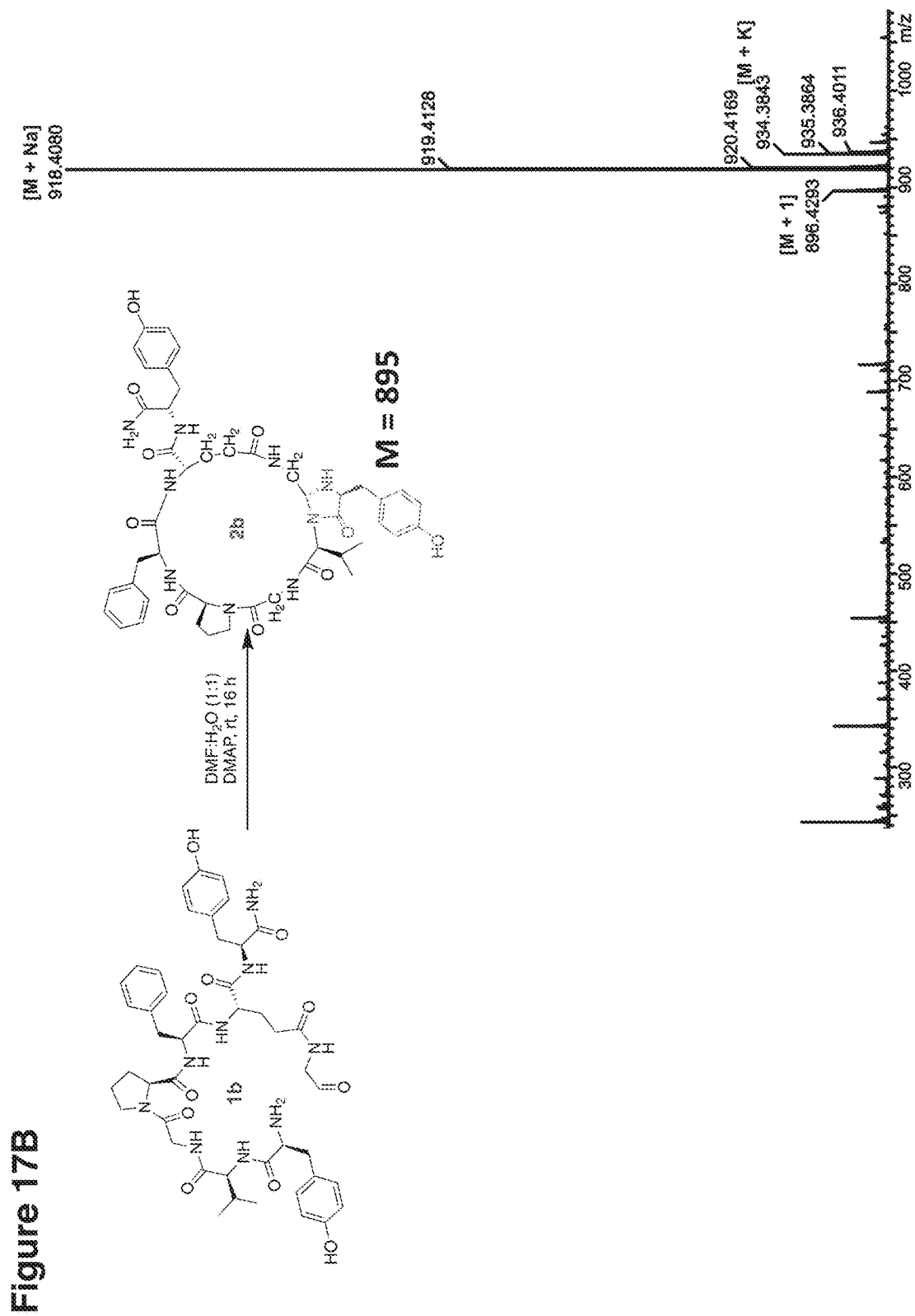
FIG. 17, comprising
FIG. 17B depicts a schematic representation of the synthesis of cyclic peptide 2b and the corresponding HRMS trace. cyc(Tyr-Val-Gly-Pro-Phe-Glu)-Tyr (SEQ ID NO: 15) (2b). LCMS: m/z 896.4 (calcd [M+Na]=896.3), m/z 918.4 (calcd [M+Na]+=918.4), m/z 934.3 (calcd [M+K]+=934.4), Purity: >95% (HPLC analysis at 220 nm). Retention time: 18.3.
Figures 17, 17E:
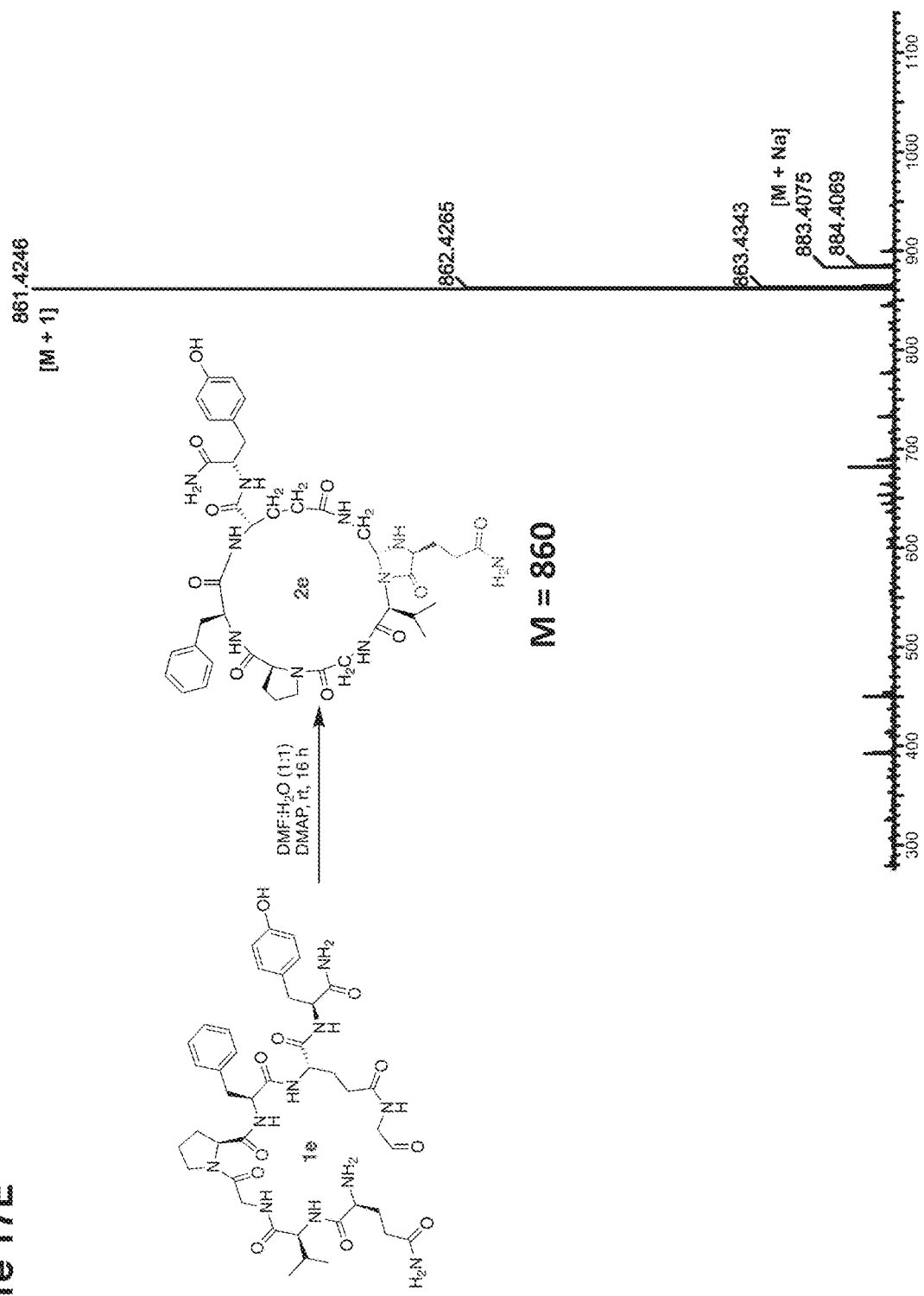
FIG. 17E depicts a schematic representation of the synthesis of cyclic peptide 2e and the corresponding HRMS trace. cyc(Gln-Val-Gly-Pro-Phe-Glu)-Tyr (SEQ ID NO: 18) (2e). LCMS: m/z 861.4 (calcd [M+H]+=861.3), m/z 883.4 (calcd [M+Na]+=883.3), Purity: >95% (HPLC analysis at 220 nm). Retention time: 13.6.
Figures 17, 17F:
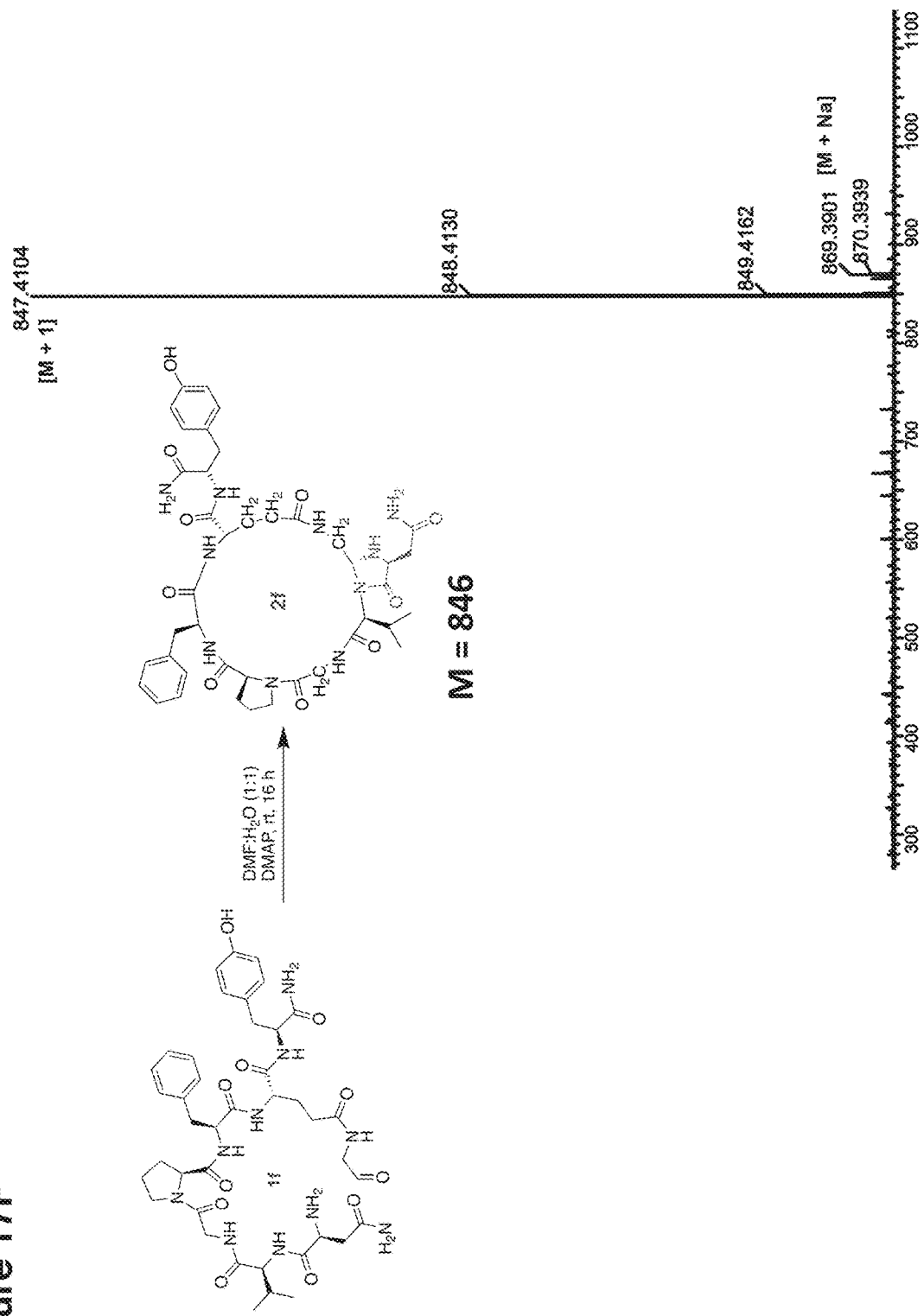
FIG. 17F depicts a schematic representation of the synthesis of cyclic peptide 2f and the corresponding HRMS trace, cyc(Asn-Val-Gly-Pro-Phe-Glu)-Tyr (SEQ ID NO: 19) (2f). LCMS: m/z 847.4 (calcd [M+H]+=847.4), m/z 869.4 (calcd [M+Na]+=869.4), Purity: >95% (HPLC analysis at 220 nm). Retention time: 14.4.
Figure 17:
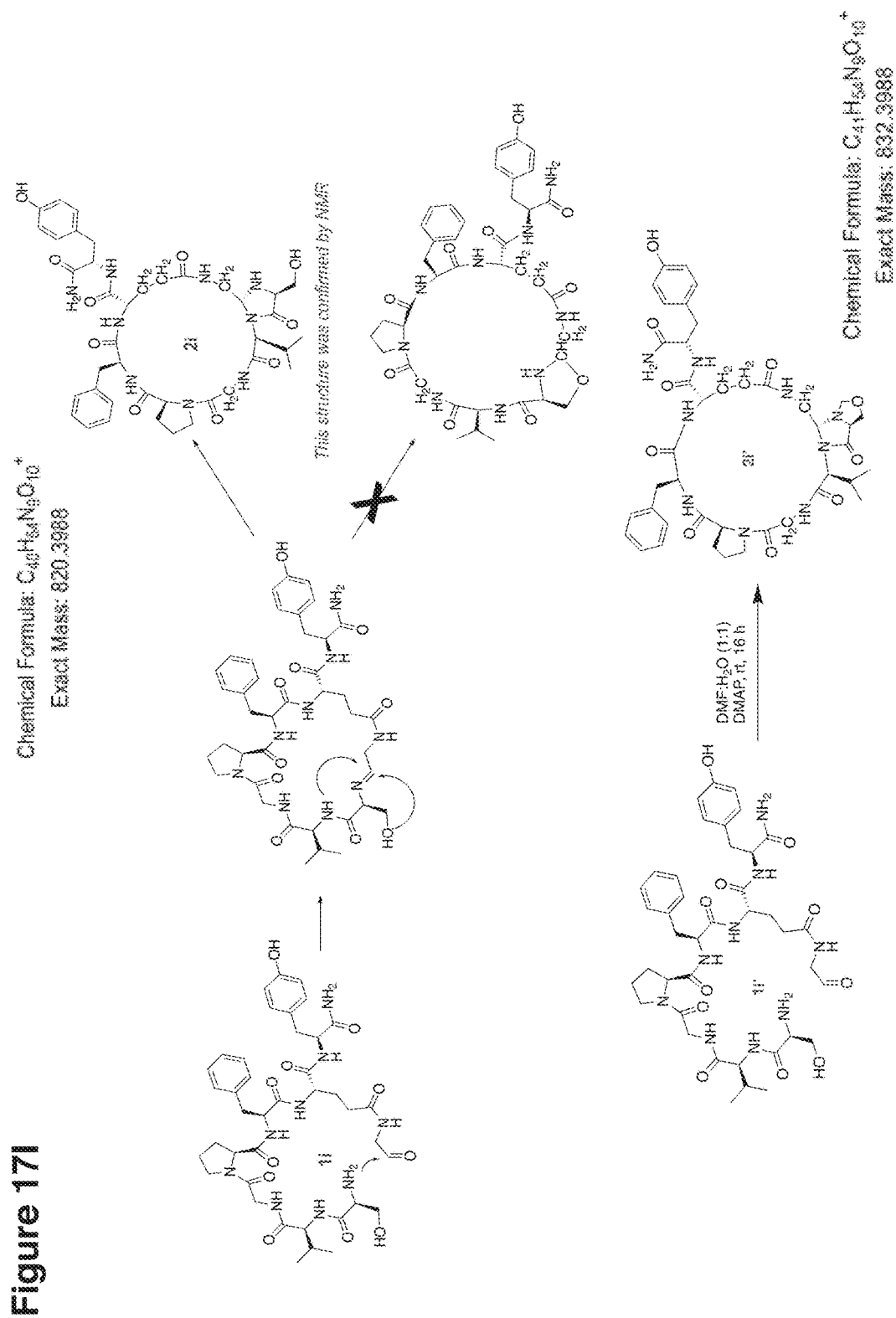
Figures 17, 17K:
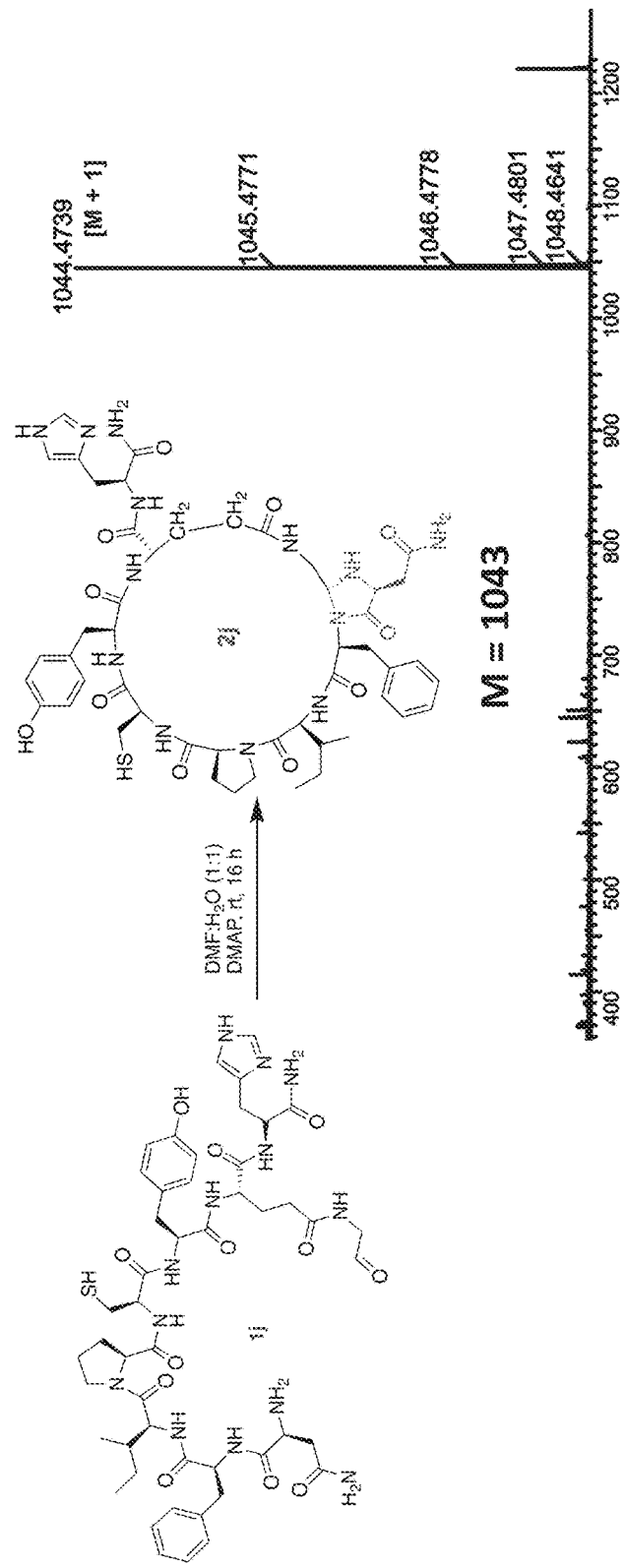
FIG. 17K depicts a schematic representation of the synthesis of cyclic peptide 2j and the corresponding HRMS trace. cyc(Asn-Phe-Ile-Pro-Cys-Tyr-Glu)-His (SEQ ID NO: 23) (2j). LCMS: m/z 1044.5 (calcd [M+H]+1044.4), Purity: >95% (HPLC analysis at 220 nm). Retention time: 16.8.
Figures 17, 17M:
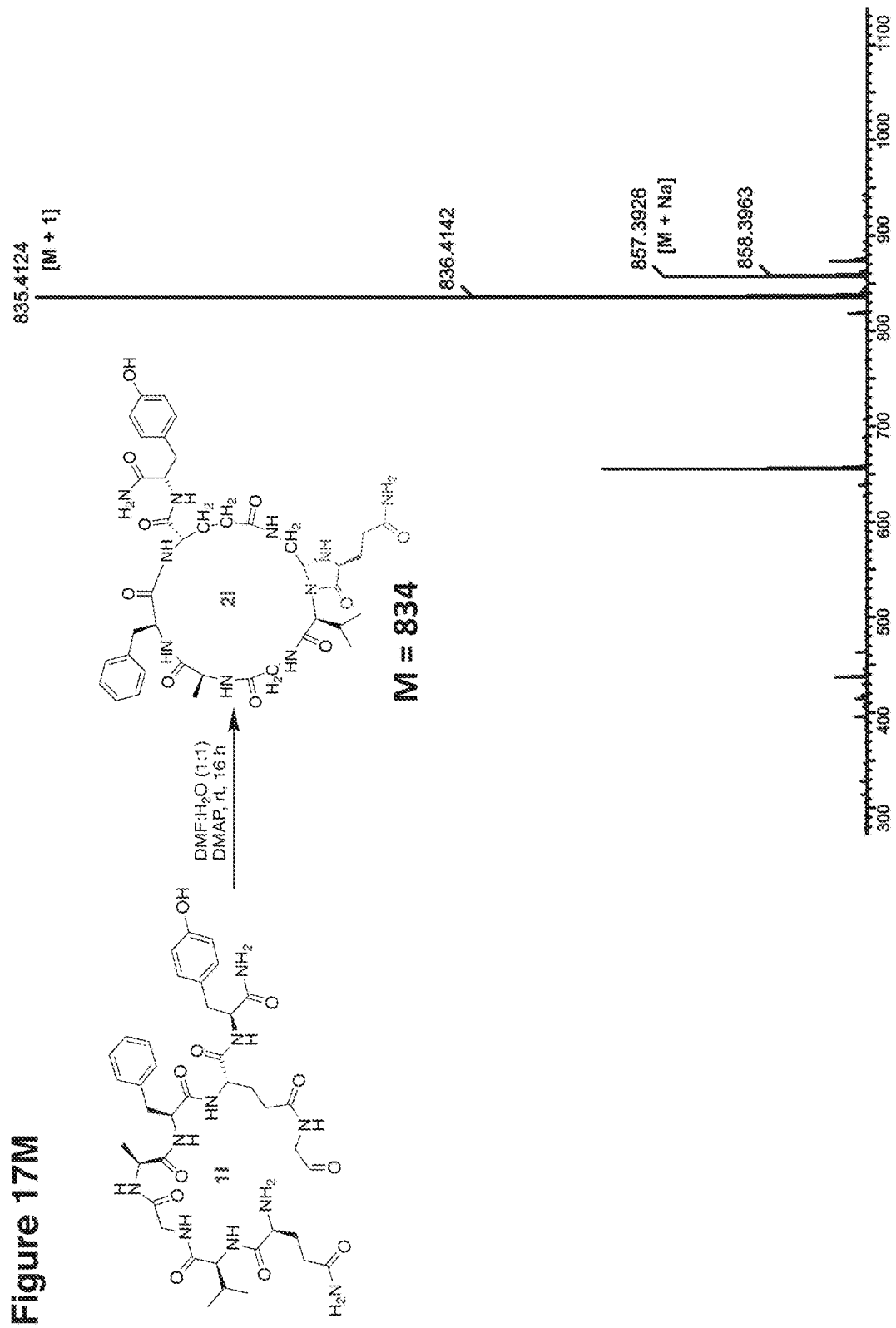
FIG. 17M depicts a schematic representation of the synthesis of cyclic peptide 2l and the corresponding HRMS trace, cyc(Gln-Val-Gly-Ala-Phe-Glu)-Tyr (SEQ ID NO: 25) (2l). LCMS: m/z 835.4 (calcd [M+H]+=835.4), m/z 857.4 (calcd [M+Na]+=857.4), Purity: >95% (HPLC analysis at 220 nm). Retention time: 12.5.
Figure 17N:
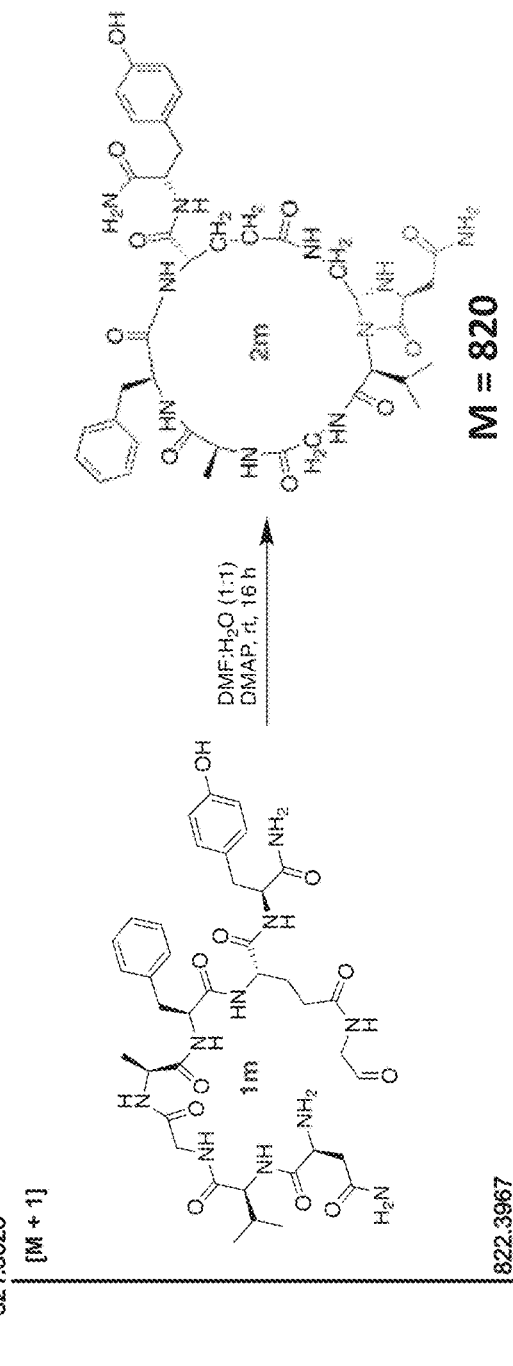
FIG. 17N depicts a schematic representation of the synthesis of cyclic peptide 2m and the corresponding HRMS trace. cyc(Asn-Val-Gly-Ala-Phe-Glu)-Tyr (SEQ ID NO: 26) (2m). LCMS: m/z 821.4 (calcd [M+H]+=821.4), m/z 844.4 (calcd [M+H]+=844.4), Purity: >95% (HPLC analysis at 220 nm). Retention time: 12.4.
Figure 17:
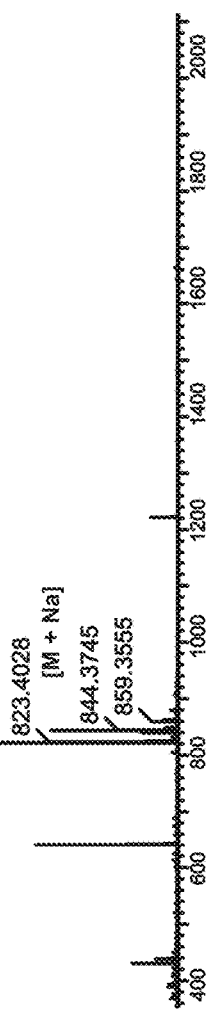
Figures 17, 17O:
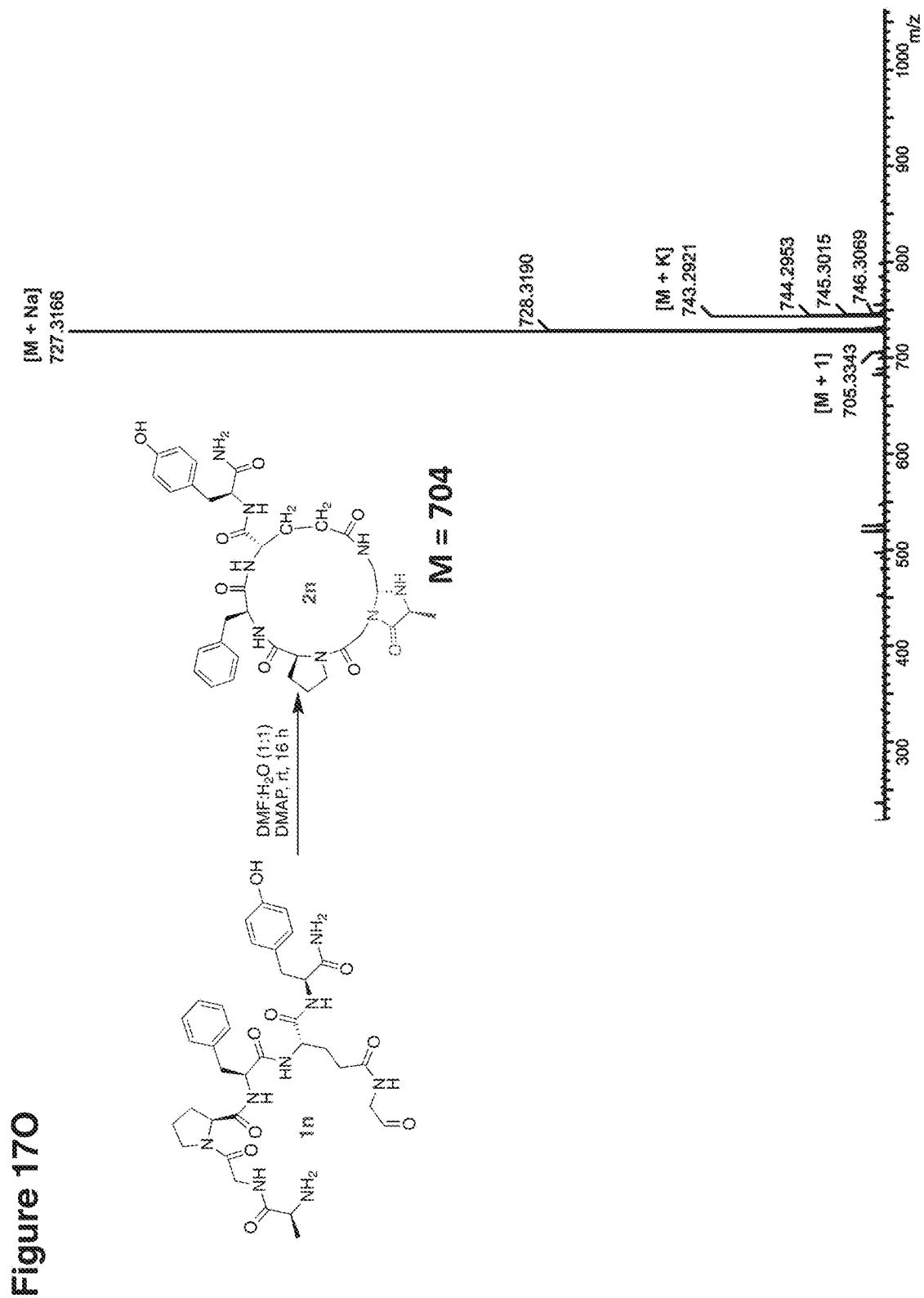
FIG. 17O depicts a schematic representation of the synthesis of cyclic peptide 2n and the corresponding HRMS trace. cyc(Ala-Gly-Pro-Phe-Glu)-Tyr (SEQ ID NO: 27) (2n). LCMS: m/z 705.3 (calcd [M+H]+=705.4), m/z 727.3 (calcd [M+Na]+=727.4), m/z 743.2 (calcd [M+K]+=743.4), Purity: >95% (HPLC analysis at 220 nm). Retention time: 12.8.
Figures 17, 17P:
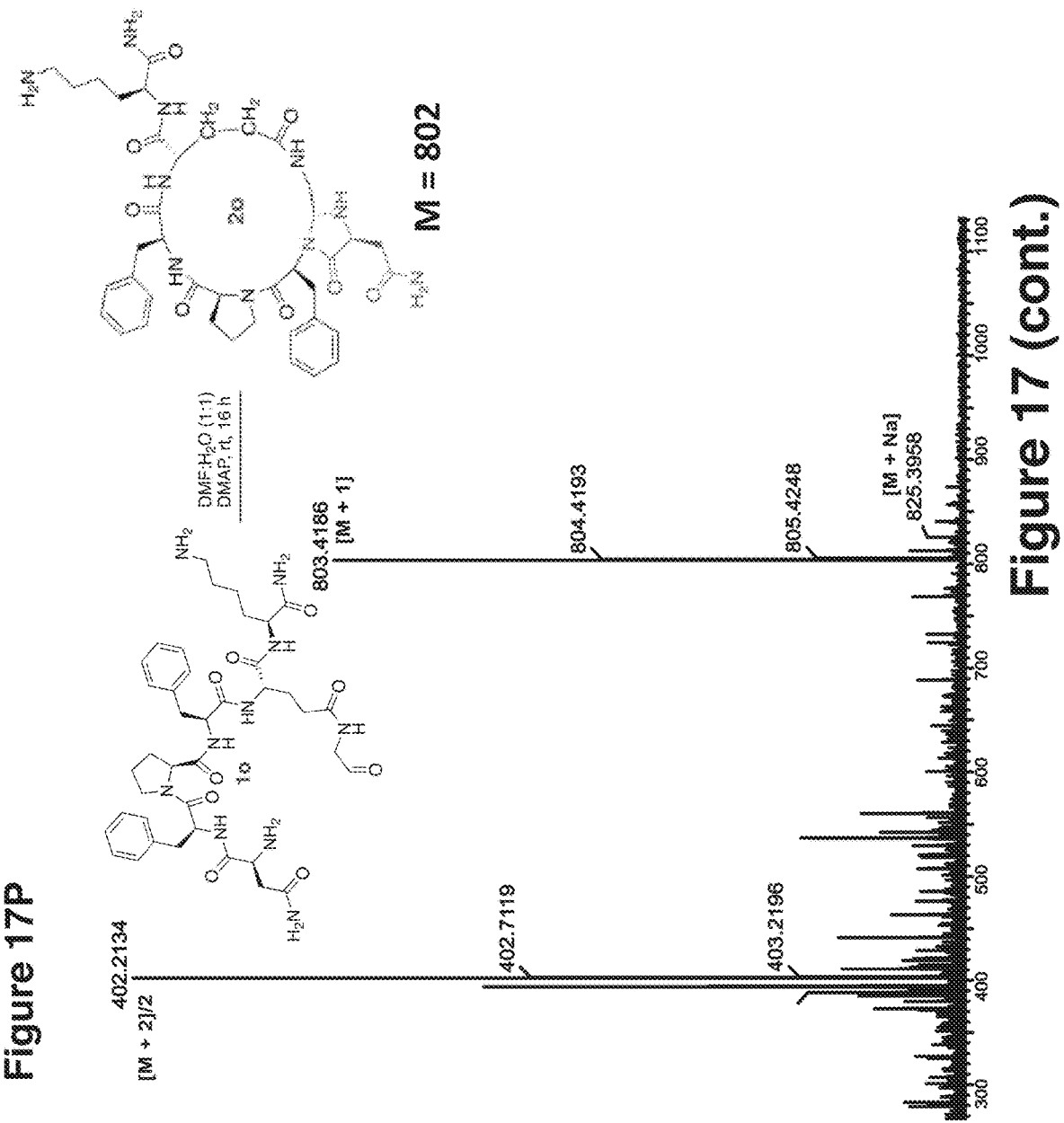
FIG. 17P depicts a schematic representation of the synthesis of cyclic peptide 2o and the corresponding HRMS trace. cyc(Asn-Phe-Pro-Phe-Glu)-Lys (SEQ ID NO: 28) (2o). LCMS: m/z 803.4 (calcd [M+H]+=803.4), m/z 402.2 (calcd [(m+2)/2=402.2), Purity: >95% (HPLC analysis at 220 nm). Retention time: 10.7.
Figures 17, 17Q:
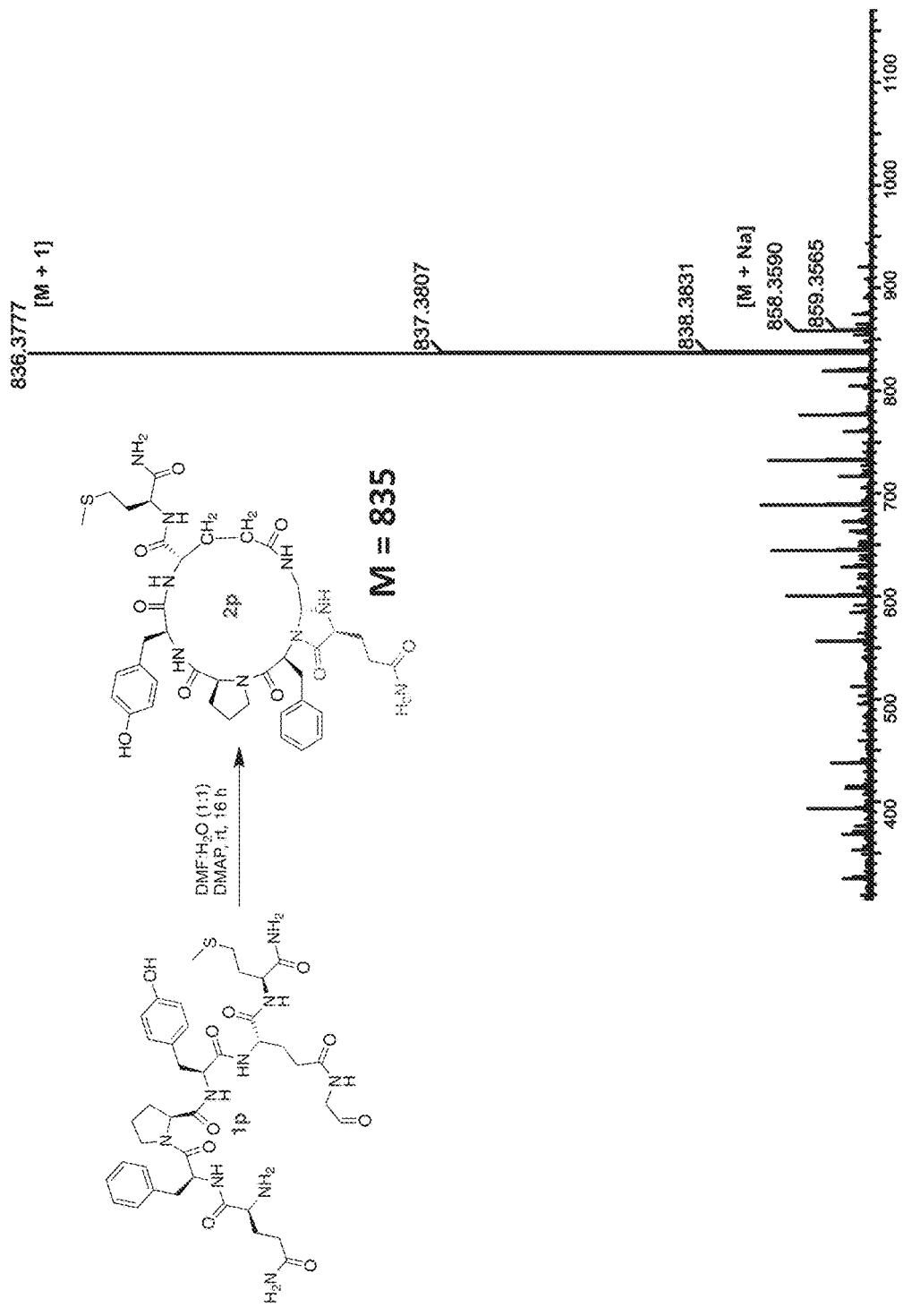
FIG. 17Q depicts a schematic representation of the synthesis of cyclic peptide 2p and the corresponding HRMS trace, cyc(Gln-Phe-Pro-Tyr-Glu)-Met (SEQ ID NO: 29) (2p). LCMS: m/z 836.4 (calcd [M+H]+=836.4), m/z 858.4 (calcd [M+Na]+=858.4), Purity: >95% (HPLC analysis at 220 nm). Retention time: 14.0.
Figures 17, 17S:
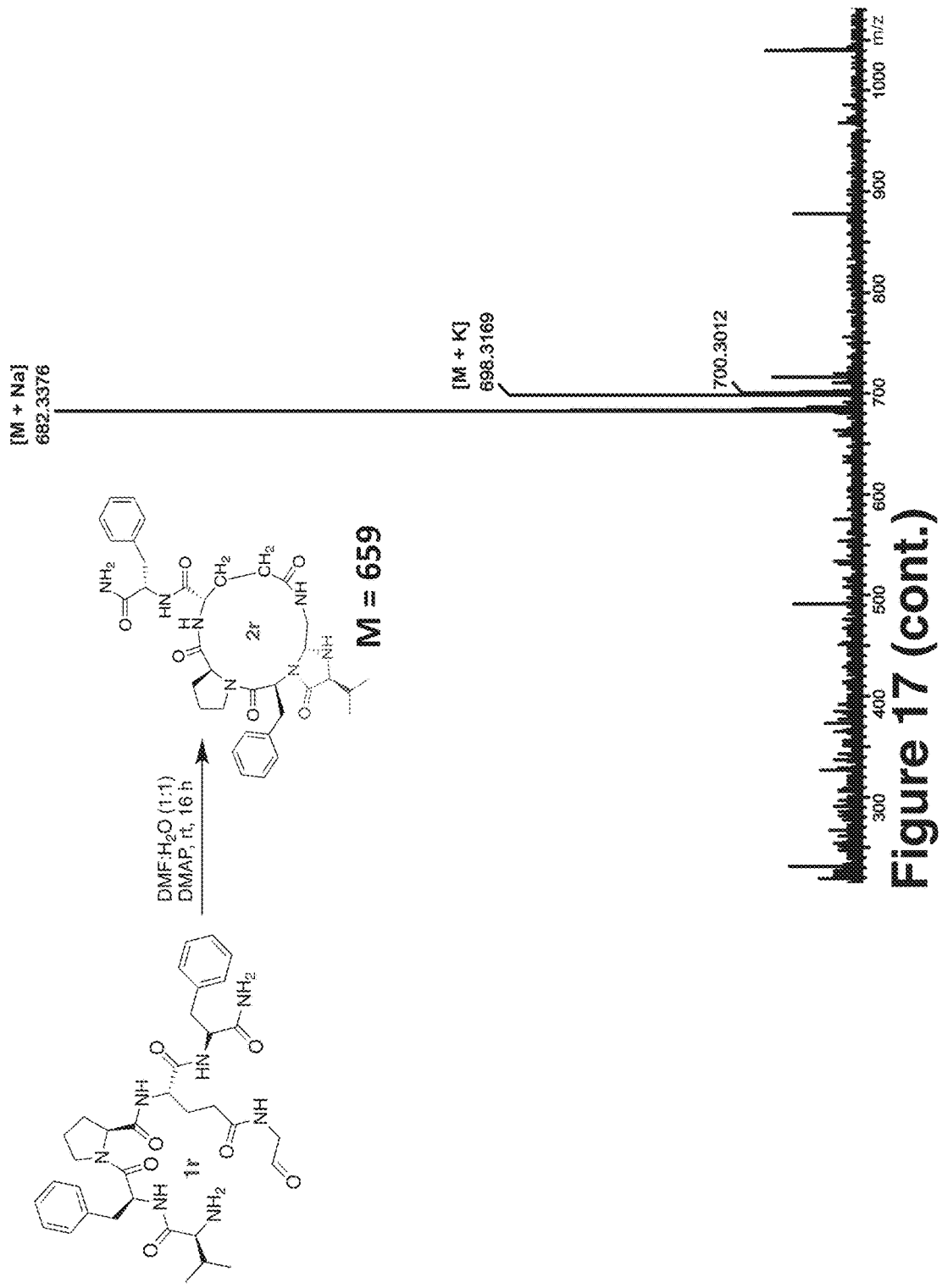
FIG. 17S depicts a schematic representation of the synthesis of cyclic peptide 2r and the corresponding HRMS trace, cyc(Val-Phe-Pro-Glu)-Phe (SEQ ID NO: 31) (2r), LCMS: m/z 682.3 (calcd [M+Na]+=682.4), m/z 698.3 (calcd [M+K]+=698.4), Purity: >95% (HPLC analysis at 220 nm). Retention time: 14.5.
Figure 17:
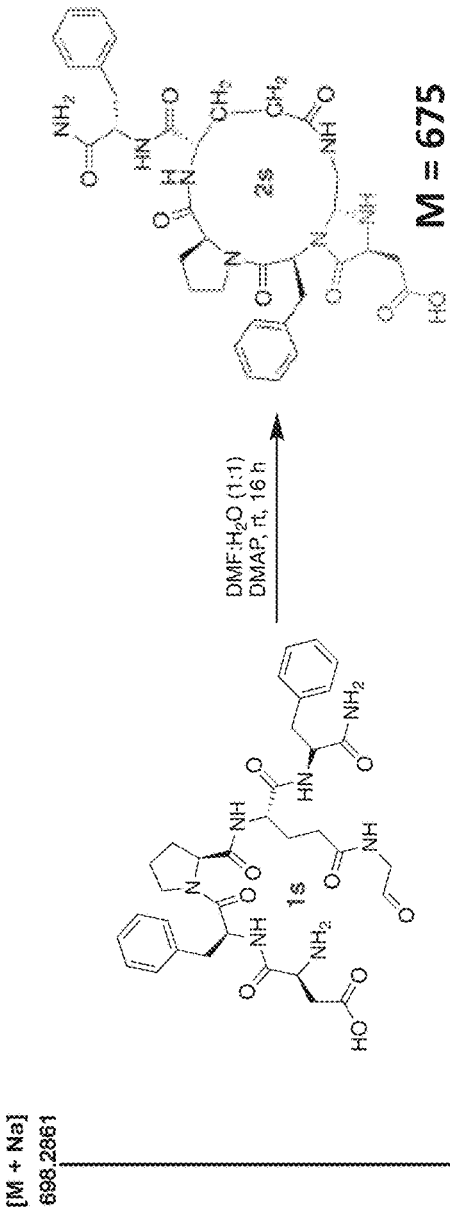
Figure 17:
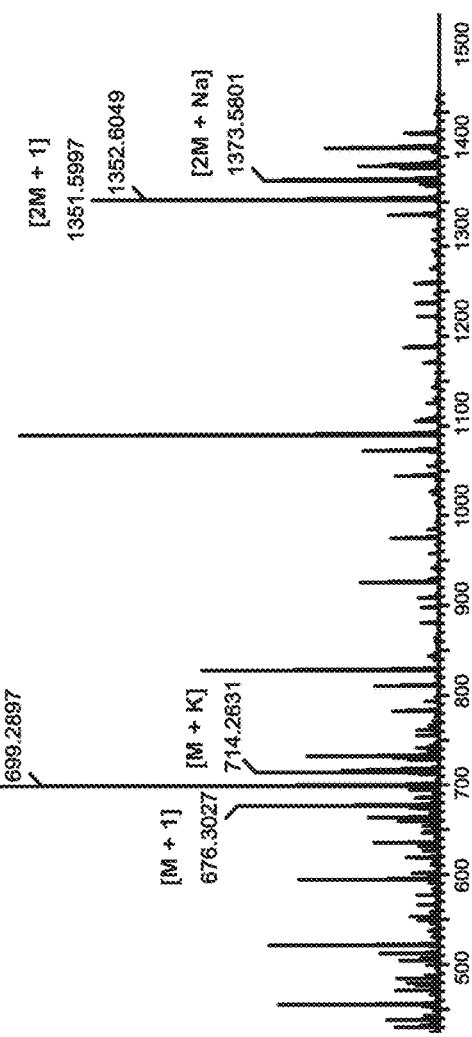
Figure 18:
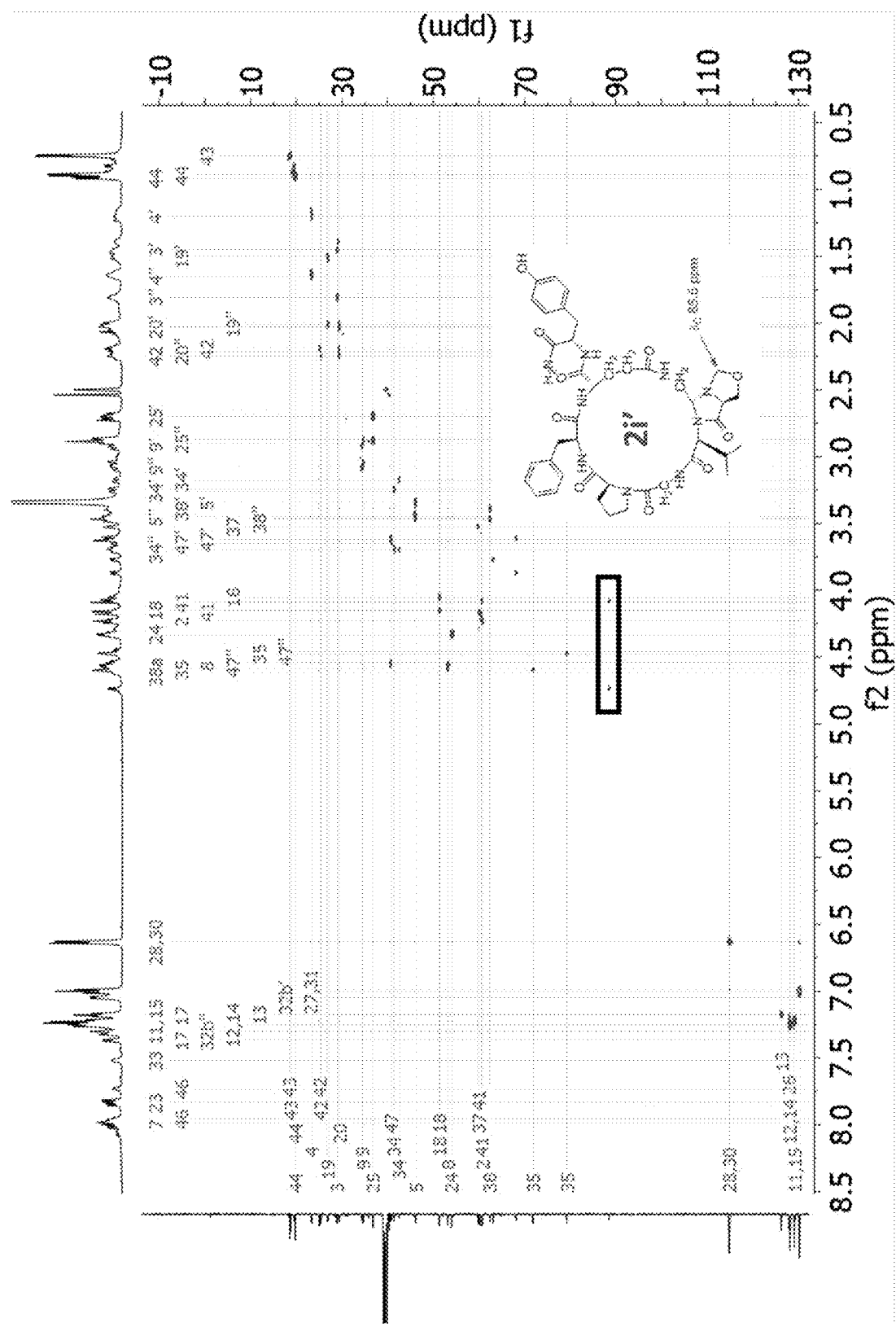
FIG. 18 depicts representative HSQC NMR data of fused bicyclic five membered 5-imino-oxazolidine cyclic peptide 2i'.

The detailed NMR and HRMS analysis of the imidazo-[1,5-c]oxazol-7-one cyclic peptide 2i' revealed the late-stage insertion of the formyl group in the 4-imidazolidinone moiety of the cyclic peptide 2i and the hydroxymethyl group of the side chain of serine (FIG. 16A, HRMS—FIG. 17, and 2i' NMR—FIG. 18; Davis A C et al., 1951, J. Chem. Soc., 3479). This was due to the formaldehyde present in the undistilled DMF. The source of formaldehyde was further validated by carrying out the reaction in H$_2$O/ACN. The formation of fused five-membered bicyclic imidazo[1,5-c]oxazol-7-one cyclic peptide 2i' was not observed in H$_2$O/ACN and the desired 4-imidazolidinone cyclic peptide 2i was obtained with 80% conversion (FIG. 16A).

Unprotected linear peptides 1j and 1k with reactive amino acids, such as Asn, Asp, His, Tyr, Cys, Gln, and Ser, afforded 23-membered cyclic peptides 2j through 2k with good conversions (45%-61%, FIG. 16A and FIG. 17), demonstrating the versatility of the CyClick reaction. The reaction was also utilized for the cyclization of the difficult sequences with all L-amino acids without any turn inducers, such as NVGAFE(CHO)Y (SEQ ID NO: 25) 1l and QVGAFE-(CHO)Y (SEQ ID NO: 26) 1m. Linear peptides 1l and 1m cyclized smoothly with high amounts of DMAP (21 equiv.) and generated corresponding cyclized products 2l and 2m (53%-65%, FIG. 16A and FIG. 17), Notably, the formation of any linear or cyclic oligomers was not observed.

Moreover, the γ-amino groups of lysine residues did not undergo CyClick reaction because of the lack of a neighboring amide group required for facile cyclization. To probe the impact of lysine residues, linear peptide aldehydes 1h and 1o bearing unprotected Lys residues were prepared and cyclized under CyClick chemistry conditions. The reactions generated 4-imidazolidinone cyclic products 2h and 2o with good conversion (2h, 84% and 2o, 70%, FIG. 16A). Peptides lacking a Lys group (2a through 2g, 2n, and 2p, FIG. 16A) produced nearly similar yields of the cyclic products, indicating that unprotected Lys did not influence the overall yield of the Cy Click products.

Encouraged by these results, subsequent studies continued to test the versatility of this procedure with different chain lengths of peptides, such as pentapeptides and hexapeptides 1n through 1x. All the substrates cyclized efficiently and provided the corresponding 14- to 17-membered macrocycles 2n through 2x with good conversions (FIG. 16A and FIG. 17). Interestingly, the reaction of linear peptides with proline at the N-terminus gave fused bicyclic five-membered 1H-pyrrolo[1,2-c]imidazole-1-one cyclic peptides 3a and 3b (FIG. 16B, HRMS—FIG. 19, and 3a NMR—FIG. 20 and Table 5; Federsel H J et al., 1990, J. Org. Chem., 55:2254),

TABLE 5

Representative NMR data for 3a.

| Residue | Atom Name | Numbering | δ$_H$ (ppm), multiplicity | δ$_C$ (ppm) |
|---|---|---|---|---|
| Pro | N | 1 | — | — |
| | C$_a$H | 2 | 4.22, d (J = 9.1 Hz) | 60.59 |
| | C$_b$H$_2$ | 3 | 1.40, m; 1.81, m | 29.14 |
| | C$_g$H$_2$ | 4 | 1.14, m; 1.62, m | 23.21 |
| | C$_d$H$_2$ | 5 | 3.34, m; 3.45, t (J = 8.9 Hz) | 46.11 |
| | CO | 6 | — | 172.15 |
| Phe | NH | 7 | 8.01, d (J = 8.7 Hz) | — |
| | C$_a$H | 8 | 4.56, ddd (J = 10.6, 9.1, 6.8 Hz) | 53.23 |
| | C$_b$H$_2$ | 9 | 2.94, dd (J = 14.3, 11.4 Hz); 3.07, m | 34.25 |
| | C$_1$ | 10 | — | 138.22 |
| | C$_2$H, C$_6$H | 11, 15 | 7.22, m | 129.01 |
| | C$_3$H, C$_5$H | 12, 14 | 7.25, m | 128.09 |
| | C$_4$ | 13 | 7.18, t (J = 6.9 Hz) | 126.18 |
| | CO | 16 | — | 170.71 |
| Glu | NH | 17 | 7.19, m | — |
| | C$_a$H | 18 | 4.11, m | 51.50 |
| | C$_b$H$_2$ | 19 | 1.48, m; 2.00, m | 26.89 |
| | C$_g$H$_2$ | 20 | 1.95, m; 2.15, dd (J = 15.2, 8.2 Hz) | 29.47 |
| | C$_d$O | 21 | — | 171.54 |
| | CO | 22 | — | 170.54 |
| Tyr | NH | 23 | 7.84, d (J = 8.7 Hz) | — |
| | C$_a$H | 24 | 4.33, td (J = 8.6, 5.0 Hz) | 54.06 |
| | C$_b$H$_2$ | 25 | 2.70, dd (J = 13.9, 9.0 Hz); 2.88, m | 36.72 |
| | C$_1$ | 26 | — | 127.88 |
| | C$_2$H, C$_6$H | 27, 31 | 7.00, d (J = 8.0 Hz) | 130.10 |
| | C$_3$H, C$_5$H | 28, 30 | 6.64, d (J = 8.0 Hz) | 114.82 |
| | C$_4$OH | 29 | 9.16, s | 155.74 |
| | CONH$_2$ | 32 | 7.04, s; 7.31, s | 172.82 |
| Linker | NH | 33 | 7.30, m | — |
| | C$_a$H$_2$ | 34 | 3.14, br d (J = 12.9 Hz); 3.74, m | 42.43 |
| | C$_b$H | 35 | 4.41, br s | 78.43 |
| Pro | NH | 36 | — | — |
| | C$_a$H | 37 | 3.60, dd (J = 8.9, 4.5 Hz) | 63.72 |
| | C$_b$H$_2$ | 38 | 1.73, m; 1.96, m | 27.88 |
| | C$_g$H$_2$ | 39 | 1.53, m; 1.59, m | 24.37 |
| | C$_d$H$_2$ | 40 | 2.65, m; 3.08, m | 55.75 |
| | CO | 41 | — | 175.71 |
| Val | N | 42 | — | — |
| | C$_a$H | 43 | 4.06, d (J = 11.1 Hz) | 60.27 |
| | C$_b$H | 44 | 2.22, m | 25.11 |
| | C$_{g1}$H$_3$, C$_{g2}$H$_3$ | 45, 46 | 0.81, d (J = 6.5 Hz); 0.93, d (J = 6.4 Hz) | 19.08, 19.85 |
| | CO | 47 | | 169.37 |
| Gly | NH | 48 | 7.60, dd (J = 8.2, 2.4 Hz) | — |
| | C$_a$H$_2$ | 49 | 3.63, dd (J = 16.6, 2.6 Hz); 4.48, dd (J = 16.9, 8.7 Hz) | 40.76 |
| | CO | 50 | — | 169.39 |

Figure 19:
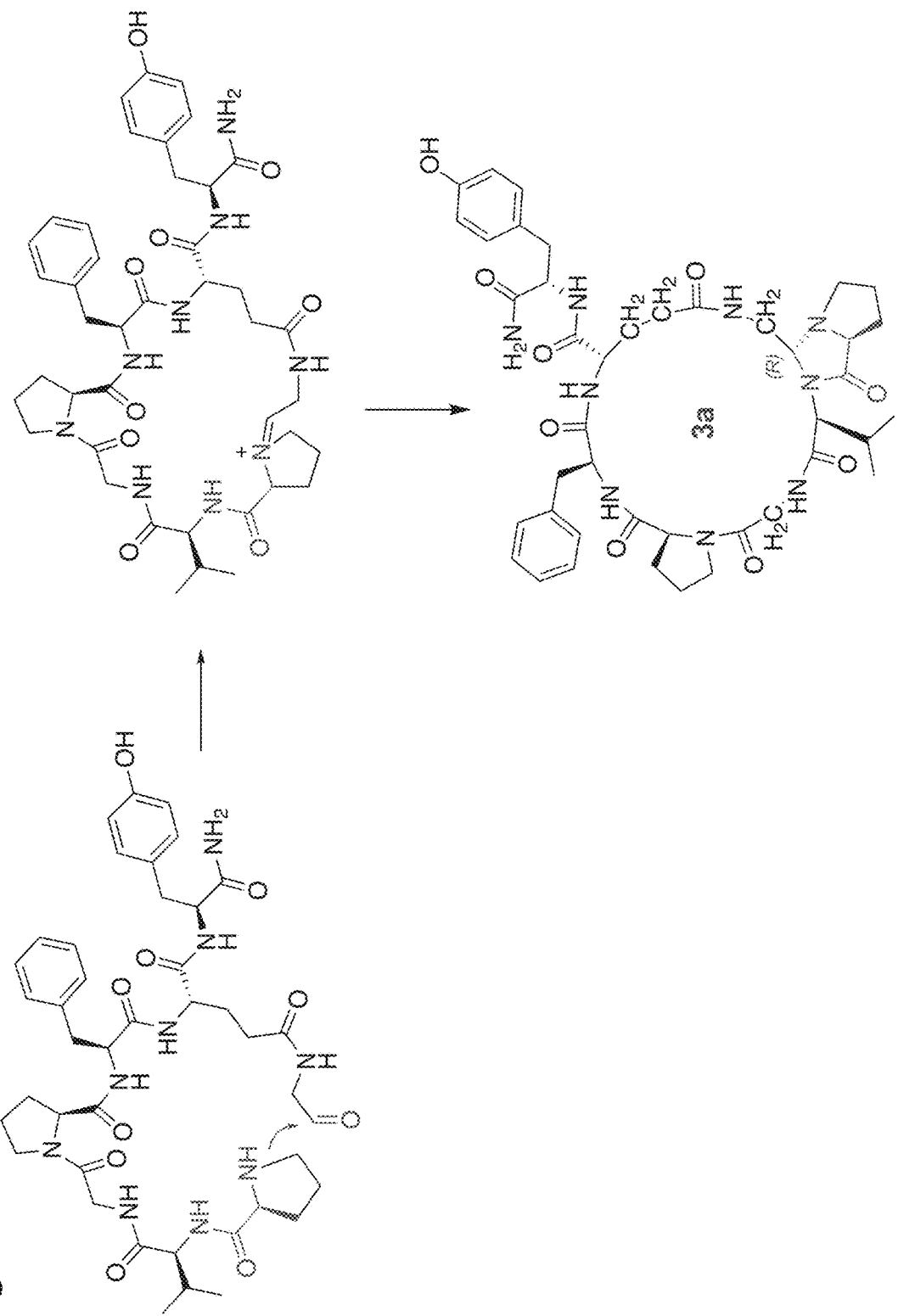
FIG. 19, comprising
Figures 19, 19B:
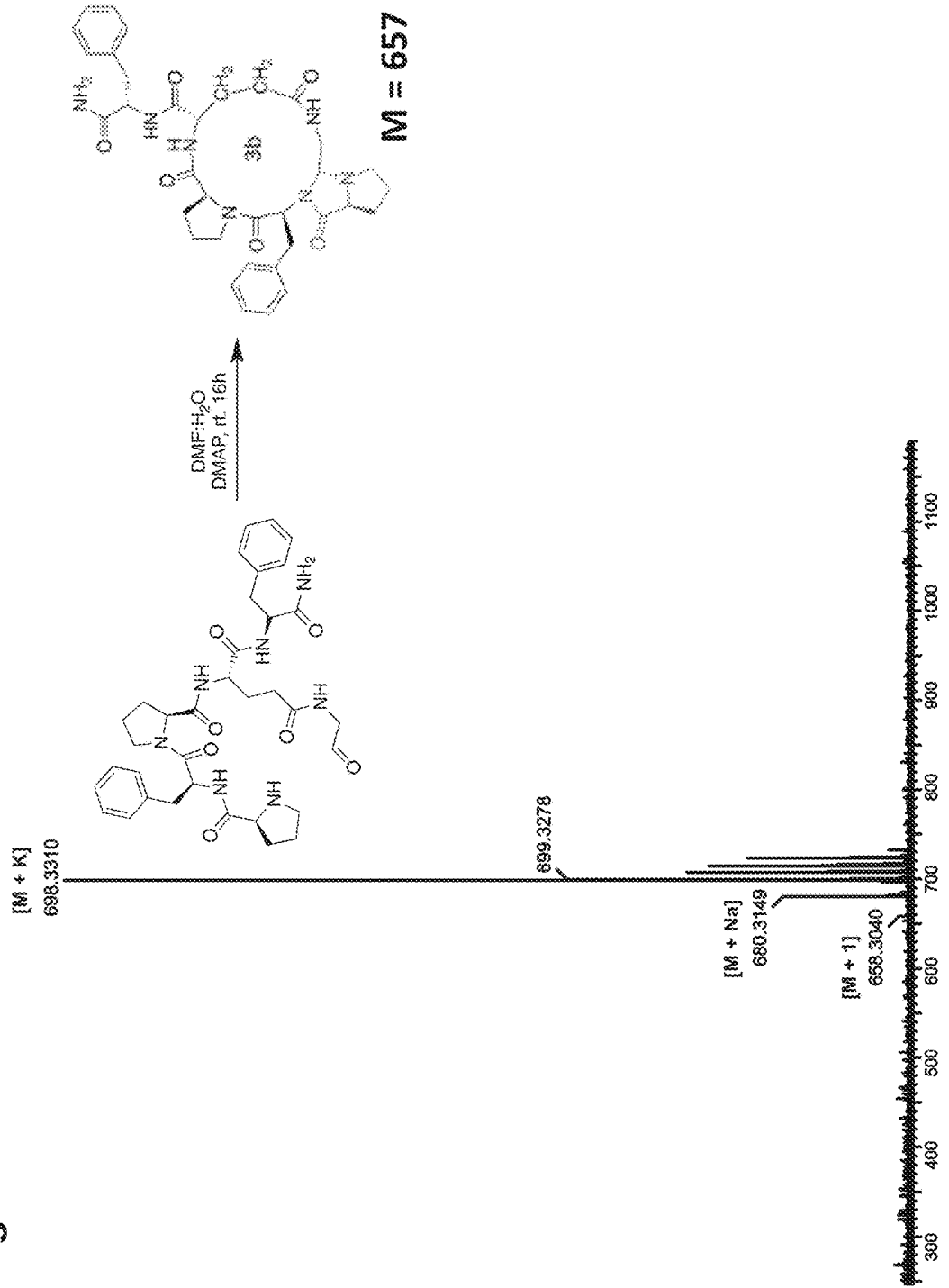
Figure 19:
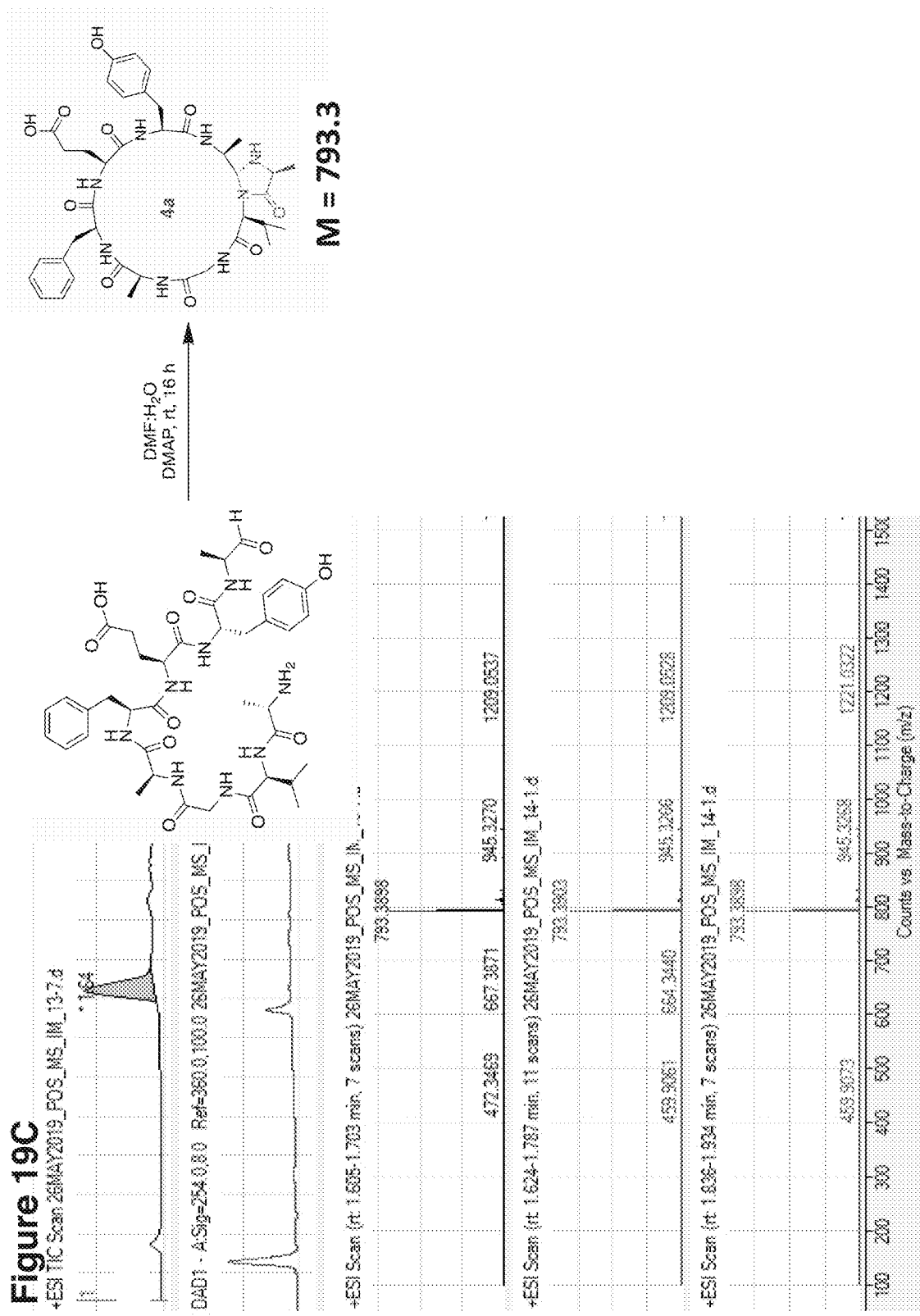
Figures 19, 19E:
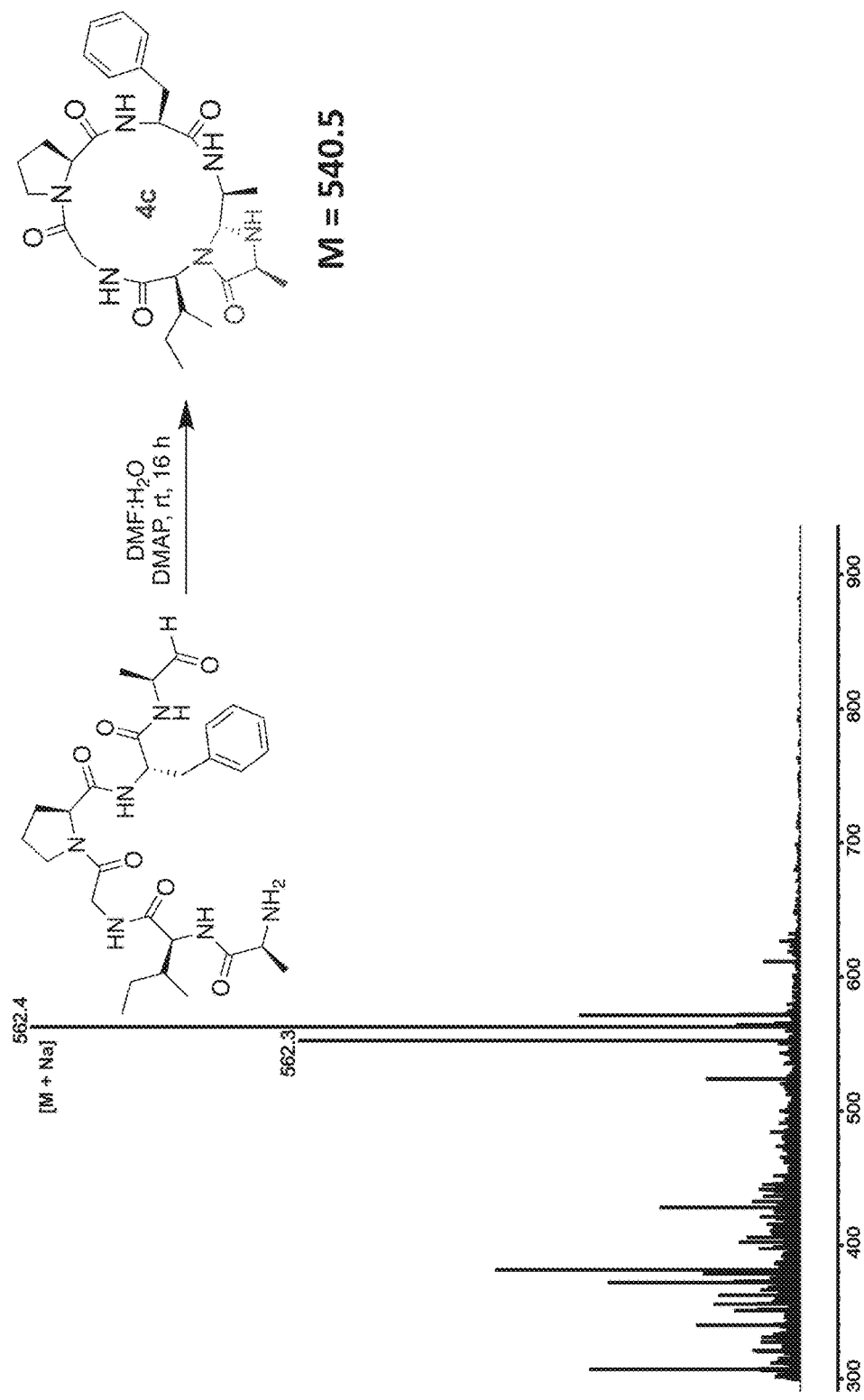
Figure 19F:
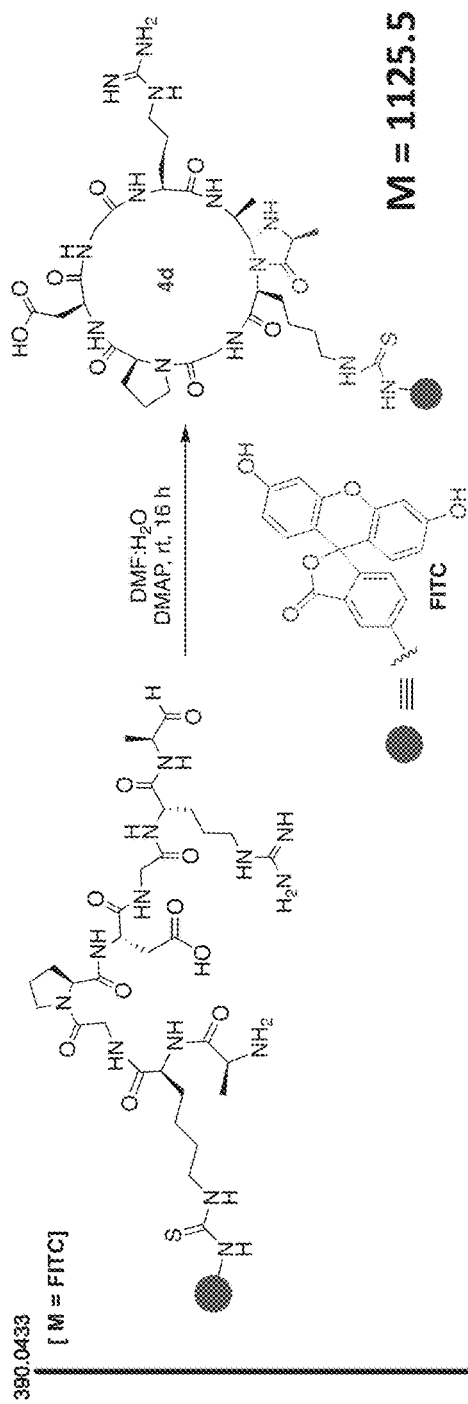
Figure 19:
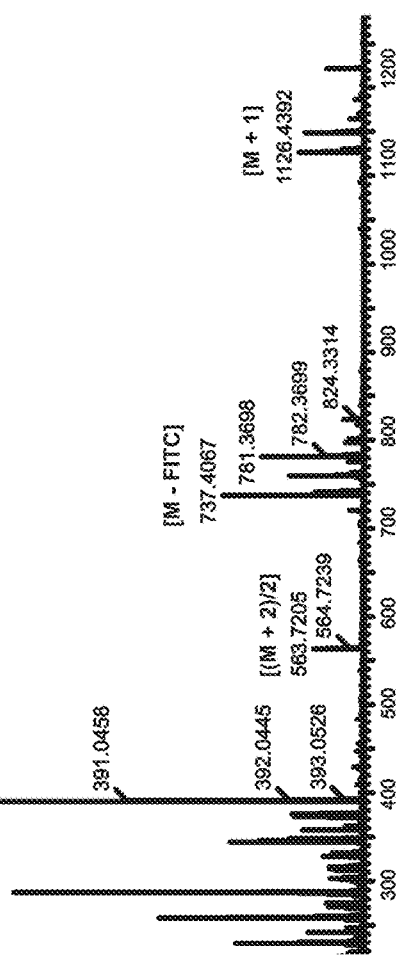
Figures 19, 19H:
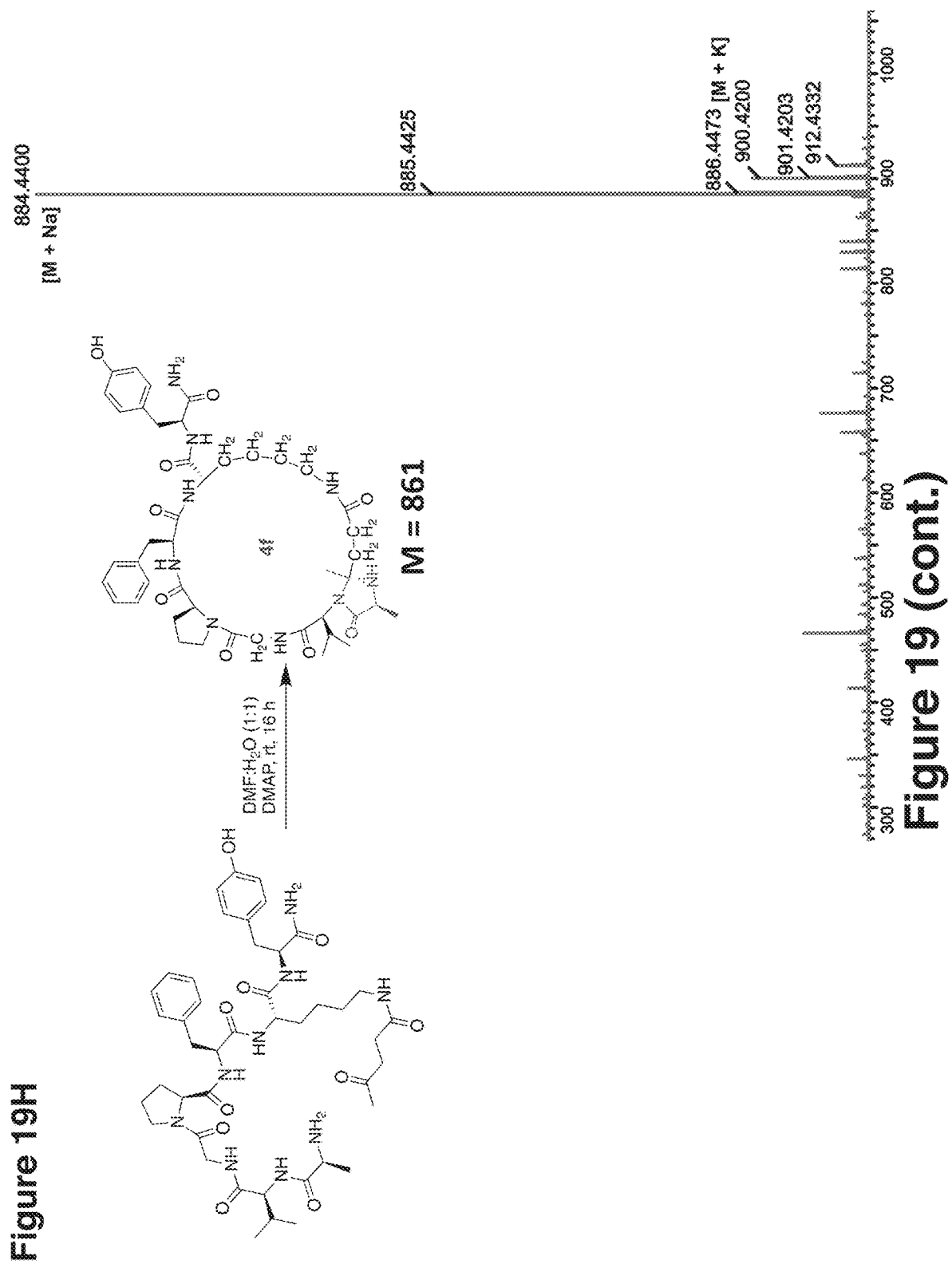
Figures 20, 20A:
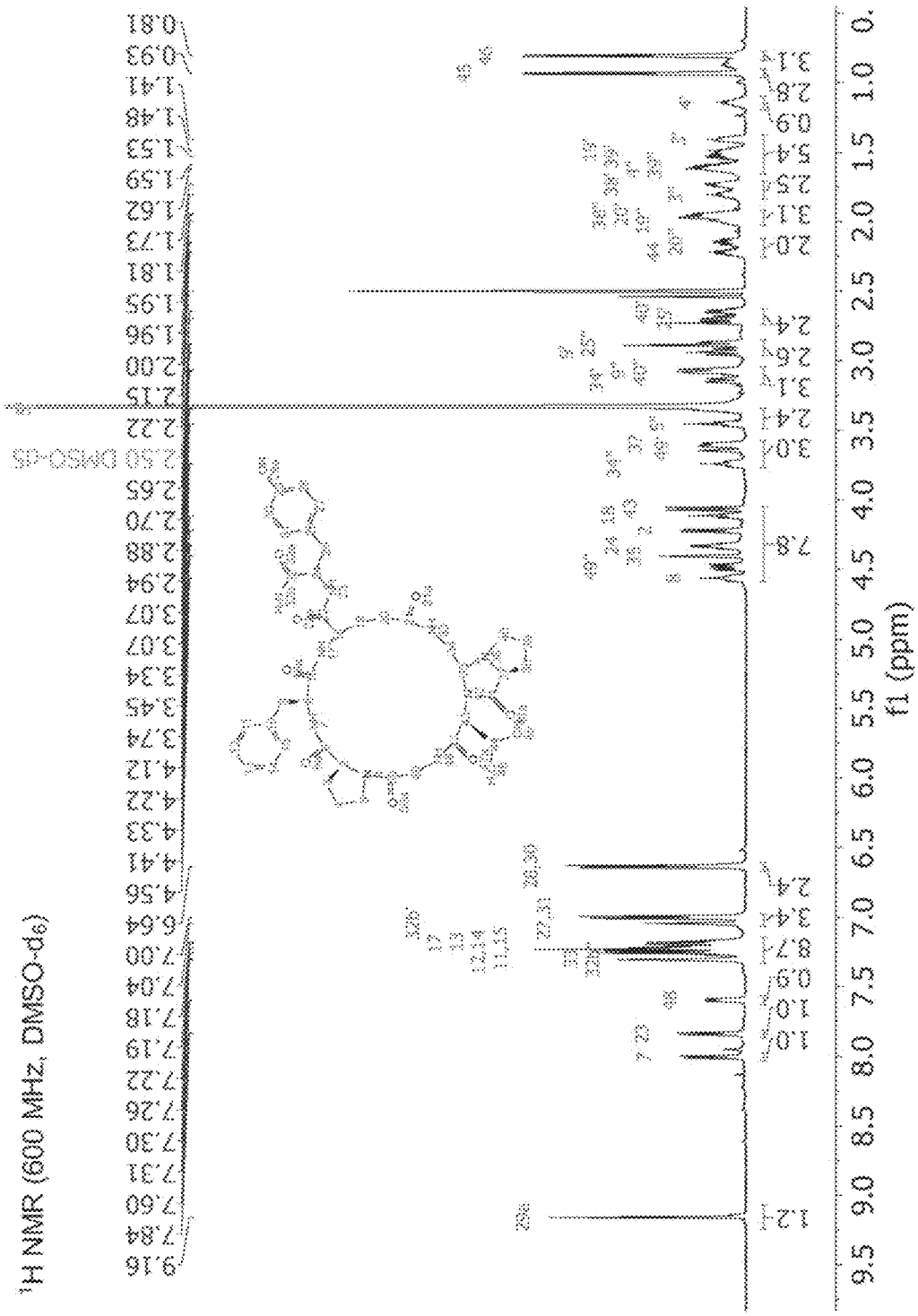
Figure 20:
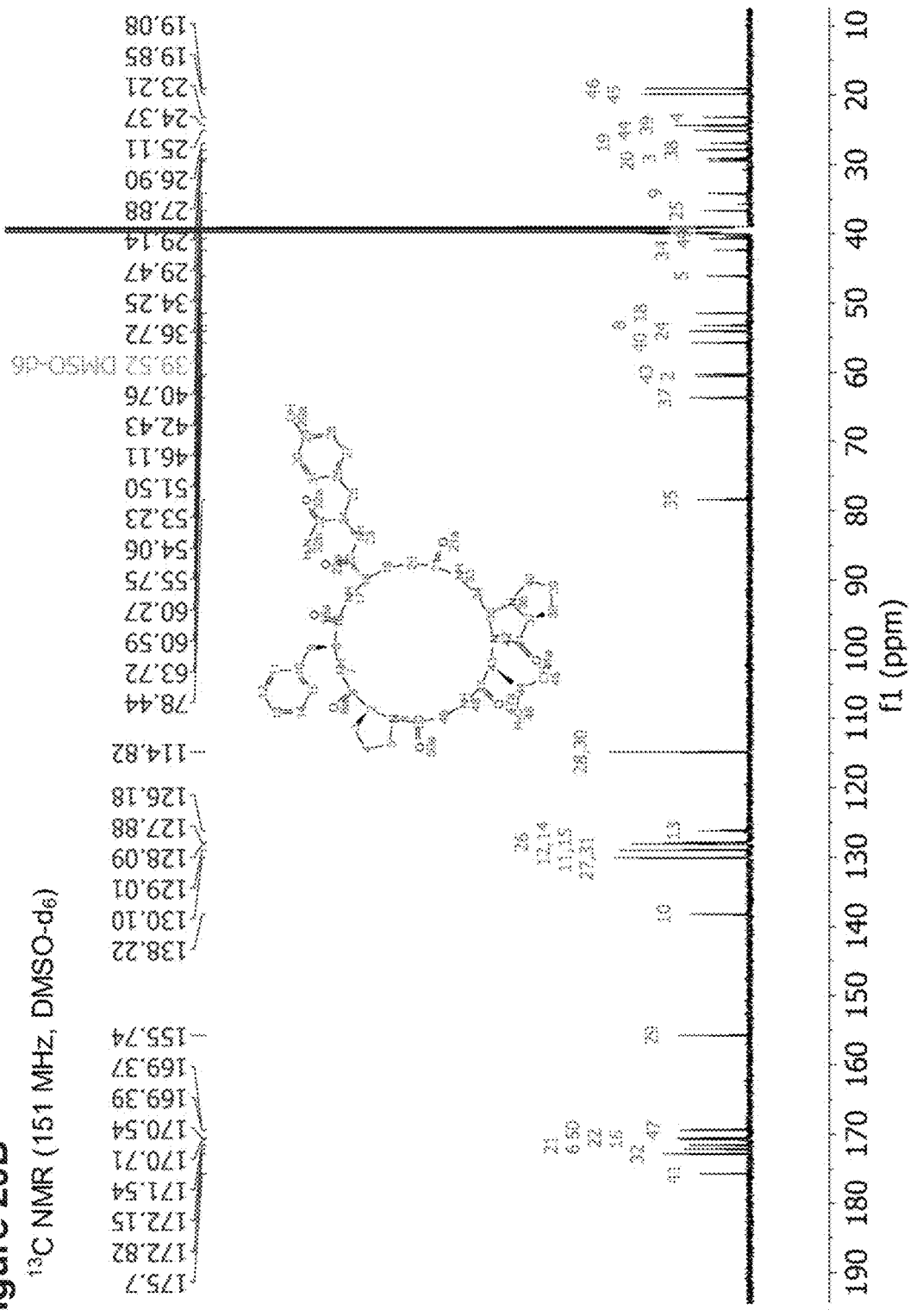
FIG. 20, comprising
Figures 20, 20D:
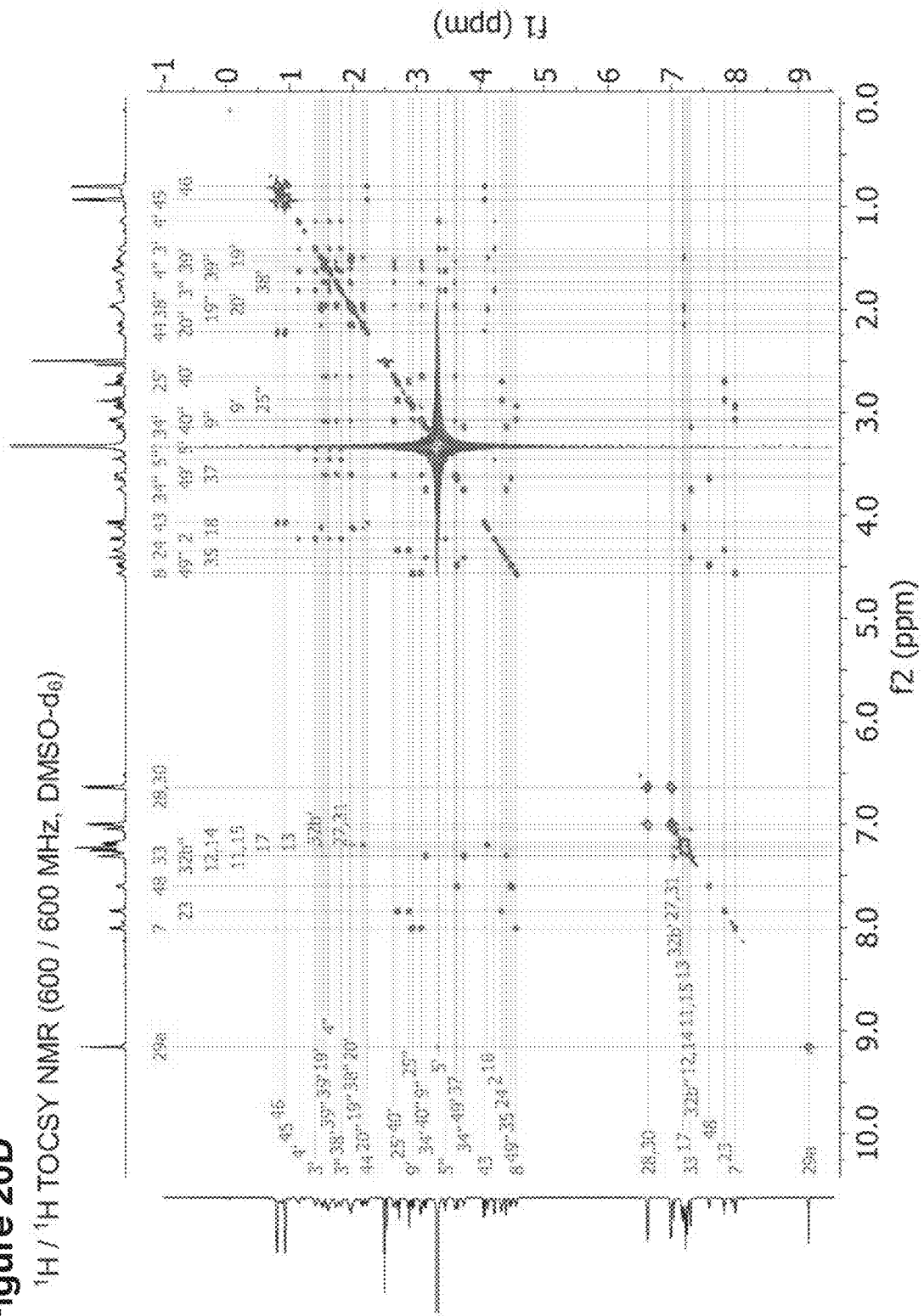
Figures 20, 20E:
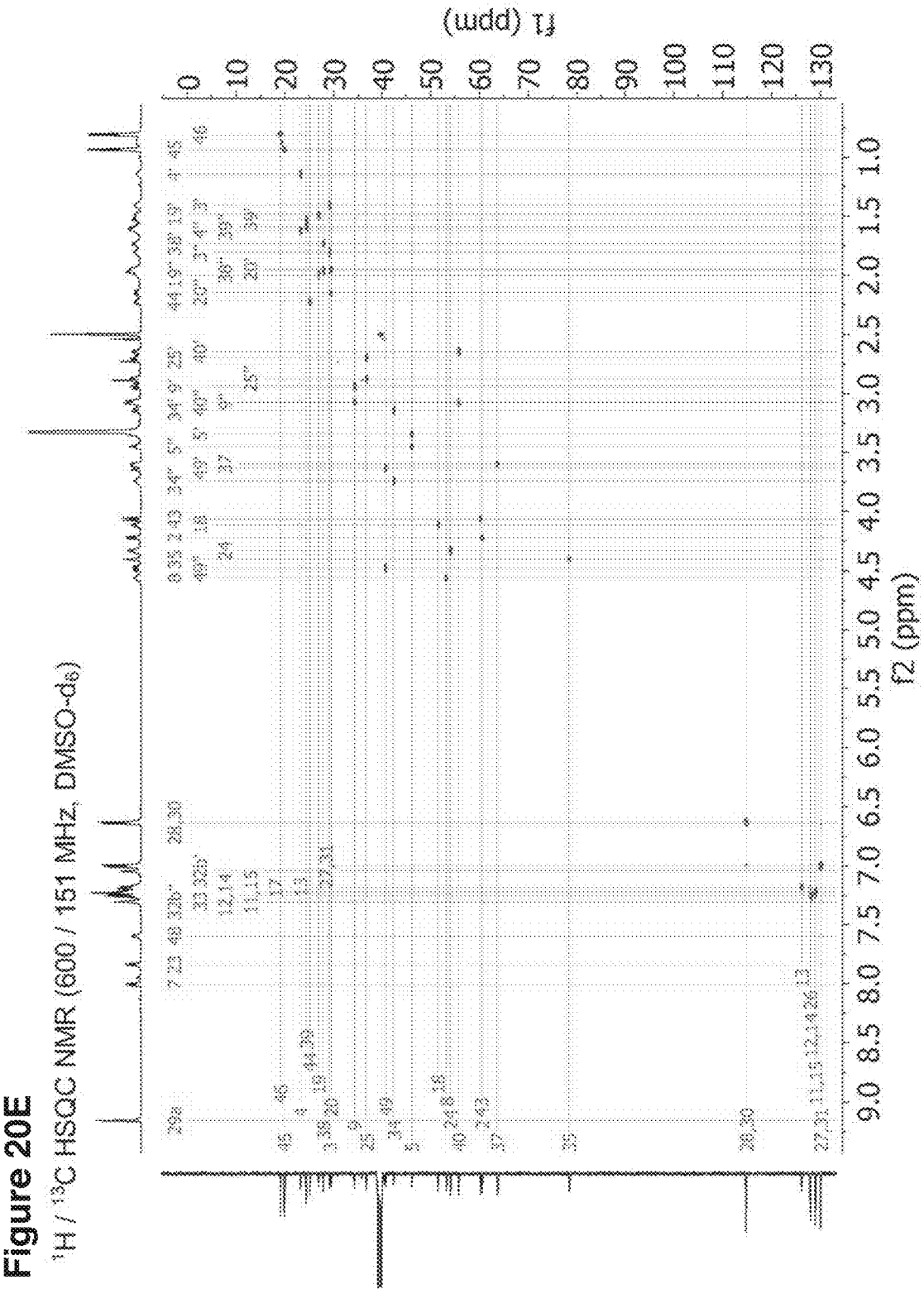
Figures 20, 20F:
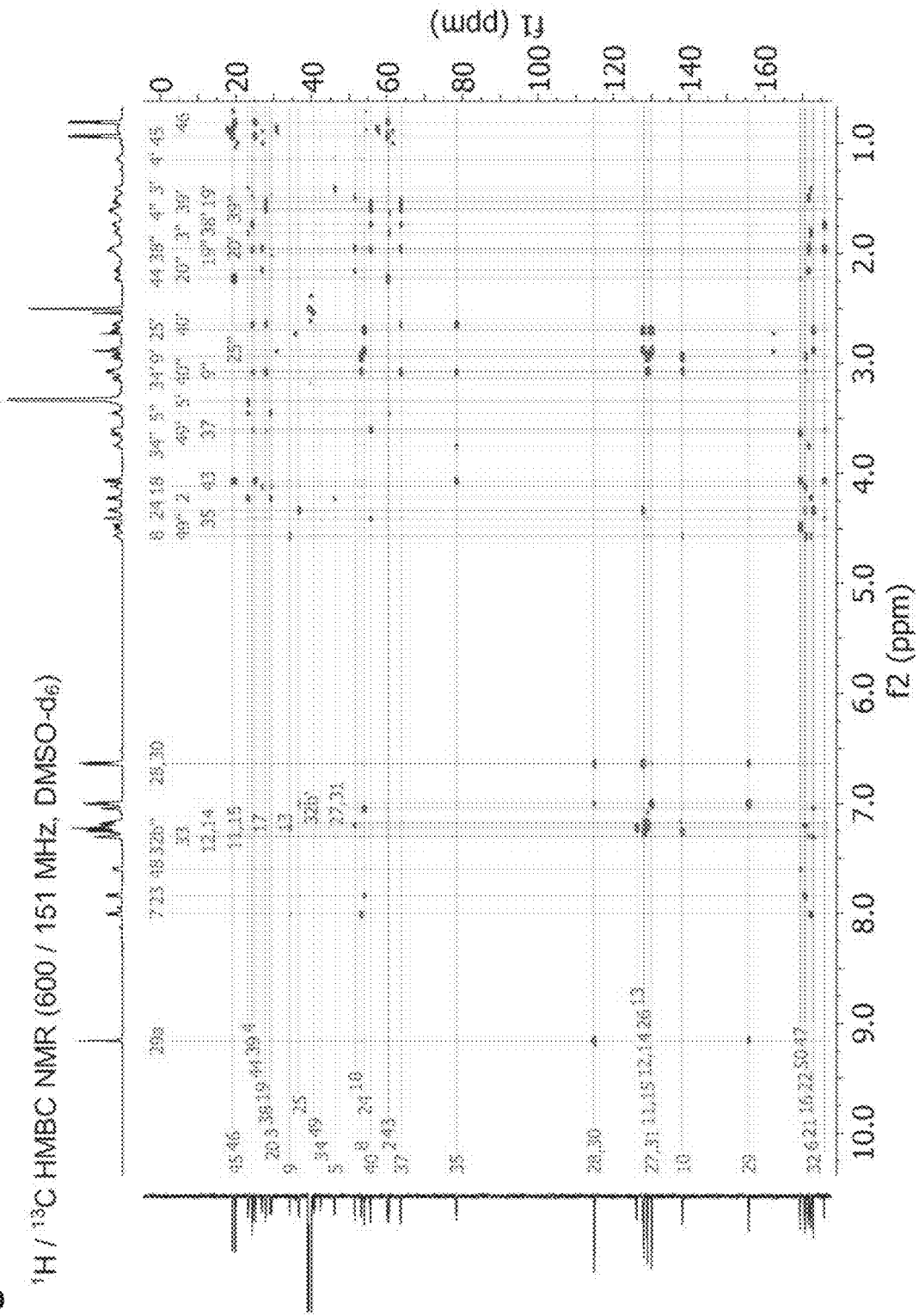
Figures 20, 20G:
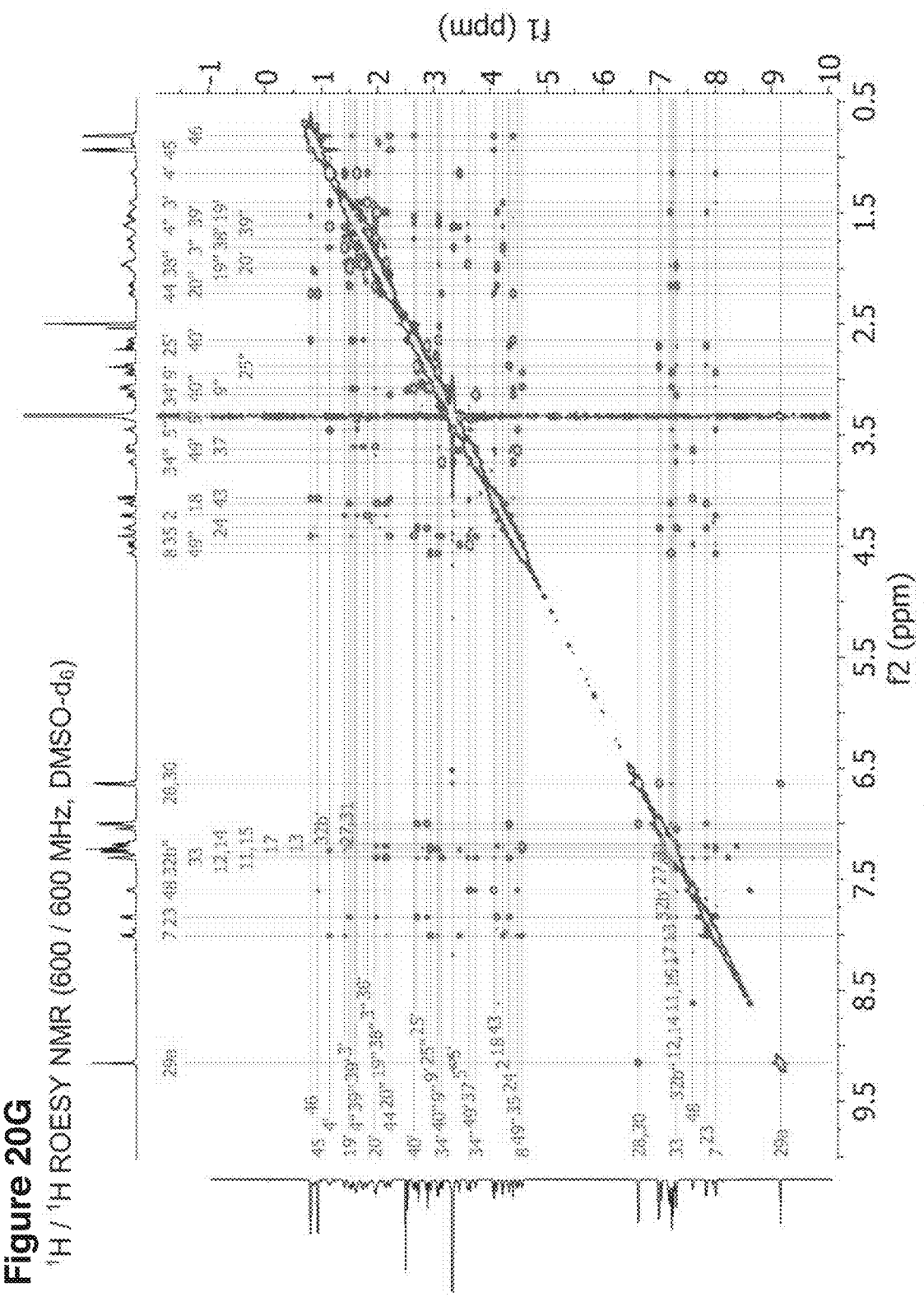

Similarly, head-to-tail macrocyclization of octa-, hepta-, and hexapeptides yielded the corresponding 15- to 21-membered macrocycles 4a through 4c with good conversions under the reaction conditions (45-75%, FIG. 16C and FIG. 19). The head-to-tail macrocyclization of the difficult sequence with all L-amino acids without any turn inducers, such as AVGAFEYA(CHO) proceeded smoothly and the corresponding cyclized product 4a was generated with good conversion without the formation of any side products due to linear and cyclic oligomerization (FIG. 16C and FIG. 19).

The utility of this protocol was further highlighted by synthesizing a fluorescent-labeled 4-imidazolidinone cyclic RGD peptide 4d, which has the potential to bind to breast cancer cells overexpressing avb3 integrin (FIG. 16C and FIG. 19; Kumagai H et al., 1991, Biochem, Biophys. Res. Commun, 177:74; Dechantsreiter M A et al., 1999, J. Med. Chem., 42:3033). This result demonstrated the validity of the present approach in synthesizing bioactive peptidomimetics. The present method was next challenged by cyclizing a head-to-tail pentapeptide, which is extremely difficult to achieve by current cyclization techniques due to their high tendency to form oligomers (White C J et al, 2011, Nat. Chem., 3:509; Lambert J N et al., 2001, J. Chem. Soc. Perkin Trans. 1, 471; Puentes A R et al., 2017, Org. Lett., 19:4022; Meutennans W D F et al., 2003, Org. Lett., 5:2711; Wong C T T et al., 2013, Angew. Chem. Int. Ed., 52:10212; Bielawski C W et al., 2002, Science, 297:2041; Lawson K V et al., 2013, Proc. Natl. Acad, Sci. USA, 110:E3753; Royo-Gracia S et al., 2009, Future Med. Chem., 1:1289; Skropeta D et al., 2004, J. Org. Chem., 69:8804; Ehrlich A et al., 1996, J. Org. Chem., 61:8831; Malesevic M et al., 2004, J. Biotechnol., 112:73; Wessjohann L A et al., 2017, Angew. Chem. Int. Ed., 56:3501; Marti-Centelles V et al., 2015, Chem. Rev., 115:8736). Nevertheless, the highly strained 12-membered cyclic peptide 4e was formed with good conversion (71%, FIG. 16C and FIG. 19).

To further challenge the present method, the cyclization of the head-to-tail tetrapeptide FGPA(CHO) was attempted using various reaction conditions, including high amounts of DMAP. A tetrapeptide aldehyde was predicted to give a 9-membered ring, which is impossible, but the formation of any linear and cyclodimer by CyClick chemistry was also not observed (FIG. 19). These results were confirmed by reducing the reaction mixture with sodium cyanoborohydride; this resulted in the formation of reduced linear tetrapeptide and reduced linear dimer. These studies further confirmed that the present method worked in intramolecular fashion only (FIG. 17 and FIG. 19).

Figures 21, 21A:
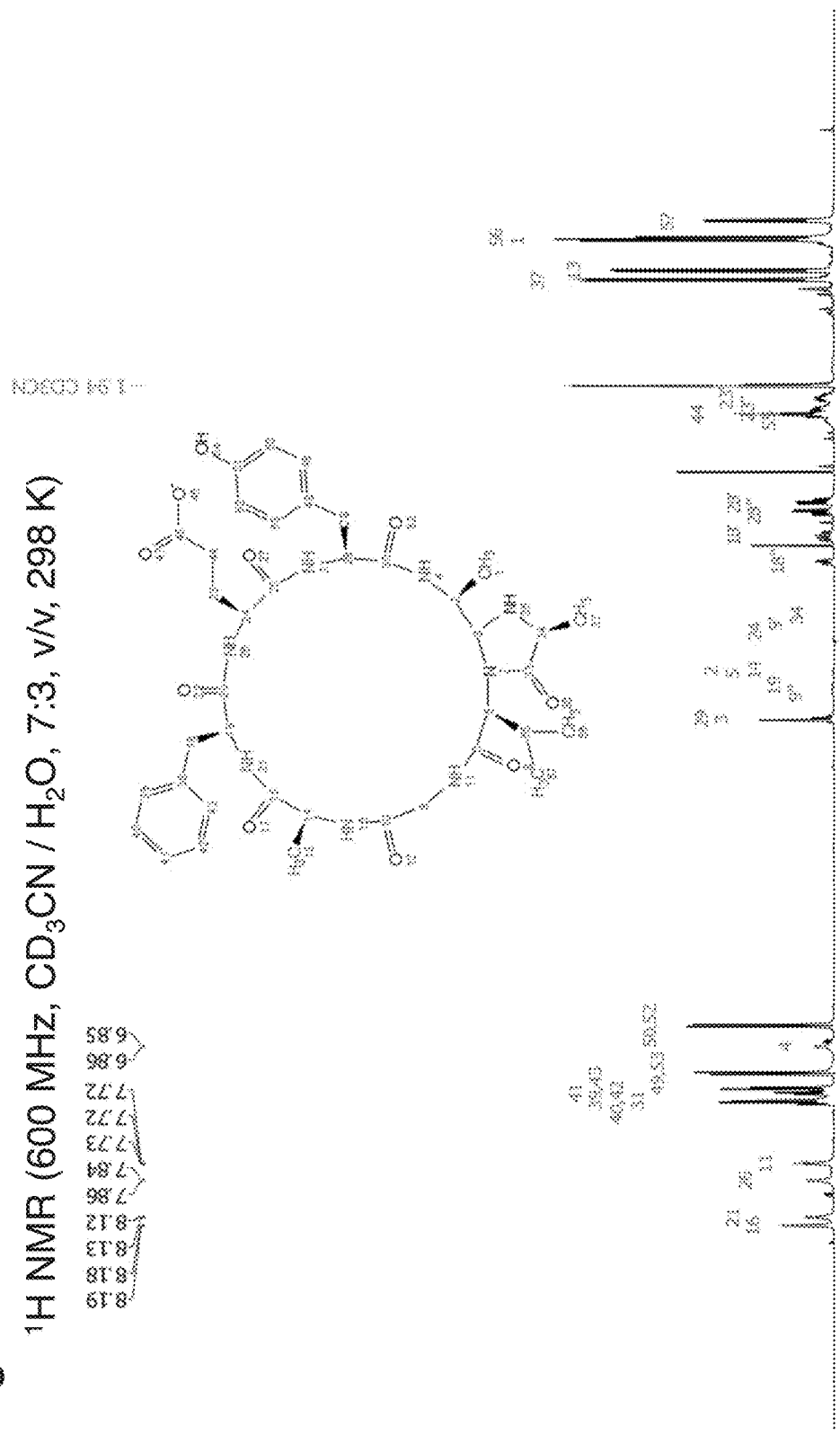
Figure 21:
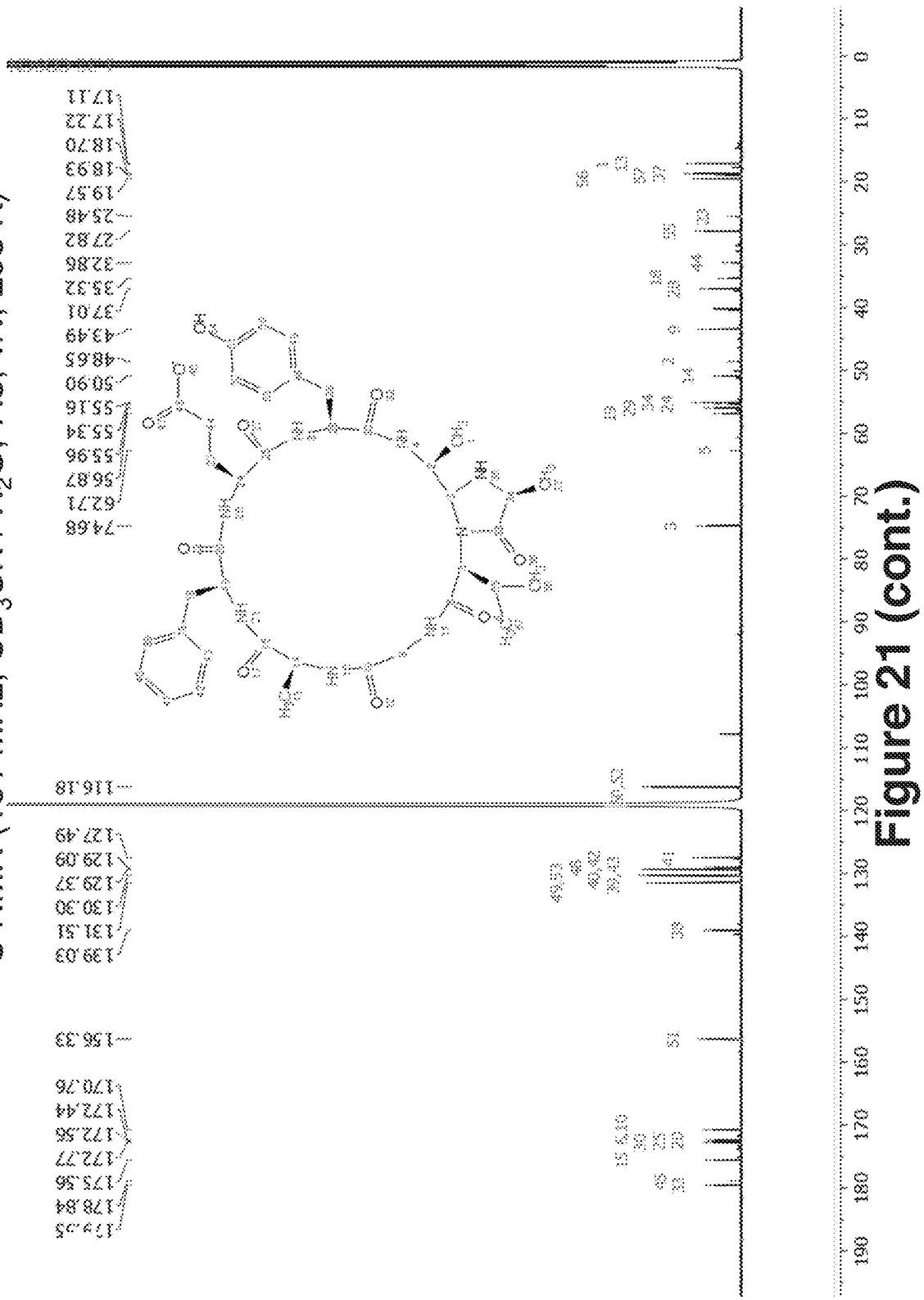
FIG. 21, comprising
Figures 21, 21C:
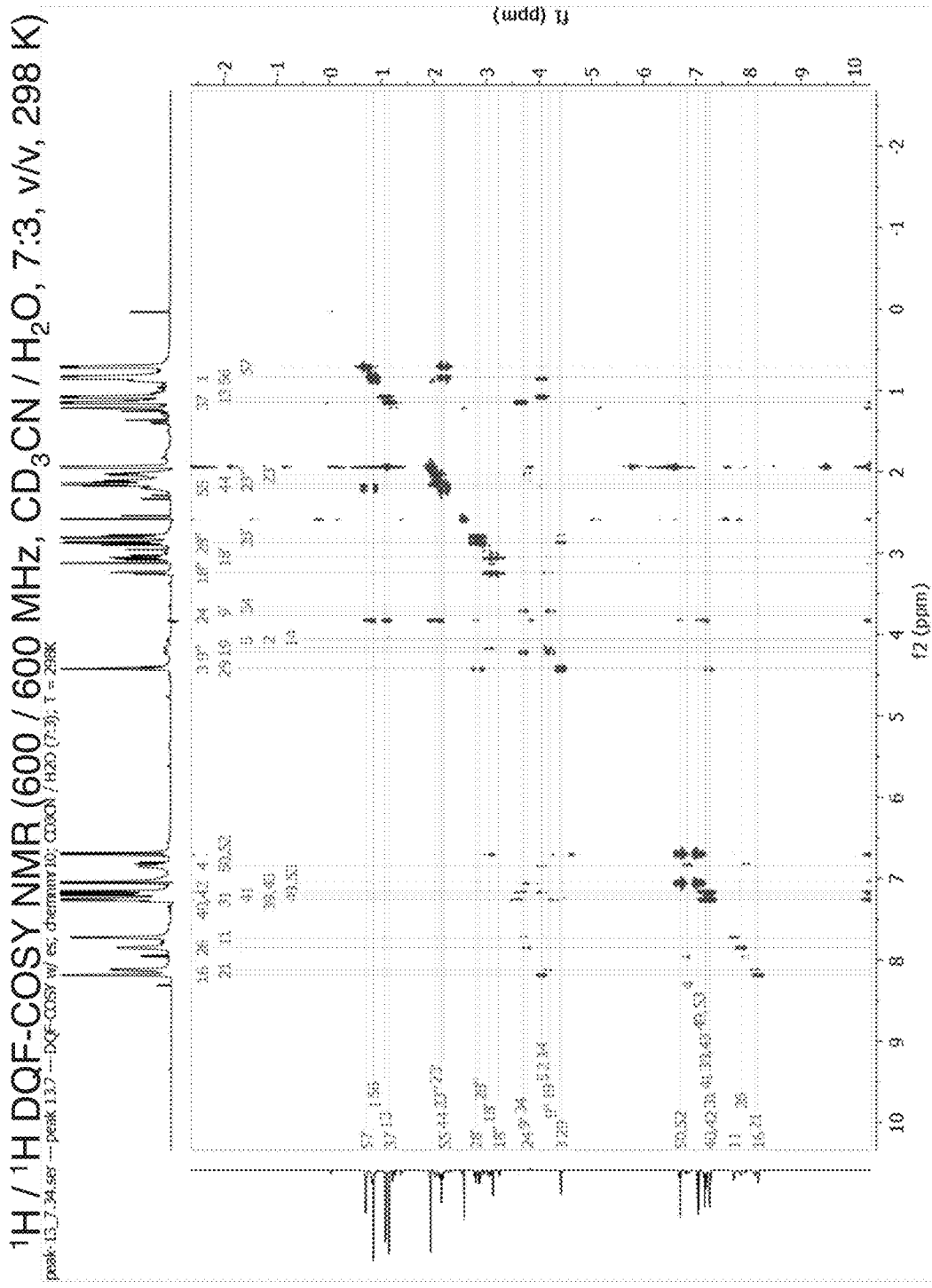
Figures 21, 21D:
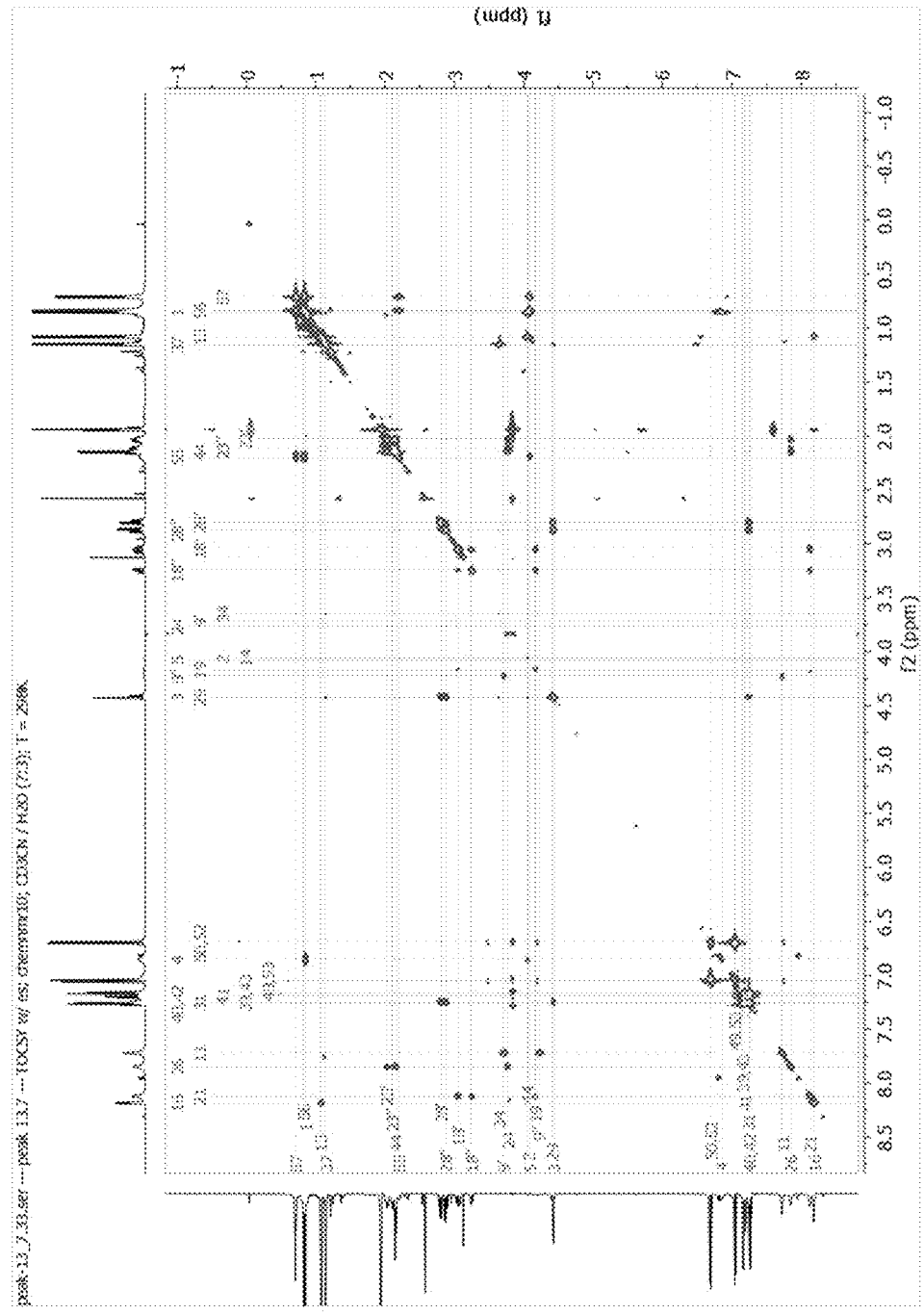
Figures 21, 21E:
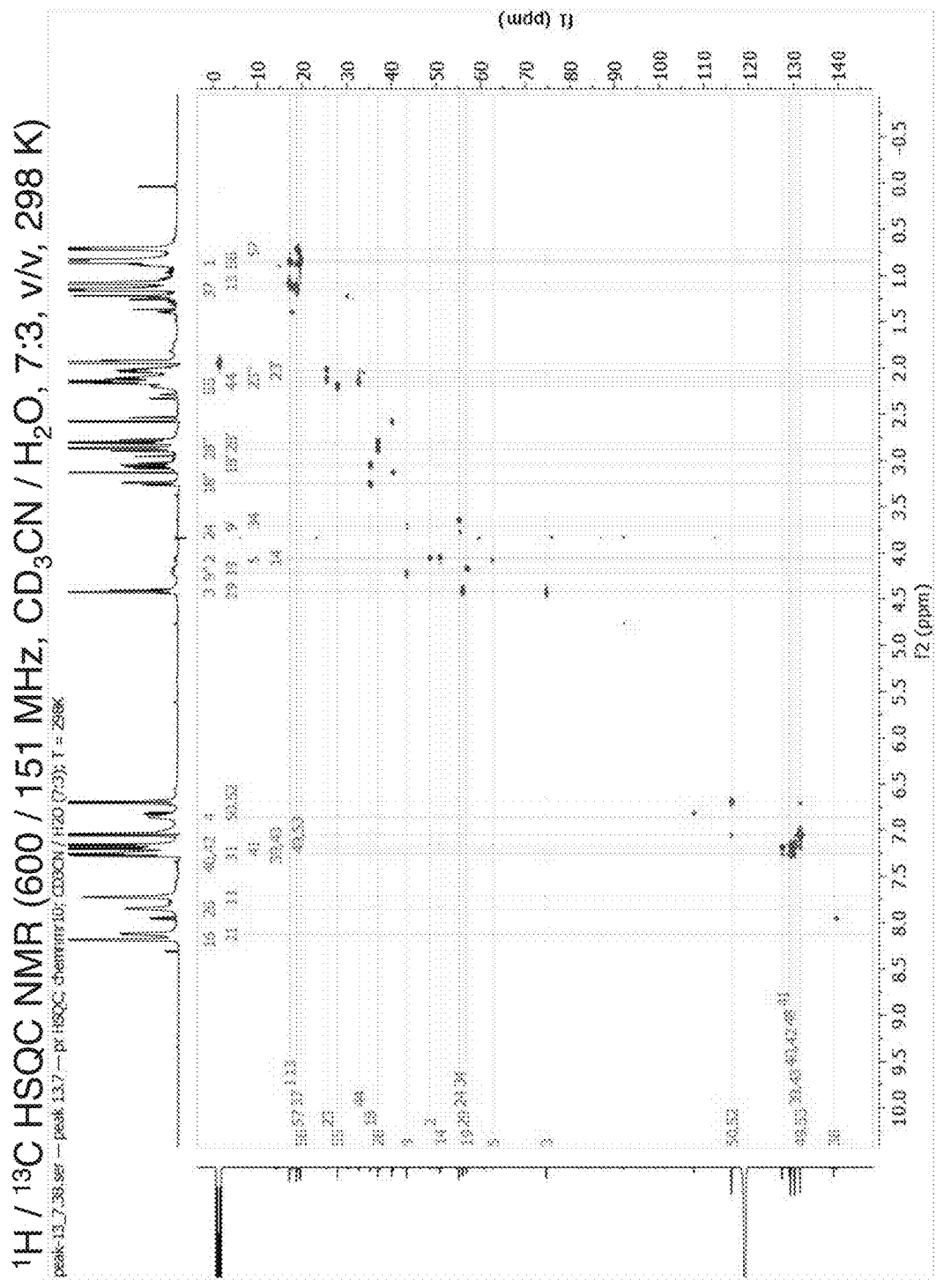
Figures 21, 21F:
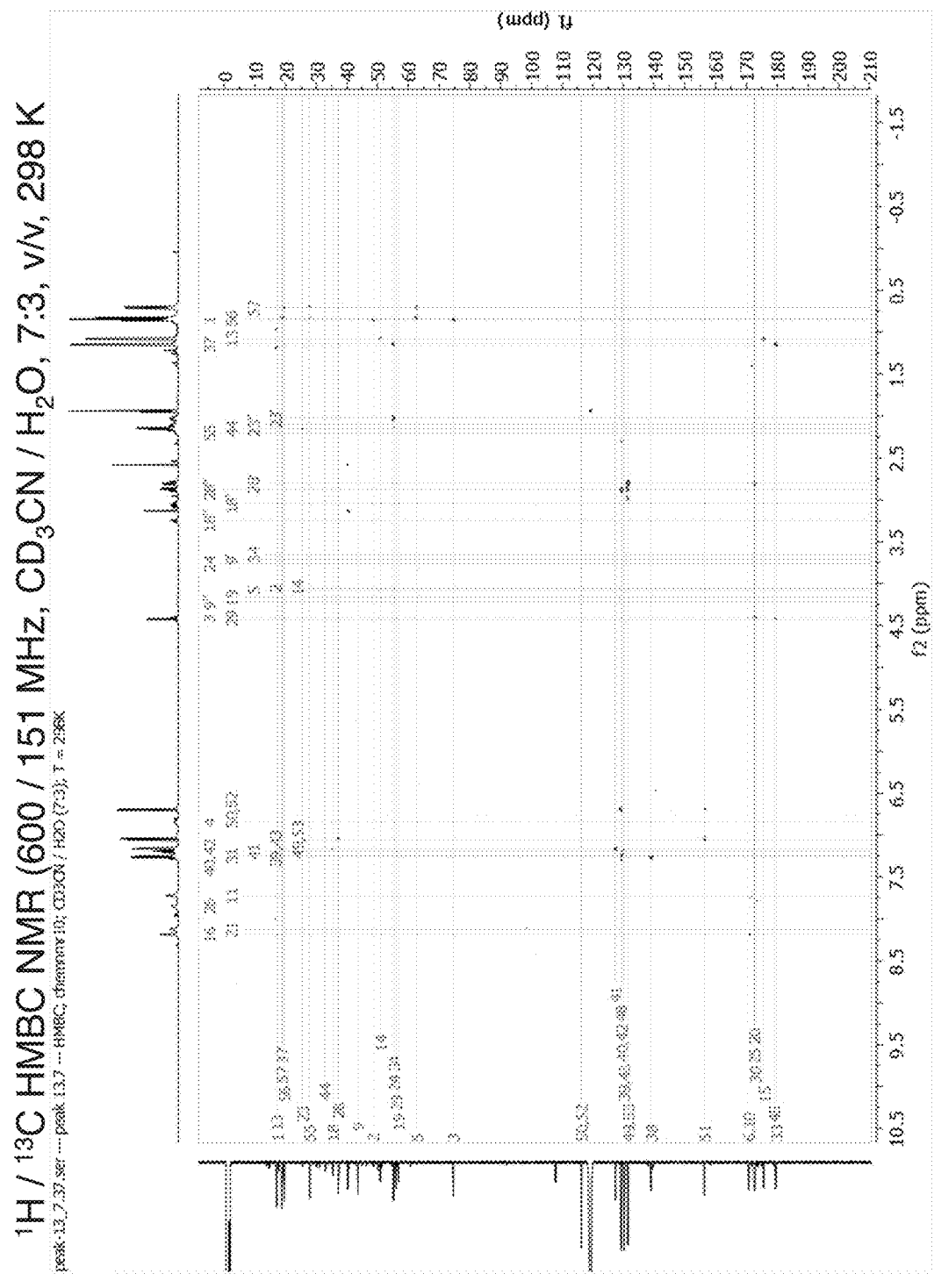
Figures 21, 21G:
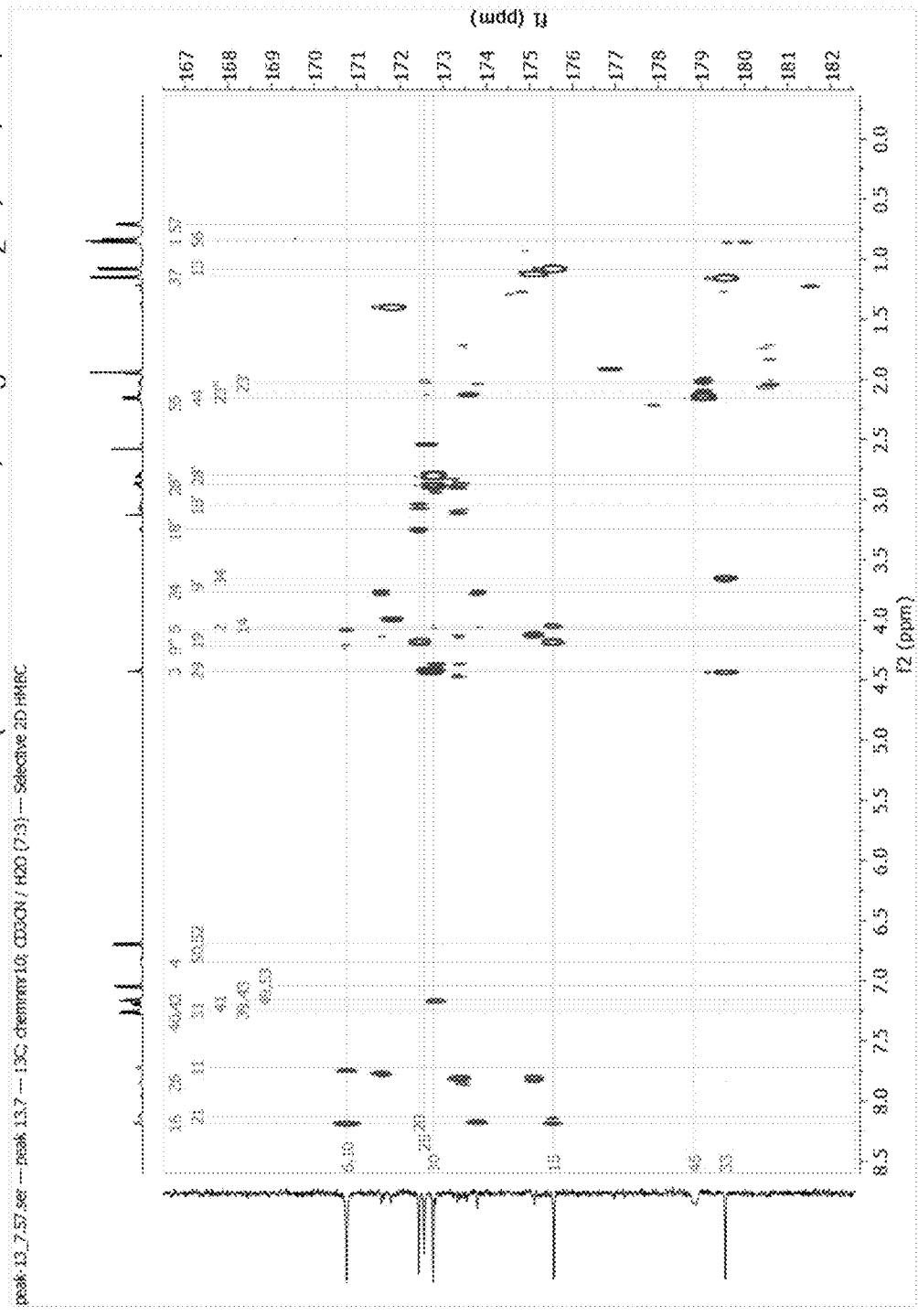
Figures 21, 21H:
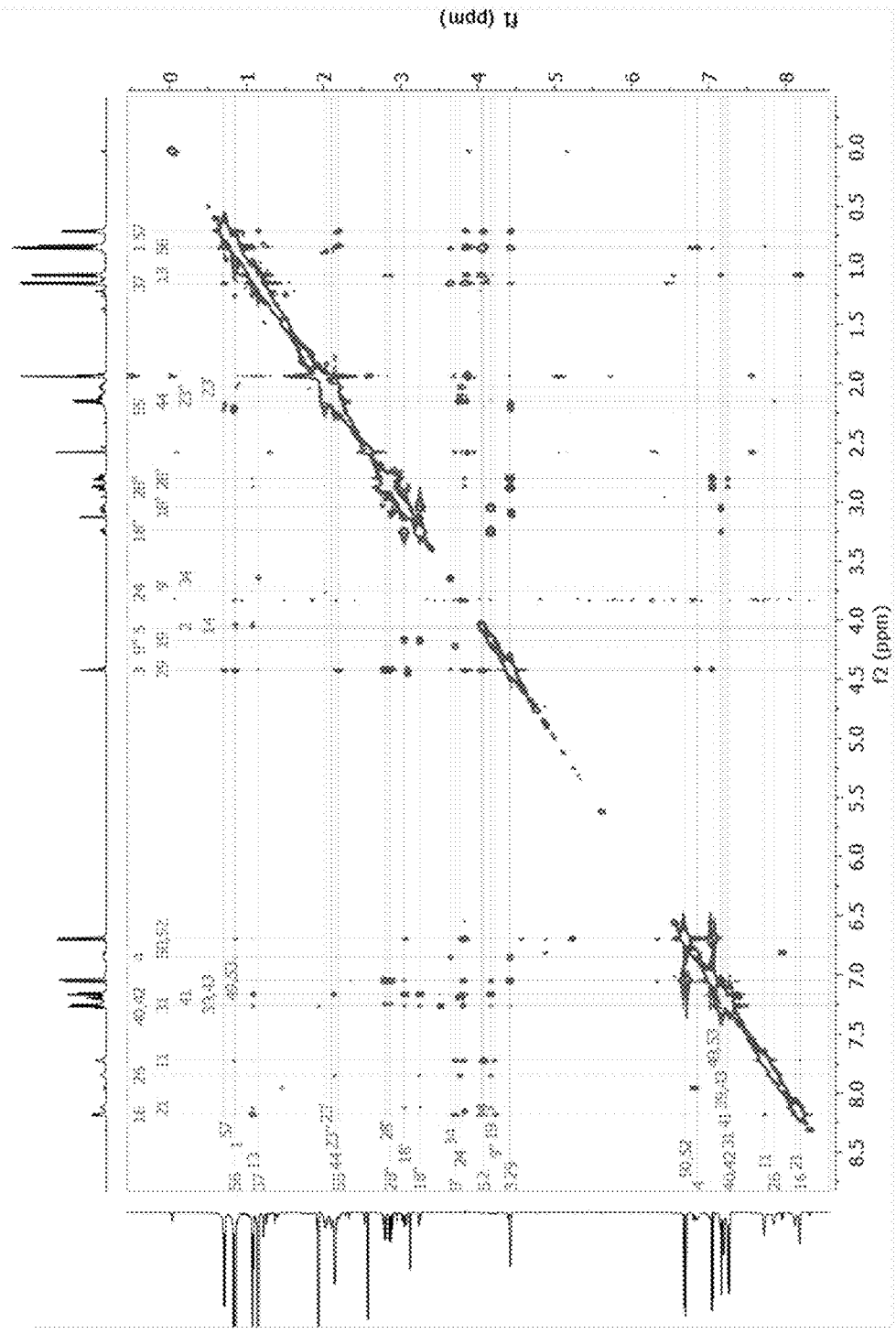
Figure 22:
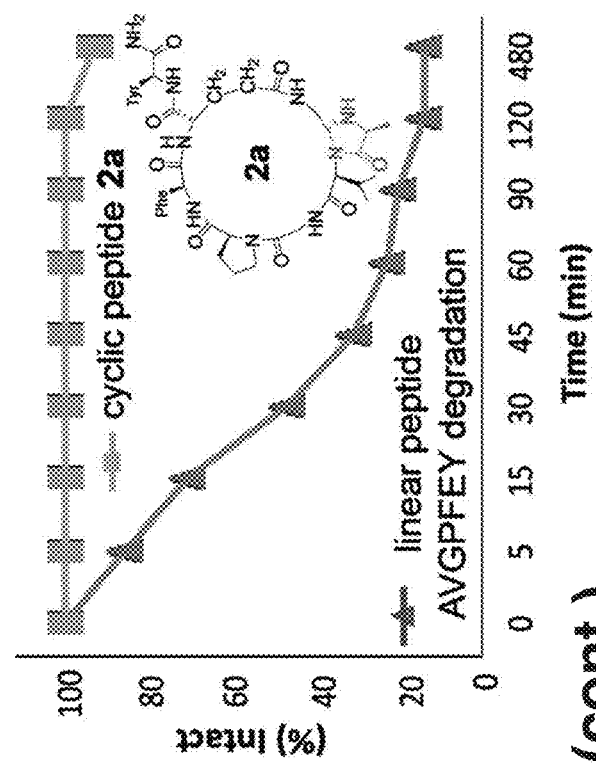
FIG. 22, comprising
Figure 22:
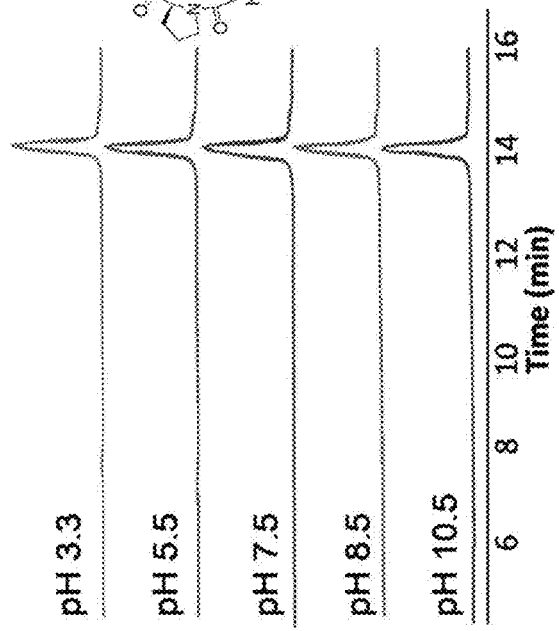
Figure 23:
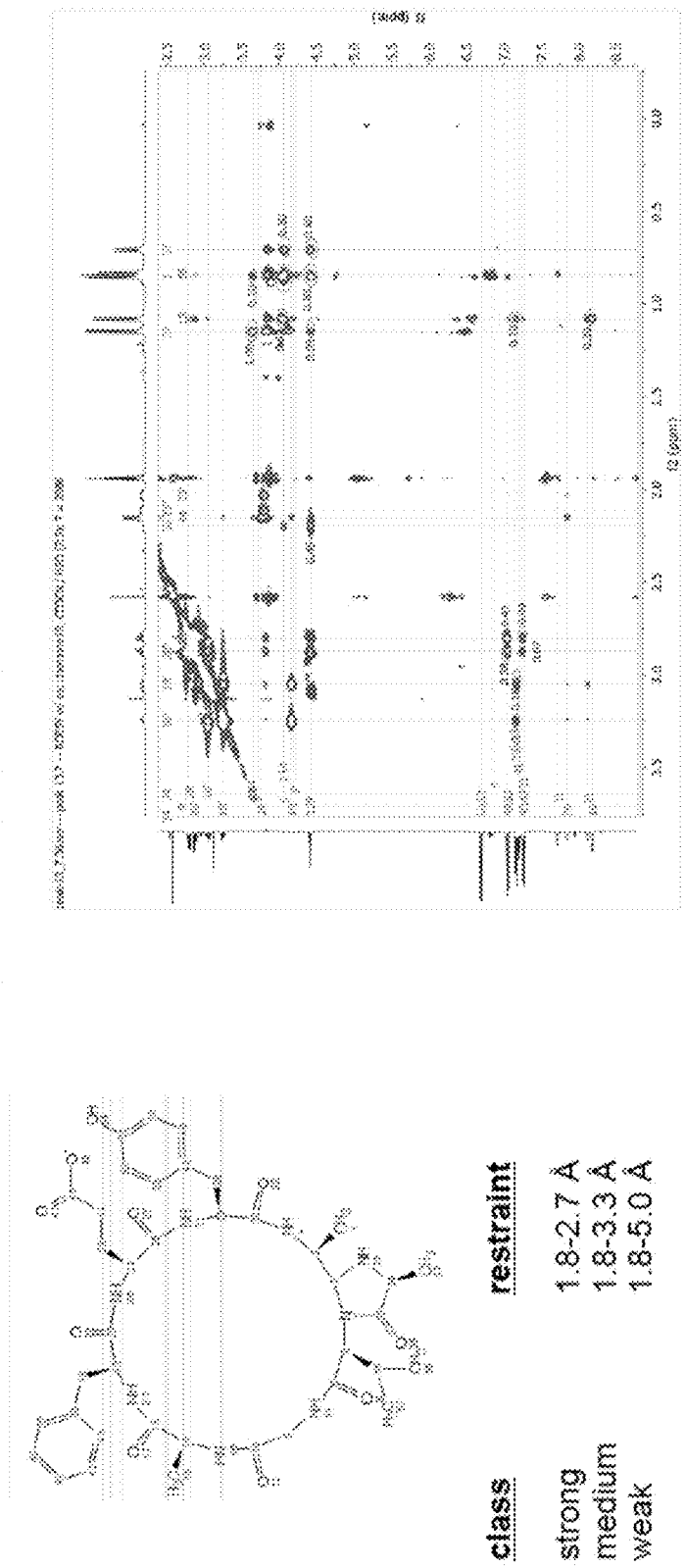
FIG. 23, comprising
Figures 24, 24D:
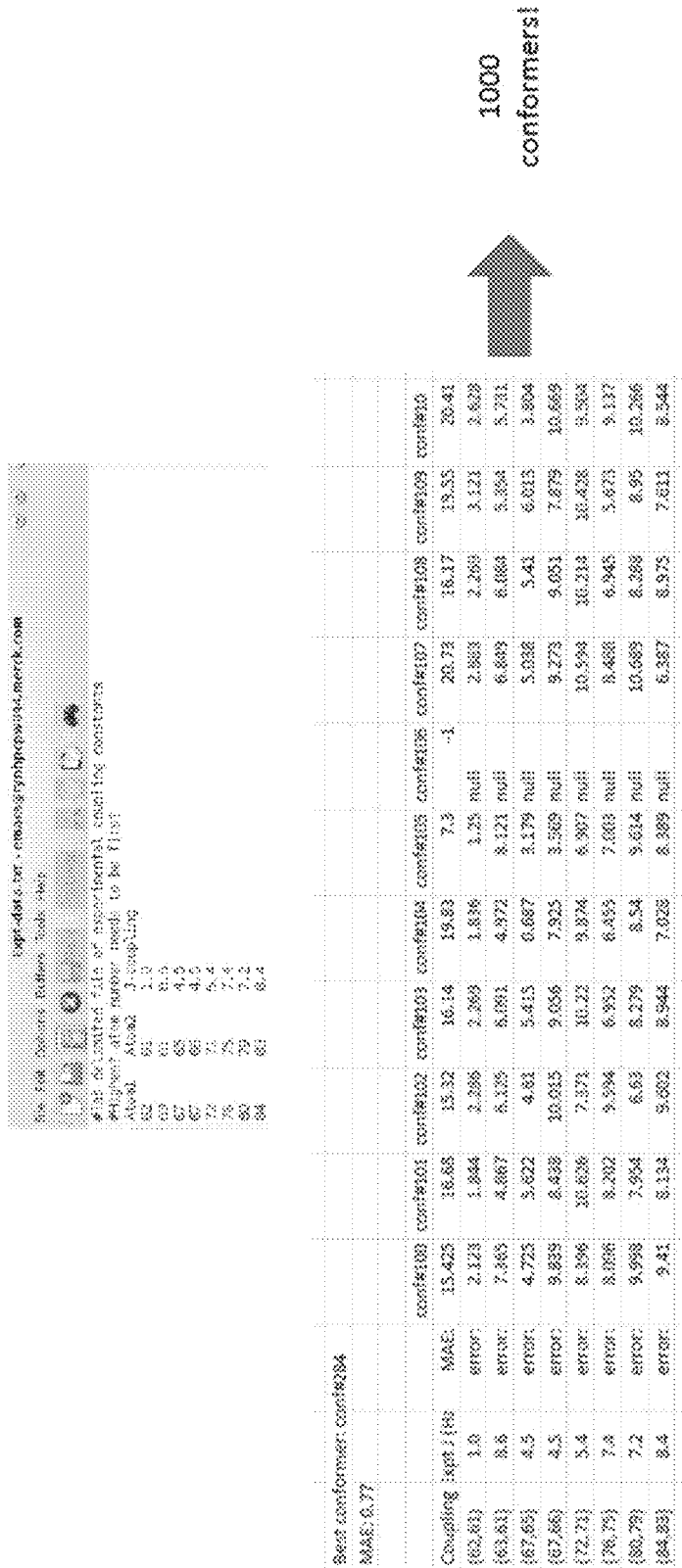

Next, the scope of CyClick chemistry was examined on less reactive peptide ketones instead of peptide aldehydes. Interestingly, cyclic peptide 4f was generated with moderate conversion from the peptide ketone with a quaternary chiral center at the site of cyclization, further expanding the substrate scope of this reaction (36%, FIG. 16C and FIG. 19). In the reactions described above, more than thirty-five cyclic peptides that vary in ring size (12- to 23-membered) and amino acid composition have synthesized highlighting that CyClick is a powerful, self-guided, intramolecular amide backbone activation approach for the efficient synthesis of cyclic peptides in high purity, free from the typical contaminating species normally encountered during the synthesis of cyclic peptides using conventional methodology, Structural Impact of 4-Imidazolidinone in Cyclic Peptides To determine the ability of the 4-imidazolidinone to induce secondary structure in cyclic peptides, NMR studies were conducted on the head-to-tail cyclic peptide cyc-(AVGAFEYA) (SEQ ID NO: 40) 4a in aqueous medium. 2D TOCSY, COSY, HSQC, HMBC, and ROESY spectra were acquired to assign the $^1$H and $^{13}$C signals of 4a (FIG. 21). Variable-temperature (VT-NMR) studies were then performed to determine the intramolecular H-bonding pattern of cyclic peptide 4a (FIG. 22A and FIG. 23), between the Tyr amide proton and Ala carbonyl oxygen. The observed ROEs were used to construct a ROE "connectivity" map, which summarizes sequential (i.e. residues i to i+1) and long-range ROEs that are commonly observed in peptides with higher order structure. Long-range ROEs were observed for peptide 4a between residues Ala (ith) and Tyr (i+3) indicating their proximity. Furthermore, the secondary structure adopted by 4a was determined by running ForceGen (Jain A N et al., 2019, J. Comput. Aided Mol. Des., 33:531) with NMR constraints (FIG. 22B and FIG. 24). Together, these NMR studies provided the first direct experimental evidence that 4-imidazolidinone was indeed a turn inducer.

Biological Evaluation of 4-Imidazolidinone Cyclic Peptides

The stability of cyclic peptides is a major concern, for pharmaceutical applications. To evaluate the stability of a 4-imidazolidinone cyclic peptide, cyclic peptide cyc (NVGPFEY) (SEQ ID NO: 19) 2f was incubated under different pH conditions. HPLC analysis showed that 4-imidazolidinone cyclic peptide 2f was resistant to hydrolysis/degradation under acidic and basic conditions and remained unchanged for up to 24 h (10 mM phosphate-buffered saline (PBS) buffer, pH 3.5-10.5, FIG. 22C).

Figure 25:
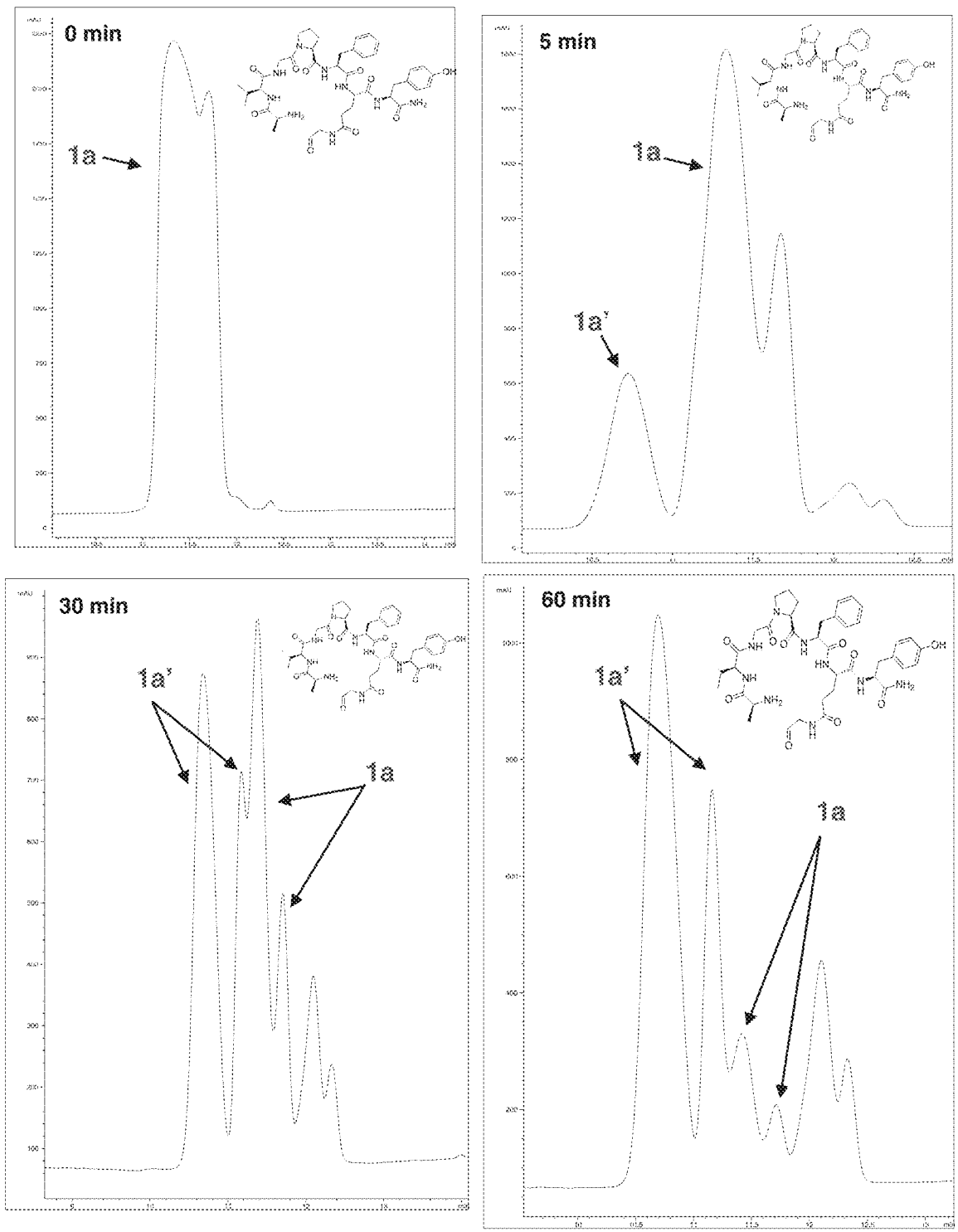
FIG. 25, comprising

To evaluate the potential of 4-imidazolidinone cyclic peptides for biological applications, the proteolytic stability of a cyclic peptide cyc(AVGPFEY) (SEQ ID NO: 13) 2a in comparison with its linear counterpart AVGPFEY (SEQ ID NO: 13) was examiner. Linear peptide AVGPFEY ID NO: 13) and cyclic peptide cyc(AVGPFEY) (SEQ ID NO: 13) 2a were incubated with chymotrypsin, which hydrolyzes peptide bonds at the C-terminal side of aromatic residues, such as Phe. Results showed that in the presence of chymotrypsin cyclic peptide 2a remained intact for up to 24 h with only 20% cleavage observed, whereas its linear counterpart AVGPFEY (SEQ ID NO: 13) degraded quickly with a half-life of 20 min and was fully consumed in 90 min, as determined by HPLC and MS analysis (FIG. 22D, FIG. 25, and Table 6).

TABLE 6

Representative results of the enzyme degradation studies.

| Time (min) | Linear AVGPFEY (SEQ ID NO: 13) | Cyclic cyc(AVGPFEY) 2a (SEQ ID NO: 13) |
| --- | --- | --- |
| 0 | 100 | 100 |
| 5 | 82.9 | 100 |
| 15 | 66.3 | 100 |
| 30 | 38.6 | 100 |
| 45 | 20.2 | 100 |
| 60 | 10.9 | 100 |
| 90 | 7.7 | 100 |
| 120 | 0 | 100 |
| 480 | 0 | 91.9 |

These results demonstrated that the 4-imdazolidinone moiety generated during cyclization significantly improved the stability of cyclic peptides against both proteolysis as well as degradation over a range of pH conditions. Together, these results demonstrated the applicability of the CyClick chemistry in generating potentially bioactive cyclic peptidomimetics as molecular tools to study biological systems.

In summary, the present studies describe the development of the CyClick reaction, an approach based on the conformationally induced activation of the amide backbone, for the cyclization of peptides. This method was highly selective for intramolecular reaction and led to the efficient synthesis of cyclic peptides even at high concentrations without the formation of any undesired side products due to linear and cyclic dimerization or oligomerization. The potency of the CyClick reaction was well demonstrated by the broad substrate scope encompassing a variety of peptides with different amino acid compositions including difficult sequences containing all L-amino acids without any turn inducers, various aldehydes and ketones, and different chain lengths, including generation of highly strained 12-membered cyclic peptide(s) as shown in FIG. 16. CyClick chemistry led to the formation of a 4-imidazolidinone moiety in a cyclic peptide, which further induced a turn structure as determined by detailed NMR investigation. The 4-imidazolidinone cyclic peptides exhibited high stability over a range of pH conditions and towards enzymatic degradation, demonstrating the utility of this chemistry for the development of pharmaceutically active compounds and biological probes. Moreover, the 4-imidazolidinone moiety introduced a secondary amine in cyclic peptides, which is utilized in additional studies for further diversification. The increasing significance of bioactive cyclic peptides containing pharmacophores render this method attractive for synthetic and medicinal chemistry.

The materials and methods employed in these experiments are now described.

General Information

All commercial materials (Sigma-Aldrich, Fluka, and Novabiochem) were used without further purification. All solvents were reagent or HPLC (Fisher) grade. All reactions were performed under air in glass vials. Yields refer to chromatographically pure compounds; % yields were obtained by comparison of HPLC peak areas of products and starting materials. HPLC was used to monitor reaction progress.

Materials

Fmoc-amino acids, Rink amide resin, 3-[bis(dimethylamino)methyliumyl]-3H-benzotriazol-1-oxide hexafluorophosphate (HBTU), 1-hydroxy-7-azabenzotriazole (HOAt), N,N'-iisopropylcarbodiimide (DIC), and N,N-diisopropylethylamine (DIEA) were obtained from CreoSalus (Louisville, Kentucky). 4-dimethylaminopyridine (DMAP), piperidine, trifluoroacetic acid (TFA), di-tert-butyl dicarbonate (BOC2O), 4-methyl morpholine (NMM) and hydrazine monohydrate were obtained from Alfa Aesar (Ward Hill, Massachusetts). N,N-dimethylformamide (DMF), dichloromethane (DCM), methanol (MeOH), acetonitrile (ACN), sodium cyanoborohydride, tetrahydrofuran (THF), and Fmoc-Ala-aldehyde were obtained from VWR (100 Matsonford Road Radnor, Pennsylvania). Sodium dimethyldithiocarbamate dihydrate (DTC) and aminoacetylaldehyde dimethyl acetal were obtained from Sigma-Aldrich (St. Louis, Missouri). Benzotriazol-1-yl-oxytripyrrolidinophosphonium hexafluorophosphate (PyBOP), phenylsilane, palladium(triphenylphosphine)tetrakis, and levulinic acid were obtained from TCI (Portland, OR). Water was purified using a Millipore Milli-Q water purification system.

Purification. HPLC

Purification was performed using high performance liquid chromatography (HPLC) on an Agilent 1100/1200 series HPLC equipped with a 5 urn particle size, C-18 reversed-phase column. All separations involved a mobile phase of 0.1% formic acid (v/v) in water (solvent A) and 0.1% formic acid (v/v) in acetonitrile (solvent B). The HPLC method employed a linear gradient of 0-80% solvent B over 30 minutes at ambient temperature with a flow rate of 1.0 mL min$^{-1}$. The separation was monitored by UV absorbance at both 220 nm unless otherwise noted.

Analytical Methods

LC-MS: Mass spectrometry to check reaction mixtures was performed using an Agilent 1100 Series HPLC with MSD VL mass spectrometer using positive polarity electrospray ionization (+ESI).

High Resolution LC-MS Conditions for All Purified Peptides: Analyses were performed on an ultra-performance LC system (ACQUITY, Waters Corp., USA) coupled with a quadrupole time-of-flight mass spectrometer (Q-ToF Premier, Waters) with electrospray ionization (ESI) in positive mode using Mass lynx software (V4.1). Unless otherwise mentioned a sample was injected either onto a C4 column (PHENOMENEX AERIS™ 3.6 μm WIDEPORE C4 200 Å, LC Column 50×2.1 mm) with a 300 μL/min flow rate of mobile phase of solution A (95% $H_2O$, 5% acetonitrile and 0.1% formic acid) and solution B (95% acetonitrile, 5% $H_2O$, and 0,1% formic acid) beginning gradient-Time-0 min 10% B; 5 min 28% B; 20 min 38% B; 22 min 90% B; C18 column (ACQUITY UPLC BEH 1.7 μm 1×50 mm) with a 200 μL/min flow rate of mobile phase of solution A (95% $H_2O$, 5% acetonitrile and 0.1% formic acid) and solution B (95% acetonitrile, 5% $H_2O$, and 0.1% formic acid) beginning gradient-Time-1 min 0% B; 1-10 min 100% B for chromatography analysis (or) directly injected with mobile phase 50% $H_2O$: 50% ACN, 0.1% formic acid at 200 μL/min flow rate in ESI positive mode.

Fmoc Solid-Phase Peptide Synthesis (Fmoc-SPPS) (Chan W C et al., 2000, Fmoc Solid Phase Peptide Synthesis: A Practical Approach, Oxford Univ. Press, New York)

Peptides were synthesized manually on a 0.25 mm scale using Rink amide resin. Resin was swollen with DCM for 1 h at room temperature. Fmoc was deprotected using 20% piperidine-DMF for 5 min to obtain a deprotected peptide-resin. First Fmoc-protected amino acid (1.25 mm/5 equiv.) was coupled using HOAt (1.25 mm/5 equiv.) and DIC (1.25 mm/5 equiv.) in DMF for 15 min at room temperature, Fmoc-protected amino acids (0.75 mm/3 equiv.) were sequentially coupled on the resin using HBTU (0.75 mm/3 equiv.) and DIEA (1.5 mm/6 equiv.) in DMF for 5 min at room temperature. Peptides were synthesized using standard protocols (Chan W C et al., 2000, Fmoc Solid Phase Peptide Synthesis: A Practical Approach, Oxford Univ. Press, New York). Any Fmoc-protected amino acid added after Fmoc-proline was subjected to the conditions of the first amino acid coupling. Peptides were cleaved from the resin using a cocktail of 95:5, trifluoroacetic acid: water for 2 h. The resin was removed by filtration and the resulting solution was concentrated. The residue was diluted with ACN/water mixture. The resulting solution was purified by HPLC.

General Procedure for Synthesis of Peptide Aldehydes

Peptide aldehydes were necessary to facilitate macrocyclization. An aldehyde was added on either the side chain of the peptide or the C-terminus.

Figure 26:
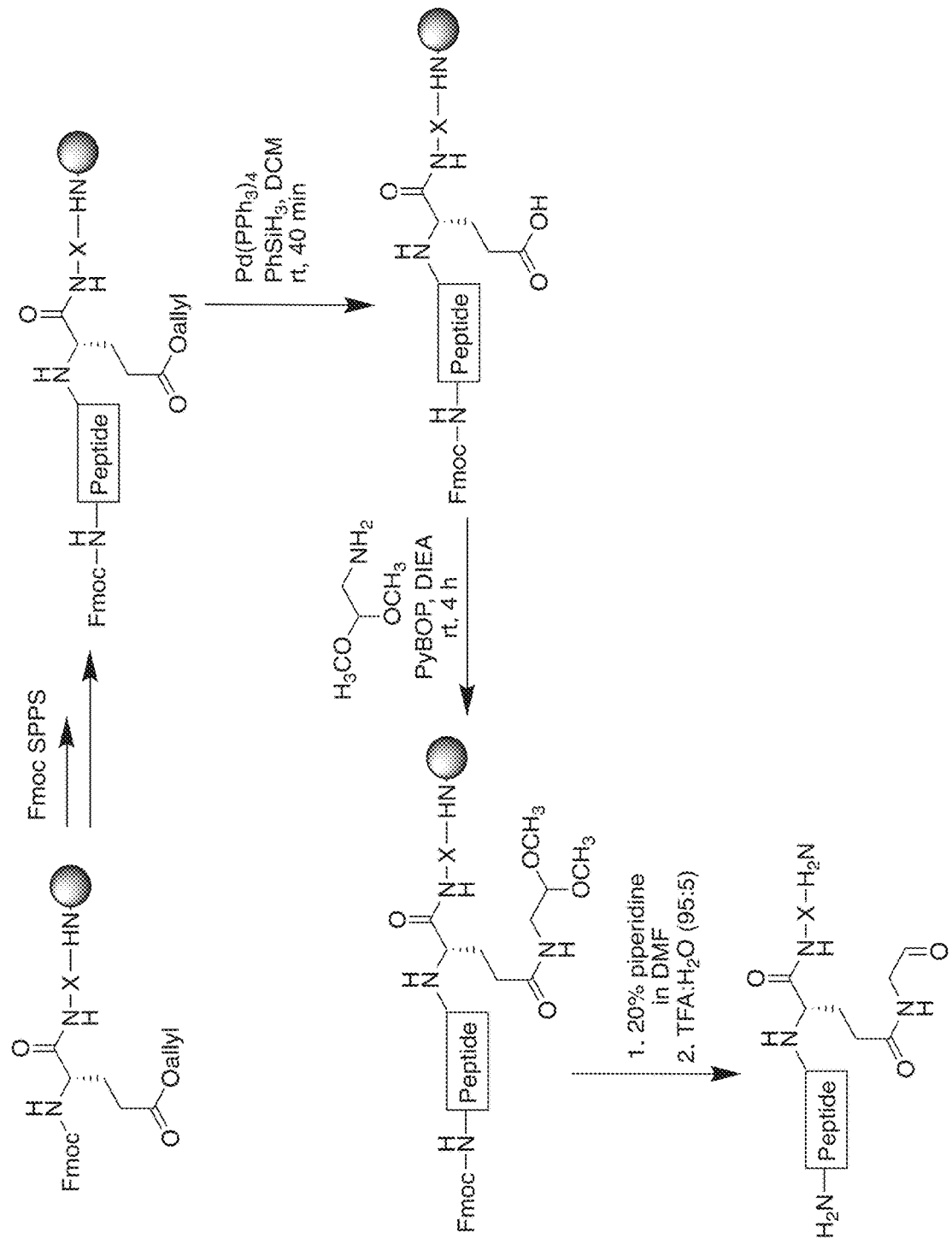
FIG. 26 depicts a schematic representation of the synthesis of side chain peptide aldehydes.

Procedure for Synthesis of Side Chain Peptide Aldehydes—FIG. 26 (Malins L R et al., 2017, J. Am. Chem. Soc., 139:5233): Peptides with Fmoc-Glu(Oall)-QH were synthesized by Fmoc solid phase peptide synthesis protocol. Fmoc-glutamic acid is commercially available with an O-allyl protected side chain. The selective deprotection of the O-allyl group from the side chain of the Glu on a peptide (0.5 mm/g) was achieved on solid support through the addition of palladium(triphenylphosphine)tetrakis (0.05 equiv.) and phenylsilane (24 equiv.) in DCM (6 mL/6.9 mM) and shake for 40 min. This process was repeated, and the resulting resin was washed with DCM (5×). Extra washings with 0.5% DIEA in DMF (2×), 0.5% mass/vol DTC in DMF (2×), and DMF (5×) were carried out to remove the palladium from the resin. Cleavage of the small amount of resin followed by LC-MS evaluation confirmed the deprotection. Next, the deprotected peptide (0.075 mm) on solid support was treated with a solution of PyBOP (0.75 mm/10 equiv.), DIEA (1.5 mm/20 equiv.), and amino acetyl aldehyde dimethyl acetal (0.75 mm/10 equiv.) and resin was shaken for 4 h at room temperature. The resulting resin was washed with three times with DMF, DCM and MeOH. This was followed by the cleavage of the peptide from solid support using cleavage cocktail TFA:$H_2O$ (95:5) for 2 h at room temperature. The resulting peptide aldehyde was analyzed by LCMS and purified by HPLC followed by lypholization to obtain pure peptide aldehyde.

Figure 27:
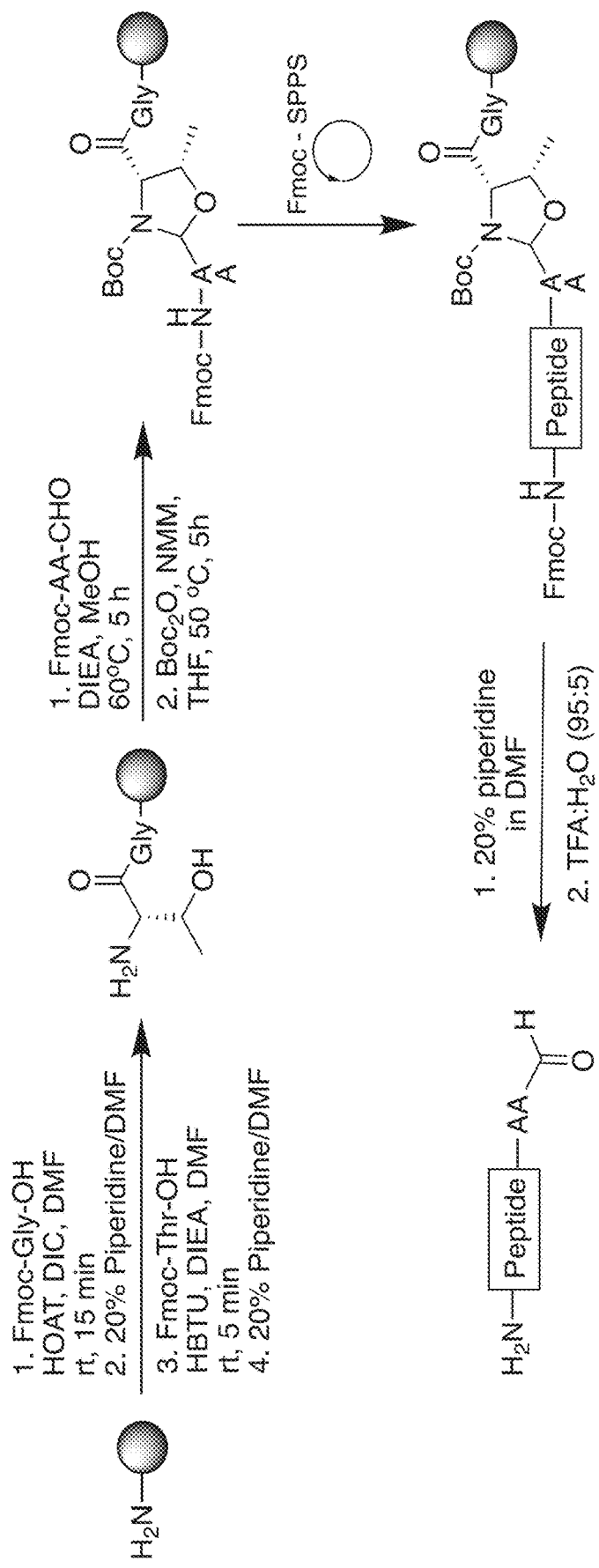
FIG. 27 depicts a schematic representation of the synthesis of C-terminal peptide aldehydes.

Procedure for Synthesis of C-Terminal Peptide Aldehydes—FIG. 27 (Malins L R et al., 2017, J. Am. Chem. Soc., 139:5233; Wang G et al., 2003, Org. Lett., 5:737): Fmoc-Gly-OH and Fmoc-Thr-GH were coupled with the general peptide synthesis procedure to swollen Rink resin (0.5 mm/g). Following Fmoc-deprotection, the resin (500 mg) was added to a solution of Fmoc-Ala-CHO (alanine aldehyde) (1 mm/4 equiv.) in 1% DIEA v/v in MeOH (2.5 mL/final conc. 0.1 M) and rocked for 5 h at 60° C. The resin was washed with MeOH (5×3 mL), DMF (5×3 ml), DCM (5×3 mL), and THF (5×3 mL). The resin was then rocked for 5 h at 50° C. in a solution of Boc anhydride BOC20 (1.25 mm/5 equiv.), NMM (1.25 mm/5 equiv.) in THF (2.5 mL/final conc. 0.1 M). The resin was washed with THF (5×3 mL), DCM (5×3 mL), and DMF (5×3 mL) followed by the coupling of rest of Fmoc-amino acid residues using Fmoc SPPS. After Fmoc-SPPS, the resulting resin was washed three times with DMF, DCM, and MeOH. This was followed by the cleavage of the peptide from the solid support using cleavage cocktail TFA:$H_2O$ (95:5) for 2 h at room temperature. The resulting C-terminal peptide aldehyde was analyzed by LCMS and purified by HPLC followed by lypholization to obtain pure peptide aldehyde.

Figure 28:
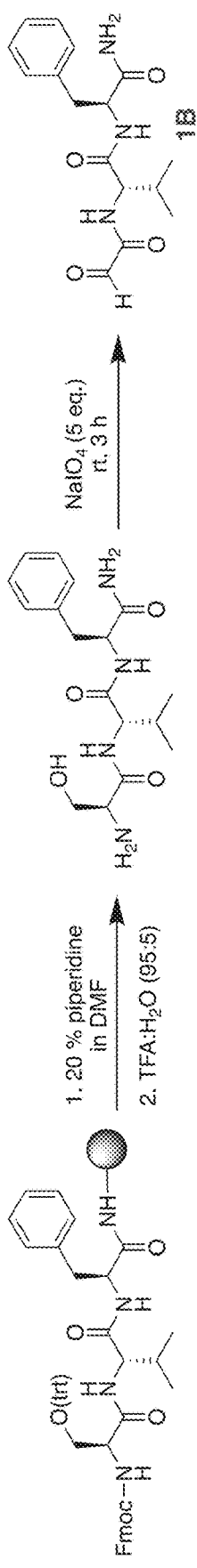
FIG. 28 depicts a schematic representation of the synthesis of N-terminal peptide aldehydes.

Procedure for synthesis of N-terminal peptide aldehydes—FIG. 28 (Witus L S et al., 2010, Curr. Protoc. Chem. Biol., 2:125): Fmoc-Phe-QH, Fmoc-Val-QH, and Fmoc Ser (trt)-OH were sequentially coupled to Rink amide resin (0.5 mm/g) using standard SPPS protocol. The peptide was cleaved with TFA:TES:$H_2O$ (95:2.5:2.5) and purified with HPLC. Lypholized peptide (10 mg) was shaken with sodium periodate (5 equiv.) in 50 mM phosphate buffer (1 mL, 31 mM) at room temperature for 3 h in the dark. The sample was analyzed by HPLC and MS.

Figure 29:
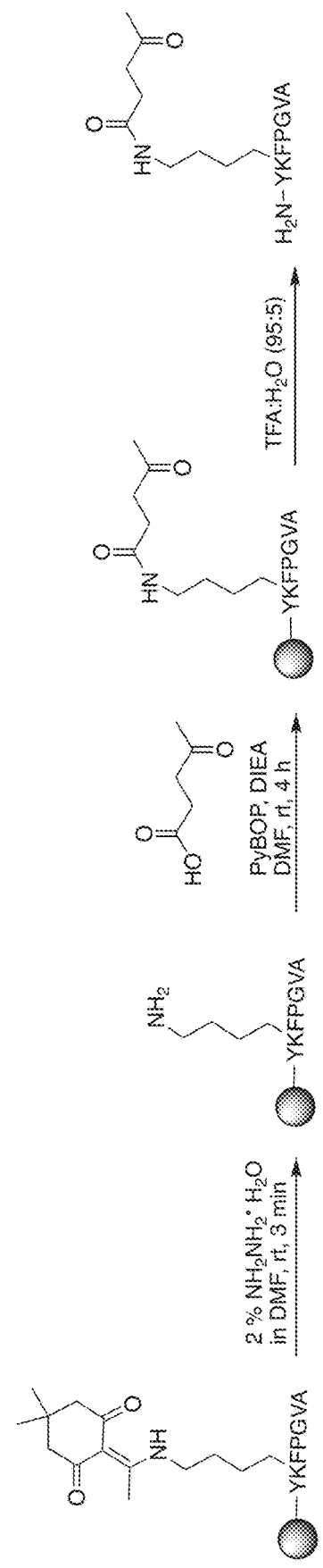
FIG. 29 depicts a schematic representation of the general synthesis of peptide ketones.

General Procedure for Synthesis of Peptide Ketones—FIG. 29

Peptide containing lysine with Dde as a protecting group on resin (0.5 mm/g) was first selectively deprotected from resin using 2% hydrazine monohydrate in DMF (260 µL) for 3 min at room temperature (3×) and washed with DMF (3×). Next, 0.05 mm of Sys-deprotected resin was treated with levulinic acid (0.5 mm/10 equiv.), PyBOP (0.5 mm/10 equiv.), DIEA (1 mm/20 equiv.), in DMF (6 mL, final conc. 0.01 M) and rocked for 4 h at room temperature. The resulting resin was washed three times with DMF, DCM and MeOH. This was followed by the cleavage of the peptide ketone from solid support using cleavage cocktail TFA:$H_2O$ (95:5) for 2 h at room temperature. The peptide ketone was analyzed by LCMS and purified by HPLC followed by lypholization to obtain pure peptide ketone.

Structure Elucidation Via NMR

An approximately 1 mg sample was dissolved in 0.15 mL of DMSO-$d_6$, and the solution was then transferred to a 3-mm NMR tube. $^1H$, $^{13}C$, COSY, TOCSY, HSQC, HMBC, and ROESY spectra were acquired at ambient temperature (298 K) using a 3-mm triple resonance (HCN) helium cryoprobe on a 600 MHz Agilent DD2 NMR spectrometer. Proton chemical shifts were referenced to residual DMSO-$d_5$ at 2.50 ppm, and carbon, chemical shifts were referenced to DMSO-$d_6$ at 39.52 ppm. Spectra were processed using Mnova ver. 12.0.4. A gradient COSY spectrum was acquired using 2048×400 increments, and 0% sine squared II apodizations were applied in both dimensions. A TOCSY spectrum was acquired using a 60 ms mixing time and 2048×512 increments; the spectrum was then linear predicted to 1048 points in the f1 dimension. An adiabatic gradient multiplicity-edited HSQC spectrum was acquired using 2048×512 increments. An adiabatic gradient HMBC spectrum was acquired using a J-optimization of 8 Hz and 2048×512 increments, and then a 0% sine squared II apodization was applied in the direct dimension. An adiabatic gradient ROESY spectrum was acquired using a 200 ms mixing time and 2048×400 increments, and 90° sine squared apodizations were applied in both dimensions.

As shown in FIG. 4B, downfield aminal carbon chemical shift at 71.15 ppm, which is much further downfield than any Ca carbon. This downfield aminal chemical shift was present in all cyclized structures described herein (i.e., 71.2, 71.6, 71.7, 72.4, 78.4 for bicyclic, and 74.7 ppm), and thus it is diagnostic for the imidazolidinone moiety. ACD labs' (ver 2015) predictions for this carbon chemical shift were between 68 to 78 ppm.

Figures 4, 4D:
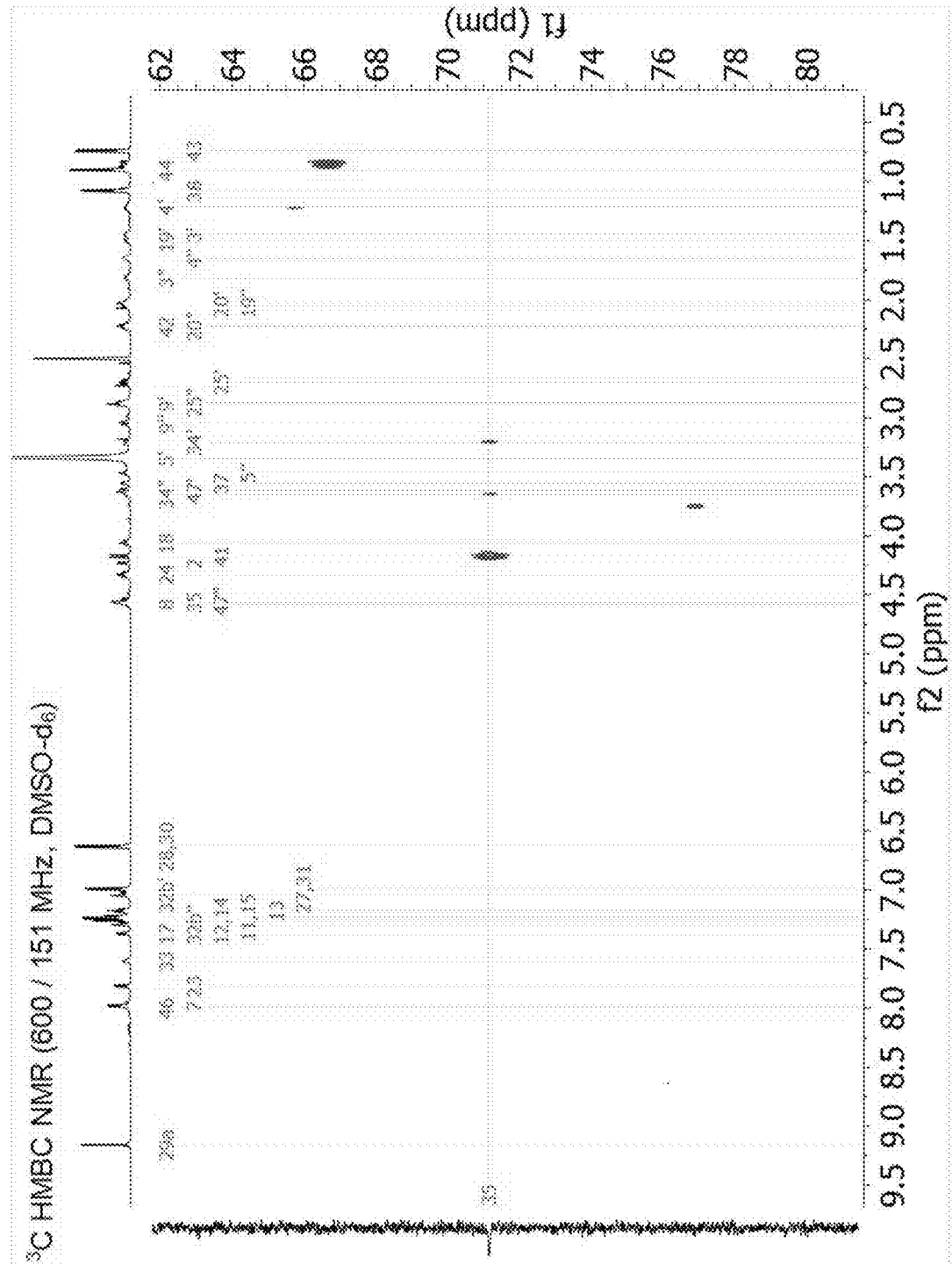
Figures 4, 4F:
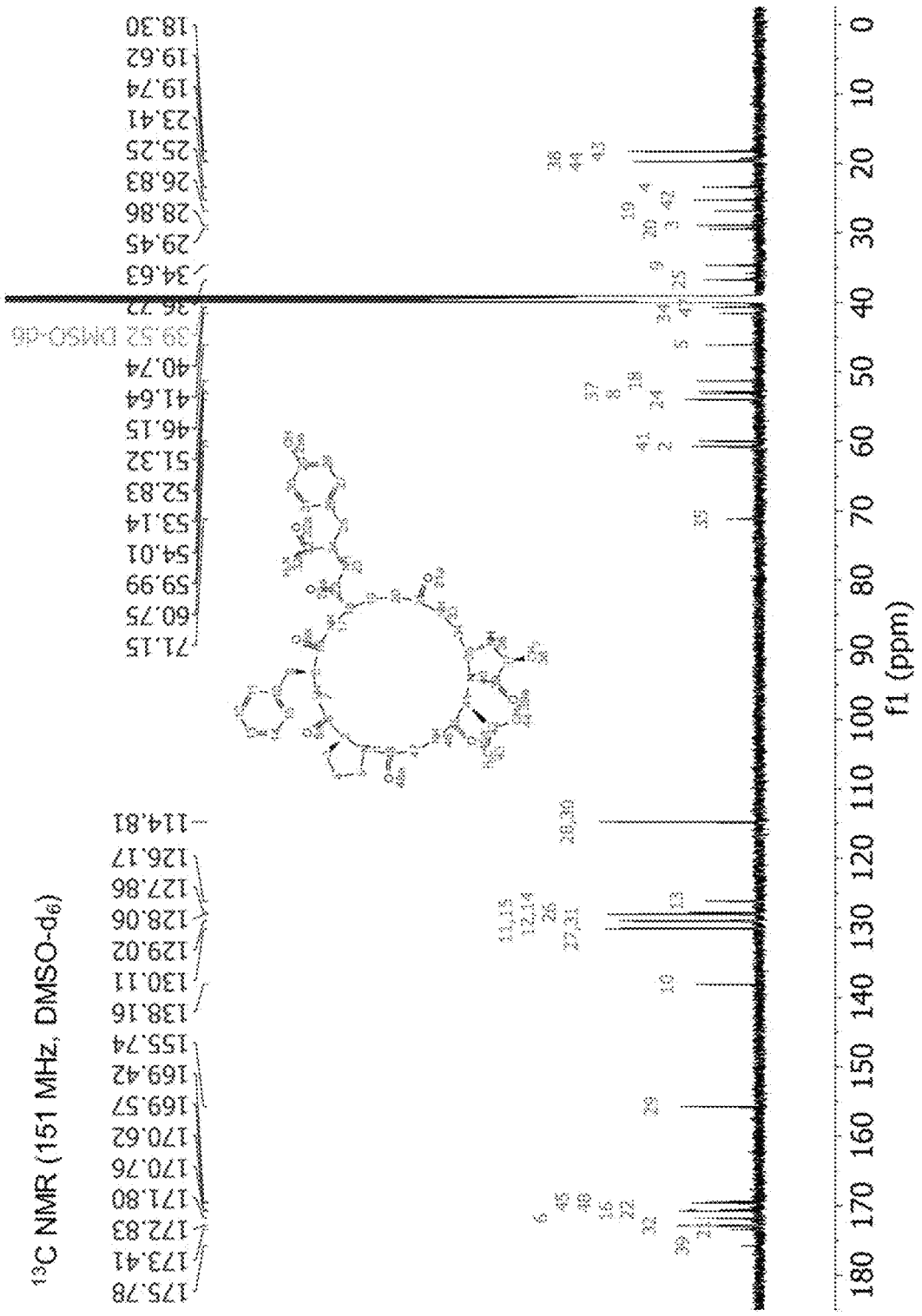
Figures 4, 4H:
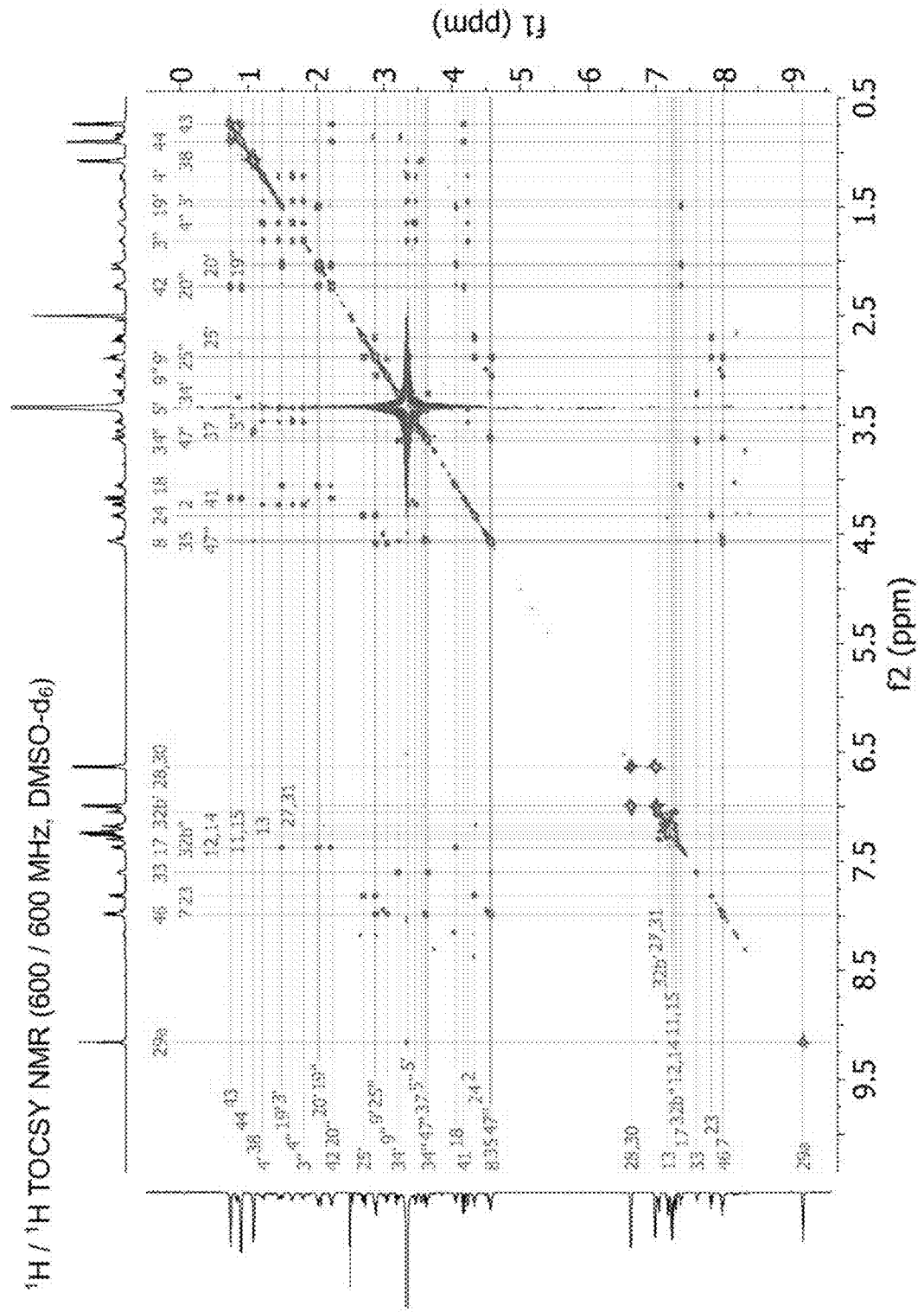
Figures 4, 4I:
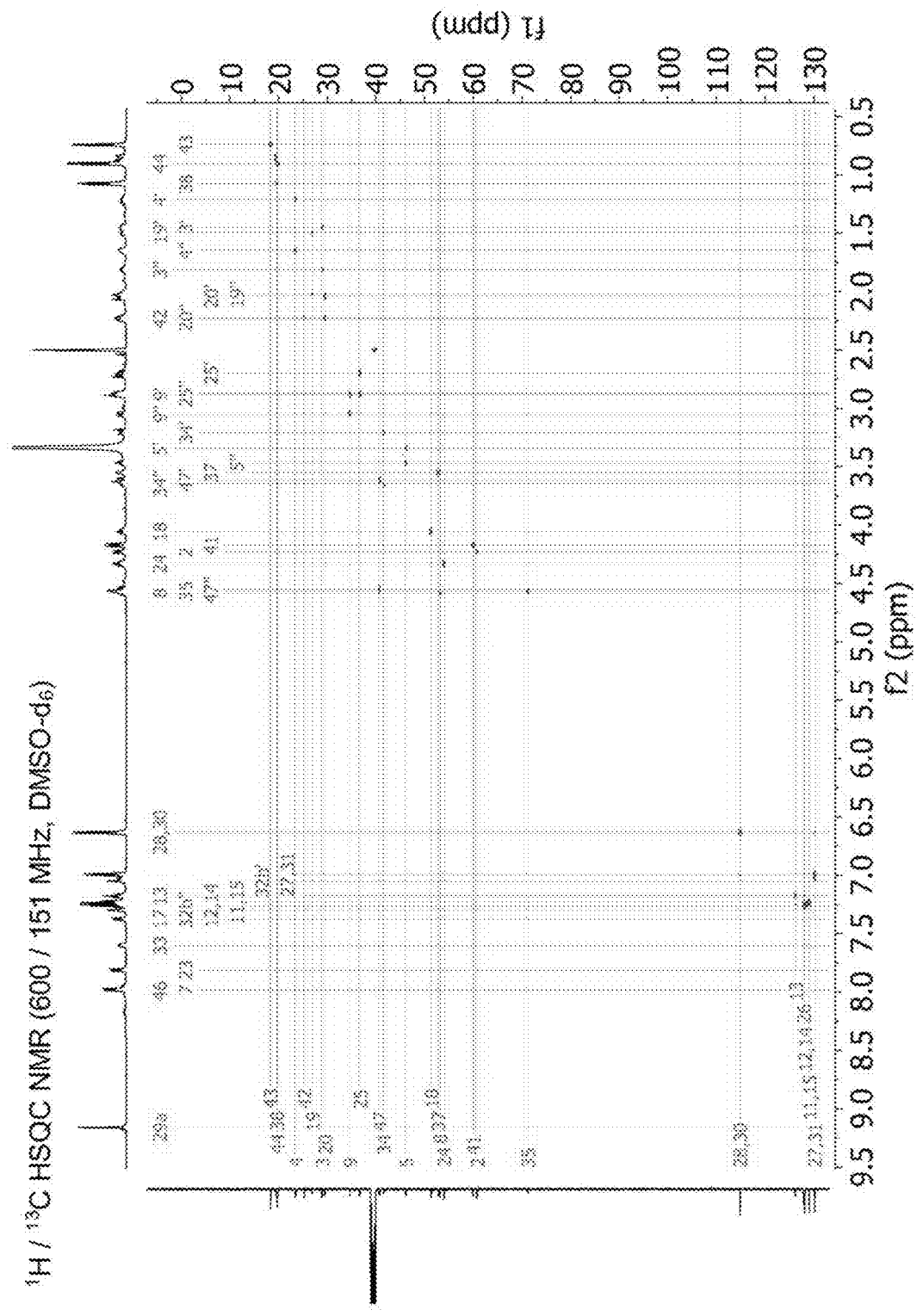
Figures 4, 4J:
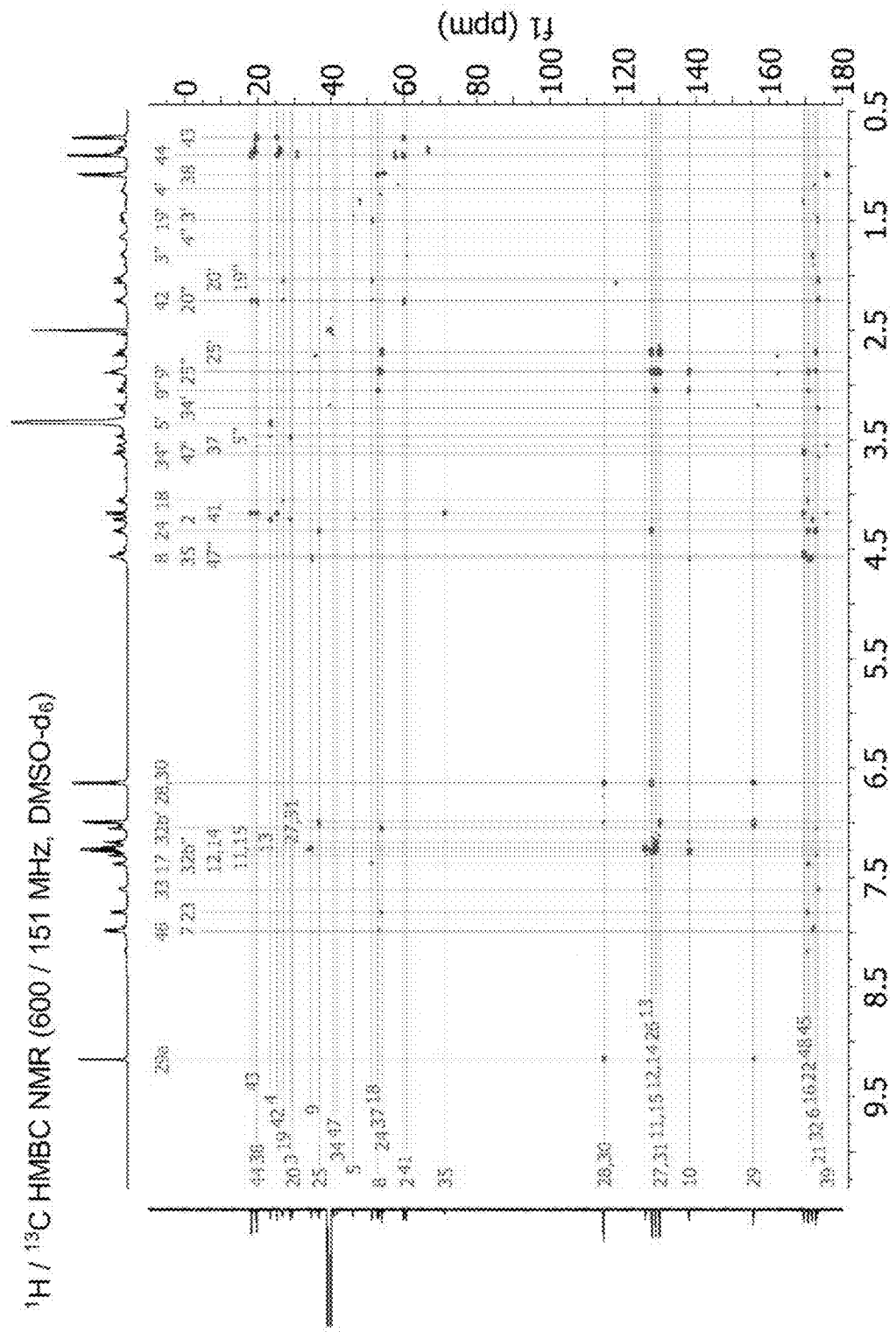
Figures 4, 4K:
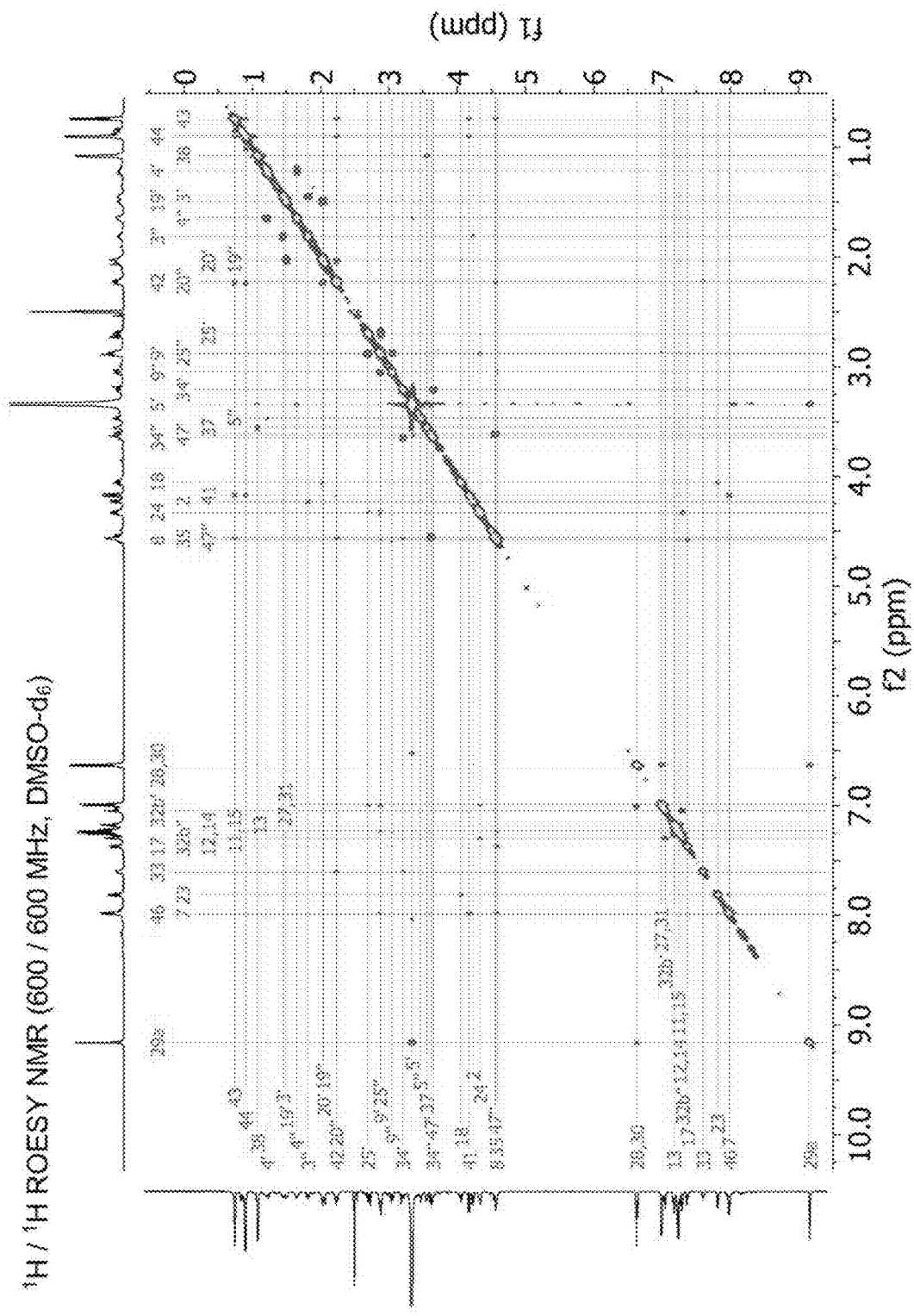

Furthermore, HMBC correlations from Val (proton 41) and Glu (protons 34' and 34") to the C35 carbon was investigated (FIG. 4C and FIG. 4D). It is also worth noting that there 2JCH correlations from H34' and H34" are weaker than the correlation from H41 to C35, which is consistent with 2JCH coupling from the 34 methylene protons to C35 being smaller than the optimization of the HMBC, which was set for 8 Hz. Overall, the data are completely consistent with the imidazolidinone moiety.

ACD Labs (Ver. 2015)$^{13}C$ Chemical Shift Predictions

Figures 5, 5A:
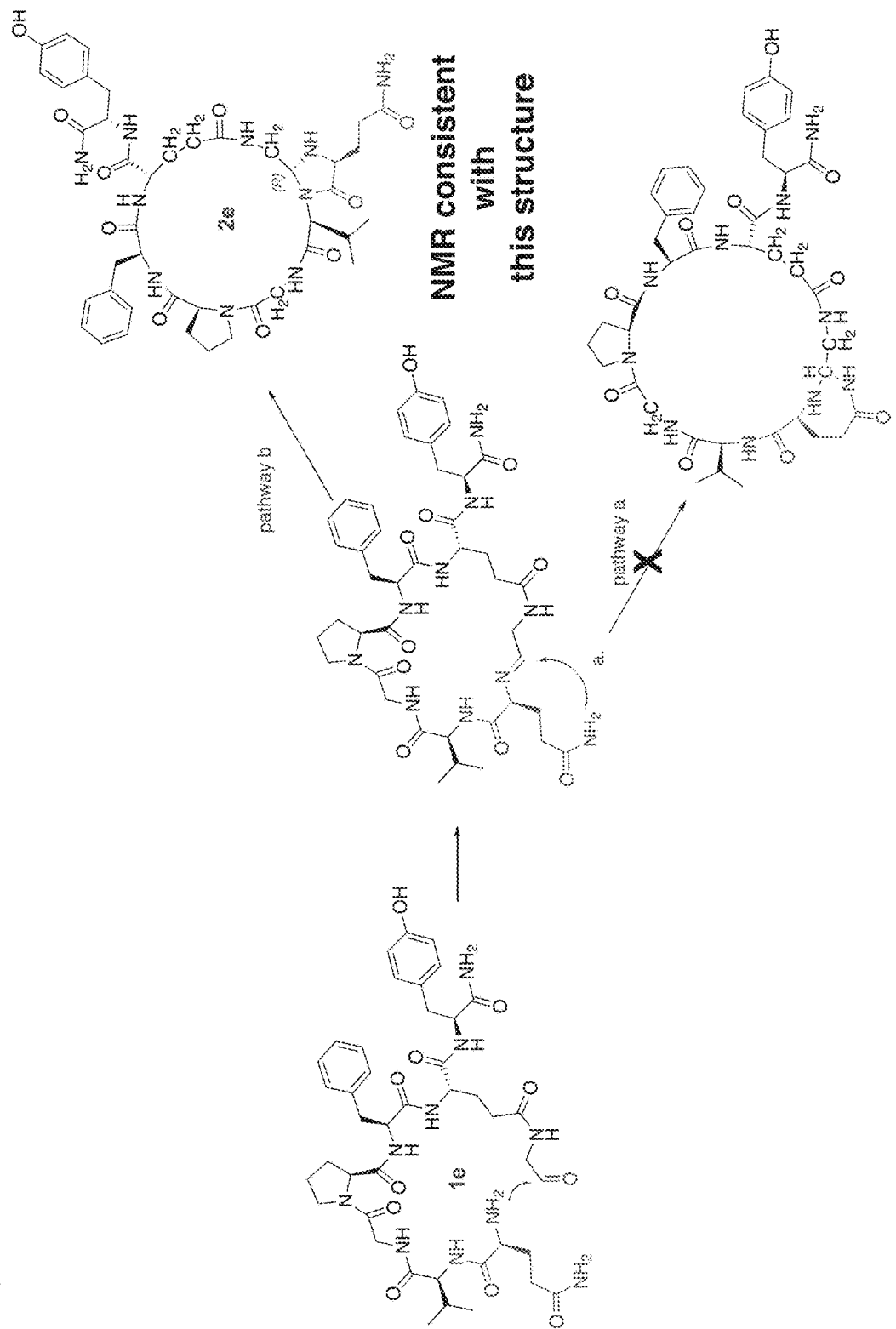
Figures 5, 5C:
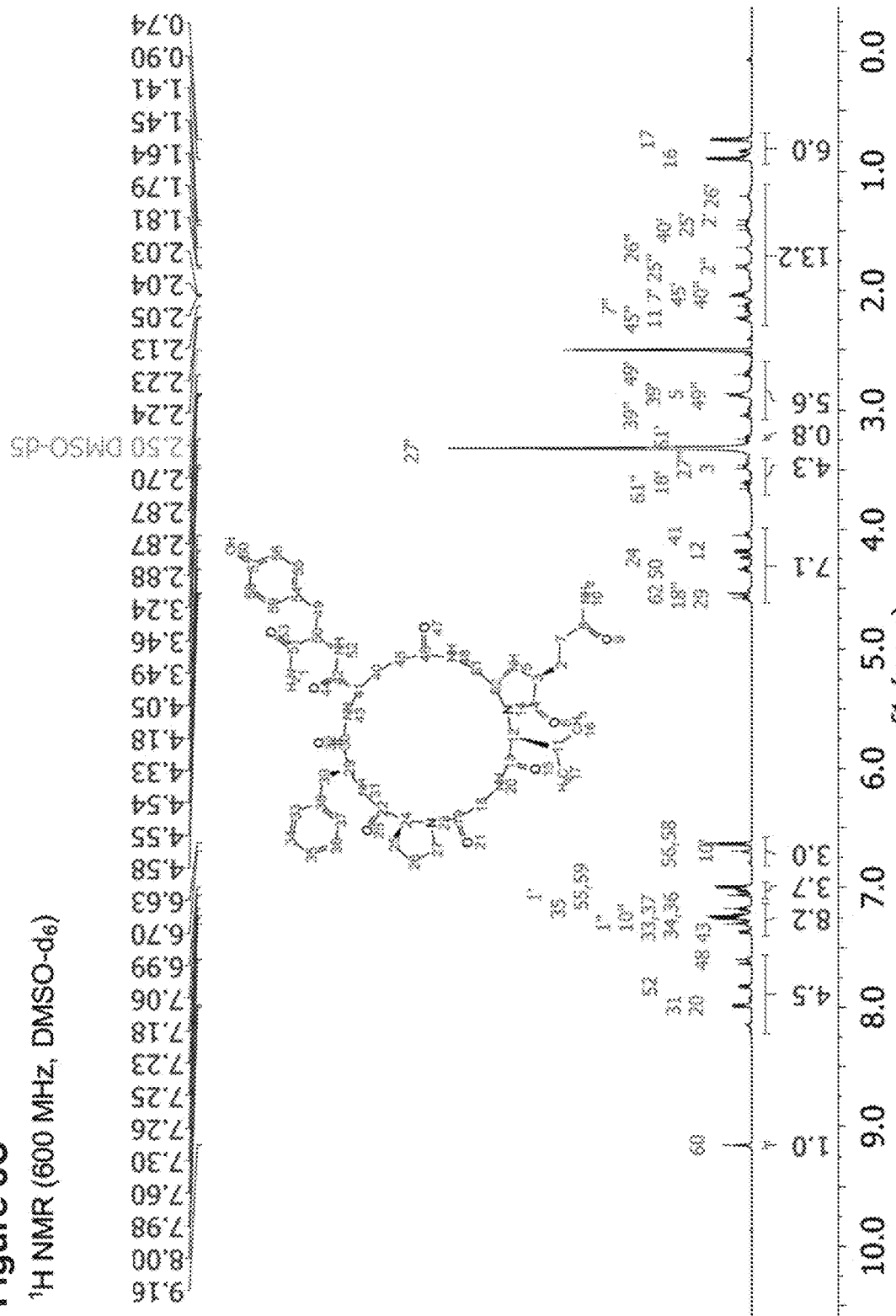
Figures 5, 5D:
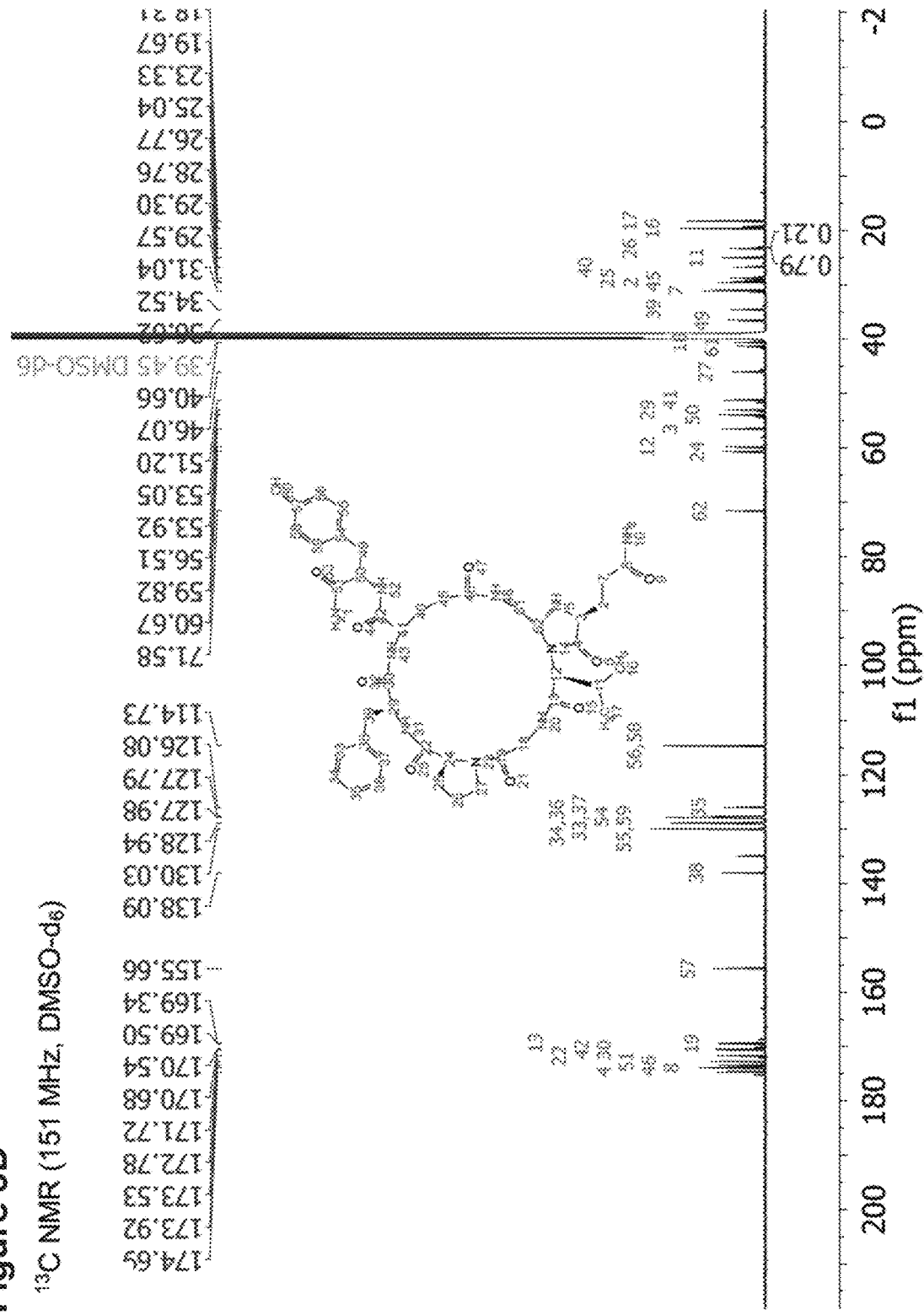
Figures 5, 5E:
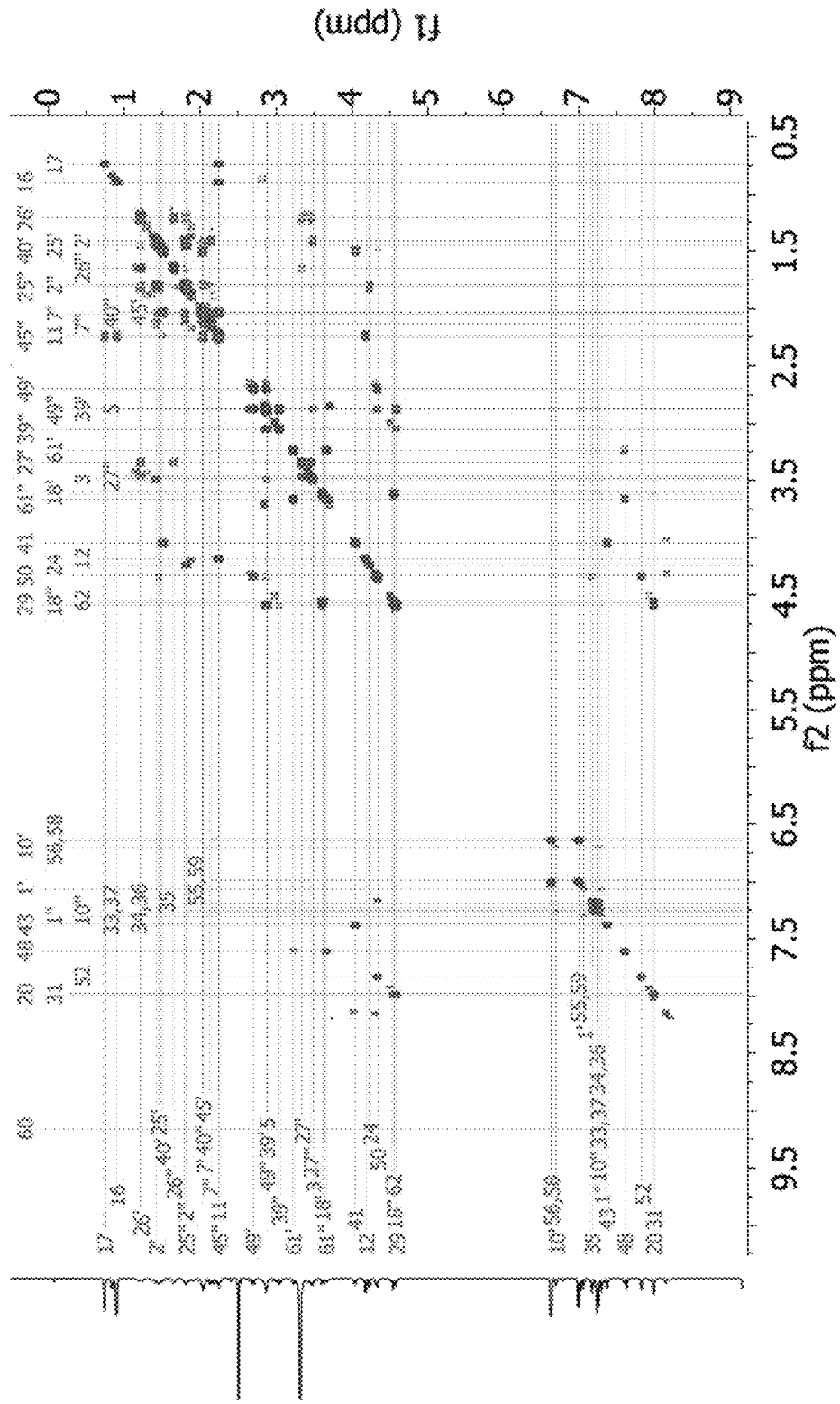
Figures 5, 5F:
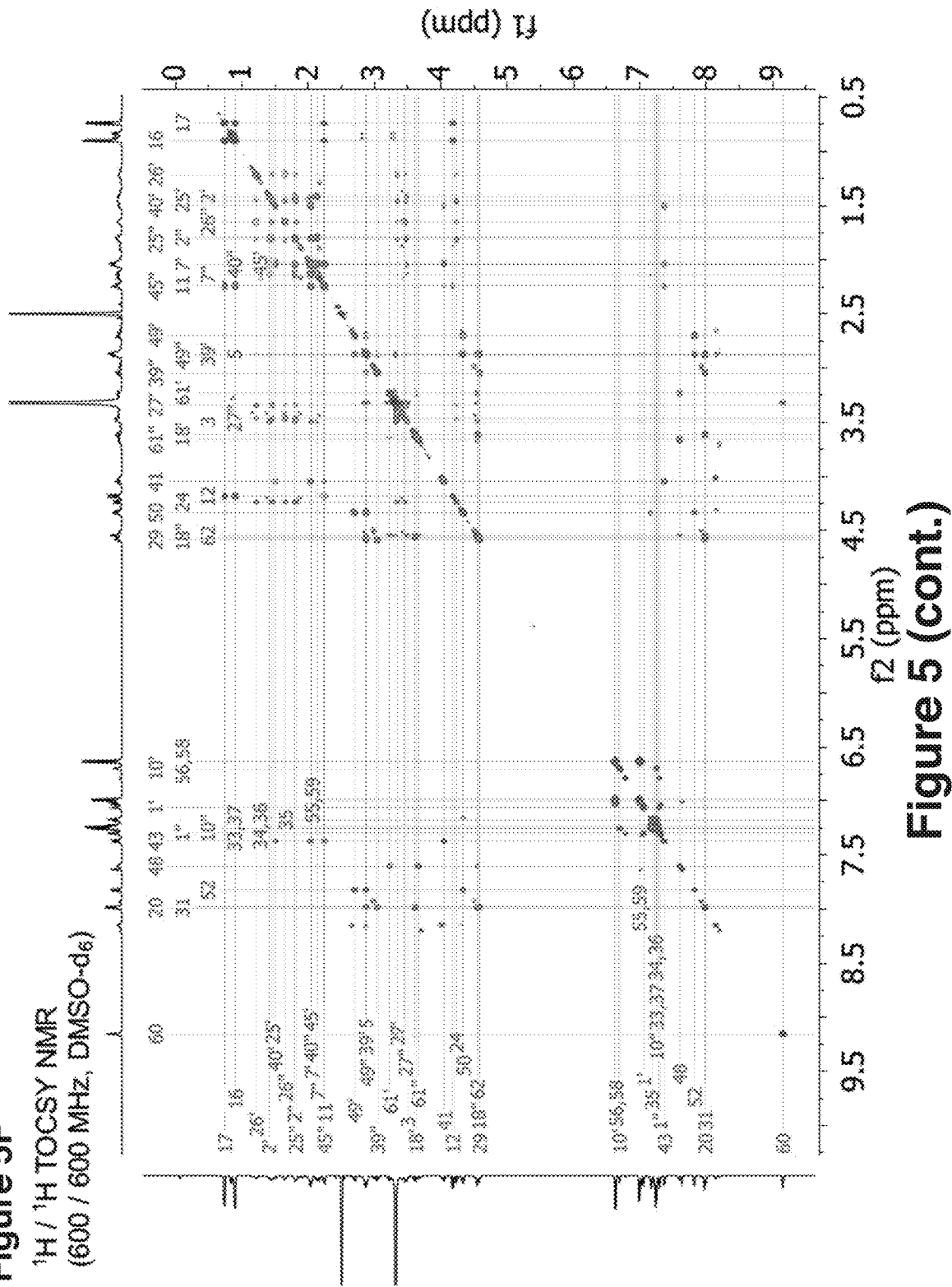
Figures 5, 5I:
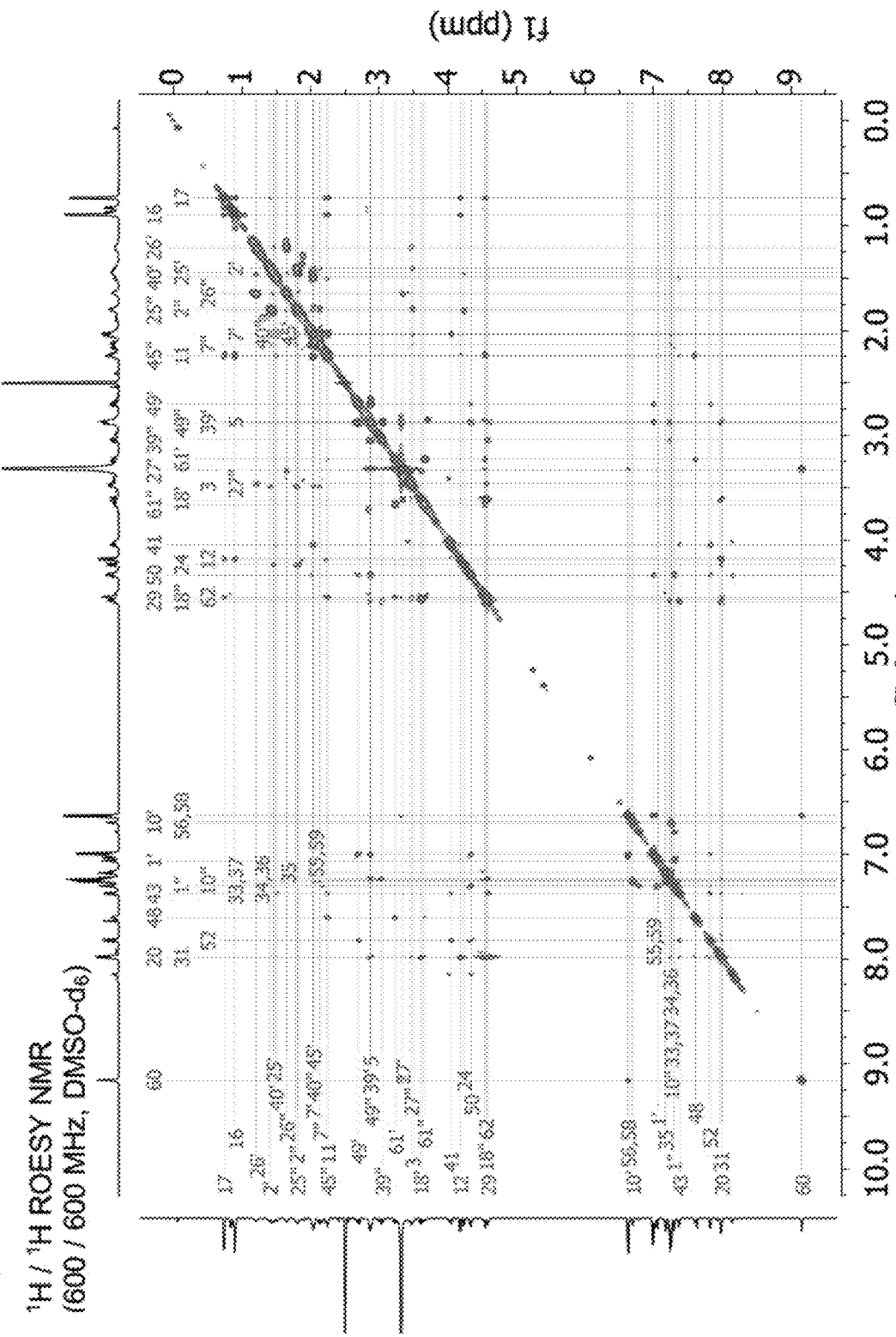
Figures 6, 6A:
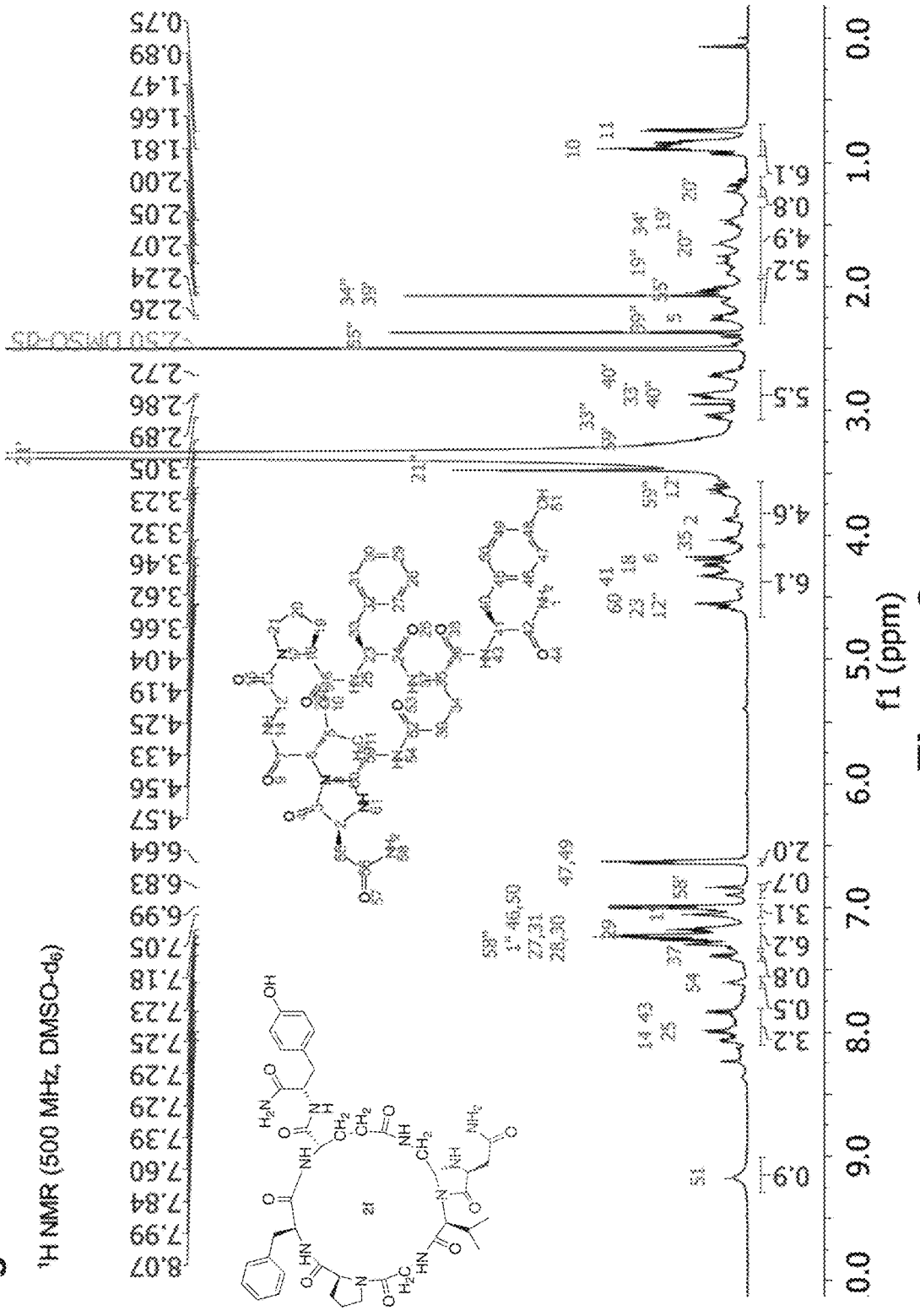
Figures 6, 6B:
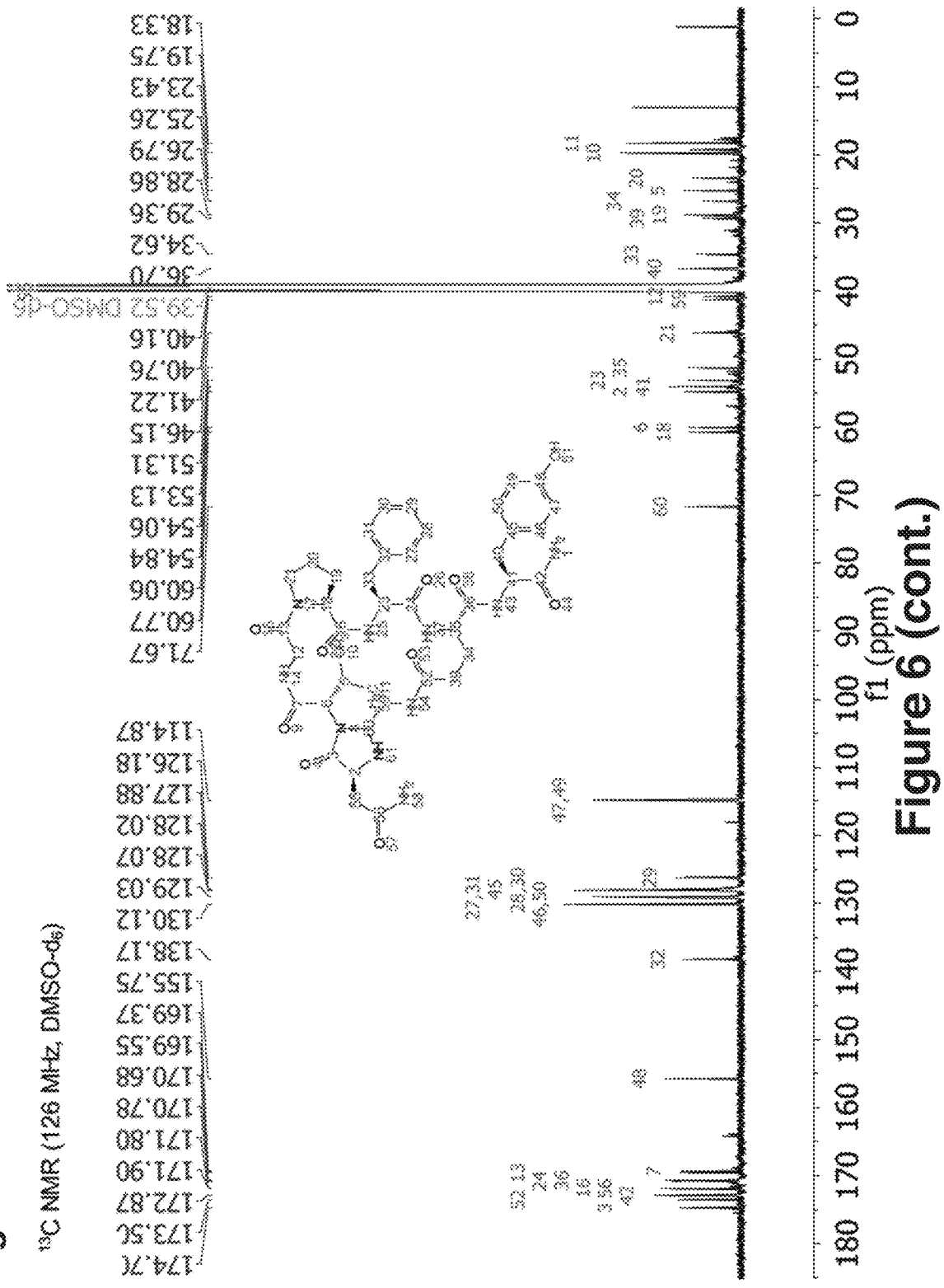
Figures 6, 6C:
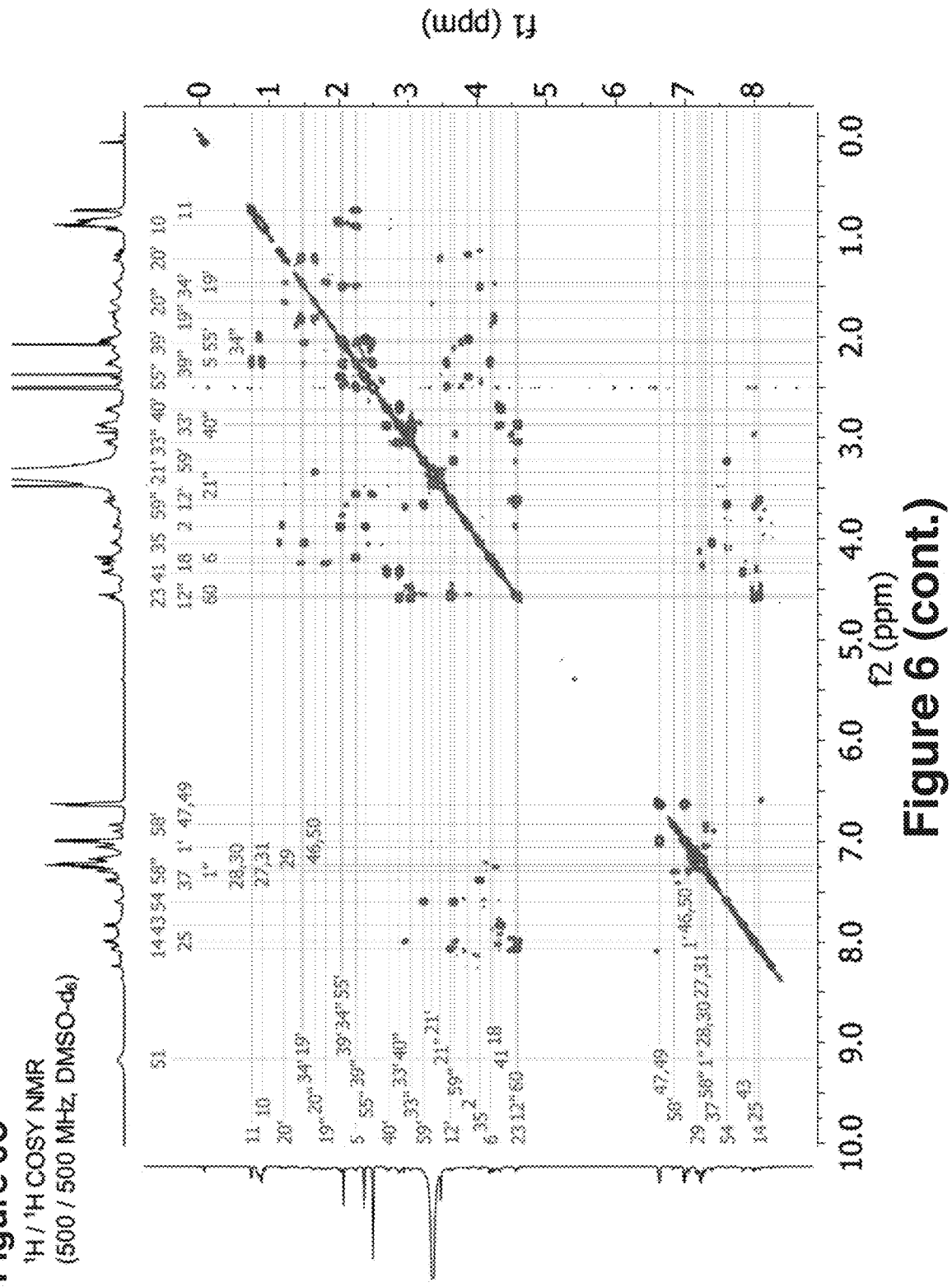
Figures 6, 6E:
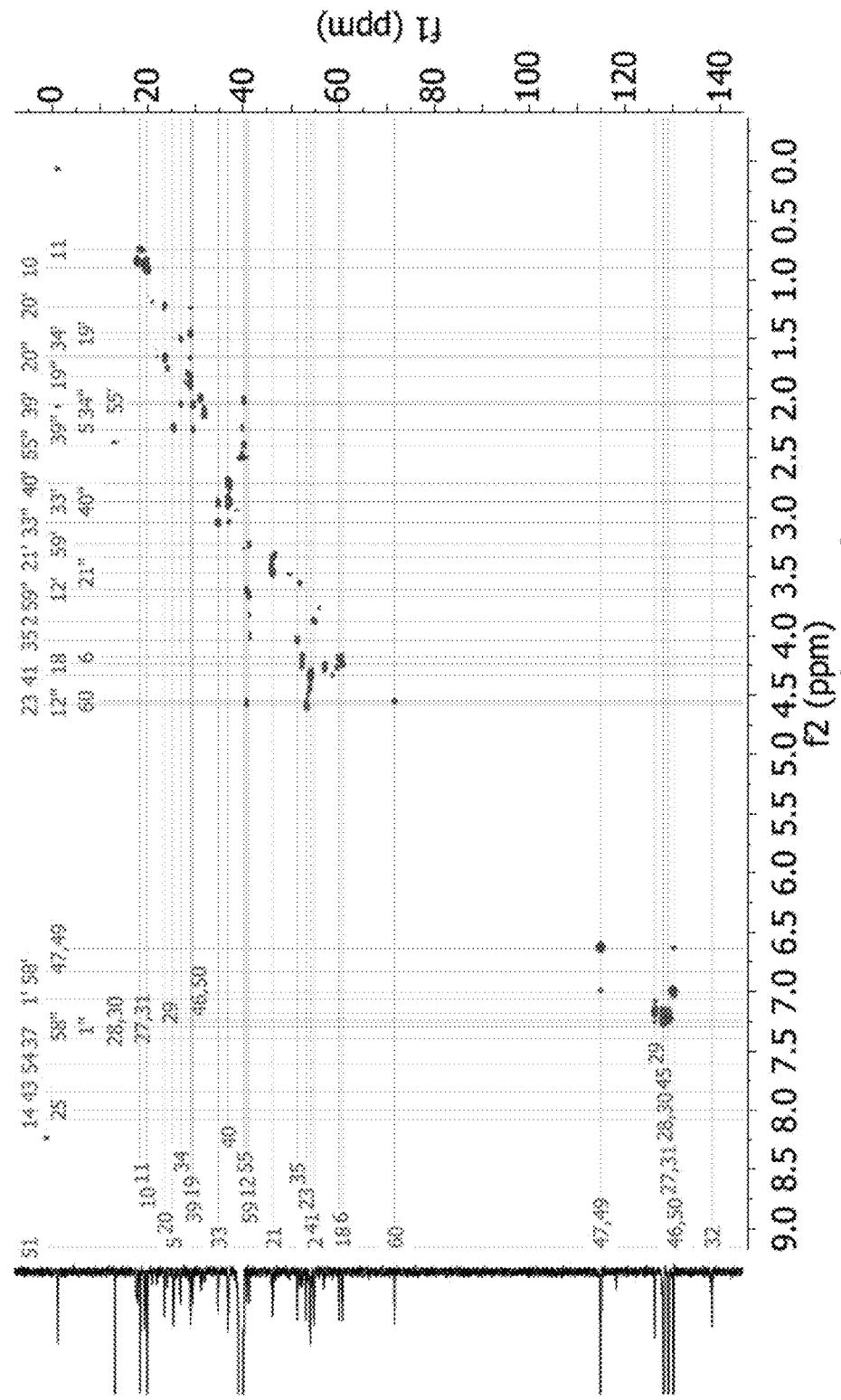
Figures 6, 6F:
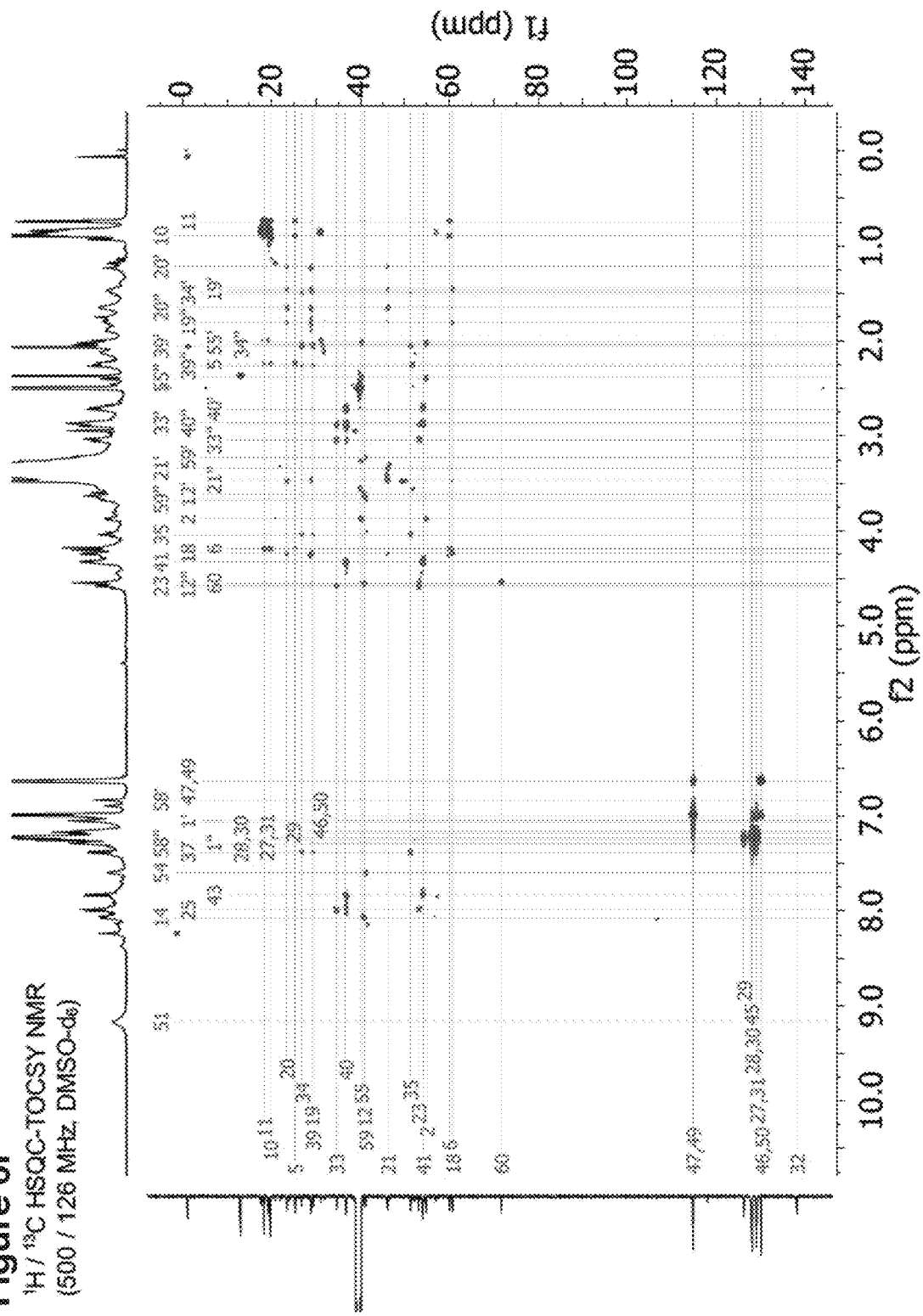
Figure 6:
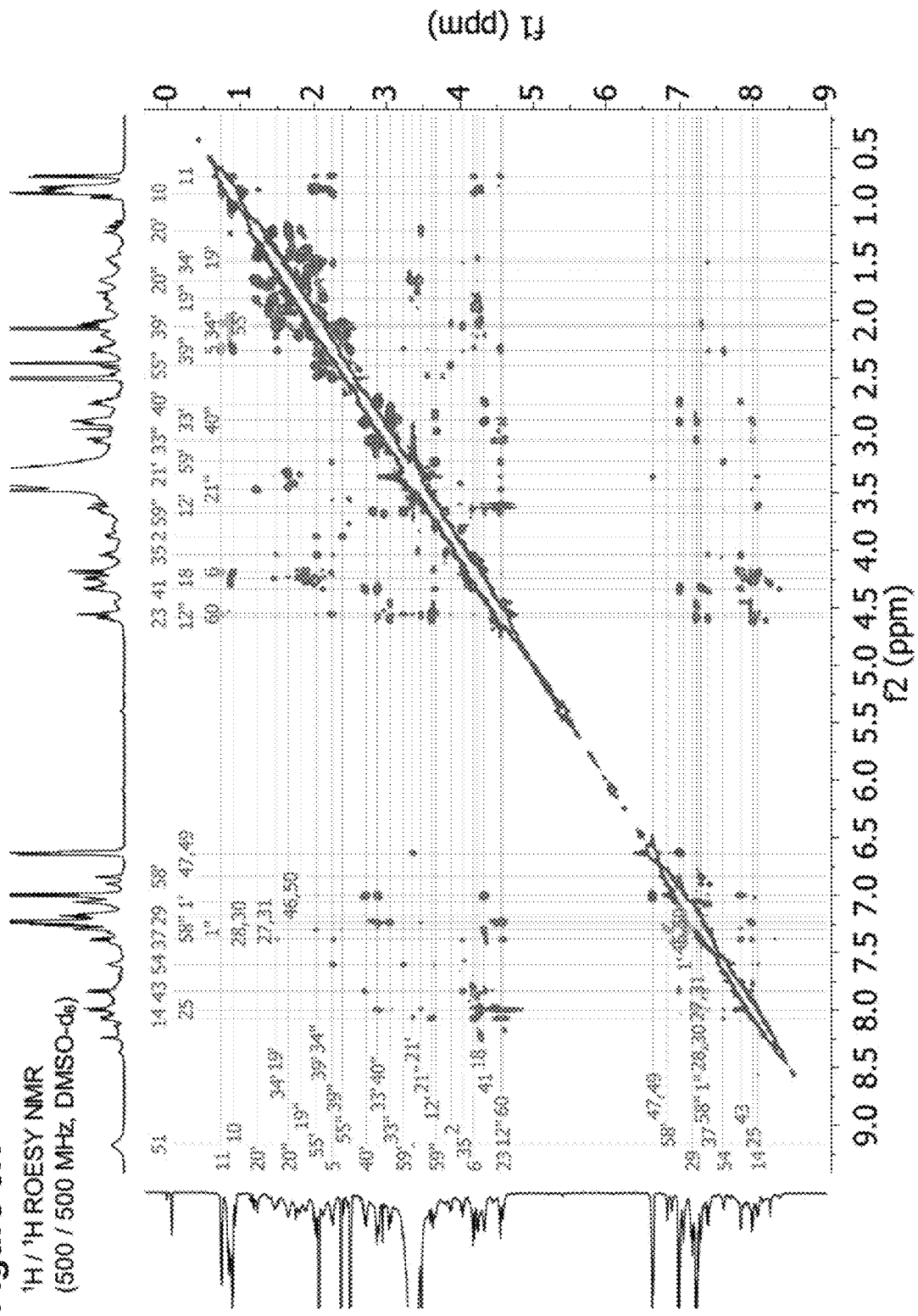
FIG. 6, comprising

From the below ACD Labs predictions (ver. 2015) of carbon chemical shifts, the aminal carbon (i.e., newly formed stereocenter) was predicted to be 62.39 ppm in the 7-membered ring structure and 73.44 ppm in the 5-membered ring structure. The observed chemical shift was 71.58 ppm, which corresponded to the 5-membered ring structure (FIG. 5B and FIG. 5D). Furthermore, both sets of $NH_2$ protons on the terminal amide were observed in the $^{15}N$ HSQC spectrum (FIG. 5J).

Mechanistic Determination of the Reason for High Stereoselectivity of New Chiral Center In an effort to determine the reason for the high stereoselectivity of new chiral center in cyclic peptide 2a cyc (AVGPFEY) (SEQ ID NO: 13) with R configuration two linear peptide aldehydes, aVGPFE(CHO)Y (SEQ ID NO: 13) and AiGPFE(CHO)Y (SEQ ID NO: 46) were synthesized with D-configured amino acids. The peptide aldehydes had D-amino acids strategically placed in either the first or the second position. This was followed by the macrocyclization of linear peptide aldehydes aVGPFE(CHO)Y (SEQ ID NO: 13) and AiGPFE(CHO)Y (SEQ ID NO: 34) under optimized CyClick reaction conditions and a new chiral center in resulting cyclic peptides cyc(aVGPFEY) (SEQ ID NO: 13) and cyc(AiGPFEY) (SEQ ID NO: 46) were analyzed by NMR (FIG. 10), which showed no stereochemical change based on the use of D-configured amino acid at the first position.

Procedure for High Concentration Studies

Linear peptide AVGPE(CHO)Y (SEQ ID NO: 13) 1a was cyclized at high concentrations (25 mM) with two different methods, the CyClick procedure and conventional reductive animation procedure and results were compared.

CyClick method: Linear peptide AVGPFE(CHO)Y (SEQ ID NO: 13) 1a (4 mg, 0.005 mmol) was dissolved in 1:1 DMF/$H_2O$ solution (200 µL, final conc. 25 mM) and DMAP (21 equiv.) was added. The resulting solution was stirred at room temperature for 19 h. The reaction was analyzed by HPLC, which showed the formation of only desired cyclic peptide 2a. The formation of any dimers or polymers was not observed under the reaction conditions.

Conventional reductive animation method (Malins L R et al., 2017, J. Am. Chem. Soc., 139:5233) Linear peptide AVGPFE(CHO)Y (SEQ ID NO: 13) 1a (4 mg, 0.005 mmol) was dissolved in 1:1 DMF/$H_2O$ solution (200 µL, final conc. 25 mM) and NaBH$_3$CN (50 equiv.) was added. The resulting solution was stirred at room temperature for 19 h. The reaction was analyzed by HPLC, which showed the formation of linear and cyclic dimers side products along with desired cyclic peptide.

Procedure for High Concentration Studies by CyClick Method

Linear peptide AVGPE(CHO)Y (SEQ ID NO: 13) 1a was cyclized at high concentrations (100 mM) with the CyClick procedure.

CyClick Method: Linear peptide AVGPFE(CHO)Y (SEQ ID NO: 13) 1a (3.5 mg, final conc. 100 mM) was dissolved in 1:1 DMF/H$_2$O solution (44 μL) and DMAP (21 equiv.) was added. The resulting solution was stirred at room temperature for 8 h. The reaction was analyzed by HPLC, which showed the formation of only desired cyclic peptide 2a with 89% conversion. The formation of any dimers or polymers was not observed under the reaction conditions.

General Procedures for Rate Studies

Linear peptide AVGPFE(CHO)Y (SEQ ID NO: 13) 1a (1 mg, 0.001 mmol) was dissolved in 1:1 DMF/H$_2$O solution (1800 μL, final conc. 0.67 mM) and DMAP (7 equiv.) was added. The resulting solution was stirred at room temperature. Samples (100 μL) were taken after regular intervals of time and reaction was quenched by adding it into 400 μL of pre-frozen water followed by freezing the sample at −80° C. The frozen samples were then lyophilized and dissolved in 120 μL of 1:1 H$_2$O/ACN and injected immediately into the HPLC for determining the % conversion to a macrocyclic peptide 2a at different time intervals. Rate study was done in triplicate. Average of three trials was used to plot the rate curve (FIG. 15), 0 min sample is sample taken after addition of all the reagents of the CyClick reaction.

Figures 30, 30A:
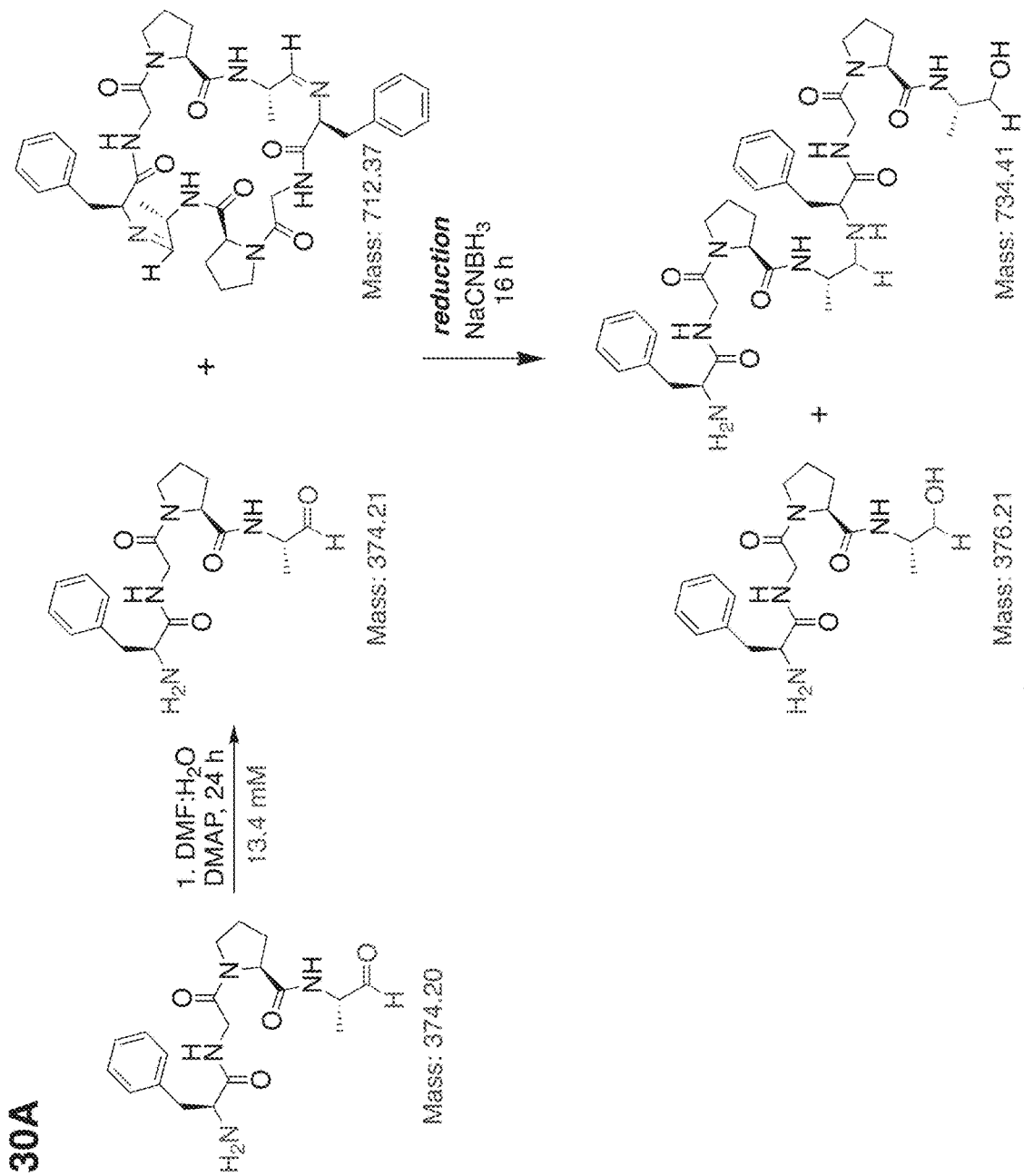
Figure 30:
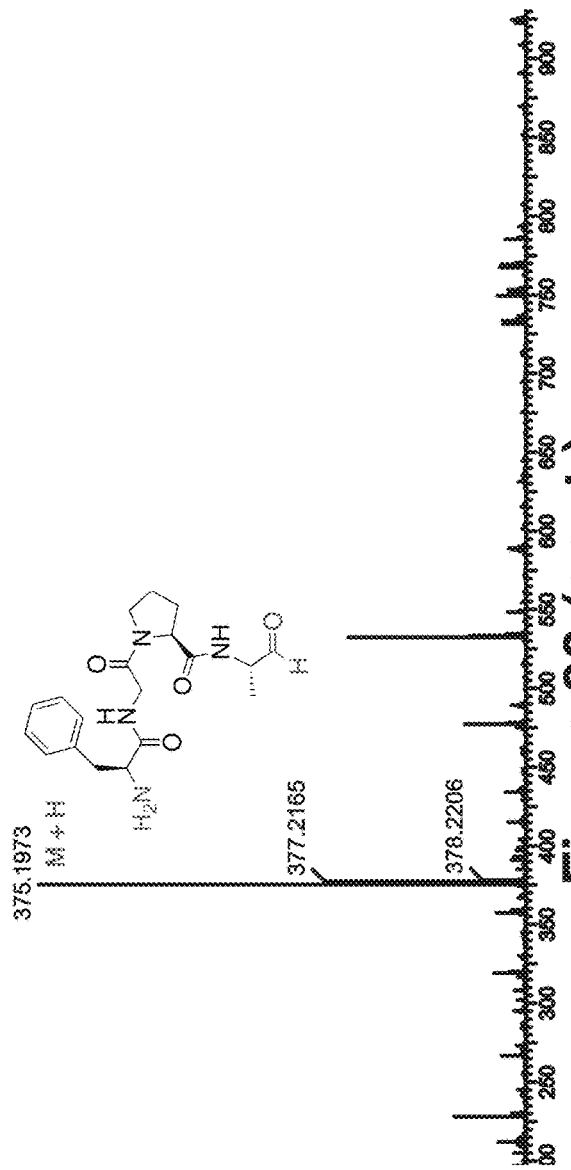
FIG. 30, comprising
Figures 30, 30C:
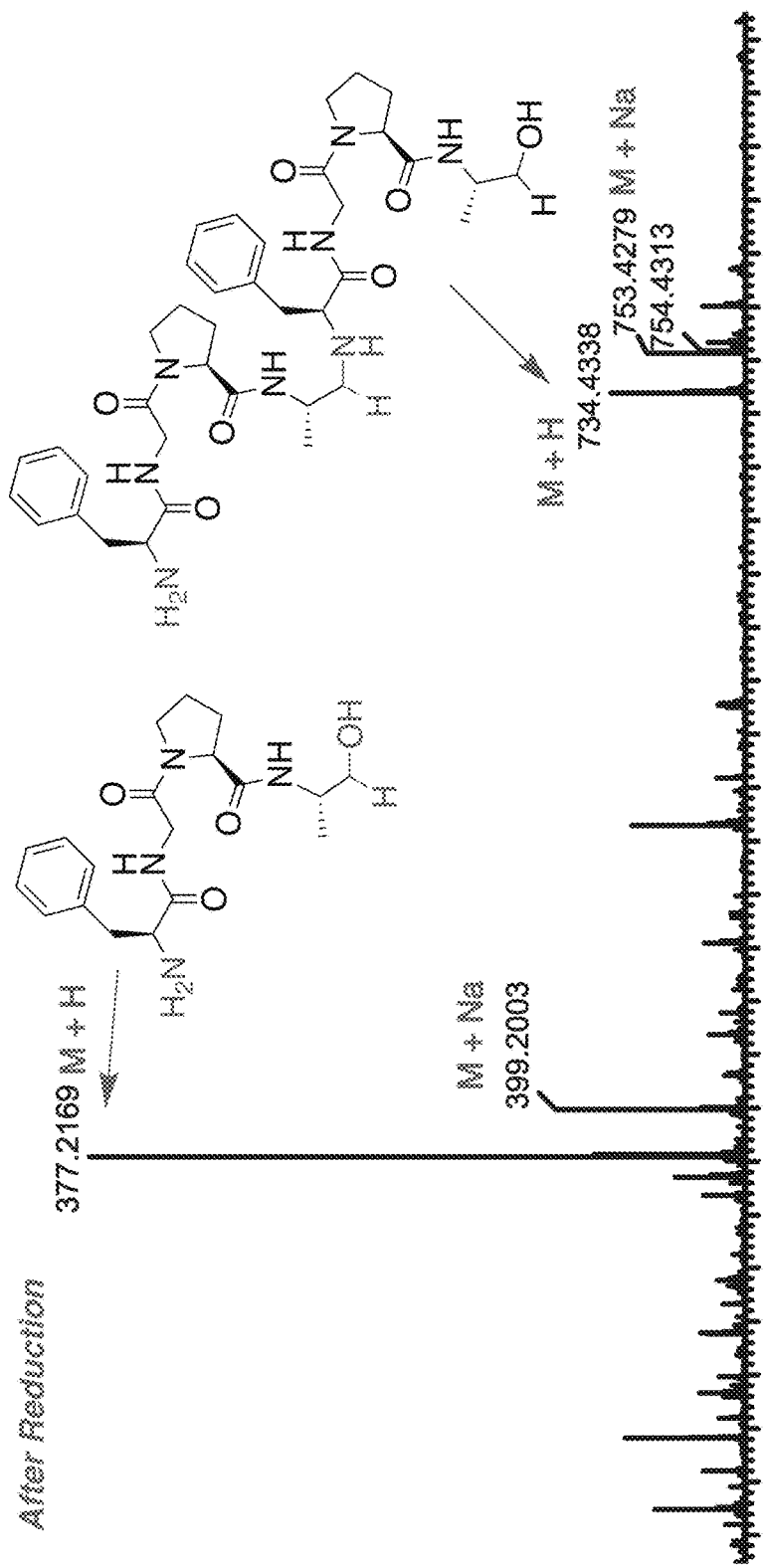

Reaction with Tetrapeptide FGPA(CHO) and Identification of the Products of Tetrapeptide Aldehyde Reaction—FIG. 30

Lypholized peptide FGPA(CHO) (SEQ ID NO: 49) (1.5 mg, 12.8 mM) was mixed with excess of DMAP (30 equiv., 384 mM) in a 1:1 DMF:H$_2$O solution (300 μL), The reaction was shaken at room temperature for 24 h. The cyclic imine intermediate exhibited mass equivalent to the desired 4-oxazolidinone products. A tetrapeptide aldehyde could not yield a 9-membered ring. To confirm the formation of any linear and cyclodimer by CyClick chemistry, reduction with sodium cyanoborohydride was carried, out. In an effort to determine the nature of the product of tetrapeptide reaction, sodium cyanoborohydride (50 equiv.) was added and reaction was stirred for additional 16 h. The resulting products were analyzed with LC-MS. The result showed the formation of reduced linear tetrapeptide and reduced dimerized peptide. No formation of any CyClick product was observed.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound comprising 4-imidazolidinone-fused cyclic peptide, wherein the compound is a compound having the structure of

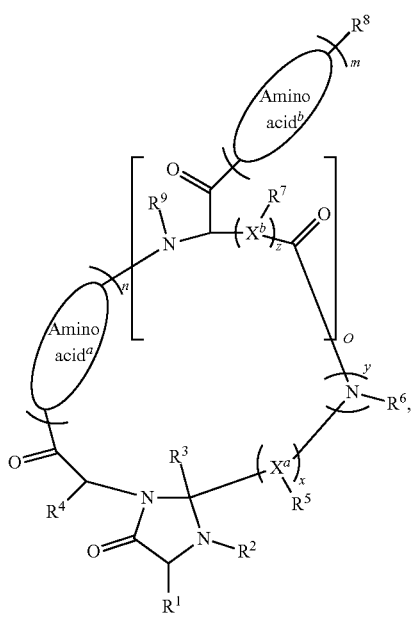

Formula (I)

or a derivative, prodrug, pharmaceutically acceptable salt, solvate, isomer, or tautomer thereof, wherein each occurrence of $R^1$, $R^2$, $R^3$, $R^4$, $R^5$, $R^6$, $R^7$, $R^8$, and $R^9$ is independently selected from the group consisting of hydrogen, deuterium, halogen, hydroxyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, acyl, ester, urea, thiourea, thiol, thioalkyl, thioxo, sulfanyl, sulfinyl, sulfonyl, phosphino, =O, nitrile, isonitrile, cyano, carbamate, guanidine, guanidine alkyl, amino acid, and any combination thereof;

wherein $R^1$ and $R^2$ are optionally fused or joined to form a ring;

each occurrence of $X^a$ and $X^b$ is independently selected from the group consisting of C, —$CR^{10}$, N, P, P=O, S=O, and any combination thereof;

wherein each occurrence of $R^{10}$ is independently selected from the group consisting of hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, and any combination thereof;

m is an integer from 1 to 5;
n is an integer from 1 to 20;
o is an integer from 0 to 10;
x is an integer from 0 to 10;
y is an integer selected from the group consisting of 0 and 1; and
z is an integer from 0 to 10.

2. The compound of claim 1, wherein each occurrence of amino acid$^a$ and amino acid$^b$ is independently selected from the group consisting of a natural amino acid, unnatural amino acid, D-amino acid, L-amino acid, functionalized natural amino acid, functionalized unnatural amino acid, functionalized D-amino acid, functionalized L-amino acid, and any combination thereof.

3. The compound of claim 1, wherein the compound having the structure of Formula (I) is a compound having the structure selected from the group consisting of

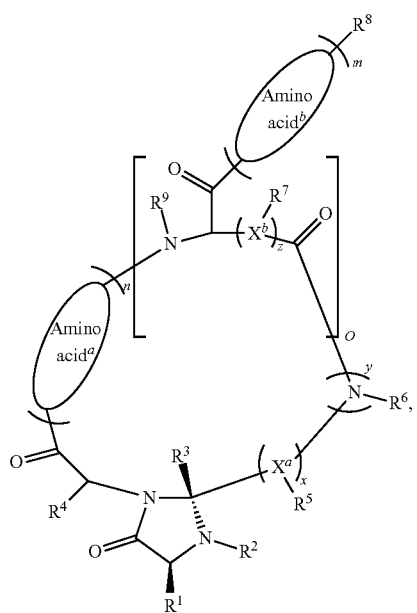

Formula (Ia)

or a derivative, prodrug, pharmaceutically acceptable salt, solvate, isomer, or tautomer thereof, and

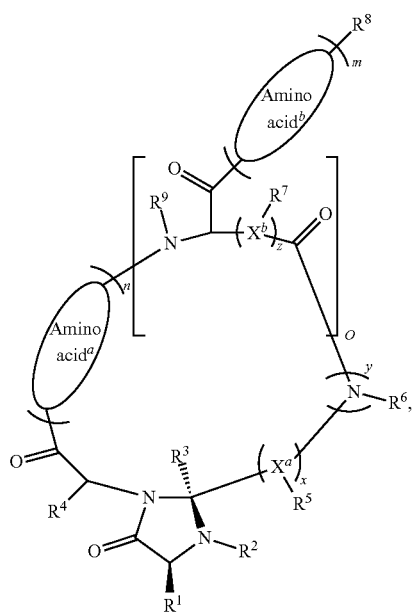

Formula (Ib)

or a derivative, prodrug, pharmaceutically acceptable salt, solvate, isomer, or tautomer thereof, wherein each occurrence of $R^1$, $R^2$, $R^3$, $R^4$, $R^5$, $R^6$, $R^7$, $R^8$, and $R^9$ is independently selected from the group consisting of hydrogen, deuterium, halogen, hydroxyl, amino,

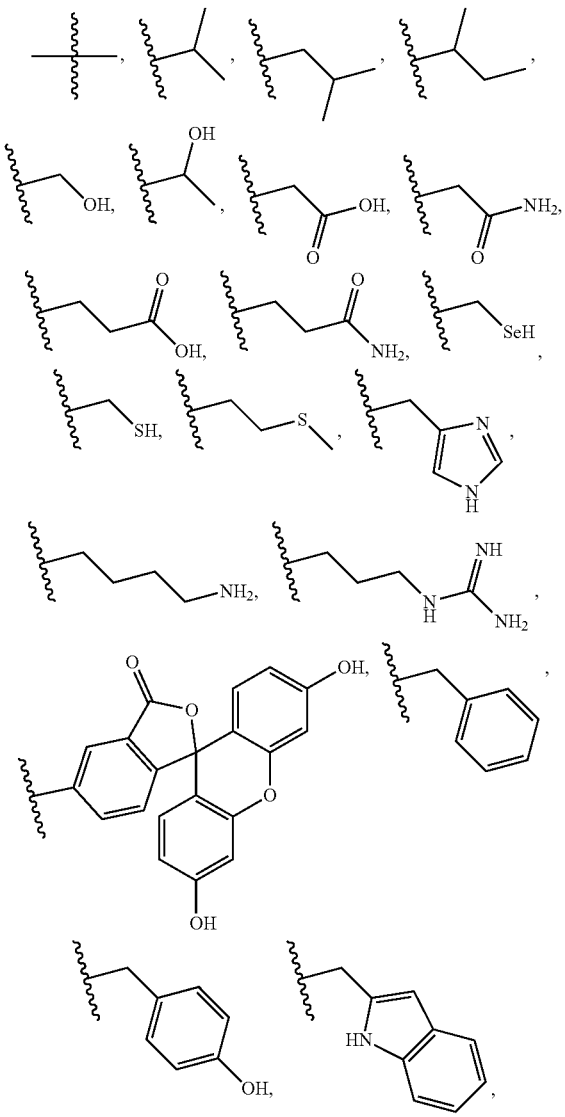

amino acid, and any combination thereof;
wherein $R^1$ and $R^2$ are optionally fused or joined to form a ring;
each occurrence of $X^a$ and $X^b$ is independently selected from the group consisting of C, —$CR^{10}$, N, P, P=O, S=O, and any combination thereof;
wherein each occurrence of $R^{10}$ is independently selected from the group consisting of hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, and any combination thereof;

m is an integer from 1 to 5;

n is an integer from 1 to 20;

o is an integer from 0 to 10;

x is an integer from 0 to 10;

y is an integer selected from the group consisting of 0 and 1; and z is an integer from 0 to 10.

4. The compound of claim 1, wherein each occurrence of $R^1$, $R^2$, $R^4$, $R^6$, and $R^9$ is independently selected from the group consisting of hydrogen, deuterium, halogen, hydroxyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, acyl, ester, urea, thiourea, thiol, thioalkyl, thioxo, sulfanyl, sulfinyl, sulfonyl, phosphino, =O, nitrile, isonitrile, cyano, carbamate, guanidine, guanidine alkyl, amino acid, and any combination thereof;

wherein $R^1$ and $R^2$ are optionally fused or joined to form a ring;

$R^3$ is selected from the group consisting of hydrogen, deuterium, alkyl, and any combination thereof;

each occurrence of $R^5$ and $R^7$ is independently selected from the group consisting of hydrogen and deuterium;

$R^8$ is amino;

each occurrence of $X^a$ and $X^b$ is independently selected from the group consisting of C and —$CR^{10}$;

wherein each occurrence of $R^{10}$ is independently selected from the group consisting of hydrogen and deuterium;

m is an integer from 1 to 5;

n is an integer from 1 to 10;

o is an integer selected from the group consisting of 0 and 1;

x is an integer selected from the group consisting of 0 and 1;

y is an integer selected from the group consisting of 0 and 1; and z is an integer selected from the group consisting of 0, 1, and 2.

5. The compound of claim 1, wherein (Amino Acid$^a$)$_n$ is selected from the group consisting of an amino acid sequence as set forth in SEQ ID NOs: 1-12.

6. The compound of claim 1, wherein o is an integer 0.

7. The compound of claim 1, wherein $R_2$ is hydrogen.

8. The compound of claim 1, wherein $R_1$ and $R_2$ are fused or joined to form a ring.

9. The compound of claim 8, wherein the compound having the structure of Formula (I) is a compound having the structure of

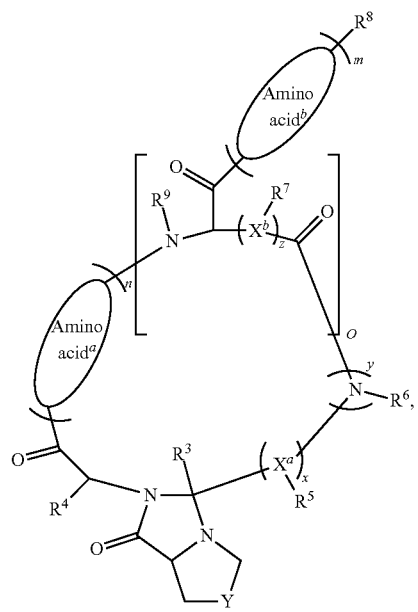

Formula (II)

or a derivative, prodrug, pharmaceutically acceptable salt, solvate, isomer, or tautomer thereof, wherein each occurrence of $R^3$, $R^4$, $R^5$, $R^6$, $R^7$, $R^8$, and $R^9$ is independently selected from the group consisting of hydrogen, deuterium, halogen, hydroxyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, acyl, ester, urea, thiourea, thiol, thioalkyl, thioxo, sulfanyl, sulfinyl, sulfonyl, phosphino, =O, nitrile, isonitrile, cyano, carbamate, guanidine, guanidine alkyl, amino acid, and any combination thereof;

each occurrence of $X^a$ and $X^b$ is independently selected from the group consisting of C, —$CR^{10}$, N, P, P=O, S=O, and any combination thereof;

wherein each occurrence of $R^{10}$ is independently selected from the group consisting of hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, and any combination thereof;

wherein Y is selected from the group consisting of O, S, NH, C=O, and $CH_2$;

m is an integer from 1 to 5;

n is an integer from 1 to 20;

o is an integer from 0 to 10;

x is an integer from 0 to 10;

y is an integer selected from the group consisting of 0 and 1; and z is an integer from 0 to 10.

10. The compound of claim 9, wherein the compound having the structure of Formula (II) is a compound having the structure selected from the group consisting of

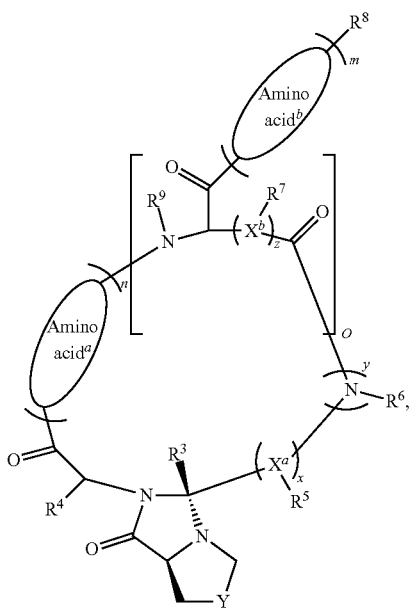

Formula (IIa)

or a derivative, prodrug, pharmaceutically acceptable salt, solvate, isomer, or tautomer thereof, and

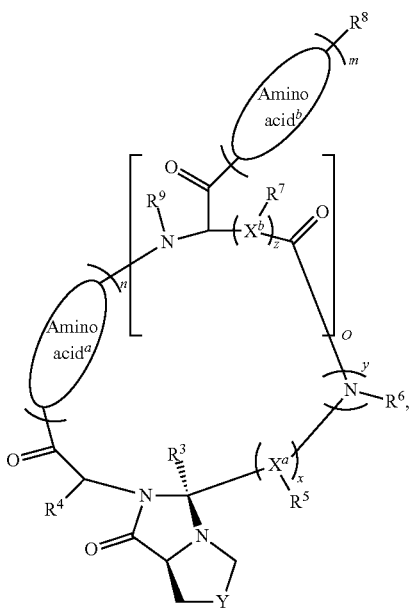

Formula (IIb)

or a derivative, prodrug, pharmaceutically acceptable salt, solvate, isomer, or tautomer thereof, wherein each occurrence of $R^3$, $R^4$, $R^5$, $R^6$, $R^7$, $R^8$, and $R^9$ is independently selected from the group consisting of hydrogen, deuterium, halogen, hydroxyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, acyl, ester, urea, thiourea, thiol, thioalkyl, thioxo, sulfanyl, sulfinyl, sulfonyl, phosphino, =O, nitrile, isonitrile, cyano, carbamate, guanidine, guanidine alkyl, amino acid, and any combination thereof;

each occurrence of $X^a$ and $X^b$ is independently selected from the group consisting of C, —$CR^{10}$, N, P, P=O, S=O, and any combination thereof;

wherein each occurrence of $R^{10}$ is independently selected from the group consisting of hydrogen, deuterium, halogen, hydroxyl, hydroxylalkyl, alkoxy, amino, aminoalkyl, carbonyl, carboxyl, carboxylic acid, alkyl, heteroalkyl, cycloalkyl, heterocycloalkyl, alkenyl, cycloalkenyl, heterocycloalkenyl, alkynyl, cycloalkynyl, heterocycloalkynyl, aryl, arylalkyl, heteroaryl, heteroarylalkyl, arylalkenyl, heteroarylalkenyl, arylalkynyl, heteroarylalkynyl, acyl, ester, urea, thiourea, thiol, thioalkyl, thioxo, sulfanyl, sulfinyl, sulfonyl, phosphino, nitrile, isonitrile, cyano, carbamate, guanidine, guanidine alkyl, amino acid, and any combination thereof;

wherein Y is selected from the group consisting of O, S, NH, C=O, and $CH_2$;

m is an integer from 1 to 5;
n is an integer from 1 to 20;
o is an integer from 0 to 10;
x is an integer from 0 to 10;
y is an integer selected from the group consisting of 0 and 1; and
z is an integer from 0 to 10.

11. The compound of claim 1, wherein the compound inhibits at least one protein-protein interaction.

12. A composition comprising at least one compound of claim 1.

13. The compound of claim 1, wherein each occurrence of $R^1$, $R^2$, $R^3$, $R^4$, $R^5$, $R^6$, $R^7$, $R^8$, and $R^9$ is independently selected from the group consisting of hydrogen, deuterium, halogen, hydroxyl, amino,

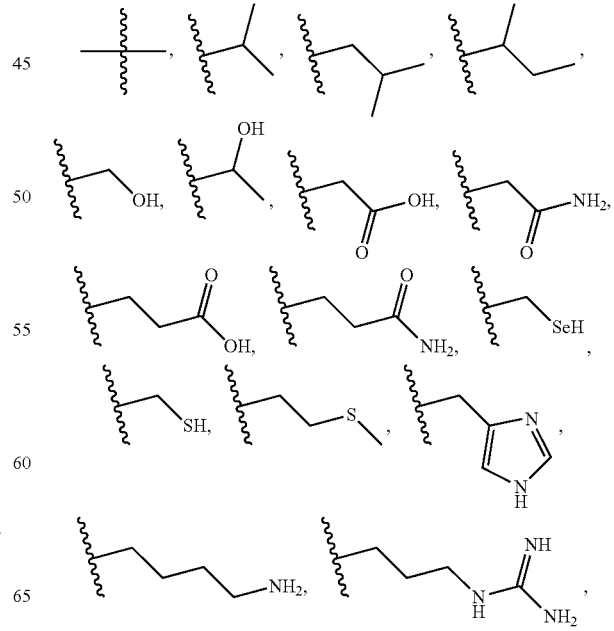

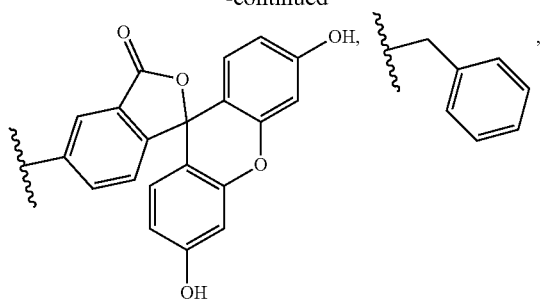
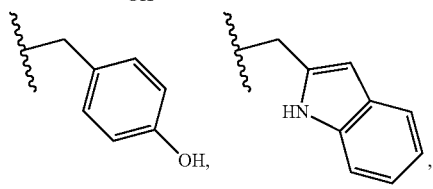
amino acid, and any combination thereof;
wherein $R^1$ and $R^2$ are optionally fused or joined to form a ring.
* * * * *